(12) United States Patent
Bevan et al.

(10) Patent No.: US 7,396,910 B2
(45) Date of Patent: Jul. 8, 2008

(54) TRANSIENT RECEPTOR POTENTIAL CHANNEL TRPV3 AND ITS USE

(75) Inventors: Stuart Bevan, London (GB); Pamposh Ganju, London (GB); Peter McIntyre, London (GB); Ardem Patapoutian, San Diego, CA (US); Andrea Peier, San Diego, CA (US); Chuanzheng Song, Warren, NJ (US)

(73) Assignees: IRM LLC, Hamilton (BM); Novartis AG, Basel (CH)

(*) Notice: Subject to any disclaimer, the term of this patent is extended or adjusted under 35 U.S.C. 154(b) by 0 days.

(21) Appl. No.: 11/384,955

(22) Filed: Mar. 20, 2006

(65) Prior Publication Data

US 2006/0251648 A1 Nov. 9, 2006

Related U.S. Application Data

(63) Continuation of application No. 10/171,319, filed on Jun. 13, 2002, now Pat. No. 7,115,414.

(60) Provisional application No. 60/381,739, filed on May 16, 2002, provisional application No. 60/381,086, filed on May 15, 2002, provisional application No. 60/357,161, filed on Feb. 12, 2002, provisional application No. 60/352,914, filed on Jan. 29, 2002, provisional application No. 60/351,238, filed on Jan. 22, 2002, provisional application No. 60/297,835, filed on Jun. 13, 2001.

(51) Int. Cl.
  *C07K 14/435* (2006.01)
  *A61K 38/17* (2006.01)

(52) U.S. Cl. ........................ 530/350; 514/12

(58) Field of Classification Search ........................ None
  See application file for complete search history.

(56) References Cited

U.S. PATENT DOCUMENTS

| 6,239,267 | B1 | 5/2001 | Duckworth et al. |
| 6,406,908 | B1 | 6/2002 | McIntyre et al. |
| 2003/0027232 | A1* | 2/2003 | Davis et al. ............... 435/7.92 |
| 2003/0219806 | A1* | 11/2003 | Glucksmann et al. ........ 435/6 |

FOREIGN PATENT DOCUMENTS

| EP | 0 943 683 | 9/1999 |
| WO | WO 01/53348 A2 | 7/2001 |

OTHER PUBLICATIONS

NCBI Sequence Viewer, Definition: *Homo sapiens* Vanilloid Receptor-like Protein-1 (VRL-1) mRNA, complete cds, Version AF129112.1 GI:4589140 (Apr. 20, 1999).
NCBI Sequence Viewer, Definition: *Rattus norvegicus* Vanilloid Receptor Subtype 1 mRNA, complete cds, Version AF029310.1 GI:2570932 (Oct. 30, 1997).
NCBI Sequence Viewer, Definition: *Homo sapiens* OTRPC4 mRNA, complete cds, Version AF258465.1 GI:10304080 (Sep. 26, 2000).
NCBI Sequence Viewer, Definition: *Homo sapiens* Similar to Vanilloid Receptor-Related Osmotically Activated Channel Protein (LOC162514), mRNA, Version XM_091604.1 GI:18587705 (Feb. 7, 2002).
NCBI Sequence Viewer, Definition: OTRPC4 Cation Channel, complete cds, Version AAG17543 GI:10443637 (Oct. 2, 2000).
NCBI Sequence Viewer, Definition: *Mus musculus*, Version Accession No. AF208026.1 GI:10443636 (Oct. 2, 2000).
Caterina et al., "The Capsaicin Receptor: A Heat-Activated Ion Channel in the Pain Pathway", Nature, vol. 389, No. 23, pp. 816-824 (1997) and Accession No. AF029310 XP002239516 (1997).
Caterina et al., "A Capsaicin-Receptor Homologue with a High Threshold for Noxious Heat", Nature, vol. 398, No. 6276, pp. 436-441 (1999).
Caterina et al., "Impaired Nociception and Pain Sensation in Mice Lacking the Capsaicin Receptor", Science, vol. 288, pp. 306-313 (2000).
Clapham, et al., "The TRP Ion Channel Family", Nature Reviews, Neuroscience, vol. 2, No. 6, pp. 387-396 (2001).
Davis et al., "Vanilloid Receptor-1 is Essential for Inflammatory Thermal Hyperalgesia", Nature, vol. 405, pp. 183-187 (2000).
Liedtke et al., "Vanilloid-Receptor-Related Osmotically Activated Channel (VR-OAC), a Candidate Vertebrate Osmoreceptor", Cell, vol. 103, pp. 525-535 (2000).
McKemy et al., "Identification of a Cold Receptor Reveals a General role for TRP Channels in Thermosensation", Nature, vol. 416, pp. 52-58 (2002).
Montell et al., "A Unified Nomenclature for the Superfamily of TRP Cation Channels", Molecular Cell, vol. 9, No. 2, pp. 229-231, (2002).
Peng et al., "Structural Conservation of the Genes Encoding CaT1, CaT2 and Related Cation Channels", Genomics, vol. 76, No. 1-3, pp. 99-109 (2001).
Peier et al, "A Heat Sensitive TRP Channel Expressed in Keratinocytes", Science, vol. 296, No. 5575, pp. 2046-2049, (2002) and Database Accession Nos. NM-145068 XP002239517 & NM_145099 XP002239518 (abstract).
Peng et al., "Structural Conversation of the Genes Encoding CaT1, CaT2, and Related Cation Channels", Genomics, vol. 76, Nos. 1-3, pp. 99-109 (2001).
Smith et al., "TRPV is a Temperature-Sensitive Vanilloid Receptor-Like Protein", Nature, vol. 418, No. 6894, pp. 186-190, (2002).
Strotmann et al., "OTRPC4, a Nonselective Cation Channel that Confers Sensitivity to Extracellular Osmolarity", Nat. Cell Biol., vol. 2, pp. 695-702 (2000).

(Continued)

*Primary Examiner*—Ruixiang Li
(74) *Attorney, Agent, or Firm*—Timothy L. Smith; Genomics Institute of the Novartis Research Foundation

(57) ABSTRACT

This invention provides novel genes and polypeptides of the transient receptor potential channel family, and use of these genes and polypeptides for the treatment of pain and identification of agents useful in the treatment of pain.

3 Claims, 17 Drawing Sheets

OTHER PUBLICATIONS

Tsavaler et al., "Trp-p8, a Novel Prostate-Specific Gene, is Up-Regulated in Prostate Cancer and Other Malignancies and Shared High Homology with Transient Receptor Potential Calcium Channel Proteins", Cancer Res., vol. 61, pp. 3760-3769 (2001).

Peng et al., "Structural Conservation of the Genes Encoding CaT1, CaT2, and Related Cation Channels", Genomics, vol. 76, Nos. 1-3, pp. 99-109 (2001).

Xu et al., "TRPV3 is a Calcium-Permeable Temperature-Sensitive Cation Channel", Nature, vol. 418, No. 6894, pp. 181-186, (2002).

* cited by examiner

FIGURE 6A

```
TRPM7    1  MSQKSWIESTLTKRECVY-----------------------------IIPSSKDPHRCLPGCQICQQLVRCFCGRLVKQHA
TRPM1    1  ------------------------------------------------------------------------------
TRPM2    1  KEPSALRKAGSEQEEGIEGLPRRVTDLGMVSNLRRSNSSLFKSWRLQCPFGNNDKQESLSSWIPENIKKKECVYPVSSSK
TRPM8    1  KSFEGARLSMPSPRNGTNGSTK------TLYSSVSRST---------IVSYSDSD------LVNFIQANFKKRECVFFTHLSK

TRPM7   53  CFTASLAMKYSDVKLGEHFNQA-------IEEWSVSKHTEQSPTDAYGVINFQGSSHSYRAKYVRLSYDTKPEIILQLLL
TRPM1    1  --------------------------------------------------MSIRVSYDTKFQSLLHLNV
TRPM2   81  LSDAGKVVCQCGYTHEQHLEEATKPHTFQGTQWDPKKHVQEMPTDAFGDIVFTGLSQKV-SKIVRMGQDTFSSVIYHIMT
TRPM8   63  AMFN----ICKCGYAQSQHIEGT---QINQNSKWNYKEHTKKPFTDAFGDIQFETLGKKG-K-YLRLSCHTLSETLYKLLT

TRPM7  126  KEWQMELPKLVISVHGGMQKFELHPRIKQLLGKGLIKAAVTTGAWIITGGVNTGVAKHVGDALKEHASRSSRK---ICTI
TRPM1   20  KDWQLELPKLLISVHCGLQNPEMQPRIKQVFGKGLIKAAMTTGAWIFTGGVSTGVISHVGDALKDHSSKSPGR-----VCAI
TRPM2  160  QHWGLDVPNLLISVTQGAKNENMKPRLKSIFRNGLVKVAQITCAWIITGGSHTGVMRKQVGEAVRDFSLSSSVKESELITI
TRPM8  135  QHWHLKPPNLVISVTGGAKNFALKPRMRKIFSR-LIYIAQSKGAWILTGGTHYGLMKYIGEVVRENTISPNSEE-NIVAI

TRPM7  203  GIAPWGVIENRNDLVG-----RDVVAPYQTLLNPLSKLNVLNNLRSHFILVDDGTVCKYGAEVRLRRELEKTINQQP-IH
TRPM1   97  SIAPWGIVENKEDLVG-----IDVTRVYQTMSNPLSKLSVLNNSGTHPILADNGTLGKYGAEVKLRRLLEKHISLQE-IN
TRPM2  240  GVATWYTVHRREGLIHPT---GSPAEYILDEDGQGNLTCLDSNHSHFILVDDGTHGQYGVEIPLRTRLEKFISEQTKER
TRPM8  213  GIAAWGMVSNRDTLIRSCDDEGHFSAQYIMDDFTRDPLYILDNNSIHLLLVDNGCHGHPTVEAKLRNQLEKYISERTSQD

TRPM7  277  ARIGQCVPVVALIFEGGPNVILTVLSYLQESPPVEVVVEGTGRAADLLAYIHKQTEEGGNLPDAAEPDIISTIKMTPNS
TRPM1  171  TRLSQSVPLVGLVVEGGPNVVSIVLETLQEEPPIPVVICTGSGRASDILSPAHKYCEEGGIINESLREQLIATIQKTFNY
TRPM2  317  GGVAIKIPIVCVVLEGGPGTLHTTDNATTN---GTPCVVVEGSGRVADVIAQVANLPVSDITISLIQQKLSVFFQEMFETF
TRPM8  293  SNYGGKIPIVCFAQGGGRETLKAINTSVKS---KIPCVVVEGSGQIADVIASLVEV-EDVLTSSMVKEKLVRFLPRTVSRL

TRPM7  357  GQSEAVHLFYTNRECMKKKELITVHIGSEDHQDIDVAILTALLKGTNASAFD------QLILTIAWDRVDIAKNHVFV
TRPM1  251  NKAQSHQLFAIIMECMKKKELVTVFRMGSEGQQDIEMAILTALLKGTNVSAPD------QLSLALAWNRVDIARSQIFV
TRPM2  395  TEEPIVEWTKKIQDIVARRQLITVFREGKDKGQQDVDVAILQALLKASRSQDHFGHENWDHQLKLAVAWNRVDIAKSEIFM
TRPM8  370  PEEEIESWIRWLKEILESSHLLTVIKMEEAGDEIVSRAESYALYKAFSTNEQD-KINWNGQLRLLLEWNQLPLASGEIFT

TRPM7  430  YGQQWL-----------------------------------------------------VGSLEQAMLDALVMDR
TRPM1  325  FGPHWTFLGSLAPPTDSKATEKEKKPPMATTKGGRGKGKGKKKGKVKEEVEEETDPRKIELLNWVNALEQAMLDALVIDR
TRPM2  475  DEWQWKP---------------------------------------------SDLHPTNTAALISNK
TRPM8  449  NDRSWES---------------------------------------------ADLQEVMFTALIKDR

TRPM7  452  VSPVKLLIENGVSMHKELTKPRLSELYNTKQGPTNDMLFHLIRDVKQGR----LPRQYRITLIDIGLVIEVLMGGTYRCT
TRPM1  404  VEPVKLLIEAGVMMQHELTKPLSELYNTRLGPPN-TIHDLVRDVKSN---LEPDYHISLIDIGLVLEYLMGGAYRCN
TRPM2  497  FEFVKLFLENGVQLKEFVTWDTLLYLYENLDPSCLFHSKLQRVLVEDPERPACAPAAPRLQMHHVAQVLRELLGDPTQFL
TRPM8  471  PFFVRLFLENGINLQRFLTNEVLTELFS-THFSTLVYRNLQIAKNSYN-------------DALLTFVWKLVANFRRGF

TRPM7  528  YTRRFRLIYMSLGGNRMRRSGRNTSSSTFQLRKSHETFGNRADKRKKMRHNHFIRTAQPYRPKMDASMEEGKKKRTKDEI
TRPM1  479  YTKEMFRILYNRLFG------PKRPKALFLFKGMEDIEPPAEGK--------------KKKKKKKEEEID
TRPM2  577  YPRPRHEDRLRLLP-----------VPKVKLNVQGVSLRSLYKRSSGB---------
TRPM8  536  WKEDRSSR-------------EULQVEIHDASIT-----------

TRPM7  608  VDIDDFETKRFPYPLNELLIWACLMKRQVMARPIMQHGERESMAKALVACKTYRSMAYEAKQSDLVDPKSEEKQYSNDFG
TRPM1  528  IDVQDPAVERFQYPPEELMVWAVLMKEQMMAVFLMQPGEEESMAKALVACKLYKAMAHESSESRLVDRISQDLDMNSKDFG
TRPM2  615  -------VTFTMDPIEELLIWAIVQNRRELAGIIWAQSQDTIAAALACSKILKELSKEEED------TDSSEEMLALAEEYE
TRPM8  557  ---------TRHFLQALFIWAILQNKKELSKVIWEQTKGCTLAALGASFLLKTLAKVKND----INAAGESEELANEYE

TRPM7  688  QLAVELLEQSFTQDETNAMKLLTYELDNWSNSTCLKLAVSSRLRPFVAHTCTQMLLSEDMWMGRLNMRKNSWYEVILSILV
TRPM1  608  QLALELLDQSYRHDRQIAMKLLTYELKNWSNGTCLELAVAAKHRDLPIAHPCSQMLLTDMMGRLRKRKNPGLKVTMGILL
TRPM2  684  HRAIGVFTECYRKDERRAQNLLTRVSEAWSKTTCLQLALEAKLMKEPVSHEGIQAFLTEVVWSQLSVDNGLWRVTLCMEAF
TRPM8  623  TRAVELFTECYSNDEDLAEQLLVYSCEAWGGSNCLELAVEATDQHFIAQFGVQNFLSKQKYGEISRDTRNNKILLCLFKI

TRPM7  768  PPAIEMLEYFTNAEKSHIPQSQDAHQMTMEDSENNFSNITEEIPMEVFKEVFTLDSSDGKNEMEIKIKSEKLFITPKEYA
TRPM1  688  PFITLFLEFRTYDDPSYQTSKENEDGKEKEE-EN---------TIANADAGSRKGDEENEHKKQRSIPIGTKICE
TRPM2  764  PLESTGLISFRERKRLQDVG-----------------TPAARAPA
TRPM8  703  RIVGGLVSFRKKPIDKHK-------------------EILWYYVA
```

FIGURE 6A (continued)

```
TRPM7    1  MSQKSWIESTLTKRECVY---------------------------IIPSSKDPHRCLPGCQICQQLVRCFCGRLVKQHA
TRPM1    1  --------------------------------------------------------------------------------
TRPM2    1  MEPSALRKAGSEQEEGFEGLPRVTDLGMVSNLRRSNSSLFKSWRLQCFPGNNDKQESLGSWIPENIKKKECVYFVESSK
TRPM8    1  MSFEGARLSMRSRRNGTMGSTR------TLYGSVSRST----------DVSYSJSD----LVNFIQANFKKRECVFFTRDSK

TRPM7   53  CFTASLAMKYSDVKLGEHFNQA-------IEENGVEKRFEQSFPTDAYGVINPQGGSHSYRAKYVRLSYDFKPEIILQLIL
TRPM1    1  --------------------------------------------------MYIRVSXDFKPDSLLHLMV
TRPM2   81  LSDAGKVVQQYYTHEQMLEEATKPHTFQGTQWDPERHVQEMFTDAPSDIVFIGLSQKV-KKYVRVSQDFPSSVIYHLMT
TRPM8   63  AMEN----ICKCGYAQSQHIEGT---QINQNEKWNYKKRTKEFPTDAFGDIQFETLGKKG-K-XLRLSCDYDSETLYELLS

TRPM7  126  KEWQMELFKLVISVHSGMQKFELHPRIKQLLGKGLIKAAVTPQAWTDTGGVNTSVAEHVGDALKEHASKSSFK----ICTI
TRPM1   20  KLWQLRLFELLISVHEGLQNPRMQPKLKQVPGKSLIRAAMTPGAWIPTGGVSTDVISHVSDALKDHSSKERGR----VCAI
TRPM2  160  QHSGLDVPNLLISVTGGAKNFNMKPRLKSIFRRGLVEVAQTTSAMLITGCGHTSAMKQVGEAVRDFSLSSSYKEGELITI
TRPM8  135  QHWHLRTFNLVISVTGGAKNFALKPRMRRIEGR-LIYIAQSKDAWILTGGTHYGLMKYIGEVVRDNYISRNGEE-NIYAI

TRPM7  203  GIAPWGVIENRNDLVG------RDVVAPYQELLNFLSKQNVRNNLLSRFTLYEDGTVGKYGAEVRLRRELEKTINQQR-IH
TRPM1   97  GIAPWGIVENREDLVG-----KDVTRVVQTMSNPLSKLSVLNNSNTFSILADNGFLGKYGAEVKLRRLLEKHISLQK-IN
TRPM2  240  SVATWGTVHRREGLIHPT---GSFPAEYILDEDGQGNLTCLDRNHSHFILVDGTHGQKGVEIPLRTRLEKFISEQTKER
TRPM8  213  GIAANNVSNRDTLIRSCDLEGHFSAQYIMDDFTRDPLVILDNNENMLLLVGNGGRGHFTVBAKLPNQLEKYISRETSQD

TRPM7  277  ARIEKGVPVVALIFEGGPNVILTVEEYLQESFPVPVVVCEGSGRAADDLAYIKRQTEEGRMLPDAAEPDIISTKKNFNF
TRPM1  171  TRLGQSVFLVGGLVVEGGPNVVSIVLEYLQREFPIPVVICDGSGRASDILSFAHKYCESGGIINESLREQLVPTQRFNY
TRPM2  317  GCVAIKIFIVCVVLEGGPGTLHTTDNATTN---CTFCVVVEGSGRVADVIAQVANLPVSDITISLIQQFLSVFFQEMPETF
TRPM8  293  SNYQGKIFIVCFAQGGGRETLRAINTSVKS--KIFCVVVEGSGQIADVIASLVEN-EDVLTSSMVREKLVRELFRTVSRL

TRPM7  357  GQSRAVHLFQTMMBCMKKKELITVFHIGSEDHQDIDVALLTALLKGTHASAFQ------QLLSHANDFVDIARNHVYV
TRPM1  251  NKAQSHQLFAIINECMKRKELATVFRMGSEGQQDIEMAILPALLKQVNYSAFQ------QLSIALAWNRVDIARSQIFV
TRPM2  395  TRRLVENTKRIQDIVRREQLLTVFREGKDQGQDVDVALLQALLKASRSQDHFGHENNDRQLKLAVAWNRVDIARSEIPM
TRPM8  370  PKFRIESWIKWLKEILESSHLLTVIEMFEAQDEIVSNAISYALYKAFSINEQD-KDNWNGQLKELLEWNQLDLASDEIFT

TRPM7  430  YGQQWL-----------------------------------------------VGSLEQAMLDALVMDR
TRPM1  325  FGPHWTPLGSLAPPTDSKATEKEKKPPMATTKGGRGKGKGKKKGKVKEEVEEETDFPRKIELLNWWNALEQAMLDSLVLDR
TRPM2  475  DEWQWKP-------------------------------------------STRHPTMFAALISNK
TRPM8  449  NDRRWES--------------------------------------------ADLQEVMFTALIKDR

TRPM7  452  VSFVKLLIENGVSMHRFLTIFRLEELYNTRQGFPNPMLFHLIRDVRQGN----LPPGYKITLIDIGLVIEYLMGNTYRCT
TRPM1  404  VDFVKLLIENGVNMQHFLTIFRLSELVNTRLGFPN-TELLVRDVRFSN----LPFGYHIRLIDIGLVLEYLMGGAVRSN
TRPM2  497  PEFVKLFLENGVQLKEFVTWDTLLYLYENLDPSCLFHSELQKVLVEDFERPACARAAPRLQMHHVAQVGRELLNDFTQPL
TRPM8  471  PKFVRLFLENGLNLQKFLTNEVLTELFS-THFSTLVYRNLQIAKNSYN-------------DALLTFVWKLVANPRRSF

TRPM7  528  YTRKRFRLIYNSLGGNNRRSGRNFSSSTPQLRKGSHETFGNRADKREKMRHNHPIRTAQPYRPKMDASMEEGKKKRTKDEI
TRPM1  479  YTPKNFRTLYNLPG-------------PKRPKALKLLGMEDDEPPAKGK-----------KKKKKKKEEEID
TRPM2  577  YPKPRHNDKLRLLLP-------------VPHVRLNVQGVSLRSLYKPSSGH---------------------
TRPM8  536  WKEDKSSR-----------------EDLDVELHDASLT------------------------

TRPM7  608  VDIDDPETKRFPYPLNELLIKACLMKRQVMARELWQHGEESMAKALVACKIYRSMAYEAKQSSLVEDTSRSLKQYSNDFG
TRPM1  528  IDVDDPAVSRFQYPFHELMWAVLMKRQRMAVFLWQRGEESMAKAIVACKLFKAMAHESSESDLVDDISQDLRNNSKDFG
TRPM2  615  -------VTFTMPPIRDLLIWAIVQNRRELAGIIWAQSQDCIAAALACSKILKELSKEEED----TKSSEEMLALAEEYE
TRPM8  557  -----------TRHPLQALFIWAILQNKKELSKVIWEQTKGCTLAALGASKLLKTLAKVKND-----INAAGSSRELANEVE

TRPM7  688  QLAVELLEQSFRQDETMAMKLLTYELKNWSNSTCLKLAVSSRLRPFVAHTCTQMLLSDMWMGRLNMRKNSWYKVILSIIV
TRPM1  608  QLALELLDQSFKREEQIAMKLLGTYELKNWSNSTCLKLAVAAKHRDFIAHTCSQMLLTDMWMGRLRMRKNPGLKVIMGIIL
TRPM2  684  HRALSVFTECYRKDEERAQKLLTRVSEAWGKTTCLQLALEAKDMKFVSHGGIQAFLTKVWWGQLSVDNGLMRVTLCMLAF
TRPM8  623  TRAVELFTECYSNDEDLAEQLLVYQCEAWGGSNCLELAVEATLQHFTAQPGVQNFLSKQWYGEISRDTKNWKIIDCLFTI

TRPM7  768  PPAILMLEYKTKAEMSHTPQSQDAHQMTMEDSEKNFHNITEEIPMEVFREVKILDSSDGKNEMEIHIKSKKLPITRKFVA
TRPM1  688  PPTILPLEFRTTYDPFSYQFSKENEDGKEKEE-EN-------TDAMAUAGSRKGDERNEHKRQRSIFIGTKICE
TRPM2  764  PLLLTGLISFREKFLQDVG--------------------------------------TPAAKARA
TRPM8  703  PLNGCLLVSERFKFIIKHK----------------------------------------KLLWYYVA
```

A

B

A

B

SEQUENCE LISTING

```
<160> NUMBER OF SEQ ID NOS: 114

<210> SEQ ID NO 1
<211> LENGTH: 2440
<212> TYPE: DNA
<213> ORGANISM: Mus musculus
<220> FEATURE:
<221> NAME/KEY: CDS
<222> LOCATION: (65)...(2440)

<400> SEQUENCE: 1
gatctcaagg caaggactgc caccaccatc tggaacctgc cagcatatgc cttaggctcc          60 agca atg aat gcc cac tcc aag gag atg gtg ccc ctc atg ggc aaa aga         109
     Met Asn Ala His Ser Lys Glu Met Val Pro Leu Met Gly Lys Arg
     1               5                  10                  15 acc acg gca cct ggc ggg aac cct gtt gta ctg aca gag aag agg cca         157
Thr Thr Ala Pro Gly Gly Asn Pro Val Val Leu Thr Glu Lys Arg Pro
                20                  25                  30 gca gat ctc acc ccc acc aag aag agt gca cac ttc ttc ctg gag ata         205
Ala Asp Leu Thr Pro Thr Lys Lys Ser Ala His Phe Phe Leu Glu Ile
            35                  40                  45 gaa gga ttt gag ccc aac ccc acg gtc acc aag acc tct cca ccc atc         253
Glu Gly Phe Glu Pro Asn Pro Thr Val Thr Lys Thr Ser Pro Pro Ile
        50                  55                  60 ttc tcc aag ccg atg gac tcc aac atc cgg cag tgc ctc tct ggc aac         301
Phe Ser Lys Pro Met Asp Ser Asn Ile Arg Gln Cys Leu Ser Gly Asn
    65                  70                  75 tgt gat gac atg gac tct ccc cag tct cct cag gat gat gtg aca gag         349
Cys Asp Asp Met Asp Ser Pro Gln Ser Pro Gln Asp Asp Val Thr Glu
80                  85                  90                  95 acc cca tcc aat ccc aac agt ccg agc gca aac ctg gcc aag gaa gaa         397
Thr Pro Ser Asn Pro Asn Ser Pro Ser Ala Asn Leu Ala Lys Glu Glu
                100                 105                 110 cag agg cag aag aag aag cga ctg aag aag cgc atc ttc gcg gct gtg         445
Gln Arg Gln Lys Lys Lys Arg Leu Lys Lys Arg Ile Phe Ala Ala Val
            115                 120                 125 tcc gag ggc tgc gtg gag gag ctg cgg gaa ctc cta cag gat ctg cag         493
Ser Glu Gly Cys Val Glu Glu Leu Arg Glu Leu Leu Gln Asp Leu Gln
        130                 135                 140 gac ctc tgc agg agg cgc cgc ggc ctg gat gtg cct gac ttc ctc atg         541
Asp Leu Cys Arg Arg Arg Arg Gly Leu Asp Val Pro Asp Phe Leu Met
    145                 150                 155 cac aag ctg aca gcc tca gac acc ggg aag acc tgc ctg atg aag gct         589
His Lys Leu Thr Ala Ser Asp Thr Gly Lys Thr Cys Leu Met Lys Ala
160                 165                 170                 175 ttg ctc aac atc aat ccc aac acc aaa gag atc gtg cgg att ctg ctt         637
Leu Leu Asn Ile Asn Pro Asn Thr Lys Glu Ile Val Arg Ile Leu Leu
                180                 185                 190
```

```
gcc ttc gct gag gag aac gac atc ctg gac agg ttc atc aac gct gag      685
Ala Phe Ala Glu Glu Asn Asp Ile Leu Asp Arg Phe Ile Asn Ala Glu
            195                 200                 205 tac acg gaa gag gcc tat gaa ggg cag aca gcg ctg aac atc gcc atc      733
Tyr Thr Glu Glu Ala Tyr Glu Gly Gln Thr Ala Leu Asn Ile Ala Ile
        210                 215                 220 gag cgg cgc cag gga gac atc aca gca gtg ctt ata gca gcg ggt gct      781
Glu Arg Arg Gln Gly Asp Ile Thr Ala Val Leu Ile Ala Ala Gly Ala
225                 230                 235 gac gtc aat gct cac gcc aag ggg gtc ttc ttc aac ccc aaa tac cag      829
Asp Val Asn Ala His Ala Lys Gly Val Phe Phe Asn Pro Lys Tyr Gln
240                 245                 250                 255 cat gaa ggc ttc tat ttt ggc gag aca ccc ctg gct ttg gca gcg tgt      877
His Glu Gly Phe Tyr Phe Gly Glu Thr Pro Leu Ala Leu Ala Ala Cys
                260                 265                 270 act aac cag cct gag att gtg cag ctg ctg atg gag aat gag cag aca      925
Thr Asn Gln Pro Glu Ile Val Gln Leu Leu Met Glu Asn Glu Gln Thr
            275                 280                 285 gac atc act tcc cag gat tcc cgg gga aac aac atc ctg cac gcg ctg      973
Asp Ile Thr Ser Gln Asp Ser Arg Gly Asn Asn Ile Leu His Ala Leu
        290                 295                 300 gtg aca gtg gct gag gac ttc aag act cag aat gac ttc gtt aag cgc     1021
Val Thr Val Ala Glu Asp Phe Lys Thr Gln Asn Asp Phe Val Lys Arg
305                 310                 315 atg tat gac atg atc ctg ctg agg agt ggc aac tgg gag ctg gag acc     1069
Met Tyr Asp Met Ile Leu Leu Arg Ser Gly Asn Trp Glu Leu Glu Thr
320                 325                 330                 335 atg cgc aac aac gat ggg ctc aca cca ctg cag ctg gct gcc aag atg     1117
Met Arg Asn Asn Asp Gly Leu Thr Pro Leu Gln Leu Ala Ala Lys Met
                340                 345                 350 ggc aag gct gag atc ctg aag tac atc ctc agc cgc gag atc aag gag     1165
Gly Lys Ala Glu Ile Leu Lys Tyr Ile Leu Ser Arg Glu Ile Lys Glu
            355                 360                 365 aag cct ctc cgg agc ttg tcc agg aag ttc acg gac tgg gcg tat ggg     1213
Lys Pro Leu Arg Ser Leu Ser Arg Lys Phe Thr Asp Trp Ala Tyr Gly
        370                 375                 380 cct gtg tca tcc tca ctc tat gac ctc acc aat gta gac aca acg acg     1261
Pro Val Ser Ser Ser Leu Tyr Asp Leu Thr Asn Val Asp Thr Thr Thr
385                 390                 395 gat aac tct gtg ctg gaa atc atc gtc tac aac acc aac att gat aac     1309
Asp Asn Ser Val Leu Glu Ile Ile Val Tyr Asn Thr Asn Ile Asp Asn
400                 405                 410                 415 cga cat gag atg ctg acc ctg gag cct ctg cat acg ctg cta cac acg     1357
Arg His Glu Met Leu Thr Leu Glu Pro Leu His Thr Leu Leu His Thr
                420                 425                 430 aaa tgg aag aaa ttt gcc aag tac atg ttc ttc ttg tcc ttc tgc ttc     1405
Lys Trp Lys Lys Phe Ala Lys Tyr Met Phe Phe Leu Ser Phe Cys Phe
            435                 440                 445 tat ttc ttc tac aac atc acc ctg acc ctt gtc tct tac tac cgt cct     1453
Tyr Phe Phe Tyr Asn Ile Thr Leu Thr Leu Val Ser Tyr Tyr Arg Pro
        450                 455                 460 cgg gaa gat gag gat ctc cca cac ccc ttg gcc ctg aca cac aaa atg     1501
Arg Glu Asp Glu Asp Leu Pro His Pro Leu Ala Leu Thr His Lys Met
465                 470                 475 agt tgg ctt cag ctc cta ggg agg atg ttt gtc ctc atc tgg gcc aca     1549
Ser Trp Leu Gln Leu Leu Gly Arg Met Phe Val Leu Ile Trp Ala Thr
480                 485                 490                 495 tgc atc tct gtg aaa gaa ggc att gcc att ttc ctg ctg aga ccc tcc     1597
Cys Ile Ser Val Lys Glu Gly Ile Ala Ile Phe Leu Leu Arg Pro Ser
```

```
                    500             505             510
gat ctt cag tcc atc ctg tca gat gcc tgg ttt cac ttt gtc ttt ttt         1645
Asp Leu Gln Ser Ile Leu Ser Asp Ala Trp Phe His Phe Val Phe Phe
            515                 520                 525 gtc caa gct gta ctt gtg ata ctg tct gta ttc ttg tac ttg ttt gcc         1693
Val Gln Ala Val Leu Val Ile Leu Ser Val Phe Leu Tyr Leu Phe Ala
            530                 535                 540 tac aaa gaa tac ctc gcc tgc ctc gtg ctg gcc atg gcc ctg ggc tgg         1741
Tyr Lys Glu Tyr Leu Ala Cys Leu Val Leu Ala Met Ala Leu Gly Trp
545                 550                 555 gcg aac atg ctc tac tac acg aga ggc ttc cag tct atg ggc atg tac         1789
Ala Asn Met Leu Tyr Tyr Thr Arg Gly Phe Gln Ser Met Gly Met Tyr
    560                 565                 570                 575 agc gtc atg atc cag aag gtc att ttg cat gat gtc ctc aag ttc ttg         1837
Ser Val Met Ile Gln Lys Val Ile Leu His Asp Val Leu Lys Phe Leu
                580                 585                 590 ttt gtt tac atc ctg ttc tta ctt gga ttt gga gta gcg ctg gcc tca         1885
Phe Val Tyr Ile Leu Phe Leu Leu Gly Phe Gly Val Ala Leu Ala Ser
                    595                 600                 605 ctg att gag aag tgc tcc aag gac aaa aag gac tgc agt tcc tat ggc         1933
Leu Ile Glu Lys Cys Ser Lys Asp Lys Lys Asp Cys Ser Ser Tyr Gly
                        610                 615                 620 agc ttc agc gac gcg gtg ctg gag ctc ttc aag ctc acc ata ggc ctg         1981
Ser Phe Ser Asp Ala Val Leu Glu Leu Phe Lys Leu Thr Ile Gly Leu
625                 630                 635 ggc gac ctg aac atc cag cag aac tcc acc tac ccc atc ctc ttt ctc         2029
Gly Asp Leu Asn Ile Gln Gln Asn Ser Thr Tyr Pro Ile Leu Phe Leu
640                 645                 650                 655 ttc cta ctc atc acc tat gtc atc ctc acc ttc gtc ctc ctc aac              2077
Phe Leu Leu Ile Thr Tyr Val Ile Leu Thr Phe Val Leu Leu Leu Asn
            660                 665                 670 atg ctc atc gcc ctg atg ggg gag acg gtg gag aac gtc tcc aaa gaa         2125
Met Leu Ile Ala Leu Met Gly Glu Thr Val Glu Asn Val Ser Lys Glu
                675                 680                 685 agt gag cgg atc tgg cgc ttg cag aga gcc agg acc atc ttg gag ttt         2173
Ser Glu Arg Ile Trp Arg Leu Gln Arg Ala Arg Thr Ile Leu Glu Phe
                    690                 695                 700 gag aaa atg tta cca gaa tgg ctg aga agc aga ttc cgc atg ggc gag         2221
Glu Lys Met Leu Pro Glu Trp Leu Arg Ser Arg Phe Arg Met Gly Glu
705                 710                 715 ctg tgc aaa gta gca gat gag gac ttc cgg ctg tgt ctg cgg atc aac         2269
Leu Cys Lys Val Ala Asp Glu Asp Phe Arg Leu Cys Leu Arg Ile Asn
720                 725                 730                 735 gag gtg aag tgg acg gaa tgg aaa aca cac gtg tcc ttc ctt aat gaa         2317
Glu Val Lys Trp Thr Glu Trp Lys Thr His Val Ser Phe Leu Asn Glu
            740                 745                 750 gac ccg gga ccc ata aga cgg aca gca gat tta aac aag att caa gat         2365
Asp Pro Gly Pro Ile Arg Arg Thr Ala Asp Leu Asn Lys Ile Gln Asp
                755                 760                 765 tct tcc agg agc aat agc aaa acc acc ctc tat gcg ttt gat gaa tta         2413
Ser Ser Arg Ser Asn Ser Lys Thr Thr Leu Tyr Ala Phe Asp Glu Leu
                    770                 775                 780 gat gaa ttc cca gaa acg tcg gtg tag                                      2440
Asp Glu Phe Pro Glu Thr Ser Val *
785                 790

<210> SEQ ID NO 2
<211> LENGTH: 791
<212> TYPE: PRT
<213> ORGANISM: Mus musculus
```

<400> SEQUENCE: 2

```
Met Asn Ala His Ser Lys Glu Met Val Pro Leu Met Gly Lys Arg Thr
 1               5                  10                  15

Thr Ala Pro Gly Gly Asn Pro Val Val Leu Thr Glu Lys Arg Pro Ala
             20                  25                  30

Asp Leu Thr Pro Thr Lys Lys Ser Ala His Phe Phe Leu Glu Ile Glu
         35                  40                  45

Gly Phe Glu Pro Asn Pro Thr Val Thr Lys Thr Ser Pro Pro Ile Phe
     50                  55                  60

Ser Lys Pro Met Asp Ser Asn Ile Arg Gln Cys Leu Ser Gly Asn Cys
65                  70                  75                  80

Asp Asp Met Asp Ser Pro Gln Ser Pro Gln Asp Val Thr Glu Thr
                 85                  90                  95

Pro Ser Asn Pro Asn Ser Pro Ser Ala Asn Leu Ala Lys Glu Glu Gln
                100                 105                 110

Arg Gln Lys Lys Lys Arg Leu Lys Lys Arg Ile Phe Ala Ala Val Ser
             115                 120                 125

Glu Gly Cys Val Glu Glu Leu Arg Glu Leu Leu Gln Asp Leu Gln Asp
        130                 135                 140

Leu Cys Arg Arg Arg Gly Leu Asp Val Pro Asp Phe Leu Met His
145                 150                 155                 160

Lys Leu Thr Ala Ser Asp Thr Gly Lys Thr Cys Leu Met Lys Ala Leu
                165                 170                 175

Leu Asn Ile Asn Pro Asn Thr Lys Glu Ile Val Arg Ile Leu Leu Ala
            180                 185                 190

Phe Ala Glu Glu Asn Asp Ile Leu Asp Arg Phe Ile Asn Ala Glu Tyr
        195                 200                 205

Thr Glu Glu Ala Tyr Glu Gly Gln Thr Ala Leu Asn Ile Ala Ile Glu
    210                 215                 220

Arg Arg Gln Gly Asp Ile Thr Ala Val Leu Ile Ala Ala Gly Ala Asp
225                 230                 235                 240

Val Asn Ala His Ala Lys Gly Val Phe Phe Asn Pro Lys Tyr Gln His
                245                 250                 255

Glu Gly Phe Tyr Phe Gly Glu Thr Pro Leu Ala Leu Ala Ala Cys Thr
            260                 265                 270

Asn Gln Pro Glu Ile Val Gln Leu Leu Met Glu Asn Glu Gln Thr Asp
        275                 280                 285

Ile Thr Ser Gln Asp Ser Arg Gly Asn Asn Ile Leu His Ala Leu Val
    290                 295                 300

Thr Val Ala Glu Asp Phe Lys Thr Gln Asn Asp Phe Val Lys Arg Met
305                 310                 315                 320

Tyr Asp Met Ile Leu Leu Arg Ser Gly Asn Trp Glu Leu Glu Thr Met
                325                 330                 335

Arg Asn Asn Asp Gly Leu Thr Pro Leu Gln Leu Ala Ala Lys Met Gly
            340                 345                 350

Lys Ala Glu Ile Leu Lys Tyr Ile Leu Ser Arg Glu Ile Lys Glu Lys
        355                 360                 365

Pro Leu Arg Ser Leu Ser Arg Lys Phe Thr Asp Trp Ala Tyr Gly Pro
    370                 375                 380

Val Ser Ser Ser Leu Tyr Asp Leu Thr Asn Val Asp Thr Thr Thr Asp
385                 390                 395                 400

Asn Ser Val Leu Glu Ile Ile Val Tyr Asn Thr Asn Ile Asp Asn Arg
```

```
                405                 410                 415
His Glu Met Leu Thr Leu Glu Pro Leu His Thr Leu His Thr Lys
            420                 425                 430
Trp Lys Lys Phe Ala Lys Tyr Met Phe Phe Leu Ser Phe Cys Phe Tyr
            435                 440                 445
Phe Phe Tyr Asn Ile Thr Leu Thr Leu Val Ser Tyr Arg Pro Arg
450                 455                 460
Glu Asp Glu Asp Leu Pro His Pro Leu Ala Leu Thr His Lys Met Ser
465                 470                 475                 480
Trp Leu Gln Leu Leu Gly Arg Met Phe Val Leu Ile Trp Ala Thr Cys
            485                 490                 495
Ile Ser Val Lys Glu Gly Ile Ala Ile Phe Leu Leu Arg Pro Ser Asp
            500                 505                 510
Leu Gln Ser Ile Leu Ser Asp Ala Trp Phe His Phe Val Phe Phe Val
            515                 520                 525
Gln Ala Val Leu Val Ile Leu Ser Val Phe Leu Tyr Leu Phe Ala Tyr
            530                 535                 540
Lys Glu Tyr Leu Ala Cys Leu Val Leu Ala Met Ala Leu Gly Trp Ala
545                 550                 555                 560
Asn Met Leu Tyr Tyr Thr Arg Gly Phe Gln Ser Met Gly Met Tyr Ser
                565                 570                 575
Val Met Ile Gln Lys Val Ile Leu His Asp Val Leu Lys Phe Leu Phe
            580                 585                 590
Val Tyr Ile Leu Phe Leu Leu Gly Phe Gly Val Ala Leu Ala Ser Leu
            595                 600                 605
Ile Glu Lys Cys Ser Lys Asp Lys Lys Asp Cys Ser Ser Tyr Gly Ser
            610                 615                 620
Phe Ser Asp Ala Val Leu Glu Leu Phe Lys Leu Thr Ile Gly Leu Gly
625                 630                 635                 640
Asp Leu Asn Ile Gln Gln Asn Ser Thr Tyr Pro Ile Leu Phe Leu Phe
                645                 650                 655
Leu Leu Ile Thr Tyr Val Ile Leu Thr Phe Val Leu Leu Leu Asn Met
                660                 665                 670
Leu Ile Ala Leu Met Gly Glu Thr Val Glu Asn Val Ser Lys Glu Ser
            675                 680                 685
Glu Arg Ile Trp Arg Leu Gln Arg Ala Arg Thr Ile Leu Glu Phe Glu
            690                 695                 700
Lys Met Leu Pro Glu Trp Leu Arg Ser Arg Phe Arg Met Gly Glu Leu
705                 710                 715                 720
Cys Lys Val Ala Asp Glu Asp Phe Arg Leu Cys Leu Arg Ile Asn Glu
                725                 730                 735
Val Lys Trp Thr Glu Trp Lys Thr His Val Ser Phe Leu Asn Glu Asp
            740                 745                 750
Pro Gly Pro Ile Arg Arg Thr Ala Asp Leu Asn Lys Ile Gln Asp Ser
            755                 760                 765
Ser Arg Ser Asn Ser Lys Thr Thr Leu Tyr Ala Phe Asp Glu Leu Asp
            770                 775                 780
Glu Phe Pro Glu Thr Ser Val
785                 790

<210> SEQ ID NO 3
<211> LENGTH: 2373
<212> TYPE: DNA
<213> ORGANISM: Artificial Sequence
```

-continued

```
<220> FEATURE:
<221> NAME/KEY: CDS
<222> LOCATION: (1)...(2373)
<223> OTHER INFORMATION: Generic sequence that encompasses all
      nucleotide sequences that encode mouse TRPV3 having an amino acid
      sequence as shown in SEQ ID NO:2
<220> FEATURE:
<221> NAME/KEY: misc_feature
<222> LOCATION: 15,120,180,195,210,231,255,264,294,306,312,384,495,873,
      882,984,1086,1116,1122,1155,1158,1161,1206,1332,1377,1440,1494,
      1533,1545,1554,1608,1713,1728,1821,1839,1860,1863,1872,1878,
      1941,2055,2064,2139,2241,2304,2307,2313,2370
<223> OTHER INFORMATION: n = A,C,G, or T if after TC;
      n = T or C if after AG
<220> FEATURE:
<221> NAME/KEY: misc_feature
<222> LOCATION: 45,90,339,354,366,408,441,444,447,450,564,606,675,678,
      885,957,981,1011,1089,1113,1125,1248,1386,1392,1461,1527,1701,
      2070,2079,2088,2094,2136,2142,2148,2187,2199,2271,2274,2310
<223> OTHER INFORMATION: n = A,C,G, or T if after CG;
      n = A or G if after AG
<220> FEATURE:
<221> NAME/KEY: misc_feature
<222> LOCATION: all "n" not specified above
<223> OTHER INFORMATION: n = A,T,C or G

<400> SEQUENCE: 3 atg aay gcn cay wsn aar gar atg gtn ccn ytn atg ggn aar mgn acn         48
Met Asn Ala His Ser Lys Glu Met Val Pro Leu Met Gly Lys Arg Thr
1               5                   10                  15 acn gcn ccn ggn ggn aay ccn gtn gtn ytn acn gar aar mgn ccn gcn         96
Thr Ala Pro Gly Gly Asn Pro Val Val Leu Thr Glu Lys Arg Pro Ala
            20                  25                  30 gay ytn acn ccn acn aar aar wsn gcn cay tty tty ytn gar ath gar        144
Asp Leu Thr Pro Thr Lys Lys Ser Ala His Phe Phe Leu Glu Ile Glu
        35                  40                  45 ggn tty gar ccn aay ccn acn gtn acn aar acn wsn ccn ccn ath tty        192
Gly Phe Glu Pro Asn Pro Thr Val Thr Lys Thr Ser Pro Pro Ile Phe
    50                  55                  60 wsn aar ccn atg gay wsn aay ath mgn car tgy ytn wsn ggn aay tgy        240
Ser Lys Pro Met Asp Ser Asn Ile Arg Gln Cys Leu Ser Gly Asn Cys
65                  70                  75                  80 gay gay atg gay wsn ccn car wsn ccn car gay gay gtn acn gar acn        288
Asp Asp Met Asp Ser Pro Gln Ser Pro Gln Asp Asp Val Thr Glu Thr
                85                  90                  95 ccn wsn aay ccn aay wsn ccn wsn gcn aay ytn gcn aar gar gar car        336
Pro Ser Asn Pro Asn Ser Pro Ser Ala Asn Leu Ala Lys Glu Glu Gln
            100                 105                 110 mgn car aar aar aar mgn ytn aar aar mgn ath tty gcn gcn gtn wsn        384
Arg Gln Lys Lys Lys Arg Leu Lys Lys Arg Ile Phe Ala Ala Val Ser
        115                 120                 125 gar ggn tgy gtn gar gar ytn mgn gar ytn ytn car gay ytn car gay        432
Glu Gly Cys Val Glu Glu Leu Arg Glu Leu Leu Gln Asp Leu Gln Asp
    130                 135                 140 ytn tgy mgn mgn mgn mgn ggn ytn gay gtn ccn gay tty ytn atg cay        480
Leu Cys Arg Arg Arg Arg Gly Leu Asp Val Pro Asp Phe Leu Met His
145                 150                 155                 160 aar ytn acn gcn wsn gay acn ggn aar acn tgy ytn atg aar gcn ytn        528
Lys Leu Thr Ala Ser Asp Thr Gly Lys Thr Cys Leu Met Lys Ala Leu
                165                 170                 175 ytn aay ath aay ccn aay acn aar gar ath gtn mgn ath ytn ytn gcn        576
Leu Asn Ile Asn Pro Asn Thr Lys Glu Ile Val Arg Ile Leu Leu Ala
            180                 185                 190 tty gcn gar gar aay gay ath ytn gay mgn tty ath aay gcn gar tay        624
Phe Ala Glu Glu Asn Asp Ile Leu Asp Arg Phe Ile Asn Ala Glu Tyr
        195                 200                 205
```

```
acn gar gar gcn tay gar ggn car acn gcn ytn aay ath gcn ath gar      672
Thr Glu Glu Ala Tyr Glu Gly Gln Thr Ala Leu Asn Ile Ala Ile Glu
    210                 215                 220 mgn mgn car ggn gay ath acn gcn gtn ytn ath gcn gcn ggn gcn gay      720
Arg Arg Gln Gly Asp Ile Thr Ala Val Leu Ile Ala Ala Gly Ala Asp
225                 230                 235                 240 gtn aay gcn cay gcn aar ggn gtn tty tty aay ccn aar tay car cay      768
Val Asn Ala His Ala Lys Gly Val Phe Phe Asn Pro Lys Tyr Gln His
                245                 250                 255 gar ggn tty tay tty ggn gar acn ccn ytn gcn ytn gcn gcn tgy acn      816
Glu Gly Phe Tyr Phe Gly Glu Thr Pro Leu Ala Leu Ala

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 515 |     |     |     | 520 |     |     |     |     | 525 |     |     |     |     |      |
| car | gcn | gtn | ytn | gtn | ath | ytn | wsn | gtn | tty | ytn | tay | ytn | tty | gcn | tay | 1632 |
| Gln | Ala | Val | Leu | Val | Ile | Leu | Ser | Val | Phe | Leu | Tyr | Leu | Phe | Ala | Tyr |      |
|     | 530 |     |     |     |     | 535 |     |     |     |     | 540 |     |     |     |     |      |
| aar | gar | tay | ytn | gcn | tgy | ytn | gtn | ytn | gcn | atg | gcn | ytn | ggn | tgg | gcn | 1680 |
| Lys | Glu | Tyr | Leu | Ala | Cys | Leu | Val | Leu | Ala | Met | Ala | Leu | Gly | Trp | Ala |      |
| 545 |     |     |     |     | 550 |     |     |     |     | 555 |     |     |     |     | 560 |      |
| aay | atg | ytn | tay | tay | acn | mgn | ggn | tty | car | wsn | atg | ggn | at

<400> SEQUENCE: 4

```
gacatgcggt gatctcaggg caagggttgc cacgaccacc cagaacctca ccagcc atg    59
                                                               Met
                                                                 1 aaa gcc cac ccc aag gag atg gtg cct ctc atg ggc aag aga gtt gct    107
Lys Ala His Pro Lys Glu Met Val Pro Leu Met Gly Lys Arg Val Ala
          5                  10                  15 gcc ccc agt ggg aac cct gcc gtc ctg cca gag aag agg ccg gcg gag    155
Ala Pro Ser Gly Asn Pro Ala Val Leu Pro Glu Lys Arg Pro Ala Glu
     20                  25                  30 atc acc ccc aca aag aag agt gca cac ttc ttc ctg gag ata gaa ggg    203
Ile Thr Pro Thr Lys Lys Ser Ala His Phe Phe Leu Glu Ile Glu Gly
 35                  40                  45 ttt gaa ccc aac ccc aca gtt gcc aag acc tct cct cct gtc ttc tcc    251
Phe Glu Pro Asn Pro Thr Val Ala Lys Thr Ser Pro Pro Val Phe Ser
 50                  55                  60                  65 aag ccc atg gat tcc aac atc cgg cag tgc atc tct ggt aac tgt gat    299
Lys Pro Met Asp Ser Asn Ile Arg Gln Cys Ile Ser Gly Asn Cys Asp
                 70                  75                  80 gac atg gac tcc ccc cag tct cct cag gat gat gtg aca gag acc cca    347
Asp Met Asp Ser Pro Gln Ser Pro Gln Asp Asp Val Thr Glu Thr Pro
             85                  90                  95 tcc aat ccc aac agc ccc agt gca cag ctg gcc aag gaa gag cag agg    395
Ser Asn Pro Asn Ser Pro Ser Ala Gln Leu Ala Lys Glu Glu Gln Arg
        100                 105                 110 agg aaa aag agg cgg ctg aag aag cgc atc ttt gca gcc gtg tct gag    443
Arg Lys Lys Arg Arg Leu Lys Lys Arg Ile Phe Ala Ala Val Ser Glu
    115                 120                 125 ggc tgc gtg gag gag ttg gta gag ttg ctg gtg gag ctg cag gag ctt    491
Gly Cys Val Glu Glu Leu Val Glu Leu Leu Val Glu Leu Gln Glu Leu
130                 135                 140                 145 tgc agg cgg cgc cat gat gag gat gtg cct gac ttc ctc atg cac aag    539
Cys Arg Arg Arg His Asp Glu Asp Val Pro Asp Phe Leu Met His Lys
                150                 155                 160 ctg acg gcc tcc gac acg ggg aag acc tgc ctg atg aag gcc ttg tta    587
Leu Thr Ala Ser Asp Thr Gly Lys Thr Cys Leu Met Lys Ala Leu Leu
            165                 170                 175 aac atc aac ccc aac acc aag gag ata gtg cgg atc ctg ctt gcc ttt    635
Asn Ile Asn Pro Asn Thr Lys Glu Ile Val Arg Ile Leu Leu Ala Phe
        180                 185                 190 gct gaa gag aac gac atc ctg ggc agg ttc atc aac gcc gag tac aca    683
Ala Glu Glu Asn Asp Ile Leu Gly Arg Phe Ile Asn Ala Glu Tyr Thr
    195                 200                 205 gag gag gcc tat gaa ggg cag acg gcg ctg aac atc gcc atc gag cgg    731
Glu Glu Ala Tyr Glu Gly Gln Thr Ala Leu Asn Ile Ala Ile Glu Arg
210                 215                 220                 225 cgg cag ggg gac atc gca gcc ctg ctc atc gcc gcc ggc gcc gac gtc    779
Arg Gln Gly Asp Ile Ala Ala Leu Leu Ile Ala Ala Gly Ala Asp Val
                230                 235                 240 aac gcg cac gcc aag ggg gcc ttc ttc aac ccc aag tac caa cac gaa    827
Asn Ala His Ala Lys Gly Ala Phe Phe Asn Pro Lys Tyr Gln His Glu
            245                 250                 255 ggc ttc tac ttc ggt gag acg ccc ctg gcc ctg gca gca tgc acc aac    875
Gly Phe Tyr Phe Gly Glu Thr Pro Leu Ala Leu Ala Ala Cys Thr Asn
        260                 265                 270 cag ccc gag att gtg cag ctg ctg atg gag cac gag cag acg gac atc    923
Gln Pro Glu Ile Val Gln Leu Leu Met Glu His Glu Gln Thr Asp Ile
    275                 280                 285 acc tcg cgg gac tca cga ggc aac aac atc ctt cac gcc ctg gtg acc    971
```

```
Thr Ser Arg Asp Ser Arg Gly Asn Asn Ile Leu His Ala Leu Val Thr
290             295                 300                 305 gtg gcc gag gac ttc aag acg cag aat gac ttt gtg aag cgc atg tac      1019
Val Ala Glu Asp Phe Lys Thr Gln Asn Asp Phe Val Lys Arg Met Tyr
            310                 315                 320 gac atg atc cta ctg cgg agt ggc aac tgg gag ctg gag acc act cgc      1067
Asp Met Ile Leu Leu Arg Ser Gly Asn Trp Glu Leu Glu Thr Thr Arg
                325                 330                 335 aac aac gat ggc ctc acg ccg ctg cag ctg gcc gcc aag atg ggc aag      1115
Asn Asn Asp Gly Leu Thr Pro Leu Gln Leu Ala Ala Lys Met Gly Lys
            340                 345                 350 gcg gag atc ctg aag tac atc ctc agt cgt gag atc aag gag aag cgg      1163
Ala Glu Ile Leu Lys Tyr Ile Leu Ser Arg Glu Ile Lys Glu Lys Arg
355                 360                 365 ctc cgg agc ctg tcc agg aag ttc acc gac tgg gcg tac gga ccc gtg      1211
Leu Arg Ser Leu Ser Arg Lys Phe Thr Asp Trp Ala Tyr Gly Pro Val
370                 375                 380                 385 tca tcc tcc ctc tac gac ctc acc aac gtg gac acc acc acg gac aac      1259
Ser Ser Ser Leu Tyr Asp Leu Thr Asn Val Asp Thr Thr Thr Asp Asn
                390                 395                 400 tca gtg ctg gaa atc act gtc tac aac acc aac atc gac aac cgg cat      1307
Ser Val Leu Glu Ile Thr Val Tyr Asn Thr Asn Ile Asp Asn Arg His
            405                 410                 415 gag atg ctg acc ctg gag ccg ctg cac acg ctg ctg cat atg aag tgg      1355
Glu Met Leu Thr Leu Glu Pro Leu His Thr Leu Leu His Met Lys Trp
        420                 425                 430 aag aag ttt gcc aag cac atg ttc ttt ctg tcc ttc tgc ttt tat ttc      1403
Lys Lys Phe Ala Lys His Met Phe Phe Leu Ser Phe Cys Phe Tyr Phe
435                 440                 445 ttc tac aac atc acc ctg acc ctc gtc tcg tac tac cgc ccc cgg gag      1451
Phe Tyr Asn Ile Thr Leu Thr Leu Val Ser Tyr Tyr Arg Pro Arg Glu
450                 455                 460                 465 gag gag gcc atc ccg cac ccc ttg gcc ctg acg cac aag atg ggg tgg      1499
Glu Glu Ala Ile Pro His Pro Leu Ala Leu Thr His Lys Met Gly Trp
                470                 475                 480 ctg cag ctc cta ggg agg atg ttt gtg ctc atc tgg gcc atg tgc atc      1547
Leu Gln Leu Leu Gly Arg Met Phe Val Leu Ile Trp Ala Met Cys Ile
            485                 490                 495 tct gtg aaa gag ggc att gcc atc ttc ctg ctg aga ccc tcg gat ctg      1595
Ser Val Lys Glu Gly Ile Ala Ile Phe Leu Leu Arg Pro Ser Asp Leu
        500                 505                 510 cag tcc atc ctc tcg gat gcc tgg ttc cac ttt gtc ttt ttt atc caa      1643
Gln Ser Ile Leu Ser Asp Ala Trp Phe His Phe Val Phe Phe Ile Gln
515                 520                 525 gct gtg ctt gtg ata ctg tct gtc ttc ttg tac ttg ttt gcc tac aaa      1691
Ala Val Leu Val Ile Leu Ser Val Phe Leu Tyr Leu Phe Ala Tyr Lys
530                 535                 540                 545 gag tac ctc gcc tgc ctc gtg ctg gcc atg gcc ctg ggc tgg gcg aac      1739
Glu Tyr Leu Ala Cys Leu Val Leu Ala Met Ala Leu Gly Trp Ala Asn
                550                 555                 560 atg ctc tac tat acg cgg ggt ttc cag tcc atg ggc atg tac agc gtc      1787
Met Leu Tyr Tyr Thr Arg Gly Phe Gln Ser Met Gly Met Tyr Ser Val
            565                 570                 575 atg atc cag aag gtc att ttg cat gat gtt ctg aag ttc ttg ttt gta      1835
Met Ile Gln Lys Val Ile Leu His Asp Val Leu Lys Phe Leu Phe Val
        580                 585                 590 tat atc gtg ttt ttg ctt gga ttt gga gta gcc ttg gcc tcg ctg atc      1883
Tyr Ile Val Phe Leu Leu Gly Phe Gly Val Ala Leu Ala Ser Leu Ile
595                 600                 605
```

```
gag aag tgt ccc aaa gac aac aag gac tgc agc tcc tac ggc agc ttc    1931
Glu Lys Cys Pro Lys Asp Asn Lys Asp Cys Ser Ser Tyr Gly Ser Phe
610             615                 620                 625 agc gac gca gtg ctg gaa ctc ttc aag ctc acc ata ggc ctg ggt gac    1979
Ser Asp Ala Val Leu Glu Leu Phe Lys Leu Thr Ile Gly Leu Gly Asp
            630                 635                 640 ctg aac atc cag cag aac tcc aag tat ccc att ctc ttt ctg ttc ctg    2027
Leu Asn Ile Gln Gln Asn Ser Lys Tyr Pro Ile Leu Phe Leu Phe Leu
        645                 650                 655 ctc atc acc tat gtc atc ctc acc ttt gtt ctc ctc aac atg ctc        2075
Leu Ile Thr Tyr Val Ile Leu Thr Phe Val Leu Leu Asn Met Leu
    660                 665                 670 att gct ctg atg ggc gag act gtg gag aac gtc tcc aag gag agc gaa    2123
Ile Ala Leu Met Gly Glu Thr Val Glu Asn Val Ser Lys Glu Ser Glu
675                 680                 685 cgc atc tgg cgc ctg cag aga gcc agg acc atc ttg gag ttt gag aaa    2171
Arg Ile Trp Arg Leu Gln Arg Ala Arg Thr Ile Leu Glu Phe Glu Lys
690                 695                 700                 705 atg tta cca gaa tgg ctg agg agc aga ttc cgg atg gga gag ctg tgc    2219
Met Leu Pro Glu Trp Leu Arg Ser Arg Phe Arg Met Gly Glu Leu Cys
            710                 715                 720 aaa gtg gcc gag gat gat ttc cga ctg tgt ttg cgg atc aat gag gtg    2267
Lys Val Ala Glu Asp Asp Phe Arg Leu Cys Leu Arg Ile Asn Glu Val
        725                 730                 735 aag tgg act gaa tgg aag acg cac gtc tcc ttc ctt aac gaa gac ccg    2315
Lys Trp Thr Glu Trp Lys Thr His Val Ser Phe Leu Asn Glu Asp Pro
    740                 745                 750 ggg cct gta aga cga aca gca gat ttc aac aaa atc caa gat tct tcc    2363
Gly Pro Val Arg Arg Thr Ala Asp Phe Asn Lys Ile Gln Asp Ser Ser
755                 760                 765 agg aac aac agc aaa acc act ctc aat gca ttt gaa gaa gtc gag gaa    2411
Arg Asn Asn Ser Lys Thr Thr Leu Asn Ala Phe Glu Glu Val Glu Glu
770                 775                 780                 785 ttc ccg gaa acc tcg gtg tag                                        2432
Phe Pro Glu Thr Ser Val *
            790

<210> SEQ ID NO 5
<211> LENGTH: 791
<212> TYPE: PRT
<213> ORGANISM: Human

<400> SEQUENCE: 5

Met Lys Ala His Pro Lys Glu Met Val Pro Leu Met Gly Lys Arg Val
1               5                   10                  15

Ala Ala Pro Ser Gly Asn Pro Ala Val Leu Pro Glu Lys Arg Pro Ala
            20                  25                  30

Glu Ile Thr Pro Thr Lys Lys Ser Ala His Phe Phe Leu Glu Ile Glu
        35                  40                  45

Gly Phe Glu Pro Asn Pro Thr Val Ala Lys Thr Ser Pro Pro Val Phe
    50                  55                  60

Ser Lys Pro Met Asp Ser Asn Ile Arg Gln Cys Ile Ser Gly Asn Cys
65                  70                  75                  80

Asp Asp Met Asp Ser Pro Gln Ser Pro Gln Asp Val Thr Glu Thr
                85                  90                  95

Pro Ser Asn Pro Asn Ser Pro Ala Gln Leu Ala Lys Glu Glu Gln
            100                 105                 110

Arg Arg Lys Lys Arg Arg Leu Lys Lys Arg Ile Phe Ala Ala Val Ser
        115                 120                 125
```

```
Glu Gly Cys Val Glu Glu Leu Val Glu Leu Leu Val Glu Leu Gln Glu
    130                 135                 140

Leu Cys Arg Arg Arg His Asp Glu Asp Val Pro Asp Phe Leu Met His
145                 150                 155                 160

Lys Leu Thr Ala Ser Asp Thr Gly Lys Thr Cys Leu Met Lys Ala Leu
                165                 170                 175

Leu Asn Ile Asn Pro Asn Thr Lys Glu Ile Val Arg Ile Leu Leu Ala
            180                 185                 190

Phe Ala Glu Glu Asn Asp Ile Leu Gly Arg Phe Ile Asn Ala Glu Tyr
        195                 200                 205

Thr Glu Glu Ala Tyr Glu Gly Gln Thr Ala Leu Asn Ile Ala Ile Glu
    210                 215                 220

Arg Arg Gln Gly Asp Ile Ala Ala Leu Leu Ile Ala Ala Gly Ala Asp
225                 230                 235                 240

Val Asn Ala His Ala Lys Gly Ala Phe Phe Asn Pro Lys Tyr Gln His
                245                 250                 255

Glu Gly Phe Tyr Phe Gly Glu Thr Pro Leu Ala Leu Ala Ala Cys Thr
            260                 265                 270

Asn Gln Pro Glu Ile Val Gln Leu Leu Met Glu His Glu Gln Thr Asp
        275                 280                 285

Ile Thr Ser Arg Asp Ser Arg Gly Asn Asn Ile Leu His Ala Leu Val
    290                 295                 300

Thr Val Ala Glu Asp Phe Lys Thr Gln Asn Asp Phe Val Lys Arg Met
305                 310                 315                 320

Tyr Asp Met Ile Leu Leu Arg Ser Gly Asn Trp Glu Leu Glu Thr Thr
                325                 330                 335

Arg Asn Asn Asp Gly Leu Thr Pro Leu Gln Leu Ala Ala Lys Met Gly
            340                 345                 350

Lys Ala Glu Ile Leu Lys Tyr Ile Leu Ser Arg Glu Ile Lys Glu Lys
        355                 360                 365

Arg Leu Arg Ser Leu Ser Arg Lys Phe Thr Asp Trp Ala Tyr Gly Pro
    370                 375                 380

Val Ser Ser Ser Leu Tyr Asp Leu Thr Asn Val Asp Thr Thr Thr Asp
385                 390                 395                 400

Asn Ser Val Leu Glu Ile Thr Val Tyr Asn Thr Asn Ile Asp Asn Arg
                405                 410                 415

His Glu Met Leu Thr Leu Glu Pro Leu His Thr Leu Leu His Met Lys
            420                 425                 430

Trp Lys Lys Phe Ala Lys His Met Phe Phe Leu Ser Phe Cys Phe Tyr
        435                 440                 445

Phe Phe Tyr Asn Ile Thr Leu Thr Leu Val Ser Tyr Tyr Arg Pro Arg
    450                 455                 460

Glu Glu Glu Ala Ile Pro His Pro Leu Ala Leu Thr His Lys Met Gly
465                 470                 475                 480

Trp Leu Gln Leu Leu Gly Arg Met Phe Val Leu Ile Trp Ala Met Cys
                485                 490                 495

Ile Ser Val Lys Glu Gly Ile Ala Ile Phe Leu Leu Arg Pro Ser Asp
            500                 505                 510

Leu Gln Ser Ile Leu Ser Asp Ala Trp Phe His Phe Val Phe Phe Ile
        515                 520                 525

Gln Ala Val Leu Val Ile Leu Ser Val Phe Leu Tyr Leu Phe Ala Tyr
    530                 535                 540
```

-continued

```
Lys Glu Tyr Leu Ala Cys Leu Val Leu Ala Met Ala Leu Gly Trp Ala
545                 550                 555                 560

Asn Met Leu Tyr Tyr Thr Arg Gly Phe Gln Ser Met Gly Met Tyr Ser
                565                 570                 575

Val Met Ile Gln Lys Val Ile Leu His Asp Val Leu Lys Phe Leu Phe
            580                 585                 590

Val Tyr Ile Val Phe Leu Leu Gly Phe Gly Val Ala Leu Ala Ser Leu
        595                 600                 605

Ile Glu Lys Cys Pro Lys Asp Asn Lys Asp Cys Ser Ser Tyr Gly Ser
    610                 615                 620

Phe Ser Asp Ala Val Leu Glu Leu Phe Lys Leu Thr Ile Gly Leu Gly
625                 630                 635                 640

Asp Leu Asn Ile Gln Gln Asn Ser Lys Tyr Pro Ile Leu Phe Leu Phe
                645                 650                 655

Leu Leu Ile Thr Tyr Val Ile Leu Thr Phe Val Leu Leu Leu Asn Met
                660                 665                 670

Leu Ile Ala Leu Met Gly Glu Thr Val Glu Asn Val Ser Lys Glu Ser
        675                 680                 685

Glu Arg Ile Trp Arg Leu Gln Arg Ala Arg Thr Ile Leu Glu Phe Glu
    690                 695                 700

Lys Met Leu Pro Glu Trp Leu Arg Ser Arg Phe Arg Met Gly Glu Leu
705                 710                 715                 720

Cys Lys Val Ala Glu Asp Asp Phe Arg Leu Cys Leu Arg Ile Asn Glu
                725                 730                 735

Val Lys Trp Thr Glu Trp Lys Thr His Val Ser Phe Leu Asn Glu Asp
            740                 745                 750

Pro Gly Pro Val Arg Arg Thr Ala Asp Phe Asn Lys Ile Gln Asp Ser
        755                 760                 765

Ser Arg Asn Asn Ser Lys Thr Thr Leu Asn Ala Phe Glu Glu Val Glu
    770                 775                 780

Glu Phe Pro Glu Thr Ser Val
785                 790

<210> SEQ ID NO 6
<211> LENGTH: 2373
<212> TYPE: DNA
<213> ORGANISM: Artificial Sequence
<220> FEATURE:
<221> NAME/KEY: CDS
<222> LOCATION: (1)...(2373)
<223> OTHER INFORMATION: Generic sequence that encompasses all
      nucleotide sequences that encode human TRPV3 having an amino
      acid sequence as shown in SEQ ID NO:5
<220> FEATURE:
<221> NAME/KEY: misc_feature
<222> LOCATION: 60,120,180,195,210,231,255,264,294,306,312,384,495,873,
      882,984,1086,1116,1122,1158,1161,1164,1206,1332,1377,1494,1533,
      1545,1554,1608,1713,1728,1821,1860,1863,1872,1878,1944,2055,
      2064,2139,2241,2304,2307,2319,2370
<223> OTHER INFORMATION: n = A,T,C or G if after TC;
      n = T or C if after AG
<220> FEATURE:
<221> NAME/KEY: misc_feature
<222> LOCATION: 45,90,219,339,342,351,354,366,441,444,447,564,606,675,
      678,876,885,957,981,1011,1089,1107,1113,1125,1248,1386,1392,
      1461,1527,1701,2070,2079,2088,2136,2142,2148,2187,2199,2271,2274,
      2310
<223> OTHER INFORMATION: n = A,T,C or G if after CG;
      n = A or G if after AG
<220> FEATURE:
<221> NAME/KEY: misc_feature
<222> LOCATION: all "n" not specified above
<223> OTHER INFORMATION: n = A,T,C or G
```

-continued

```
<400> SEQUENCE: 6 atg aar gcn cay ccn aar gar atg gtn ccn ytn atg ggn aar mgn gtn         48
Met Lys Ala His Pro Lys Glu Met Val Pro Leu Met Gly Lys Arg Val
 1               5                  10                  15 gcn gcn ccn wsn ggn aay ccn gcn gtn ytn ccn gar aar mgn ccn gcn         96
Ala Ala Pro Ser Gly Asn Pro Ala Val Leu Pro Glu Lys Arg Pro Ala
             20                  25                  30 gar ath acn ccn acn aar aar wsn gcn cay tty tty ytn gar ath gar        144
Glu Ile Thr Pro Thr Lys Lys Ser Ala His Phe Phe Leu Glu Ile Glu
         35                  40                  45 ggn tty gar ccn aay ccn acn gtn gcn aar acn wsn ccn ccn gtn tty        192
Gly Phe Glu Pro Asn Pro Thr Val Ala Lys Thr Ser Pro Pro Val Phe
     50                  55                  60 wsn aar ccn atg gay wsn aay ath mgn car tgy ath wsn ggn aay tgy        240
Ser Lys Pro Met Asp Ser Asn Ile Arg Gln Cys Ile Ser Gly Asn Cys
 65                  70                  75                  80 gay gay atg gay wsn ccn car wsn ccn car gay gay gtn acn gar acn        288
Asp Asp Met Asp Ser Pro Gln Ser Pro Gln Asp Asp Val Thr Glu Thr
                 85                  90                  95 ccn wsn aay ccn aay wsn ccn wsn gcn car ytn gcn aar gar gar car        336
Pro Ser Asn Pro Asn Ser Pro Ser Ala Gln Leu Ala Lys Glu Glu Gln
            100                 105                 110 mgn mgn aar aar mgn mgn ytn aar aar mgn ath tty gcn gcn gtn wsn        384
Arg Arg Lys Lys Arg Arg Leu Lys Lys Arg Ile Phe Ala Ala Val Ser
        115                 120                 125 gar ggn tgy gtn gar gar ytn gtn gar ytn ytn gtn gar ytn car gar        432
Glu Gly Cys Val Glu Glu Leu Val Glu Leu Leu Val Glu Leu Gln Glu
    130                 135                 140 ytn tgy mgn mgn mgn cay gay gar gay gtn ccn gay tty ytn atg cay        480
Leu Cys Arg Arg Arg His Asp Glu Asp Val Pro Asp Phe Leu Met His
145                 150                 155                 160 aar ytn acn gcn wsn gay acn ggn aar acn tgy ytn atg aar gcn ytn        528
Lys Leu Thr Ala Ser Asp Thr Gly Lys Thr Cys Leu Met Lys Ala Leu
                165                 170                 175 ytn aay ath aay ccn aay acn aar gar ath gtn mgn ath ytn ytn gcn        576
Leu Asn Ile Asn Pro Asn Thr Lys Glu Ile Val Arg Ile Leu Leu Ala
            180                 185                 190 tty gcn gar gar aay gay ath ytn ggn mgn tty ath aay gcn gar tay        624
Phe Ala Glu Glu Asn Asp Ile Leu Gly Arg Phe Ile Asn Ala Glu Tyr
        195                 200                 205 acn gar gar gcn tay gar ggn car acn gcn ytn aay ath gcn ath gar        672
Thr Glu Glu Ala Tyr Glu Gly Gln Thr Ala Leu Asn Ile Ala Ile Glu
    210                 215                 220 mgn mgn car ggn gay ath gcn gcn ytn ytn ath gcn gcn ggn gcn gay        720
Arg Arg Gln Gly Asp Ile Ala Ala Leu Leu Ile Ala Ala Gly Ala Asp
225                 230                 235                 240 gtn aay gcn cay gcn aar ggn gcn tty tty aay ccn aar tay car cay        768
Val Asn Ala His Ala Lys Gly Ala Phe Phe Asn Pro Lys Tyr Gln His
                245                 250                 255 gar ggn tty tay tty ggn gar acn ccn ytn gcn ytn gcn gcn tgy acn        816
Glu Gly Phe Tyr Phe Gly Glu Thr Pro Leu Ala Leu Ala Ala Cys Thr
            260                 265                 270 aay car ccn gar ath gtn car ytn ytn atg gar cay gar car acn gay        864
Asn Gln Pro Glu Ile Val Gln Leu Leu Met Glu His Glu Gln Thr Asp
        275                 280                 285 ath acn wsn mgn gay wsn mgn ggn aay aay ath ytn cay gcn ytn gtn        912
Ile Thr Ser Arg Asp Ser Arg Gly Asn Asn Ile Leu His Ala Leu Val
    290                 295                 300
```

-continued

```
acn gtn gcn gar gay tty aar acn car aay gay tty gtn aar mgn atg      960
Thr Val Ala Glu Asp Phe Lys Thr Gln Asn Asp Phe Val Lys Arg Met
305                 310                 315                 320 tay gay atg ath ytn ytn mgn wsn ggn aay tgg gar ytn gar acn acn     1008
Tyr Asp Met Ile Leu Leu Arg Ser Gly Asn Trp Glu Leu Glu Thr Thr
                325                 330                 335 mgn aay aay gay ggn ytn acn ccn ytn car ytn gcn gcn aar atg ggn     1056
Arg Asn Asn Asp Gly Leu Thr Pro Leu Gln Leu Ala Ala Lys Met Gly
            340                 345                 350 aar gcn gar ath ytn aar tay ath ytn wsn mgn gar ath aar gar aar     1104
Lys Ala Glu Ile Leu Lys Tyr Ile Leu Ser Arg Glu Ile Lys Glu Lys
        355                 360                 365 mgn ytn mgn wsn ytn wsn mgn aar tty acn gay tgg gcn tay ggn ccn     1152
Arg Leu Arg Ser Leu Ser Arg Lys Phe Thr Asp Trp Ala Tyr Gly Pro
370                 375                 380 gtn wsn wsn wsn ytn tay gay ytn acn aay gtn gay acn acn acn gay     1200
Val Ser Ser Ser Leu Tyr Asp Leu Thr Asn Val Asp Thr Thr Thr Asp
385                 390                 395                 400 aay wsn gtn ytn gar ath acn gtn tay aay acn aay ath gay aay mgn     1248
Asn Ser Val Leu Glu Ile Thr Val Tyr Asn Thr Asn Ile Asp Asn Arg
                405                 410                 415 cay gar atg ytn acn ytn gar ccn ytn cay acn ytn ytn cay atg aar     1296
His Glu Met Leu Thr Leu Glu Pro Leu His Thr Leu Leu His Met Lys
            420                 425                 430 tgg aar aar tty gcn aar cay atg tty tty ytn wsn tty tgy tty tay     1344
Trp Lys Lys Phe Ala Lys His Met Phe Phe Leu Ser Phe Cys Phe Tyr
        435                 440                 445 tty tty tay aay ath acn ytn acn ytn gtn wsn tay tay mgn ccn mgn     1392
Phe Phe Tyr Asn Ile Thr Leu Thr Leu Val Ser Tyr Tyr Arg Pro Arg
450                 455                 460 gar gar gar gcn ath ccn cay ccn ytn gcn ytn acn cay aar atg ggn     1440
Glu Glu Glu Ala Ile Pro His Pro Leu Ala Leu Thr His Lys Met Gly
465                 470                 475                 480 tgg ytn car ytn ytn ggn mgn atg tty gtn ytn ath tgg gcn atg tgy     1488
Trp Leu Gln Leu Leu Gly Arg Met Phe Val Leu Ile Trp Ala Met Cys
                485                 490                 495 ath wsn gtn aar gar ggn ath gcn ath tty ytn ytn mgn ccn wsn gay     1536
Ile Ser Val Lys Glu Gly Ile Ala Ile Phe Leu Leu Arg Pro Ser Asp
            500                 505                 510 ytn car wsn ath ytn wsn gay gcn tgg tty cay tty gtn tty tty ath     1584
Leu Gln Ser Ile Leu Ser Asp Ala Trp Phe His Phe Val Phe Phe Ile
        515                 520                 525 car gcn gtn ytn gtn ath ytn wsn gtn tty ytn tay ytn tty gcn tay     1632
Gln Ala Val Leu Val Ile Leu Ser Val Phe Leu Tyr Leu Phe Ala Tyr
530                 535                 540 aar gar tay ytn gcn tgy ytn gtn ytn gcn atg gcn ytn ggn tgg gcn     1680
Lys Glu Tyr Leu Ala Cys Leu Val Leu Ala Met Ala Leu Gly Trp Ala
545                 550                 555                 560 aay atg ytn tay tay acn mgn ggn tty car wsn atg ggn atg tay wsn     1728
Asn Met Leu Tyr Tyr Thr Arg Gly Phe Gln Ser Met Gly Met Tyr Ser
                565                 570                 575 gtn atg ath car aar gtn ath ytn cay gay gtn ytn aar tty ytn tty     1776
Val Met Ile Gln Lys Val Ile Leu His Asp Val Leu Lys Phe Leu Phe
            580                 585                 590 gtn tay ath gtn tty ytn ytn ggn tty ggn gtn gcn ytn gcn wsn ytn     1824
Val Tyr Ile Val Phe Leu Leu Gly Phe Gly Val Ala Leu Ala Ser Leu
        595                 600                 605 ath gar aar tgy ccn aar gay aay aar gay tgy wsn wsn tay ggn wsn     1872
Ile Glu Lys Cys Pro Lys Asp Asn Lys Asp Cys Ser Ser Tyr Gly Ser
610                 615                 620
```

| | | | | | | | | | | | | | | | |
|---|---|---|---|---|---|---|---|---|---|---|---|---|---|---|---|
| tty | wsn | gay | gcn | gtn | ytn | gar | ytn | tty | aar | ytn | acn | ath | ggn | ytn | ggn | 1920 |
| Phe | Ser | Asp | Ala | Val | Leu | Glu | Leu | Phe | Lys | Leu | Thr | Ile | Gly | Leu | Gly |
| 625 | | | | 630 | | | | | 635 | | | | | 640 |

```
tty wsn gay gcn gtn ytn gar ytn tty aar ytn acn ath ggn ytn ggn    1920
Phe Ser Asp Ala Val Leu Glu Leu Phe Lys Leu Thr Ile Gly Leu Gly
625                 630                 635                 640 gay ytn aay ath car car aay wsn aar tay ccn ath ytn tty ytn tty    1968
Asp Leu Asn Ile Gln Gln Asn Ser Lys Tyr Pro Ile Leu Phe Leu Phe
                    645                 650                 655 ytn ytn ath acn tay gtn ath ytn acn tty gtn ytn ytn aay atg        2016
Leu Leu Ile Th

```
Ser Ser Val Ser Arg Ser Thr Asp Val Ser Tyr Ser Asp Ser Asp Leu
            30                  35                  40 gtg aat ttt att cag gca aat ttt aaa aaa cga gaa tgt gtc ttc ttt     618
Val Asn Phe Ile Gln Ala Asn Phe Lys Lys Arg Glu Cys Val Phe Phe
            45                  50                  55 acc aga gac tcc aag gcc atg gag aac ata tgc aag tgt ggt tat gcc     666
Thr Arg Asp Ser Lys Ala Met Glu Asn Ile Cys Lys Cys Gly Tyr Ala
        60                  65                  70 cag agc cag cac atc gaa ggc acc cag atc aac caa aat gag aag tgg     714
Gln Ser Gln His Ile Glu Gly Thr Gln Ile Asn Gln Asn Glu Lys Trp
    75                  80                  85 aac tac aaa aaa cat acc aag gag ttt cca aca gac gcc ttc ggg gac     762
Asn Tyr Lys Lys His Thr Lys Glu Phe Pro Thr Asp Ala Phe Gly Asp
 90                  95                 100                 105 att cag ttt gag act ctg ggg aag aaa ggc aag tac tta cgc ttg tcc     810
Ile Gln Phe Glu Thr Leu Gly Lys Lys Gly Lys Tyr Leu Arg Leu Ser
            110                 115                 120 tgt gac acc gac tct gaa act ctc tac gaa ctg ctg acc cag cac tgg     858
Cys Asp Thr Asp Ser Glu Thr Leu Tyr Glu Leu Leu Thr Gln His Trp
            125                 130                 135 cac ctc aaa aca ccc aac ctg gtc att tca gtg acg ggt gga gcc aaa     906
His Leu Lys Thr Pro Asn Leu Val Ile Ser Val Thr Gly Gly Ala Lys
        140                 145                 150 aac ttt gct ttg aag cca cgc atg cgc aag atc ttc agc agg ctg att     954
Asn Phe Ala Leu Lys Pro Arg Met Arg Lys Ile Phe Ser Arg Leu Ile
    155                 160                 165 tac atc gca cag tct aaa ggt gcg tgg att ctc act gga ggc act cac    1002
Tyr Ile Ala Gln Ser Lys Gly Ala Trp Ile Leu Thr Gly Gly Thr His
170                 175                 180                 185 tac ggc ctg atg aag tac ata ggc gag gtg gtg aga gac aac acc atc    1050
Tyr Gly Leu Met Lys Tyr Ile Gly Glu Val Val Arg Asp Asn Thr Ile
            190                 195                 200 agc agg aac tca gaa gag aac atc gtg gcc att ggc atc gca gca tgg    1098
Ser Arg Asn Ser Glu Glu Asn Ile Val Ala Ile Gly Ile Ala Ala Trp
            205                 210                 215 ggc atg gtc tcc aac agg gac acc ctc atc agg agc tgt gat gat gag    1146
Gly Met Val Ser Asn Arg Asp Thr Leu Ile Arg Ser Cys Asp Asp Glu
        220                 225                 230 gga cat ttt tca gct caa tac atc atg gat gac ttt acc aga gac cct    1194
Gly His Phe Ser Ala Gln Tyr Ile Met Asp Asp Phe Thr Arg Asp Pro
    235                 240                 245 cta tac atc ctg gac aac aac cat acc cac ctg ctg ctt gtg gac aac    1242
Leu Tyr Ile Leu Asp Asn Asn His Thr His Leu Leu Leu Val Asp Asn
250                 255                 260                 265 ggt tgt cat gga cac ccc aca gtg gaa gcc aag ctc cgg aat cag ctg    1290
Gly Cys His Gly His Pro Thr Val Glu Ala Lys Leu Arg Asn Gln Leu
            270                 275                 280 gaa aag tac atc tct gag cgc acc agt caa gat tcc aac tat ggt ggt    1338
Glu Lys Tyr Ile Ser Glu Arg Thr Ser Gln Asp Ser Asn Tyr Gly Gly
            285                 290                 295 aag atc ccc atc gtg tgt ttt gcc caa gga ggt gga aga gag act cta    1386
Lys Ile Pro Ile Val Cys Phe Ala Gln Gly Gly Gly Arg Glu Thr Leu
        300                 305                 310 aaa gcc atc aac acc tct gtc aaa agc aag atc cct tgt gtg gtg gtg    1434
Lys Ala Ile Asn Thr Ser Val Lys Ser Lys Ile Pro Cys Val Val Val
    315                 320                 325 gaa ggc tcg ggg cag att gct gat gtg atc gcc agc ctg gtg gag gtg    1482
Glu Gly Ser Gly Gln Ile Ala Asp Val Ile Ala Ser Leu Val Glu Val
330                 335                 340                 345
```

-continued

| | |
|---|---|
| gag gat gtt tta acc tct tcc atg gtc aaa gag aag ctg gta cgc ttt<br>Glu Asp Val Leu Thr Ser Ser Met Val Lys Glu Lys Leu Val Arg Phe<br>350 355 360 | 1530 |
| tta cca cgc act gtg tcc cgg ctg cct gaa gag gaa att gag agc tgg<br>Leu Pro Arg Thr Val Ser Arg Leu Pro Glu Glu Glu Ile Glu Ser Trp<br>365 370 375 | 1578 |
| atc aaa tgg ctc aaa gaa att ctt gag agt tct cac cta ctc aca gta<br>Ile Lys Trp Leu Lys Glu Ile Leu Glu Ser Ser His Leu Leu Thr Val<br>380 385 390 | 1626 |
| att aag atg gaa gag gct gga gat gag att gtg agc aac gcc att tcc<br>Ile Lys Met Glu Glu Ala Gly Asp Glu Ile Val Ser Asn Ala Ile Ser<br>395 400 405 | 1674 |
| tat gcg ctg tac aaa gcc ttc agc act aat gag caa gac aag gac aac<br>Tyr Ala Leu Tyr Lys Ala Phe Ser Thr Asn Glu Gln Asp Lys Asp Asn<br>410 415 420 425 | 1722 |
| tgg aat gga cag ctg aag ctt ctg ctg gag tgg aac cag ttg gac ctt<br>Trp Asn Gly Gln Leu Lys Leu Leu Leu Glu Trp Asn Gln Leu Asp Leu<br>430 435 440 | 1770 |
| gcc agt gat gag atc ttc acc aat gac cgc cgc tgg gag tct gcc gac<br>Ala Ser Asp Glu Ile Phe Thr Asn Asp Arg Arg Trp Glu Ser Ala Asp<br>445 450 455 | 1818 |
| ctt cag gag gtc atg ttc acg gct ctc ata aag gac aga ccc aag ttt<br>Leu Gln Glu Val Met Phe Thr Ala Leu Ile Lys Asp Arg Pro Lys Phe<br>460 465 470 | 1866 |
| gtc cgc ctc ttt ctg gag aat ggc ctg aat ctg cag aag ttt ctc acc<br>Val Arg Leu Phe Leu Glu Asn Gly Leu Asn Leu Gln Lys Phe Leu Thr<br>475 480 485 | 1914 |
| aat gaa gtc ctc aca gag ctc ttc tcc acc cac ttc agc acc cta gtg<br>Asn Glu Val Leu Thr Glu Leu Phe Ser Thr His Phe Ser Thr Leu Val<br>490 495 500 505 | 1962 |
| tac cgg aac ctg cag atc gcc aag aac tcc tac aat gac gca ctc ctc<br>Tyr Arg Asn Leu Gln Ile Ala Lys Asn Ser Tyr Asn Asp Ala Leu Leu<br>510 515 520 | 2010 |
| acc ttt gtc tgg aag ttg gtg gca aac ttc cgt cga agc ttc tgg aaa<br>Thr Phe Val Trp Lys Leu Val Ala Asn Phe Arg Arg Ser Phe Trp Lys<br>525 530 535 | 2058 |
| gag gac aga agc agc agg gag gac ttg gat gtg gaa ctc cat gat gca<br>Glu Asp Arg Ser Ser Arg Glu Asp Leu Asp Val Glu Leu His Asp Ala<br>540 545 550 | 2106 |
| tct ctc acc acc cgg cac ccg ctg caa gct ctc ttc atc tgg gcc att<br>Ser Leu Thr Thr Arg His Pro Leu Gln Ala Leu Phe Ile Trp Ala Ile<br>555 560 565 | 2154 |
| ctt cag aac aag aag gaa ctc tcc aag gtc att tgg gag cag acc aaa<br>Leu Gln Asn Lys Lys Glu Leu Ser Lys Val Ile Trp Glu Gln Thr Lys<br>570 575 580 585 | 2202 |
| ggc tgt act ctg gca gcc ttg ggg gcc agc aag ctt ctg aag acc ctg<br>Gly Cys Thr Leu Ala Ala Leu Gly Ala Ser Lys Leu Leu Lys Thr Leu<br>590 595 600 | 2250 |
| gcc aaa gtt aag aat gat atc aac gct gct ggg gaa tcg gag gaa ctg<br>Ala Lys Val Lys Asn Asp Ile Asn Ala Ala Gly Glu Ser Glu Glu Leu<br>605 610 615 | 2298 |
| gcc aat gaa tat gag acc cga gca gtg gag ttg ttc acc gag tgt tac<br>Ala Asn Glu Tyr Glu Thr Arg Ala Val Glu Leu Phe Thr Glu Cys Tyr<br>620 625 630 | 2346 |
| agc aat gat gaa gac ttg gca gaa cag cta ctg gtc tac tcc tgc gaa<br>Ser Asn Asp Glu Asp Leu Ala Glu Gln Leu Leu Val Tyr Ser Cys Glu<br>635 640 645 | 2394 |
| gcc tgg ggt ggg agc aac tgt ctg gag ctg gca gtg gag gct aca gat<br>Ala Trp Gly Gly Ser Asn Cys Leu Glu Leu Ala Val Glu Ala Thr Asp<br>650 655 660 665 | 2442 |

```
cag cat ttc atc gct cag cct ggg gtc cag aat ttc ctt tct aag caa      2490
Gln His Phe Ile Ala Gln Pro Gly Val Gln Asn Phe Leu Ser Lys Gln
                670                 675                 680 tgg tat gga gag att tcc cga gac acg aag aac tgg aag att atc ctg      2538
Trp Tyr Gly Glu Ile Ser Arg Asp Thr Lys Asn Trp Lys Ile Ile Leu
            685                 690                 695 tgt cta ttc att atc ccc tta gtg ggc tgt ggc ctc gta tca ttt agg      2586
Cys Leu Phe Ile Ile Pro Leu Val Gly Cys Gly Leu Val Ser Phe Arg
        700                 705                 710 aag aaa ccc att gac aag cac aag aag ctg ctg tgg tac tat gtg gcc      2634
Lys Lys Pro Ile Asp Lys His Lys Lys Leu Leu Trp Tyr Tyr Val Ala
    715                 720                 725 ttc ttc acg tcg ccc ttc gtg gtc ttc tcc tgg aac gtg gtc ttc tac      2682
Phe Phe Thr Ser Pro Phe Val Val Phe Ser Trp Asn Val Val Phe Tyr
730                 735                 740                 745 atc gcc ttc ctc ctg ctg ttt gcc tat gtg ctg ctc atg gac ttc cac      2730
Ile Ala Phe Leu Leu Leu Phe Ala Tyr Val Leu Leu Met Asp Phe His
                750                 755                 760 tca gtg cca cac acc ccc gag ctg atc ctc tac gcc ctg gtc ttc gtc      2778
Ser Val Pro His Thr Pro Glu Leu Ile Leu Tyr Ala Leu Val Phe Val
            765                 770                 775 ctc ttc tgt gat gaa gtg agg cag tgg tac atg aac gga gtg aat tat      2826
Leu Phe Cys Asp Glu Val Arg Gln Trp Tyr Met Asn Gly Val Asn Tyr
        780                 785                 790 ttc acc gac cta tgg aac gtt atg gac acc ctg gga ctc ttc tac ttc      2874
Phe Thr Asp Leu Trp Asn Val Met Asp Thr Leu Gly Leu Phe Tyr Phe
    795                 800                 805 ata gcg ggt att gta ttc cgg ctc cac tct tct aat aaa agc tcg ttg      2922
Ile Ala Gly Ile Val Phe Arg Leu His Ser Ser Asn Lys Ser Ser Leu
810                 815                 820                 825 tac tct ggg cgc gtc att ttc tgt ctg gat tac att ata ttc acg cta      2970
Tyr Ser Gly Arg Val Ile Phe Cys Leu Asp Tyr Ile Ile Phe Thr Leu
                830                 835                 840 agg ctc atc cac att ttc acc gtc agc agg aac ttg gga ccc aag att      3018
Arg Leu Ile His Ile Phe Thr Val Ser Arg Asn Leu Gly Pro Lys Ile
            845                 850                 855 ata atg ctg cag cgg atg ctg atc gac gtt ttc ttc ctg ttc ctc      3066
Ile Met Leu Gln Arg Met Leu Ile Asp Val Phe Phe Phe Leu Phe Leu
        860                 865                 870 ttt gct gtg tgg atg gtg gcc ttt ggc gtg gcc aga cag ggg atc cta      3114
Phe Ala Val Trp Met Val Ala Phe Gly Val Ala Arg Gln Gly Ile Leu
    875                 880                 885 agg caa aat gaa cag cgc tgg aga tgg atc ttc cgc tct gtc atc tat      3162
Arg Gln Asn Glu Gln Arg Trp Arg Trp Ile Phe Arg Ser Val Ile Tyr
890                 895                 900                 905 gag ccc tac ctg gcc atg ttt ggc cag gtt ccc agt gac gtg gat agt      3210
Glu Pro Tyr Leu Ala Met Phe Gly Gln Val Pro Ser Asp Val Asp Ser
                910                 915                 920 acc aca tat gac ttc tcc cac tgt acc ttc tcg gga aat gag tcc aag      3258
Thr Thr Tyr Asp Phe Ser His Cys Thr Phe Ser Gly Asn Glu Ser Lys
            925                 930                 935 cca ctg tgt gtg gag ctg gat gag cac aac ctg ccc cgc ttc cct gag      3306
Pro Leu Cys Val Glu Leu Asp Glu His Asn Leu Pro Arg Phe Pro Glu
        940                 945                 950 tgg atc acc att ccg ctg gtg tgc atc tac atg ctc tcc acc aat atc      3354
Trp Ile Thr Ile Pro Leu Val Cys Ile Tyr Met Leu Ser Thr Asn Ile
    955                 960                 965 ctt ctg gtc aac ctc ctg gtc gcc atg ttt ggc tac acg gta ggc att      3402
Leu Leu Val Asn Leu Leu Val Ala Met Phe Gly Tyr Thr Val Gly Ile
```

```
                970             975             980             985
gta cag gag aac aac gac cag gtc tgg aaa ttc cag cgg tac ttc ctg      3450
Val Gln Glu Asn Asn Asp Gln Val Trp Lys Phe Gln Arg Tyr Phe Leu
                990                 995                1000 gtg cag gag tac tgc aac cgc cta aac atc ccc ttc ccc ttc gtt gtc      3498
Val Gln Glu Tyr Cys Asn Arg Leu Asn Ile Pro Phe Pro Phe Val Val
            1005                1010                1015 ttc gct tat ttc tac atg gtg gtg aag aag tgt ttc aaa tgc tgc tgt      3546
Phe Ala Tyr Phe Tyr Met Val Val Lys Lys Cys Phe Lys Cys Cys Cys
        1020                1025                1030 aaa gag aag aat atg gag tct aat gcc tgc tgt ttc aga aat gag gac      3594
Lys Glu Lys Asn Met Glu Ser Asn Ala Cys Cys Phe Arg Asn Glu Asp
    1035                1040                1045 aat gag act ttg gcg tgg gag ggt gtc atg aag gag aat tac ctt gtc      3642
Asn Glu Thr Leu Ala Trp Glu Gly Val Met Lys Glu Asn Tyr Leu Val
1050                1055                1060                1065 aag atc aac acg aaa gcc aac gac aac tca gag gag atg agg cat cgg      3690
Lys Ile Asn Thr Lys Ala Asn Asp Asn Ser Glu Glu Met Arg His Arg
                1070                1075                1080 ttt aga caa ctg gac tca aag ctt aac gac ctc aaa agt ctt ctg aaa      3738
Phe Arg Gln Leu Asp Ser Lys Leu Asn Asp Leu Lys Ser Leu Leu Lys
            1085                1090                1095 gag att gct aat aac atc aag taa ggctggcgat gcttgtgggg agaaaccaaa    3792
Glu Ile Ala Asn Asn Ile Lys  *
        1100 tcacaatgag gtcacagcaa cccctggat gtggaggctc atgggacact gatggacagt    3852 actgctaatg acttctaaag gagacatttt caggtccctg agcacagggt ggatgactct    3912 tagtcaccct caagggcata ggtcagggag caaagtgtac agaggacttt acacctgaag    3972 agggggtgcaa aggaccatgt tcttctgtga aggtgcctgt gttttctgca tctcagagcc   4032 ttgtcctgat gctgagggat taggtgttga cactcctttc ccacgactgt gactctggcc   4092 ctgattttat acttatactg c                                              4113

<210> SEQ ID NO 8
<211> LENGTH: 1104
<212> TYPE: PRT
<213> ORGANISM: Mus musculus

<400> SEQUENCE: 8

Met Ser Phe Glu Gly Ala Arg Leu Ser Met Arg Ser Arg Arg Asn Gly
  1               5                  10                  15

Thr Met Gly Ser Thr Arg Thr Leu Tyr Ser Ser Val Ser Arg Ser Thr
             20                  25                  30

Asp Val Ser Tyr Ser Asp Ser Asp Leu Val Asn Phe Ile Gln Ala Asn
         35                  40                  45

Phe Lys Lys Arg Glu Cys Val Phe Phe Thr Arg Asp Ser Lys Ala Met
     50                  55                  60

Glu Asn Ile Cys Lys Cys Gly Tyr Ala Gln Ser Gln His Ile Glu Gly
 65                  70                  75                  80

Thr Gln Ile Asn Gln Asn Glu Lys Trp Asn Tyr Lys Lys His Thr Lys
                 85                  90                  95

Glu Phe Pro Thr Asp Ala Phe Gly Asp Ile Gln Phe Glu Thr Leu Gly
            100                 105                 110

Lys Lys Gly Lys Tyr Leu Arg Leu Ser Cys Asp Thr Asp Ser Glu Thr
        115                 120                 125

Leu Tyr Glu Leu Leu Thr Gln His Trp His Leu Lys Thr Pro Asn Leu
```

```
                130                 135                 140
Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
                195                 200                 205

Ile Val Ala Ile Gly Ile Ala Ala Trp Gly Met Val Ser Asn Arg Asp
210                 215                 220

Thr Leu Ile Arg Ser Cys Asp Glu Gly His Phe Ser Ala Gln Tyr
225                 230                 235                 240

Ile Met Asp Asp Phe Thr Arg Asp Pro Leu Tyr Ile Leu Asp Asn Asn
                245                 250                 255

His Thr His Leu Leu Val Asp Asn Gly Cys His Gly His Pro Thr
                260                 265                 270

Val Glu Ala Lys Leu Arg Asn Gln Leu Glu Lys Tyr Ile Ser Glu Arg
                275                 280                 285

Thr Ser Gln Asp Ser Asn Tyr Gly Gly Lys Ile Pro Ile Val Cys Phe
                290                 295                 300

Ala Gln Gly Gly Gly Arg Glu Thr Leu Lys Ala Ile Asn Thr Ser Val
305                 310                 315                 320

Lys Ser Lys Ile Pro Cys Val Val Glu Gly Ser Gly Gln Ile Ala
                325                 330                 335

Asp Val Ile Ala Ser Leu Val Glu Val Glu Asp Val Leu Thr Ser Ser
                340                 345                 350

Met Val Lys Glu Lys Leu Val Arg Phe Leu Pro Arg Thr Val Ser Arg
                355                 360                 365

Leu Pro Glu Glu Glu Ile Glu Ser Trp Ile Lys Trp Leu Lys Glu Ile
                370                 375                 380

Leu Glu Ser Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Asn Glu Gln Asp Lys Asp Asn Trp Asn Gly Gln Leu Lys Leu
                420                 425                 430

Leu Leu Glu Trp Asn Gln Leu Asp Leu Ala Ser Asp Glu Ile Phe Thr
                435                 440                 445

Asn Asp Arg Arg Trp Glu Ser Ala Asp Leu Gln Glu Val Met Phe Thr
                450                 455                 460

Ala Leu Ile Lys Asp Arg Pro Lys Phe Val Arg Leu Phe Leu Glu Asn
465                 470                 475                 480

Gly Leu Asn Leu Gln Lys Phe Leu Thr Asn Glu Val Leu Thr Glu Leu
                485                 490                 495

Phe Ser Thr His Phe Ser Thr Leu Val Tyr Arg Asn Leu Gln Ile Ala
                500                 505                 510

Lys Asn Ser Tyr Asn Asp Ala Leu Leu Thr Phe Val Trp Lys Leu Val
                515                 520                 525

Ala Asn Phe Arg Arg Ser Phe Trp Lys Glu Asp Arg Ser Ser Arg Glu
                530                 535                 540

Asp Leu Asp Val Glu Leu His Asp Ala Ser Leu Thr Thr Arg His Pro
545                 550                 555                 560
```

```
Leu Gln Ala Leu Phe Ile Trp Ala Ile Leu Gln Asn Lys Lys Glu Leu
                565                 570                 575
Ser Lys Val Ile Trp Glu Gln Thr Lys Gly Cys Thr Leu Ala Ala Leu
            580                 585                 590
Gly Ala Ser Lys Leu Leu Lys Thr Leu Ala Lys Val Lys Asn Asp Ile
        595                 600                 605
Asn Ala Ala Gly Glu Ser Glu Leu Ala Asn Glu Tyr Glu Thr Arg
    610                 615                 620
Ala Val Glu Leu Phe Thr Glu Cys Tyr Ser Asn Asp Glu Asp Leu Ala
625                 630                 635                 640
Glu Gln Leu Leu Val Tyr Ser Cys Glu Ala Trp Gly Gly Ser Asn Cys
                645                 650                 655
Leu Glu Leu Ala Val Glu Ala Thr Asp Gln His Phe Ile Ala Gln Pro
            660                 665                 670
Gly Val Gln Asn Phe Leu Ser Lys Gln Trp Tyr Gly Glu Ile Ser Arg
        675                 680                 685
Asp Thr Lys Asn Trp Lys Ile Ile Leu Cys Leu Phe Ile Ile Pro Leu
    690                 695                 700
Val Gly Cys Gly Leu Val Ser Phe Arg Lys Lys Pro Ile Asp Lys His
705                 710                 715                 720
Lys Lys Leu Leu Trp Tyr Tyr Val Ala Phe Phe Thr Ser Pro Phe Val
                725                 730                 735
Val Phe Ser Trp Asn Val Val Phe Tyr Ile Ala Phe Leu Leu Leu Phe
            740                 745                 750
Ala Tyr Val Leu Leu Met Asp Phe His Ser Val Pro His Thr Pro Glu
        755                 760                 765
Leu Ile Leu Tyr Ala Leu Val Phe Val Leu Phe Cys Asp Glu Val Arg
    770                 775                 780
Gln Trp Tyr Met Asn Gly Val Asn Tyr Phe Thr Asp Leu Trp Asn Val
785                 790                 795                 800
Met Asp Thr Leu Gly Leu Phe Tyr Phe Ile Ala Gly Ile Val Phe Arg
                805                 810                 815
Leu His Ser Ser Asn Lys Ser Ser Leu Tyr Ser Gly Arg Val Ile Phe
            820                 825                 830
Cys Leu Asp Tyr Ile Ile Phe Thr Leu Arg Leu Ile His Ile Phe Thr
        835                 840                 845
Val Ser Arg Asn Leu Gly Pro Lys Ile Ile Met Leu Gln Arg Met Leu
    850                 855                 860
Ile Asp Val Phe Phe Phe Leu Phe Leu Phe Ala Val Trp Met Val Ala
865                 870                 875                 880
Phe Gly Val Ala Arg Gln Gly Ile Leu Arg Gln Asn Glu Gln Arg Trp
                885                 890                 895
Arg Trp Ile Phe Arg Ser Val Ile Tyr Glu Pro Tyr Leu Ala Met Phe
            900                 905                 910
Gly Gln Val Pro Ser Asp Val Asp Ser Thr Thr Tyr Asp Phe Ser His
        915                 920                 925
Cys Thr Phe Ser Gly Asn Glu Ser Lys Pro Leu Cys Val Glu Leu Asp
    930                 935                 940
Glu His Asn Leu Pro Arg Phe Pro Glu Trp Ile Thr Ile Pro Leu Val
945                 950                 955                 960
Cys Ile Tyr Met Leu Ser Thr Asn Ile Leu Leu Val Asn Leu Leu Val
                965                 970                 975
```

-continued

```
Ala Met Phe Gly Tyr Thr Val Gly Ile Val Gln Glu Asn Asn Asp Gln
            980             985             990

Val Trp Lys Phe Gln Arg Tyr Phe Leu Val Gln Glu Tyr Cys Asn Arg
            995            1000            1005

Leu Asn Ile Pro Phe Pro Phe Val Val Phe Ala Tyr Phe Tyr Met Val
           1010            1015            1020

Val Lys Lys Cys Phe Lys Cys Cys Lys Glu Lys Asn Met Glu Ser
1025            1030            1035            1040

Asn Ala Cys Cys Phe Arg Asn Glu Asp Asn Glu Thr Leu Ala Trp Glu
           1045             1050            1055

Gly Val Met Lys Glu Asn Tyr Leu Val Lys Ile Asn Thr Lys Ala Asn
           1060             1065            1070

Asp Asn Ser Glu Glu Met Arg His Arg Phe Arg Gln Leu Asp Ser Lys
           1075             1080            1085

Leu Asn Asp Leu Lys Ser Leu Leu Lys Glu Ile Ala Asn Asn Ile Lys
           1090             1095            1100

<210> SEQ ID NO 9
<211> LENGTH: 3312
<212> TYPE: DNA
<213> ORGANISM: Artificial Sequence
<220> FEATURE:
<223> OTHER INFORMATION: Generic sequence that encompasses all
      nucleotide sequences that encode mouse TRPM8 having an amino
      acid sequence as shown in SEQ ID NO:8
<220> FEATURE:
<221> NAME/KEY: CDS
<222> LOCATION: (1)...(3312)
<220> FEATURE:
<221> NAME/KEY: misc_feature
<222> LOCATION: 6,27,36,60,78,81,87,93,105,111,117,183,225,363,378,441,
      498,522,606,615,663,687,711,858,870,879,957,966,1053,1056,1101,
      1128,1161,1164,1215,1227,1251,1329,1365,1494,1506,1545,1602,1623,
      1626,1662,1731,1785,1842,1902,1941,1962,2037,2061,2133,2199,2217,
      2286,2457,2460,2469,2472,2481,2550,2706,2751,2763,2781,2796,2808,
      2898,3120,3225,3261,3282
<223> OTHER INFORMATION: n = A,T,C or G if after TC;
      n = T or C if after AG
<220> FEATURE:
<221> NAME/KEY: misc_feature
<222> LOCATION: 21,33,39,42,66,90,156,177,357,480,486,501,591,609,669,
      684,741,834,864,930,1080,1092,1104,1353,1356,1410,1425,1521,1596,
      1599,1620,1629,1674,1872,2064,2139,2352,2448,2487,2526,2553,2586,
      2655,2670,2685,2691,2703,2850,2994,3024,3138,3237,3243,3249
<223> OTHER INFORMATION: n = A,T,C or G if after CG;
      n = T or C if after AG
<220> FEATURE:
<221> NAME/KEY: misc_feature
<222> LOCATION: all "n" not specified above
<223> OTHER INFORMATION: n = A,T,C or G

<400> SEQUENCE: 9 atg wsn tty gar

-continued

```
              65                  70                  75                  80
acn car ath aay car aay gar aar tgg aay tay aar aar cay acn aar        288
Thr Gln Ile Asn Gln Asn Glu Lys Trp Asn Tyr Lys Lys His Thr Lys
                    85                  90                  95 gar tty ccn acn gay gcn tty ggn gay ath car tty gar acn ytn ggn        336
Glu Phe Pro Thr Asp Ala Phe Gly Asp Ile Gln Phe Glu Thr Leu Gly
                100                 105                 110 aar aar ggn aar tay ytn mgn ytn wsn tgy gay acn gay wsn gar acn        384
Lys Lys Gly Lys Tyr Leu Arg Leu Ser Cys Asp Thr Asp Ser Glu Thr
            115                 120                 125 ytn tay gar ytn ytn acn car cay tgg cay ytn aar acn ccn aay ytn        432
Leu Tyr Glu Leu Leu Thr Gln His Trp His Leu Lys Thr Pro Asn Leu
        130                 135                 140 gtn ath wsn gtn acn ggn ggn gcn aar aay tty gcn ytn aar ccn mgn        480
Val Ile Ser Val Thr Gly Gly Ala Lys Asn Phe

```
Leu Glu Ser Ser His Leu Leu Thr Val Ile Lys Met Glu Glu Ala Gly
385                 390                 395                 400 gay

```
gtn ggn tgy ggn ytn gtn wsn tty mgn aar aar ccn ath gay aar cay    2160
Val Gly Cys Gly Leu Val Ser Phe Arg Lys Lys Pro Ile Asp Lys His
705             710                 715                 720 aar aar ytn ytn tgg tay tay gtn gcn tty tty acn wsn ccn tty gtn    2208
Lys Lys Leu Leu Trp Tyr Tyr Val Ala Phe Phe Thr Ser Pro Phe Val
            725                 730                 735 gtn tty wsn tgg aay gtn gtn tty tay ath gcn tty ytn ytn ytn tty    2256
Val Phe Ser Trp Asn Val Val Phe Tyr Ile Ala Phe Leu Leu Leu Phe
                740                 745                 750 gcn tay gtn ytn ytn atg gay tty cay wsn gtn ccn cay acn ccn gar    2304
Ala Tyr Val Leu Leu Met Asp Phe His Ser Val Pro His Thr Pro Glu
            755                 760                 765 ytn ath ytn tay gcn ytn gtn tty gtn ytn tty tgy gay gar gtn mgn    2352
Leu Ile Leu Tyr Ala Leu Val Phe Val Leu Phe Cys Asp Glu Val Arg
    770                 775                 780 car tgg tay atg aay ggn gtn aay tay tty acn gay ytn tgg aay gtn    2400
Gln Trp Tyr Met Asn Gly Val Asn Tyr Phe Thr Asp Leu Trp Asn Val
785             790                 795                 800 atg gay acn ytn ggn ytn tty tay tty ath gcn ggn ath gtn tty mgn    2448
Met Asp Thr Leu Gly Leu Phe Tyr Phe Ile Ala Gly Ile Val Phe Arg
                805                 810                 815 ytn cay wsn wsn aay aar wsn wsn ytn tay wsn ggn mgn gtn ath tty    2496
Leu His Ser Ser Asn Lys Ser Ser Leu Tyr Ser Gly Arg Val Ile Phe
            820                 825                 830 tgy ytn gay tay ath ath tty acn ytn mgn ytn ath cay ath tty acn    2544
Cys Leu Asp Tyr Ile Ile Phe Thr Leu Arg Leu Ile His Ile Phe Thr
        835                 840                 845 gtn wsn mgn aay ytn ggn ccn aar ath ath atg ytn car mgn atg ytn    2592
Val Ser Arg Asn Leu Gly Pro Lys Ile Ile Met Leu Gln Arg Met Leu
850             855                 860 ath gay gtn tty tty tty ytn tty ytn tty gcn gtn tgg atg gtn gcn    2640
Ile Asp Val Phe Phe Phe Leu Phe Leu Phe Ala Val Trp Met Val Ala
865             870                 875                 880 tty ggn gtn gcn mgn car ggn ath ytn mgn car aay gar car mgn tgg    2688
Phe Gly Val Ala Arg Gln Gly Ile Leu Arg Gln Asn Glu Gln Arg Trp
                885                 890                 895 mgn tgg ath tty mgn wsn gtn ath tay gar ccn tay ytn gcn atg tty    2736
Arg Trp Ile Phe Arg Ser Val Ile Tyr Glu Pro Tyr Leu Ala Met Phe
            900                 905                 910 ggn car gtn ccn wsn gay gtn gay wsn acn acn tay gay tty wsn cay    2784
Gly Gln Val Pro Ser Asp Val Asp Ser Thr Thr Tyr Asp Phe Ser His
        915                 920                 925 tgy acn tty wsn ggn aay gar wsn aar ccn ytn tgy gtn gar ytn gay    2832
Cys Thr Phe Ser Gly Asn Glu Ser Lys Pro Leu Cys Val Glu Leu Asp
930             935                 940 gar cay aay ytn ccn mgn tty ccn gar tgg ath acn ath ccn ytn gtn    2880
Glu His Asn Leu Pro Arg Phe Pro Glu Trp Ile Thr Ile Pro Leu Val
945             950                 955                 960 tgy ath tay atg ytn wsn acn aay ath ytn ytn gtn aay ytn ytn gtn    2928
Cys Ile Tyr Met Leu Ser Thr Asn Ile Leu Leu Val Asn Leu Leu Val
                965                 970                 975 gcn atg tty ggn tay acn gtn ggn ath gtn car gar aay aay gay car    2976
Ala Met Phe Gly Tyr Thr Val Gly Ile Val Gln Glu Asn Asn Asp Gln
            980                 985                 990 gtn tgg aar tty car mgn tay tty ytn gtn car gar tay tgy aay mgn    3024
Val Trp Lys Phe Gln Arg Tyr Phe Leu Val Gln Glu Tyr Cys Asn Arg
        995                 1000                1005 ytn aay ath ccn tty ccn tty gtn gtn tty gcn tay tty tay atg gtn    3072
Leu Asn Ile Pro Phe Pro Phe Val Val Phe Ala Tyr Phe Tyr Met Val
    1010                1015                1020
```

| | | | | | | | | | | | | | | |
|---|---|---|---|---|---|---|---|---|---|---|---|---|---|---|
| gtn | aar | aar | tgy | tty | aar | tgy | tgy | tgy | aar | gar | aar | aay | atg | gar | wsn | 3120 |
| Val | Lys | Lys | Cys | Phe | Lys | Cys | Cys | Cys | Lys | Glu | Lys | Asn | Met | Glu | Ser |
| 1025 | | | | 1030 | | | | | 1035 | | | | | 1040 | aay gcn tgy tgy tty mgn aay gar gay aay gar acn ytn gcn tgg gar    3168
Asn Ala Cys Cys Phe Arg Asn Glu Asp Asn Glu Thr Leu Ala Trp Glu
              1045                1050                1055 ggn gtn atg aar gar aay tay ytn gtn aar ath aay acn aar gcn aay    3216
Gly Val Met Lys Glu Asn Tyr Leu Val Lys Ile Asn Thr Lys Ala Asn
              1060                1065                1070 gay aay wsn gar gar atg mgn cay mgn tty mgn car ytn gay wsn aar    3264
Asp Asn Ser Glu Glu Met Arg His Arg Phe Arg Gln Leu Asp Ser Lys
          1075                1080                1085 ytn aay gay ytn aar wsn ytn ytn aar gar ath gcn aay aay ath aar    3312
Leu Asn Asp Leu Lys Ser Leu Leu Lys Glu Ile Ala Asn Asn Ile Lys
          1090                1095                1100

<210> SEQ ID NO 10
<211> LENGTH: 3867
<212> TYPE: DNA
<213> ORGANISM: Homo sapiens
<220> FEATURE:
<221> NAME/KEY: CDS
<222> LOCATION: (61)...(3867)

<400> SEQUENCE: 10
cagaaggaag atggagcagt tctgctaacc cgagtggtcc tggaatgtgt ttttcttccc    60 atg ccg tta cca cat aaa agt ggt cag aaa tca ctc aga tct tat ttt    108
Met Pro Leu Pro His Lys Ser Gly Gln Lys Ser Leu Arg Ser Tyr Phe
 1               5                  10                  15 gtc ttc tca atc caa gtt tcg gta att cag ata aaa ggc aca gaa agc    156
Val Phe Ser Ile Gln Val Ser Val Ile Gln Ile Lys Gly Thr Glu Ser
             20                  25                  30 cct ggg ttt gcc tgg tgg gca ttc tct gga cca ctc ttc cgg ttc ttg    204
Pro Gly Phe Ala Trp Trp Ala Phe Ser Gly Pro Leu Phe Arg Phe Leu
         35                  40                  45 cct ttc tcc gtg ttg ctg gcc ttg gag ctg acc gtg gtg ctg aca gga    252
Pro Phe Ser Val Leu Leu Ala Leu Glu Leu Thr Val Val Leu Thr Gly
     50                  55                  60 gtc tgg cgc ctc ctg cgc cct tgc tat cat tgt gtg tac tgt gga ccc    300
Val Trp Arg Leu Leu Arg Pro Cys Tyr His Cys Val Tyr Cys Gly Pro
 65                  70                  75                  80 gca gca tcg gct cac ctg ttt ata aaa cag tgg ctg gat ggt tgg agg    348
Ala Ala Ser Ala His Leu Phe Ile Lys Gln Trp Leu Asp Gly Trp Arg
                 85                  90                  95 atg cag gtg gac aga aga cgt gga gcc tgc aga agt aaa ggc ttg gtg    396
Met Gln Val Asp Arg Arg Arg Gly Ala Cys Arg Ser Lys Gly Leu Val
            100                 105                 110 cag gtt gaa ggg gct aca cag gca ggt gag cac ttg ctc agc ctg ggc    444
Gln Val Glu Gly Ala Thr Gln Ala Gly Glu His Leu Leu Ser Leu Gly
        115                 120                 125 att gtg ggg cat ctc cct gaa gaa atg atg agt gag ctg agc ctg gag    492
Ile Val Gly His Leu Pro Glu Glu Met Met Ser Glu Leu Ser Leu Glu
    130                 135                 140 gat gag cag gag atg aca gct gga ggg gta tgg gga aga ggg ctc tgg    540
Asp Glu Gln Glu Met Thr Ala Gly Gly Val Trp Gly Arg Gly Leu Trp
145                 150                 155                 160 aca gaa gaa aag atg tcc ttt cgg gca gcc agg ctc agc atg agg aac    588
Thr Glu Glu Lys Met Ser Phe Arg Ala Ala Arg Leu Ser Met Arg Asn
                165                 170                 175 aga agg aat gac act ctg gac agc acc cgg acc ctg tac tcc agc gcg    636

```
                    Arg Arg Asn Asp Thr Leu Asp Ser Thr Arg Thr Leu Tyr Ser Ser Ala
                                180                 185                 190 tct cgg agc aca gac ttg tct tac agt gaa agc gac ttg gtg aat ttt            684
Ser Arg Ser Thr Asp Leu Ser Tyr Ser Glu Ser Asp Leu Val Asn Phe
            195                 200                 205 att caa gca aat ttt aag aaa cga gaa tgt gtc ttc ttt atc aaa gat            732
Ile Gln Ala Asn Phe Lys Lys Arg Glu Cys Val Phe Phe Ile Lys Asp
        210                 215                 220 tcc aag gcc acg gag aat gtg tgc aag tgt ggc tat gcc cag agc cag            780
Ser Lys Ala Thr Glu Asn Val Cys Lys Cys Gly Tyr Ala Gln Ser Gln
225                 230                 235                 240 cac atg gaa ggc acc cag atc aac caa agt gag aaa tgg aac tac aag            828
His Met Glu Gly Thr Gln Ile Asn Gln Ser Glu Lys Trp Asn Tyr Lys
                245                 250                 255 aaa cac acc aag gaa ttt cct acc gac gcc ttt ggg gat att cag ttt            876
Lys His Thr Lys Glu Phe Pro Thr Asp Ala Phe Gly Asp Ile Gln Phe
            260                 265                 270 gag aca ctg ggg aag aaa ggg aag tat ata cgt ctg tcc tgc gac acg            924
Glu Thr Leu Gly Lys Lys Gly Lys Tyr Ile Arg Leu Ser Cys Asp Thr
        275                 280                 285 gac gcg gaa atc ctt tac gag ctg ctg acc cag cac tgg cac ctg aaa            972
Asp Ala Glu Ile Leu Tyr Glu Leu Leu Thr Gln His Trp His Leu Lys
290                 295                 300 aca ccc aac ctg gtc att tct gtg acc ggg ggc gcc aag aac ttc gcc           1020
Thr Pro Asn Leu Val Ile Ser Val Thr Gly Gly Ala Lys Asn Phe Ala
305                 310                 315                 320 ctg aag ccg cgg atg cgc aag atc ttc agc cgg ctc atc tac atc gcg           1068
Leu Lys Pro Arg Met Arg Lys Ile Phe Ser Arg Leu Ile Tyr Ile Ala
            325                 330                 335 cag tcc aaa ggt gct tgg att ctc acg gga ggc acc cat tat ggc ctg           1116
Gln Ser Lys Gly Ala Trp Ile Leu Thr Gly Gly Thr His Tyr Gly Leu
        340                 345                 350 atg aag tac atc ggg gag gtg gtg aga gat aac acc atc agc agg agt           1164
Met Lys Tyr Ile Gly Glu Val Val Arg Asp Asn Thr Ile Ser Arg Ser
    355                 360                 365 tca gag gag aat att gtg gcc att ggc ata gca gct tgg ggc atg gtc           1212
Ser Glu Glu Asn Ile Val Ala Ile Gly Ile Ala Ala Trp Gly Met Val
370                 375                 380 tcc aac cgg gac acc ctc atc agg aat tgc gat gct gag ggc tat ttt           1260
Ser Asn Arg Asp Thr Leu Ile Arg Asn Cys Asp Ala Glu Gly Tyr Phe
385                 390                 395                 400 tta gcc cag tac ctt atg gat gac ttc aca aga gat cca ctg tat atc           1308
Leu Ala Gln Tyr Leu Met Asp Asp Phe Thr Arg Asp Pro Leu Tyr Ile
            405                 410                 415 ctg gac aac aac cac aca cat ttg ctc ctc gtg gac aat ggc tgt cat           1356
Leu Asp Asn Asn His Thr His Leu Leu Leu Val Asp Asn Gly Cys His
        420                 425                 430 gga cat ccc act gtc gaa gca aag ctc cgg aat cag cta gag aag tat           1404
Gly His Pro Thr Val Glu Ala Lys Leu Arg Asn Gln Leu Glu Lys Tyr
    435                 440                 445 atc tct gag cgc act att caa gat tcc aac tat ggt ggc aag atc ccc           1452
Ile Ser Glu Arg Thr Ile Gln Asp Ser Asn Tyr Gly Gly Lys Ile Pro
450                 455                 460 att gtg tgt ttt gcc caa gga ggt gga aaa gag act ttg aaa gcc atc           1500
Ile Val Cys Phe Ala Gln Gly Gly Gly Lys Glu Thr Leu Lys Ala Ile
465                 470                 475                 480 aat acc tcc atc aaa aat aaa att cct tgt gtg gtg gtg gaa ggc tcg           1548
Asn Thr Ser Ile Lys Asn Lys Ile Pro Cys Val Val Val Glu Gly Ser
            485                 490                 495
```

| | | |
|---|---|---|
| ggc cag atc gct gat gtg atc gct agc ctg gtg gag gtg gag gat gcc<br>Gly Gln Ile Ala Asp Val Ile Ala Ser Leu Val Glu Val Glu Asp Ala<br>500 505 510 | | 1596 |
| ctg aca tct tct gcc gtc aag gag aag ctg gtg cgc ttt tta ccc cgc<br>Leu Thr Ser Ser Ala Val Lys Glu Lys Leu Val Arg Phe Leu Pro Arg<br>515 520 525 | | 1644 |
| acg gtg tcc cgg ctg cct gag gag gag act gag agt tgg atc aaa tgg<br>Thr Val Ser Arg Leu Pro Glu Glu Glu Thr Glu Ser Trp Ile Lys Trp<br>530 535 540 | | 1692 |
| ctc aaa gaa att ctc gaa tgt tct cac cta tta aca gtt att aaa atg<br>Leu Lys Glu Ile Leu Glu Cys Ser His Leu Leu Thr Val Ile Lys Met<br>545 550 555 560 | | 1740 |
| gaa gaa gct ggg gat gaa att gtg agc aat gcc atc tcc tac gct cta<br>Glu Glu Ala Gly Asp Glu Ile Val Ser Asn Ala Ile Ser Tyr Ala Leu<br>565 570 575 | | 1788 |
| tac aaa gcc ttc agc acc agt gag caa gac aag gat aac tgg aat ggg<br>Tyr Lys Ala Phe Ser Thr Ser Glu Gln Asp Lys Asp Asn Trp Asn Gly<br>580 585 590 | | 1836 |
| cag ctg aag ctt ctg ctg gag tgg aac cag ctg gac tta gcc aat gat<br>Gln Leu Lys Leu Leu Leu Glu Trp Asn Gln Leu Asp Leu Ala Asn Asp<br>595 600 605 | | 1884 |
| gag att ttc acc aat gac cgc cga tgg gag tct gct gac ctt caa gaa<br>Glu Ile Phe Thr Asn Asp Arg Arg Trp Glu Ser Ala Asp Leu Gln Glu<br>610 615 620 | | 1932 |
| gtc atg ttt acg gct ctc ata aag gac aga ccc aag ttt gtc cgc ctc<br>Val Met Phe Thr Ala Leu Ile Lys Asp Arg Pro Lys Phe Val Arg Leu<br>625 630 635 640 | | 1980 |
| ttt ctg gag aat ggc ttg aac cta cgg aag ttt ctc acc cat gat gtc<br>Phe Leu Glu Asn Gly Leu Asn Leu Arg Lys Phe Leu Thr His Asp Val<br>645 650 655 | | 2028 |
| ctc act gaa ctc ttc tcc aac cac ttc agc acg ctt gtg tac cgg aat<br>Leu Thr Glu Leu Phe Ser Asn His Phe Ser Thr Leu Val Tyr Arg Asn<br>660 665 670 | | 2076 |
| ctg cag atc gcc aag aat tcc tat aat gat gcc ctc ctc acg ttt gtc<br>Leu Gln Ile Ala Lys Asn Ser Tyr Asn Asp Ala Leu Leu Thr Phe Val<br>675 680 685 | | 2124 |
| tgg aaa ctg gtt gcg aac ttc cga aga ggc ttc cgg aag gaa gac aga<br>Trp Lys Leu Val Ala Asn Phe Arg Arg Gly Phe Arg Lys Glu Asp Arg<br>690 695 700 | | 2172 |
| aat ggc cgg gac gag atg gac ata gaa ctc cac gac gtg tct cct att<br>Asn Gly Arg Asp Glu Met Asp Ile Glu Leu His Asp Val Ser Pro Ile<br>705 710 715 720 | | 2220 |
| act cgg cac ccc ctg caa gct ctc ttc atc tgg gcc att ctt cag aat<br>Thr Arg His Pro Leu Gln Ala Leu Phe Ile Trp Ala Ile Leu Gln Asn<br>725 730 735 | | 2268 |
| aag aag gaa ctc tcc aaa gtc att tgg gag cag acc agg ggc tgc act<br>Lys Lys Glu Leu Ser Lys Val Ile Trp Glu Gln Thr Arg Gly Cys Thr<br>740 745 750 | | 2316 |
| ctg gca gcc ctg gga gcc agc aag ctt ctg aag act ctg gcc aaa gtg<br>Leu Ala Ala Leu Gly Ala Ser Lys Leu Leu Lys Thr Leu Ala Lys Val<br>755 760 765 | | 2364 |
| aag aac gac atc aat gct gct ggg gag tcc gag gag ctg gct aat gag<br>Lys Asn Asp Ile Asn Ala Ala Gly Glu Ser Glu Glu Leu Ala Asn Glu<br>770 775 780 | | 2412 |
| tac gag acc cgg gct gtt gag ctg ttc act gag tgt tac agc agc gat<br>Tyr Glu Thr Arg Ala Val Glu Leu Phe Thr Glu Cys Tyr Ser Ser Asp<br>785 790 795 800 | | 2460 |
| gaa gac ttg gca gaa cag ctg ctg gtc tat tcc tgt gaa gct tgg ggt<br>Glu Asp Leu Ala Glu Gln Leu Leu Val Tyr Ser Cys Glu Ala Trp Gly<br>805 810 815 | | 2508 |

```
gga agc aac tgt ctg gag ctg gcg gtg gag gcc aca gac cag cat ttc    2556
Gly Ser Asn Cys Leu Glu Leu Ala Val Glu Ala Thr Asp Gln His Phe
        820                 825                 830 atc gcc cag cct ggg gtc cag aat ttt ctt tct aag caa tgg tat gga    2604
Ile Ala Gln Pro Gly Val Gln Asn Phe Leu Ser Lys Gln Trp Tyr Gly
                835                 840                 845 gag att tcc cga gac acc aag aac tgg aag att atc ctg tgt ctg ttt    2652
Glu Ile Ser Arg Asp Thr Lys Asn Trp Lys Ile Ile Leu Cys Leu Phe
850                 855                 860 att ata ccc ttg gtg ggc tgt ggc ttt gta tca ttt agg aag aaa cct    2700
Ile Ile Pro Leu Val Gly Cys Gly Phe Val Ser Phe Arg Lys Lys Pro
865                 870                 875                 880 gtc gac aag cac aag aag ctg ctt tgg tac tat gtg gcg ttc ttc acc    2748
Val Asp Lys His Lys Lys Leu Leu Trp Tyr Tyr Val Ala Phe Phe Thr
                885                 890                 895 tcc ccc ttc gtg gtc ttc tcc tgg aat gtg gtc ttc tac atc gcc ttc    2796
Ser Pro Phe Val Val Phe Ser Trp Asn Val Val Phe Tyr Ile Ala Phe
                900                 905                 910 ctc ctg ctg ttt gcc tac gtg ctg ctc atg gat ttc cat tcg gtg cca    2844
Leu Leu Leu Phe Ala Tyr Val Leu Leu Met Asp Phe His Ser Val Pro
            915                 920                 925 cac ccc ccc gag ctg gtc ctg tac tcg ctg gtc ttt gtc ctc ttc tgt    2892
His Pro Pro Glu Leu Val Leu Tyr Ser Leu Val Phe Val Leu Phe Cys
        930                 935                 940 gat gaa gtg aga cag tgg tac gta aat ggg gtg aat tat ttt act gac    2940
Asp Glu Val Arg Gln Trp Tyr Val Asn Gly Val Asn Tyr Phe Thr Asp
945                 950                 955                 960 ctg tgg aat gtg atg gac acg ctg ggg ctt ttt tac ttc ata gca gga    2988
Leu Trp Asn Val Met Asp Thr Leu Gly Leu Phe Tyr Phe Ile Ala Gly
                965                 970                 975 att gta ttt cgg ctc cac tct tct aat aaa agc tct ttg tat tct gga    3036
Ile Val Phe Arg Leu His Ser Ser Asn Lys Ser Ser Leu Tyr Ser Gly
                980                 985                 990 cga gtc att ttc tgt ctg gac tac att att ttc act cta aga ttg atc    3084
Arg Val Ile Phe Cys Leu Asp Tyr Ile Ile Phe Thr Leu Arg Leu Ile
            995                 1000                1005 cac att ttt act gta agc aga aac tta gga ccc aag att ata atg ctg    3132
His Ile Phe Thr Val Ser Arg Asn Leu Gly Pro Lys Ile Ile Met Leu
        1010                1015                1020 cag agg atg ctg atc gat gtg ttc ttc ttc ctg ttc ctc ttt gcg gtg    3180
Gln Arg Met Leu Ile Asp Val Phe Phe Phe Leu Phe Leu Phe Ala Val
1025                1030                1035                1040 tgg atg gtg gcc ttt ggc gtg gcc agg caa ggg atc ctt agg cag aat    3228
Trp Met Val Ala Phe Gly Val Ala Arg Gln Gly Ile Leu Arg Gln Asn
                1045                1050                1055 gag cag cgc tgg agg tgg ata ttc cgt tcg gtc atc tac gag ccc tac    3276
Glu Gln Arg Trp Arg Trp Ile Phe Arg Ser Val Ile Tyr Glu Pro Tyr
                1060                1065                1070 ctg gcc atg ttc ggc cag gtg ccc agt gac gtg gat ggt acc acg tat    3324
Leu Ala Met Phe Gly Gln Val Pro Ser Asp Val Asp Gly Thr Thr Tyr
            1075                1080                1085 gac ttt gcc cac tgc acc ttc act ggg aat gag tcc aag cca ctg tgt    3372
Asp Phe Ala His Cys Thr Phe Thr Gly Asn Glu Ser Lys Pro Leu Cys
        1090                1095                1100 gtg gag ctg gat gag cac aac ctg ccc cgg ttc ccc gag tgg atc acc    3420
Val Glu Leu Asp Glu His Asn Leu Pro Arg Phe Pro Glu Trp Ile Thr
1105                1110                1115                1120 atc ccc ctg gtg tgc atc tac atg tta tcc acc aac atc ctg ctg gtc    3468
Ile Pro Leu Val Cys Ile Tyr Met Leu Ser Thr Asn Ile Leu Leu Val
```

```
                  1125                1130                1135
aac ctg ctg gtc gcc atg ttt ggc tac acg gtg ggc acc gtc cag gag    3516
Asn Leu Leu Val Ala Met Phe Gly Tyr Thr Val Gly Thr Val Gln Glu
            1140                1145                1150 aac aat gac cag gtc tgg aag ttc cag agg tac ttc ctg gtg cag gag    3564
Asn Asn Asp Gln Val Trp Lys Phe Gln Arg Tyr Phe Leu Val Gln Glu
        1155                1160                1165 tac tgc agc cgc ctc aat atc ccc ttc ccc ttc atc gtc ttc gct tac    3612
Tyr Cys Ser Arg Leu Asn Ile Pro Phe Pro Phe Ile Val Phe Ala Tyr
    1170                1175                1180 ttc tac atg gtg gtg aag aag tgc ttc aag tgt tgc tgc aag gag aaa    3660
Phe Tyr Met Val Val Lys Lys Cys Phe Lys Cys Cys Cys Lys Glu Lys
1185                1190                1195                1200 aac atg gag tct tct gtc tgc tgt ttc aaa aat gaa gac aat gag act    3708
Asn Met Glu Ser Ser Val Cys Cys Phe Lys Asn Glu Asp Asn Glu Thr
                1205                1210                1215 ctg gca tgg gag ggt gtc atg aag gaa aac tac ctt gtc aag atc aac    3756
Leu Ala Trp Glu Gly Val Met Lys Glu Asn Tyr Leu Val Lys Ile Asn
            1220                1225                1230 aca aaa gcc aac gac acc tca gag gaa atg agg cat cga ttt aga caa    3804
Thr Lys Ala Asn Asp Thr Ser Glu Glu Met Arg His Arg Phe Arg Gln
        1235                1240                1245 ctg gat aca aag ctt aat gat ctc aag ggt ctt ctg aaa gag att gct    3852
Leu Asp Thr Lys Leu Asn Asp Leu Lys Gly Leu Leu Lys Glu Ile Ala
    1250                1255                1260 aat aaa atc aaa taa                                                3867
Asn Lys Ile Lys *
1265

<210> SEQ ID NO 11
<211> LENGTH: 1268
<212> TYPE: PRT
<213> ORGANISM: Homo sapiens

<400> SEQUENCE: 11

Met Pro Leu Pro His Lys Ser Gly Gln Lys Ser Leu Arg Ser Tyr Phe
 1               5                  10                  15

Val Phe Ser Ile Gln Val Ser Val Ile Gln Ile Lys Gly Thr Glu Ser
                20                  25                  30

Pro Gly Phe Ala Trp Trp Ala Phe Ser Gly Pro Leu Phe Arg Phe Leu
            35                  40                  45

Pro Phe Ser Val Leu Leu Ala Leu Glu Leu Thr Val Val Leu Thr Gly
        50                  55                  60

Val Trp Arg Leu Leu Arg Pro Cys Tyr His Cys Val Tyr Cys Gly Pro
65                  70                  75                  80

Ala Ala Ser Ala His Leu Phe Ile Lys Gln Trp Leu Asp Gly Trp Arg
                85                  90                  95

Met Gln Val Asp Arg Arg Gly Ala Cys Arg Ser Lys Gly Leu Val
            100                 105                 110

Gln Val Glu Gly Ala Thr Gln Ala Gly Glu His Leu Leu Ser Leu Gly
        115                 120                 125

Ile Val Gly His Leu Pro Glu Glu Met Met Ser Glu Leu Ser Leu Glu
    130                 135                 140

Asp Glu Gln Glu Met Thr Ala Gly Gly Val Trp Gly Arg Gly Leu Trp
145                 150                 155                 160

Thr Glu Glu Lys Met Ser Phe Arg Ala Ala Arg Leu Ser Met Arg Asn
                165                 170                 175
```

-continued

```
Arg Arg Asn Asp Thr Leu Asp Ser Thr Arg Thr Leu Tyr Ser Ser Ala
            180                 185                 190

Ser Arg Ser Thr Asp Leu Ser Tyr Ser Glu Ser Asp Leu Val Asn Phe
        195                 200                 205

Ile Gln Ala Asn Phe Lys Lys Arg Glu Cys Val Phe Ile Lys Asp
        210                 215                 220

Ser Lys Ala Thr Glu Asn Val Cys Lys Cys Gly Tyr Ala Gln Ser Gln
225                 230                 235                 240

His Met Glu Gly Thr Gln Ile Asn Gln Ser Glu Lys Trp Asn Tyr Lys
                245                 250                 255

Lys His Thr Lys Glu Phe Pro Thr Asp Ala Phe Gly Asp Ile Gln Phe
                260                 265                 270

Glu Thr Leu Gly Lys Lys Gly Lys Tyr Ile Arg Leu Ser Cys Asp Thr
        275                 280                 285

Asp Ala Glu Ile Leu Tyr Glu Leu Leu Thr Gln His Trp His Leu Lys
        290                 295                 300

Thr Pro Asn Leu Val Ile Ser Val Thr Gly Gly Ala Lys Asn Phe Ala
305                 310                 315                 320

Leu Lys Pro Arg Met Arg Lys Ile Phe Ser Arg Leu Ile Tyr Ile Ala
                325                 330                 335

Gln Ser Lys Gly Ala Trp Ile Leu Thr Gly Gly Thr His Tyr Gly Leu
                340                 345                 350

Met Lys Tyr Ile Gly Glu Val Val Arg Asp Asn Thr Ile Ser Arg Ser
                355                 360                 365

Ser Glu Glu Asn Ile Val Ala Ile Gly Ile Ala Ala Trp Gly Met Val
        370                 375                 380

Ser Asn Arg Asp Thr Leu Ile Arg Asn Cys Asp Ala Glu Gly Tyr Phe
385                 390                 395                 400

Leu Ala Gln Tyr Leu Met Asp Asp Phe Thr Arg Asp Pro Leu Tyr Ile
                405                 410                 415

Leu Asp Asn Asn His Thr His Leu Leu Leu Val Asp Asn Gly Cys His
                420                 425                 430

Gly His Pro Thr Val Glu Ala Lys Leu Arg Asn Gln Leu Glu Lys Tyr
                435                 440                 445

Ile Ser Glu Arg Thr Ile Gln Asp Ser Asn Tyr Gly Gly Lys Ile Pro
        450                 455                 460

Ile Val Cys Phe Ala Gln Gly Gly Gly Lys Glu Thr Leu Lys Ala Ile
465                 470                 475                 480

Asn Thr Ser Ile Lys Asn Lys Ile Pro Cys Val Val Val Glu Gly Ser
                485                 490                 495

Gly Gln Ile Ala Asp Val Ile Ala Ser Leu Val Glu Val Glu Asp Ala
                500                 505                 510

Leu Thr Ser Ser Ala Val Lys Glu Lys Leu Val Arg Phe Leu Pro Arg
        515                 520                 525

Thr Val Ser Arg Leu Pro Glu Glu Glu Thr Glu Ser Trp Ile Lys Trp
        530                 535                 540

Leu Lys Glu Ile Leu Glu Cys Ser His Leu Leu Thr Val Ile Lys Met
545                 550                 555                 560

Glu Glu Ala Gly Asp Glu Ile Val Ser Asn Ala Ile Ser Tyr Ala Leu
                565                 570                 575

Tyr Lys Ala Phe Ser Thr Ser Glu Gln Asp Lys Asp Asn Trp Asn Gly
                580                 585                 590

Gln Leu Lys Leu Leu Leu Glu Trp Asn Gln Leu Asp Leu Ala Asn Asp
```

-continued

```
              595                 600                 605
Glu Ile Phe Thr Asn Asp Arg Arg Trp Glu Ser Ala Asp Leu Gln Glu
        610                 615                 620

Val Met Phe Thr Ala Leu Ile Lys Asp Arg Pro Lys Phe Val Arg Leu
625                 630                 635                 640

Phe Leu Glu Asn Gly Leu Asn Leu Arg Lys Phe Leu Thr His Asp Val
                645                 650                 655

Leu Thr Glu Leu Phe Ser Asn His Phe Ser Thr Leu Val Tyr Arg Asn
        660                 665                 670

Leu Gln Ile Ala Lys Asn Ser Tyr Asn Asp Ala Leu Leu Thr Phe Val
        675                 680                 685

Trp Lys Leu Val Ala Asn Phe Arg Arg Gly Phe Arg Lys Glu Asp Arg
        690                 695                 700

Asn Gly Arg Asp Glu Met Asp Ile Glu Leu His Asp Val Ser Pro Ile
705                 710                 715                 720

Thr Arg His Pro Leu Gln Ala Leu Phe Ile Trp Ala Ile Leu Gln Asn
                725                 730                 735

Lys Lys Glu Leu Ser Lys Val Ile Trp Glu Gln Thr Arg Gly Cys Thr
                740                 745                 750

Leu Ala Ala Leu Gly Ala Ser Lys Leu Leu Lys Thr Leu Ala Lys Val
                755                 760                 765

Lys Asn Asp Ile Asn Ala Ala Gly Glu Ser Glu Glu Leu Ala Asn Glu
        770                 775                 780

Tyr Glu Thr Arg Ala Val Glu Leu Phe Thr Glu Cys Tyr Ser Ser Asp
785                 790                 795                 800

Glu Asp Leu Ala Glu Gln Leu Leu Val Tyr Ser Cys Glu Ala Trp Gly
                805                 810                 815

Gly Ser Asn Cys Leu Glu Leu Ala Val Glu Ala Thr Asp Gln His Phe
                820                 825                 830

Ile Ala Gln Pro Gly Val Gln Asn Phe Leu Ser Lys Gln Trp Tyr Gly
        835                 840                 845

Glu Ile Ser Arg Asp Thr Lys Asn Trp Lys Ile Ile Leu Cys Leu Phe
850                 855                 860

Ile Ile Pro Leu Val Gly Cys Gly Phe Val Ser Phe Arg Lys Lys Pro
865                 870                 875                 880

Val Asp Lys His Lys Lys Leu Leu Trp Tyr Tyr Val Ala Phe Phe Thr
                885                 890                 895

Ser Pro Phe Val Val Phe Ser Trp Asn Val Val Phe Tyr Ile Ala Phe
                900                 905                 910

Leu Leu Leu Phe Ala Tyr Val Leu Leu Met Asp Phe His Ser Val Pro
        915                 920                 925

His Pro Pro Glu Leu Val Leu Tyr Ser Leu Val Phe Val Leu Phe Cys
        930                 935                 940

Asp Glu Val Arg Gln Trp Tyr Val Asn Gly Val Asn Tyr Phe Thr Asp
945                 950                 955                 960

Leu Trp Asn Val Met Asp Thr Leu Gly Leu Phe Tyr Phe Ile Ala Gly
                965                 970                 975

Ile Val Phe Arg Leu His Ser Ser Asn Lys Ser Ser Leu Tyr Ser Gly
                980                 985                 990

Arg Val Ile Phe Cys Leu Asp Tyr Ile Ile Phe Thr Leu Arg Leu Ile
                995                 1000                1005

His Ile Phe Thr Val Ser Arg Asn Leu Gly Pro Lys Ile Ile Met Leu
        1010                1015                1020
```

```
Gln Arg Met Leu Ile Asp Val Phe Phe Leu Phe Leu Phe Ala Val
1025                1030                1035                1040

Trp Met Val Ala Phe Gly Val Ala Arg Gln Gly Ile Leu Arg Gln Asn
            1045                1050                1055

Glu Gln Arg Trp Arg Trp Ile Phe Arg Ser Val Ile Tyr Glu Pro Tyr
        1060                1065                1070

Leu Ala Met Phe Gly Gln Val Pro Ser Asp Val Asp Gly Thr Thr Tyr
            1075                1080                1085

Asp Phe Ala His Cys Thr Phe Thr Gly Asn Glu Ser Lys Pro Leu Cys
        1090                1095                1100

Val Glu Leu Asp Glu His Asn Leu Pro Arg Phe Pro Glu Trp Ile Thr
1105                1110                1115                1120

Ile Pro Leu Val Cys Ile Tyr Met Leu Ser Thr Asn Ile Leu Leu Val
                1125                1130                1135

Asn Leu Leu Val Ala Met Phe Gly Tyr Thr Val Gly Thr Val Gln Glu
            1140                1145                1150

Asn Asn Asp Gln Val Trp Lys Phe Gln Arg Tyr Phe Leu Val Gln Glu
        1155                1160                1165

Tyr Cys Ser Arg Leu Asn Ile Pro Phe Pro Phe Ile Val Phe Ala Tyr
    1170                1175                1180

Phe Tyr Met Val Val Lys Lys Cys Phe Lys Cys Cys Cys Lys Glu Lys
1185                1190                1195                1200

Asn Met Glu Ser Ser Val Cys Cys Phe Lys Asn Glu Asp Asn Glu Thr
                1205                1210                1215

Leu Ala Trp Glu Gly Val Met Lys Glu Asn Tyr Leu Val Lys Ile Asn
            1220                1225                1230

Thr Lys Ala Asn Asp Thr Ser Glu Glu Met Arg His Arg Phe Arg Gln
        1235                1240                1245

Leu Asp Thr Lys Leu Asn Asp Leu Lys Gly Leu Leu Lys Glu Ile Ala
    1250                1255                1260

Asn Lys Ile Lys
1265

<210> SEQ ID NO 12
<211> LENGTH: 3804
<212> TYPE: DNA
<213> ORGANISM: Artificial Sequence
<220> FEATURE:
<223> OTHER INFORMATION: Generic sequence that encompasses all
      nucleotide sequences that encode human TRPM8 having amino
      acid sequence as shown in SEQ ID NO:11
<220> FEATURE:
<221> NAME/KEY: CDS
<222> LOCATION: (1)...(3804)
<220> FEATURE:
<221> NAME/KEY: misc_feature
<222> LOCATION: 21,33,42,57,69,96,123,153,249,324,378,417,426,498,519,
      552,570,573,579,585,597,603,609,675,717,750,855,933,990,1014,1098,
      1104,1107,1155,1350,1371,1449,1488,1515,1545,1548,1593,1620,1656,
      1707,1719,1743,1749,1857,1986,2037,2154,2223,2277,2394,2397,2433,
      2454,2529,2553,2625,2691,2709,2778,2811,2949,2952,2961,2964,2973,
      3042,3198,3243,3300,3390,3513,3612,3615,3717
<223> OTHER INFORMATION: n = A,T,C or G if after TC;
      n = T or C if after AG
<220> FEATURE:
<221> NAME/KEY: misc_feature
<222> LOCATION: 39,138,201,210,288,303,306,309,321,471,504,513,525,531,
      534,558,582,648,849,972,978,993,1083,1101,1161,1176,1233,1326,
      1356,1572,1584,1596,1845,1848,1902,1917,1947,2013,2088,2091,2100,
      2112,2121,2166,2247,2364,2556,2631,2844,2940,2979,3018,3045,3078,
      3147,3162,3177,3183,3195,3342,3486,3516,3729,3735,3741
<223> OTHER INFORMATION: n = A,T,C or G if after CG;
```

```
        n = A or G if after AG
<220>  FEATURE:
<221>  NAME/KEY: misc_feature
<222>  LOCATION: all "n" not specified above
<223>  OTHER INFORMATION: n = A,T,C or G

<400> SEQUENCE: 12 atg ccn ytn ccn cay aar wsn ggn car aar wsn ytn mgn wsn tay tty        48
Met Pro Leu Pro His Lys Ser Gly Gln Lys Ser Leu Arg Ser Tyr Phe
 1               5                  10                  15 gtn tty wsn ath car gtn wsn gtn ath car ath aar ggn acn gar wsn        96
Val Phe Ser Ile Gln Val Ser Val Ile Gln Ile Lys Gly Thr Glu Ser
                20                  25                  30 ccn ggn tty gcn tgg tgg gcn tty wsn ggn ccn ytn tty mgn tty ytn       144
Pro Gly Phe Ala Trp Trp Ala Phe Ser Gly Pro Leu Phe Arg Phe Leu
            35                  40                  45 ccn tty wsn gtn ytn ytn gcn ytn gar ytn acn gtn gtn ytn acn ggn       192
Pro Phe Ser Val Leu Leu Ala Leu Glu Leu Thr Val Val Leu Thr Gly
 50                  55                  60 gtn tgg mgn ytn ytn mgn ccn tgy tay cay tgy gtn tay tgy ggn ccn       240
Val Trp Arg Leu Leu Arg Pro Cys Tyr His Cys Val Tyr Cys Gly Pro
 65                  70                  75                  80 gcn gcn wsn gcn cay ytn tty ath aar car tgg ytn gay ggn tgg mgn       288
Ala Ala Ser Ala His Leu Phe Ile Lys Gln Trp Leu Asp Gly Trp Arg
                85                  90                  95 atg car gtn gay mgn mgn mgn ggn gcn tgy mgn wsn aar ggn ytn gtn       336
Met Gln Val Asp Arg Arg Arg Gly Ala Cys Arg Ser Lys Gly Leu Val
            100                 105                 110 car gtn gar ggn gcn acn car gcn ggn gar cay ytn ytn wsn ytn ggn       384
Gln Val Glu Gly Ala Thr Gln Ala Gly Glu His Leu Leu Ser Leu Gly
        115                 120                 125 ath gtn ggn cay ytn ccn gar gar atg atg wsn gar ytn wsn ytn gar       432
Ile Val Gly His Leu Pro Glu Glu Met Met Ser Glu Leu Ser Leu Glu
    130                 135                 140 gay gar car gar atg acn gcn ggn ggn gtn tgg ggn mgn ggn ytn tgg       480
Asp Glu Gln Glu Met Thr Ala Gly Gly Val Trp Gly Arg Gly Leu Trp
145                 150                 155                 160 acn gar gar aar atg wsn tty mgn gcn gcn mgn ytn wsn atg mgn aay       528
Thr Glu Glu Lys Met Ser Phe Arg Ala Ala Arg Leu Ser Met Arg Asn
                165                 170                 175 mgn mgn aay gay acn ytn gay wsn acn mgn acn ytn tay wsn wsn gcn       576
Arg Arg Asn Asp Thr Leu Asp Ser Thr Arg Thr Leu Tyr Ser Ser Ala
            180                 185                 190 wsn mgn wsn acn gay ytn wsn tay wsn gar wsn gay ytn gtn aay tty       624
Ser Arg Ser Thr Asp Leu Ser Tyr Ser Glu Ser Asp Leu Val Asn Phe
        195                 200                 205 ath car gcn aay tty aar aar mgn gar tgy gtn tty tty ath aar gay       672
Ile Gln Ala Asn Phe Lys Lys Arg Glu Cys Val Phe Phe Ile Lys Asp
    210                 215                 220 wsn aar gcn acn gar aay gtn tgy aar tgy ggn tay gcn car wsn car       720
Ser Lys Ala Thr Glu Asn Val Cys Lys Cys Gly Tyr Ala Gln Ser Gln
225                 230                 235                 240 cay atg gar ggn acn car ath aay car wsn gar aar tgg aay tay aar       768
His Met Glu Gly Thr Gln Ile Asn Gln Ser Glu Lys Trp Asn Tyr Lys
                245                 250                 255 aar cay acn aar gar tty ccn acn gay gcn tty ggn gay ath car tty       816
Lys His Thr Lys Glu Phe Pro Thr Asp Ala Phe Gly Asp Ile Gln Phe
            260                 265                 270 gar acn ytn ggn aar aar ggn aar tay ath mgn ytn wsn tgy gay acn       864
Glu Thr Leu Gly Lys Lys Gly Lys Tyr Ile Arg Leu Ser Cys Asp Thr
        275                 280                 285
```

| | | |
|---|---|---|
| gay gcn gar ath ytn tay gar ytn ytn acn car cay tgg cay ytn aar<br>Asp Ala Glu Ile Leu Tyr Glu Leu Leu Thr Gln His Trp His Leu Lys<br>290                        295                        300 | 912 |
| acn ccn aay ytn gtn ath wsn gtn acn ggn ggn gcn aar aay tty gcn<br>Thr Pro Asn Leu Val Ile Ser Val Thr Gly Gly Ala Lys Asn Phe Ala<br>305                        310                        315                    320 | 960 |
| ytn aar ccn mgn atg mgn aar ath tty wsn mgn ytn ath tay ath gcn<br>Leu Lys Pro Arg Met Arg Lys Ile Phe Ser Arg Leu Ile Tyr Ile Ala<br>                       325                        330                    335 | 1008 |
| car wsn aar ggn gcn tgg ath ytn acn ggn ggn acn cay tay ggn ytn<br>Gln Ser Lys Gly Ala Trp Ile Leu Thr Gly Gly Thr His Tyr Gly Leu<br>           340                        345                        350 | 1056 |
| atg aar tay ath ggn gar gtn gtn mgn gay aay acn ath wsn mgn wsn<br>Met Lys Tyr Ile Gly Glu Val Val Arg Asp Asn Thr Ile Ser Arg Ser<br>                 355                        360                    365 | 1104 |
| wsn gar gar aay ath gtn gcn ath ggn ath gcn gcn tgg ggn atg gtn<br>Ser Glu Glu Asn Ile Val Ala Ile Gly Ile Ala Ala Trp Gly Met Val<br>370                        375                        380 | 1152 |
| wsn aay mgn gay acn ytn ath mgn aay tgy gay gcn gar ggn tay tty<br>Ser Asn Arg Asp Thr Leu Ile Arg Asn Cys Asp Ala Glu Gly Tyr Phe<br>385                        390                        395                    400 | 1200 |
| ytn gcn car tay ytn atg gay gay tty acn mgn gay ccn ytn tay ath<br>Leu Ala Gln Tyr Leu Met Asp Asp Phe Thr Arg Asp Pro Leu Tyr Ile<br>                       405                        410                    415 | 1248 |
| ytn gay aay aay cay acn cay ytn ytn ytn gtn gay aay ggn tgy cay<br>Leu Asp Asn Asn His Thr His Leu Leu Leu Val Asp Asn Gly Cys His<br>                     420                        425                    430 | 1296 |
| ggn cay ccn acn gtn gar gcn aar ytn mgn aay car ytn gar aar tay<br>Gly His Pro Thr Val Glu Ala Lys Leu Arg Asn Gln Leu Glu Lys Tyr<br>             435                        440                        445 | 1344 |
| ath wsn gar mgn acn ath car gay wsn aay tay ggn ggn aar ath ccn<br>Ile Ser Glu Arg Thr Ile Gln Asp Ser Asn Tyr Gly Gly Lys Ile Pro<br>450                        455                        460 | 1392 |
| ath gtn tgy tty gcn car ggn ggn ggn aar gar acn ytn aar gcn ath<br>Ile Val Cys Phe Ala Gln Gly Gly Gly Lys Glu Thr Leu Lys Ala Ile<br>465                        470                        475                    480 | 1440 |
| aay acn wsn ath aar aay aar ath ccn tgy gtn gtn gtn gar ggn wsn<br>Asn Thr Ser Ile Lys Asn Lys Ile Pro Cys Val Val Val Glu Gly Ser<br>                       485                        490                    495 | 1488 |
| ggn car ath gcn gay gtn ath gcn wsn ytn gtn gar gtn gar gay gcn<br>Gly Gln Ile Ala Asp Val Ile Ala Ser Leu Val Glu Val Glu Asp Ala<br>                 500                        505                    510 | 1536 |
| ytn acn wsn wsn gcn gtn aar gar aar ytn gtn mgn tty ytn ccn mgn<br>Leu Thr Ser Ser Ala Val Lys Glu Lys Leu Val Arg Phe Leu Pro Arg<br>             515                        520                        525 | 1584 |
| acn gtn wsn mgn ytn ccn gar gar gar acn gar wsn tgg ath aar tgg<br>Thr Val Ser Arg Leu Pro Glu Glu Glu Thr Glu Ser Trp Ile Lys Trp<br>530                        535                        540 | 1632 |
| ytn aar gar ath ytn gar tgy wsn cay ytn ytn acn gtn ath aar atg<br>Leu Lys Glu Ile Leu Glu Cys Ser His Leu Leu Thr Val Ile Lys Met<br>545                        550                        555                    560 | 1680 |
| gar gar gcn ggn gay gar ath gtn wsn aay gcn ath wsn tay gcn ytn<br>Glu Glu Ala Gly Asp Glu Ile Val Ser Asn Ala Ile Ser Tyr Ala Leu<br>                 565                        570                    575 | 1728 |
| tay aar gcn tty wsn acn wsn gar car gay aar gay aay tgg aay ggn<br>Tyr Lys Ala Phe Ser Thr Ser Glu Gln Asp Lys Asp Asn Trp Asn Gly<br>             580                        585                    590 | 1776 |
| car ytn aar ytn ytn ytn gar tgg aay car ytn gay ytn gcn aay gay<br>Gln Leu Lys Leu Leu Leu Glu Trp Asn Gln Leu Asp Leu Ala Asn Asp | 1824 |

-continued

```
             595                 600                 605
gar ath tty acn aay gay mgn mgn tgg gar wsn gcn gay ytn car gar    1872
Glu Ile Phe Thr Asn Asp Arg Arg Trp Glu Ser Ala Asp Leu Gln Glu
        610                 615                 620 gtn atg tty acn gcn ytn ath aar gay mgn ccn aar tty gtn mgn ytn    1920
Val Met Phe Thr Ala Leu Ile Lys Asp Arg Pro Lys Phe Val Arg Leu
625                 630                 635                 640 tty ytn gar aay ggn ytn aay ytn mgn aar tty ytn acn cay gay gtn    1968
Phe Leu Glu Asn Gly Leu Asn Leu Arg Lys Phe Leu Thr His Asp Val
                645                 650                 655 ytn acn gar ytn tty wsn aay cay tty wsn acn ytn gtn tay mgn aay    2016
Leu Thr Glu Leu Phe Ser Asn His Phe Ser Thr Leu Val Tyr Arg Asn
        660                 665                 670 ytn car ath gcn aar aay wsn tay aay gay gcn ytn ytn acn tty gtn    2064
Leu Gln Ile Ala Lys Asn Ser Tyr Asn Asp Ala Leu Leu Thr Phe Val
            675                 680                 685 tgg aar ytn gtn gcn aay tty mgn mgn ggn tty mgn aar gar gay mgn    2112
Trp Lys Leu Val Ala Asn Phe Arg Arg Gly Phe Arg Lys Glu Asp Arg
        690                 695                 700 aay ggn mgn gay gar atg gay ath gar ytn cay gay gtn wsn ccn ath    2160
Asn Gly Arg Asp Glu Met Asp Ile Glu Leu His Asp Val Ser Pro Ile
705                 710                 715                 720 acn mgn cay ccn ytn car gcn ytn tty ath tgg gcn ath ytn car aay    2208
Thr Arg His Pro Leu Gln Ala Leu Phe Ile Trp Ala Ile Leu Gln Asn
                725                 730                 735 aar aar gar ytn wsn aar gtn ath tgg gar car acn mgn ggn tgy acn    2256
Lys Lys Glu Leu Ser Lys Val Ile Trp Glu Gln Thr Arg Gly Cys Thr
        740                 745                 750 ytn gcn gcn ytn ggn gcn wsn aar ytn ytn aar acn ytn gcn aar gtn    2304
Leu Ala Ala Leu Gly Ala Ser Lys Leu Leu Lys Thr Leu Ala Lys Val
            755                 760                 765 aar aay gay ath aay gcn gcn ggn gar wsn gar gar ytn gcn aay gar    2352
Lys Asn Asp Ile Asn Ala Ala Gly Glu Ser Glu Glu Leu Ala Asn Glu
        770                 775                 780 tay gar acn mgn gcn gtn gar ytn tty acn gar tgy tay wsn wsn gay    2400
Tyr Glu Thr Arg Ala Val Glu Leu Phe Thr Glu Cys Tyr Ser Ser Asp
785                 790                 795                 800 gar gay ytn gcn gar car ytn ytn gtn tay wsn tgy gar gcn tgg ggn    2448
Glu Asp Leu Ala Glu Gln Leu Leu Val Tyr Ser Cys Glu Ala Trp Gly
                805                 810                 815 ggn wsn aay tgy ytn gar ytn gcn gtn gar gcn acn gay car cay tty    2496
Gly Ser Asn Cys Leu Glu Leu Ala Val Glu Ala Thr Asp Gln His Phe
        820                 825                 830 ath gcn car ccn ggn gtn car aay tty ytn wsn aar car tgg tay ggn    2544
Ile Ala Gln Pro Gly Val Gln Asn Phe Leu Ser Lys Gln Trp Tyr Gly
            835                 840                 845 gar ath wsn mgn gay acn aar aay tgg aar ath ath ytn tgy ytn tty    2592
Glu Ile Ser Arg Asp Thr Lys Asn Trp Lys Ile Ile Leu Cys Leu Phe
850                 855                 860 ath ath ccn ytn gtn ggn tgy ggn tty gtn wsn tty mgn aar aar ccn    2640
Ile Ile Pro Leu Val Gly Cys Gly Phe Val Ser Phe Arg Lys Lys Pro
865                 870                 875                 880 gtn gay aar cay aar aar ytn ytn tgg tay tay gtn gcn tty tty acn    2688
Val Asp Lys His Lys Lys Leu Leu Trp Tyr Tyr Val Ala Phe Phe Thr
                885                 890                 895 wsn ccn tty gtn gtn tty wsn tgg aay gtn gtn tty tay ath gcn tty    2736
Ser Pro Phe Val Val Phe Ser Trp Asn Val Val Phe Tyr Ile Ala Phe
        900                 905                 910 ytn ytn ytn tty gcn tay gtn ytn ytn atg gay tty cay wsn gtn ccn    2784
```

-continued

```
Leu Leu Leu Phe Ala Tyr Val Leu Leu Met Asp Phe His Ser Val Pro
        915                 920                 925 cay ccn ccn gar ytn gtn ytn tay wsn ytn gtn tty gtn ytn tty tgy      2832
His Pro Pro Glu Leu Val Leu Tyr Ser Leu Val Phe Val Leu Phe Cys
    930                 935                 940 gay gar gtn mgn car tgg tay gtn aay ggn gtn aay tay tty acn gay      2880
Asp Glu Val Arg Gln Trp Tyr Val Asn Gly Val Asn Tyr Phe Thr Asp
945                 950                 955                 960 ytn tgg aay gtn atg gay acn ytn ggn ytn tty tay tty ath gcn ggn      2928
Leu Trp Asn Val Met Asp Thr Leu Gly Leu Phe Tyr Phe Ile Ala Gly
                965                 970                 975 ath gtn tty mgn ytn cay wsn wsn aay aar wsn wsn ytn tay wsn ggn      2976
Ile Val Phe Arg Leu His Ser Ser Asn Lys Ser Ser Leu Tyr Ser Gly
            980                 985                 990 mgn gtn ath tty tgy ytn gay tay ath ath tty acn ytn mgn ytn ath      3024
Arg Val Ile Phe Cys Leu Asp Tyr Ile Ile Phe Thr Leu Arg Leu Ile
        995                 1000                1005 cay ath tty acn gtn wsn mgn aay ytn ggn ccn aar ath ath atg ytn      3072
His Ile Phe Thr Val Ser Arg Asn Leu Gly Pro Lys Ile Ile Met Leu
    1010                1015                1020 car mgn atg ytn ath gay gtn tty tty tty ytn tty ytn tty gcn gtn      3120
Gln Arg Met Leu Ile Asp Val Phe Phe Phe Leu Phe Leu Phe Ala Val
1025                1030                1035                1040 tgg atg gtn gcn tty ggn gtn gcn mgn car ggn ath ytn mgn car aay      3168
Trp Met Val Ala Phe Gly Val Ala Arg Gln Gly Ile Leu Arg Gln Asn
                1045                1050                1055 gar car mgn tgg mgn tgg ath tty mgn wsn gtn ath tay gar ccn tay      3216
Glu Gln Arg Trp Arg Trp Ile Phe Arg Ser Val Ile Tyr Glu Pro Tyr
            1060                1065                1070 ytn gcn atg tty ggn car gtn ccn wsn gay gtn gay ggn acn acn tay      3264
Leu Ala Met Phe Gly Gln Val Pro Ser Asp Val Asp Gly Thr Thr Tyr
        1075                1080                1085 gay tty gcn cay tgy acn tty acn ggn aay gar wsn aar ccn ytn tgy      3312
Asp Phe Ala His Cys Thr Phe Thr Gly Asn Glu Ser Lys Pro Leu Cys
    1090                1095                1100 gtn gar ytn gay gar cay aay ytn ccn mgn tty ccn gar tgg ath acn      3360
Val Glu Leu Asp Glu His Asn Leu Pro Arg Phe Pro Glu Trp Ile Thr
1105                1110                1115                1120 ath ccn ytn gtn tgy ath tay atg ytn wsn acn aay ath ytn ytn gtn      3408
Ile Pro Leu Val Cys Ile Tyr Met Leu Ser Thr Asn Ile Leu Leu Val
                1125                1130                1135 aay ytn ytn gtn gcn atg tty ggn tay acn gtn ggn acn gtn car gar      3456
Asn Leu Leu Val Ala Met Phe Gly Tyr Thr Val Gly Thr Val Gln Glu
            1140                1145                1150 aay aay gay car gtn tgg aar tty car mgn tay tty ytn gtn car gar      3504
Asn Asn Asp Gln Val Trp Lys Phe Gln Arg Tyr Phe Leu Val Gln Glu
        1155                1160                1165 tay tgy wsn mgn ytn aay ath ccn tty ccn tty ath gtn tty gcn tay      3552
Tyr Cys Ser Arg Leu Asn Ile Pro Phe Pro Phe Ile Val Phe Ala Tyr
    1170                1175                1180 tty tay atg gtn gtn aar aar tgy tty aar tgy tgy tgy aar gar aar      3600
Phe Tyr Met Val Val Lys Lys Cys Phe Lys Cys Cys Cys Lys Glu Lys
1185                1190                1195                1200 aay atg gar wsn wsn gtn tgy tgy tty aar aay gar gay aay gar acn      3648
Asn Met Glu Ser Ser Val Cys Cys Phe Lys Asn Glu Asp Asn Glu Thr
                1205                1210                1215 ytn gcn tgg gar ggn gtn atg aar gar aay tay ytn gtn aar ath aay      3696
Leu Ala Trp Glu Gly Val Met Lys Glu Asn Tyr Leu Val Lys Ile Asn
            1220                1225                1230
```

-continued

| | |
|---|---|
| acn aar gcn aay gay acn wsn gar gar atg mgn cay mgn tty mgn car<br>Thr Lys Ala Asn Asp Thr Ser Glu Glu Met Arg His Arg Phe Arg Gln<br>     1235                    1240                        1245 | 3744 |
| ytn gay acn aar ytn aay gay ytn aar ggn ytn ytn aar gar ath gcn<br>Leu Asp Thr Lys Leu Asn Asp Leu Lys Gly Leu Leu Glu Ile Ala<br>     1250                    1255                        1260 | 3792 |
| aay aar ath aar<br>Asn Lys Ile Lys<br>1265 | 3804 |

<210> SEQ ID NO 13
<211> LENGTH: 3281
<212> TYPE: DNA
<213> ORGANISM: Mus musculus
<220> FEATURE:
<221> NAME/KEY: CDS
<222> LOCATION: (156)...(2771)

<400> SEQUENCE: 13

| | |
|---|---|
| ctaatacgac tcactatagg gcaagcagtg gtaacaacgc agagtacgcg ggggaagcgc | 60 |
| agcaggagga ggacgcggcc ggagggatca ggaagcggcg gcgctgcgcc cgcgtcctga | 120 |
| gcaggccgag aagtacaaac agatctgggt ccagt atg gca gat cct ggt gat<br>                                                        Met Ala Asp Pro Gly Asp<br>                                                           1                          5 | 173 |
| ggt ccc cgt gca gcg cct ggg gag gtg gct gag ccc cct gga gat gag<br>Gly Pro Arg Ala Ala Pro Gly Glu Val Ala Glu Pro Pro Gly Asp Glu<br>          10                        15                          20 | 221 |
| agt ggt acc tct ggt ggg gag gcc ttc ccc ctc tct tcc ctg gcc aat<br>Ser Gly Thr Ser Gly Gly Glu Ala Phe Pro Leu Ser Ser Leu Ala Asn<br>        25                      30                          35 | 269 |
| ctg ttt gag ggg gag gaa ggc tcc tct tct ctt tcc ccg gtg gat gct<br>Leu Phe Glu Gly Glu Glu Gly Ser Ser Ser Leu Ser Pro Val Asp Ala<br>   40                        45                        50 | 317 |
| agc cgc cct gct ggc cct ggc gat gga cgt cca aac ctg cgt atg aag<br>Ser Arg Pro Ala Gly Pro Gly Asp Gly Arg Pro Asn Leu Arg Met Lys<br>55                     60                        65                        70 | 365 |
| ttc cag ggc gct ttc cgc aag ggg gtt ccc aac ccc att gac ctg ttg<br>Phe Gln Gly Ala Phe Arg Lys Gly Val Pro Asn Pro Ile Asp Leu Leu<br>                75                        80                        85 | 413 |
| gag tcc acc ctg tac gag tcc tca gta gtg cct ggg ccc aag aaa gcg<br>Glu Ser Thr Leu Tyr Glu Ser Ser Val Val Pro Gly Pro Lys Lys Ala<br>       90                        95                        100 | 461 |
| ccc atg gat tcc ttg ttc gac tac ggc act tac cgt cac cac ccc agt<br>Pro Met Asp Ser Leu Phe Asp Tyr Gly Thr Tyr Arg His His Pro Ser<br>105                     110                        115 | 509 |
| gac aac aag aga tgg agg aga aag gtc gtg gag aag cag cca cag agc<br>Asp Asn Lys Arg Trp Arg Arg Lys Val Val Glu Lys Gln Pro Gln Ser<br>             120                        125                        130 | 557 |
| ccc aaa gct cct gca ccc cag cca ccc ccc atc ctc aaa gtc ttc aat<br>Pro Lys Ala Pro Ala Pro Gln Pro Pro Pro Ile Leu Lys Val Phe Asn<br>135                     140                        145                        150 | 605 |
| cgg ccc atc ctc ttt gac att gtg tcc cgg ggc tcc act gcg gac cta<br>Arg Pro Ile Leu Phe Asp Ile Val Ser Arg Gly Ser Thr Ala Asp Leu<br>                    155                        160                        165 | 653 |
| gat gga ctg ctc tcc ttc ttg ttg acc cac aag aag cgc ctg act gat<br>Asp Gly Leu Leu Ser Phe Leu Leu Thr His Lys Lys Arg Leu Thr Asp<br>             170                        175                        180 | 701 |
| gag gag ttc cgg gag ccg tcc acg ggg aag acc tgc ctg ccc aag gcg<br>Glu Glu Phe Arg Glu Pro Ser Thr Gly Lys Thr Cys Leu Pro Lys Ala<br>185                     190                        195 | 749 |

```
ctg ctg aac cta agc aac ggg cgc aac gac acc atc ccg gtg ttg ctg      797
Leu Leu Asn Leu Ser Asn Gly Arg Asn Asp Thr Ile Pro Val Leu Leu
    200                 205                 210 gac att gcg gag cgc acc ggc aac atg cgt gaa ttc atc aac tcg ccc      845
Asp Ile Ala Glu Arg Thr Gly Asn Met Arg Glu Phe Ile Asn Ser Pro
215                 220                 225                 230 ttc aga gac atc tac tac cga ggc cag aca tcc ctg cac att gcc atc      893
Phe Arg Asp Ile Tyr Tyr Arg Gly Gln Thr Ser Leu His Ile Ala Ile
                235                 240                 245 gaa cgg cgc tgc aag cac tac gtg gag ctg ctg gtg gcc cag gga gcc      941
Glu Arg Arg Cys Lys His Tyr Val Glu Leu Leu Val Ala Gln Gly Ala
                250                 255                 260 gac gtg cac gcc cag gcc cgc ggc cgc ttc ttc cag ccc aag gat gag      989
Asp Val His Ala Gln Ala Arg Gly Arg Phe Phe Gln Pro Lys Asp Glu
            265                 270                 275 gga ggc tac ttc tac ttt ggg gag ctg ccc ttg tcc ctg gca gcc tgc     1037
Gly Gly Tyr Phe Tyr Phe Gly Glu Leu Pro Leu Ser Leu Ala Ala Cys
            280                 285                 290 acc aac cag ccg cac atc gtc aac tac ctg aca gag aac cct cac aag     1085
Thr Asn Gln Pro His Ile Val Asn Tyr Leu Thr Glu Asn Pro His Lys
295                 300                 305                 310 aaa gct gac atg agg cga cag gac tcg agg ggg aac acg gtg ctg cac     1133
Lys Ala Asp Met Arg Arg Gln Asp Ser Arg Gly Asn Thr Val Leu His
                315                 320                 325 gcg ctg gtg gcc atc gcc gac aac acc cga gag aac acc aag ttt gtc     1181
Ala Leu Val Ala Ile Ala Asp Asn Thr Arg Glu Asn Thr Lys Phe Val
                330                 335                 340 acc aag atg tac gac ctg ctg ctt ctc aag tgt tca cgc ctc ttc ctc     1229
Thr Lys Met Tyr Asp Leu Leu Leu Leu Lys Cys Ser Arg Leu Phe Leu
                345                 350                 355 gac agc aac ctg gag aca gtt ctc aac aat gat ggc ctt tcg cct ctc     1277
Asp Ser Asn Leu Glu Thr Val Leu Asn Asn Asp Gly Leu Ser Pro Leu
    360                 365                 370 atg atg gct gcc aag aca ggc aag atc ggg gtc ttt cag cac atc atc     1325
Met Met Ala Ala Lys Thr Gly Lys Ile Gly Val Phe Gln His Ile Ile
375                 380                 385                 390 cga cgt gag gtg aca gat gag gac acc cgg cat ctg tct cgc aag ttc     1373
Arg Arg Glu Val Thr Asp Glu Asp Thr Arg His Leu Ser Arg Lys Phe
                395                 400                 405 aag gac tgg gcc tat ggg cct gtg tat tct tct ctc tac gac ctc tcc     1421
Lys Asp Trp Ala Tyr Gly Pro Val Tyr Ser Ser Leu Tyr Asp Leu Ser
                410                 415                 420 tcc ctg gac aca tgc ggg gag gag gtg tcc gtg ctg gag atc ctg gtg     1469
Ser Leu Asp Thr Cys Gly Glu Glu Val Ser Val Leu Glu Ile Leu Val
                425                 430                 435 tac aac agc aag atc gag aac cgc cat gag atg ctg gct gta gag ccc     1517
Tyr Asn Ser Lys Ile Glu Asn Arg His Glu Met Leu Ala Val Glu Pro
    440                 445                 450 att aac gaa ctg ttg aga gac aag tgg cgt aag ttt ggg gct gtg tcc     1565
Ile Asn Glu Leu Leu Arg Asp Lys Trp Arg Lys Phe Gly Ala Val Ser
455                 460                 465                 470 ttc tac atc aac gtg gtc tcc tat ctg tgt gcc atg gtc atc ttc acc     1613
Phe Tyr Ile Asn Val Val Ser Tyr Leu Cys Ala Met Val Ile Phe Thr
                475                 480                 485 ctc acc gcc tac tat cag cca ctg gag ggc acg cca ccc tac cct tac     1661
Leu Thr Ala Tyr Tyr Gln Pro Leu Glu Gly Thr Pro Pro Tyr Pro Tyr
            490                 495                 500 cgg acc aca gtg gac tac ctg agg ctg gct ggc gag gtc atc acg ctc     1709
Arg Thr Thr Val Asp Tyr Leu Arg Leu Ala Gly Glu Val Ile Thr Leu
            505                 510                 515
```

-continued

| | | |
|---|---|---|
| ttc aca gga gtc ctg ttc ttc ttt acc agt atc aaa gac ttg ttc acg<br>Phe Thr Gly Val Leu Phe Phe Phe Thr Ser Ile Lys Asp Leu Phe Thr<br>520                                     525                                    530 | 1757 |

```
ttc aca gga gtc ctg ttc ttc ttt acc agt atc aaa gac ttg ttc acg    1757
Phe Thr Gly Val Leu Phe Phe Phe Thr Ser Ile Lys Asp Leu Phe Thr
520                     525                     530 aag aaa tgc cct gga gtg aat tct ctc ttc gtc gat ggc tcc ttc cag    1805
Lys Lys Cys Pro Gly Val Asn Ser Leu Phe Val Asp Gly Ser Phe Gln
535                 540                     545                 550 tta ctc tac ttc atc tac tct gtg ctg gtg gtt gtc tct gcg gcg ctc    1853
Leu Leu Tyr Phe Ile Tyr Ser Val Leu Val Val Val Ser Ala Ala Leu
                555                     560                     565 tac ctg gct ggg atc gag gcc tac ctg gct gtg atg gtc ttt gcc ctg    1901
Tyr Leu Ala Gly Ile Glu Ala Tyr Leu Ala Val Met Val Phe Ala Leu
            570                     575                     580 gtc ctg ggc tgg atg aat gcg ctg tac ttc acg cgc ggg ttg aag ctg    1949
Val Leu Gly Trp Met Asn Ala Leu Tyr Phe Thr Arg Gly Leu Lys Leu
        585                     590                     595 acg ggg acc tac agc atc atg att cag aag atc ctc ttc aaa gac ctc    1997
Thr Gly Thr Tyr Ser Ile Met Ile Gln Lys Ile Leu Phe Lys Asp Leu
    600                     605                     610 ttc cgc ttc ctg ctt gtg tac ctg ctc ttc atg atc ggc tat gcc tca    2045
Phe Arg Phe Leu Leu Val Tyr Leu Leu Phe Met Ile Gly Tyr Ala Ser
615                     620                     625                 630 gcc ctg gtc acc ctc ctg aat ccg tgc acc aac atg aag gtc tgt gac    2093
Ala Leu Val Thr Leu Leu Asn Pro Cys Thr Asn Met Lys Val Cys Asp
                635                     640                     645 gag gac cag agc aac tgc acg gtg ccc acg tat cct gcg tgc cgc gac    2141
Glu Asp Gln Ser Asn Cys Thr Val Pro Thr Tyr Pro Ala Cys Arg Asp
            650                     655                     660 agc gag acc ttc agc gcc ttc ctc ctg gac ctc ttc aag ctc acc atc    2189
Ser Glu Thr Phe Ser Ala Phe Leu Leu Asp Leu Phe Lys Leu Thr Ile
        665                     670                     675 ggc atg gga gac ctg gag atg ctg agc agc gcc aag tac ccc gtg gtc    2237
Gly Met Gly Asp Leu Glu Met Leu Ser Ser Ala Lys Tyr Pro Val Val
    680                     685                     690 ttc atc ctc ctg ctg gtc acc tac atc atc ctc acc ttc gtg ctc ctg    2285
Phe Ile Leu Leu Leu Val Thr Tyr Ile Ile Leu Thr Phe Val Leu Leu
695                     700                     705                 710 ttg aac atg ctt atc gcc ctc atg ggt gag acc gtg ggc cag gtg tcc    2333
Leu Asn Met Leu Ile Ala Leu Met Gly Glu Thr Val Gly Gln Val Ser
                715                     720                     725 aag gag agc aag cac atc tgg aag ttg cag tgg gcc acc acc atc ctg    2381
Lys Glu Ser Lys His Ile Trp Lys Leu Gln Trp Ala Thr Thr Ile Leu
            730                     735                     740 gac atc gag cgt tcc ttc cct gtg ttc ctg agg aag gcc ttc cgc tcc    2429
Asp Ile Glu Arg Ser Phe Pro Val Phe Leu Arg Lys Ala Phe Arg Ser
        745                     750                     755 gga gag atg gtg act gtg ggc aag agc tca gat ggc act ccg gac cgc    2477
Gly Glu Met Val Thr Val Gly Lys Ser Ser Asp Gly Thr Pro Asp Arg
    760                     765                     770 agg tgg tgc ttc agg gtg gac gag gtg aac tgg tct cac tgg aac cag    2525
Arg Trp Cys Phe Arg Val Asp Glu Val Asn Trp Ser His Trp Asn Gln
775                     780                     785                 790 aac ttg ggc atc att aac gag gac cct ggc aag agt gaa atc tac cag    2573
Asn Leu Gly Ile Ile Asn Glu Asp Pro Gly Lys Ser Glu Ile Tyr Gln
                795                     800                     805 tac tat ggc ttc tcc cac acc gtg ggg cgc ctt cgt agg gat cgt tgg    2621
Tyr Tyr Gly Phe Ser His Thr Val Gly Arg Leu Arg Arg Asp Arg Trp
            810                     815                     820 tcc tcg gtg gtg ccc cgc gta gtg gag ctg aac aag aac tca agc gca    2669
Ser Ser Val Val Pro Arg Val Val Glu Leu Asn Lys Asn Ser Ser Ala
```

| | | | |
|---|---|---|---|
| gat gaa gtg gtg gta ccc ctg gat aac cta ggg aac ccc aac tgt gac<br>Asp Glu Val Val Val Pro Leu Asp Asn Leu Gly Asn Pro Asn Cys Asp<br>840                              845                              850 | | | 2717 |
| ggc cac cag cag ggc tac gct ccc aag tgg agg acg gac gat gcc cca<br>Gly His Gln Gln Gly Tyr Ala Pro Lys Trp Arg Thr Asp Asp Ala Pro<br>855                              860                              865                              870 | | | 2765 |
| ctg tag gggccgtgcc agagctcgca cagatagtcc aggcttggcc ttcgctccca<br>Leu  * | | | 2821 |
| cctacattta ggcatttgtc cggtgtcttc cccacccgca tgggaccttg gaggtgaggg | | | 2881 |
| cctctgtggc gactctgtgg aggccccagg accctctggt ccccgccaag acttttgcct | | | 2941 |
| tcagctctac tccccacatg ggggggggcgg ggctcctggc tacctktctc gctcgctccc | | | 3001 |
| atggagtcac ctaagccagc acaaggcccc tctcctcgaa aggctcaggc cccatccctc | | | 3061 |
| ttgtgtatta tttattgctc tcctcaggaa aatgggtgg caggagtcca cccgcggctg | | | 3121 |
| gaacctggcc agggctgaag ctcatgcagg gacgctgcag ctccgacctg ccacagatct | | | 3181 |
| gacctgctgc agccctggct agtgtgggtc ttctgtactt tgaagagatc ggggccgctg | | | 3241 |
| gtgctcaata aatgtttatt ctcggtggaa aaaaaaaaa | | | 3281 |

```
<210> SEQ ID NO 14
<211> LENGTH: 871
<212> TYPE: PRT
<213> ORGANISM: Mus musculus

<400> SEQUENCE: 14
```

Met Ala Asp Pro Gly Asp Gly Pro Arg Ala Pro Gly Glu Val Ala
 1               5                  10                  15

Glu Pro Pro Gly Asp Glu Ser Gly Thr Ser Gly Gly Glu Ala Phe Pro
                20                  25                  30

Leu Ser Ser Leu Ala Asn Leu Phe Glu Gly Glu Gly Ser Ser Ser
            35                  40                  45

Leu Ser Pro Val Asp Ala Ser Arg Pro Ala Gly Pro Gly Asp Gly Arg
        50                  55                  60

Pro Asn Leu Arg Met Lys Phe Gln Gly Ala Phe Arg Lys Gly Val Pro
65                  70                  75                  80

Asn Pro Ile Asp Leu Leu Glu Ser Thr Leu Tyr Glu Ser Ser Val Val
                85                  90                  95

Pro Gly Pro Lys Lys Ala Pro Met Asp Ser Leu Phe Asp Tyr Gly Thr
            100                 105                 110

Tyr Arg His His Pro Ser Asp Asn Lys Arg Trp Arg Lys Val Val
            115                 120                 125

Glu Lys Gln Pro Gln Ser Pro Lys Ala Pro Ala Pro Gln Pro Pro
        130                 135                 140

Ile Leu Lys Val Phe Asn Arg Pro Ile Leu Phe Asp Ile Val Ser Arg
145                 150                 155                 160

Gly Ser Thr Ala Asp Leu Asp Gly Leu Leu Ser Phe Leu Thr His
                165                 170                 175

Lys Lys Arg Leu Thr Asp Glu Glu Phe Arg Glu Pro Ser Thr Gly Lys
            180                 185                 190

Thr Cys Leu Pro Lys Ala Leu Leu Asn Leu Ser Asn Gly Arg Asn Asp
        195                 200                 205

Thr Ile Pro Val Leu Leu Asp Ile Ala Glu Arg Thr Gly Asn Met Arg
    210                 215                 220

-continued

```
Glu Phe Ile Asn Ser Pro Phe Arg Asp Ile Tyr Tyr Arg Gly Gln Thr
225                 230                 235                 240

Ser Leu His Ile Ala Ile Glu Arg Arg Cys Lys His Tyr Val Glu Leu
            245                 250                 255

Leu Val Ala Gln Gly Ala Asp Val His Ala Gln Ala Arg Gly Arg Phe
        260                 265                 270

Phe Gln Pro Lys Asp Glu Gly Gly Tyr Phe Tyr Phe Gly Glu Leu Pro
    275                 280                 285

Leu Ser Leu Ala Ala Cys Thr Asn Gln Pro His Ile Val Asn Tyr Leu
290                 295                 300

Thr Glu Asn Pro His Lys Lys Ala Asp Met Arg Arg Gln Asp Ser Arg
305                 310                 315                 320

Gly Asn Thr Val Leu His Ala Leu Val Ala Ile Ala Asp Asn Thr Arg
            325                 330                 335

Glu Asn Thr Lys Phe Val Thr Lys Met Tyr Asp Leu Leu Leu Leu Lys
        340                 345                 350

Cys Ser Arg Leu Phe Leu Asp Ser Asn Leu Glu Thr Val Leu Asn Asn
    355                 360                 365

Asp Gly Leu Ser Pro Leu Met Met Ala Ala Lys Thr Gly Lys Ile Gly
370                 375                 380

Val Phe Gln His Ile Ile Arg Arg Glu Val Thr Asp Glu Asp Thr Arg
385                 390                 395                 400

His Leu Ser Arg Lys Phe Lys Asp Trp Ala Tyr Gly Pro Val Tyr Ser
            405                 410                 415

Ser Leu Tyr Asp Leu Ser Ser Leu Asp Thr Cys Gly Glu Glu Val Ser
        420                 425                 430

Val Leu Glu Ile Leu Val Tyr Asn Ser Lys Ile Glu Asn Arg His Glu
    435                 440                 445

Met Leu Ala Val Glu Pro Ile Asn Glu Leu Leu Arg Asp Lys Trp Arg
450                 455                 460

Lys Phe Gly Ala Val Ser Phe Tyr Ile Asn Val Val Ser Tyr Leu Cys
465                 470                 475                 480

Ala Met Val Ile Phe Thr Leu Thr Ala Tyr Tyr Gln Pro Leu Glu Gly
            485                 490                 495

Thr Pro Pro Tyr Pro Tyr Arg Thr Thr Val Asp Tyr Leu Arg Leu Ala
        500                 505                 510

Gly Glu Val Ile Thr Leu Phe Thr Gly Val Leu Phe Phe Phe Thr Ser
    515                 520                 525

Ile Lys Asp Leu Phe Thr Lys Lys Cys Pro Gly Val Asn Ser Leu Phe
530                 535                 540

Val Asp Gly Ser Phe Gln Leu Leu Tyr Phe Ile Tyr Ser Val Leu Val
545                 550                 555                 560

Val Val Ser Ala Ala Leu Tyr Leu Ala Gly Ile Glu Ala Tyr Leu Ala
            565                 570                 575

Val Met Val Phe Ala Leu Val Leu Gly Trp Met Asn Ala Leu Tyr Phe
        580                 585                 590

Thr Arg Gly Leu Lys Leu Thr Gly Thr Tyr Ser Ile Met Ile Gln Lys
    595                 600                 605

Ile Leu Phe Lys Asp Leu Phe Arg Phe Leu Leu Val Tyr Leu Leu Phe
610                 615                 620

Met Ile Gly Tyr Ala Ser Ala Leu Val Thr Leu Leu Asn Pro Cys Thr
625                 630                 635                 640

Asn Met Lys Val Cys Asp Glu Asp Gln Ser Asn Cys Thr Val Pro Thr
```

645                 650                 655
Tyr Pro Ala Cys Arg Asp Ser Glu Thr Phe Ser Ala Phe Leu Leu Asp
            660                 665                 670

Leu Phe Lys Leu Thr Ile Gly Met Gly Asp Leu Glu Met Leu Ser Ser
        675                 680                 685

Ala Lys Tyr Pro Val Val Phe Ile Leu Leu Val Thr Tyr Ile Ile
    690                 695                 700

Leu Thr Phe Val Leu Leu Leu Asn Met Leu Ile Ala Leu Met Gly Glu
705                 710                 715                 720

Thr Val Gly Gln Val Ser Lys Glu Ser Lys His Ile Trp Lys Leu Gln
                725                 730                 735

Trp Ala Thr Thr Ile Leu Asp Ile Glu Arg Ser Phe Pro Val Phe Leu
            740                 745                 750

Arg Lys Ala Phe Arg Ser Gly Glu Met Val Thr Val Gly Lys Ser Ser
        755                 760                 765

Asp Gly Thr Pro Asp Arg Arg Trp Cys Phe Arg Val Asp Glu Val Asn
    770                 775                 780

Trp Ser His Trp Asn Gln Asn Leu Gly Ile Ile Asn Glu Asp Pro Gly
785                 790                 795                 800

Lys Ser Glu Ile Tyr Gln Tyr Tyr Gly Phe Ser His Thr Val Gly Arg
                805                 810                 815

Leu Arg Arg Asp Arg Trp Ser Ser Val Val Pro Arg Val Val Glu Leu
            820                 825                 830

Asn Lys Asn Ser Ser Ala Asp Glu Val Val Val Pro Leu Asp Asn Leu
        835                 840                 845

Gly Asn Pro Asn Cys Asp Gly His Gln Gln Gly Tyr Ala Pro Lys Trp
    850                 855                 860

Arg Thr Asp Asp Ala Pro Leu
865                 870

<210> SEQ ID NO 15
<211> LENGTH: 2613
<212> TYPE: DNA
<213> ORGANISM: Artificial Sequence
<220> FEATURE:
<221> NAME/KEY: CDS
<222> LOCATION: (1)...(2613)
<223> OTHER INFORMATION: Generic sequence that encompasses all
      nucleotide sequences that encode mouse TRPV4 having amino
      acid sequence as shown in SEQ ID NO:14
<220> FEATURE:
<221> NAME/KEY: misc_feature
<222> LOCATION: 69,78,102,105,138,141,144,150,165,264,279,282,318,354,
      402,477,486,513,567,609,687,723,870,957,1062,1080,1116,1209,1248,
      1251,1266,1269,1296,1323,1410,1431,1584,1626,1644,1671,1689,1809,
      1890,1950,2001,2061,2064,2178,2187,2241,2274,2301,2304,2358,2406,
      2433,2469,2472,2508,2511
<223> OTHER INFORMATION: n = A,T,C or G if after TC;
      n = T or C if after AG
<220> FEATURE:
<221> NAME/KEY: misc_feature
<222> LOCATION: 27,168,192,204,228,342,366,372,375,453,480,537,558,618,
      657,672,696,711,744,747,807,813,945,948,960,1008,1065,1173,1176,
      1200,1212,1338,1380,1392,1509,1530,1782,1848,1983,2238,2259,2271,
      2322,2325,2337,2448,2454,2457,2463,2484,2595
<223> OTHER INFORMATION: n = A,T,C or G if after CG;
      n = A or G if after AG
<220> FEATURE:
<221> NAME/KEY: misc_feature
<222> LOCATION: all "n" not specified above
<223> OTHER INFORMATION: n = A,T,C or G

<400> SEQUENCE: 15

-continued

```
atg gcn gay ccn ggn gay ggn ccn mgn gcn gcn ccn ggn gar gtn gcn      48
Met Ala Asp Pro Gly Asp Gly Pro Arg Ala Ala Pro Gly Glu Val Ala
 1               5                  10                  15 gar ccn ccn ggn gay gar wsn ggn acn wsn ggn ggn gar gcn tty ccn      96
Glu Pro Pro Gly Asp Glu Ser Gly Thr Ser Gly Gly Glu Ala Phe Pro
                20                  25                  30 ytn wsn wsn ytn gcn aay ytn tty gar ggn gar gar ggn wsn wsn wsn     144
Leu Ser Ser Leu Ala Asn Leu Phe Glu Gly Glu Glu Gly Ser Ser Ser
            35                  40                  45 ytn wsn ccn gtn gay gcn wsn mgn ccn gcn ggn ccn ggn gay ggn mgn     192
Leu Ser Pro Val Asp Ala Ser Arg Pro Ala Gly Pro Gly Asp Gly Arg
     50                  55                  60 ccn aay ytn mgn atg aar tty car ggn gcn tty mgn aar ggn gtn ccn     240
Pro Asn Leu Arg Met Lys Phe Gln Gly Ala Phe Arg Lys Gly Val Pro
 65                  70                  75                  80 aay ccn ath gay ytn ytn gar wsn acn ytn tay gar wsn wsn gtn gtn     288
Asn Pro Ile Asp Leu Leu Glu Ser Thr Leu Tyr Glu Ser Ser Val Val
                85                  90                  95 ccn ggn ccn aar aar gcn ccn atg gay wsn ytn tty gay tay ggn acn     336
Pro Gly Pro Lys Lys Ala Pro Met Asp Ser Leu Phe Asp Tyr Gly Thr
            100                 105                 110 tay mgn cay cay ccn wsn gay aay aar mgn tgg mgn mgn aar gtn gtn     384
Tyr Arg His His Pro Ser Asp Asn Lys Arg Trp Arg Arg Lys Val Val
    115                 120                 125 gar aar car ccn car wsn ccn aar gcn ccn gcn ccn car ccn ccn ccn     432
Glu Lys Gln Pro Gln Ser Pro Lys Ala Pro Ala Pro Gln Pro Pro Pro
130                 135                 140 ath ytn aar gtn tty aay mgn ccn ath ytn tty gay ath gtn wsn mgn     480
Ile Leu Lys Val Phe Asn Arg Pro Ile Leu Phe Asp Ile Val Ser Arg
145                 150                 155                 160 ggn wsn acn gcn gay ytn gay ggn ytn ytn wsn tty ytn ytn acn cay     528
Gly Ser Thr Ala Asp Leu Asp Gly Leu Leu Ser Phe Leu Leu Thr His
                165                 170                 175 aar aar mgn ytn acn gay gar gar tty mgn gar ccn wsn acn ggn aar     576
Lys Lys Arg Leu Thr Asp Glu Glu Phe Arg Glu Pro Ser Thr Gly Lys
            180                 185                 190 acn tgy ytn ccn aar gcn ytn ytn aay ytn wsn aay ggn mgn aay gay     624
Thr Cys Leu Pro Lys Ala Leu Leu Asn Leu Ser Asn Gly Arg Asn Asp
        195                 200                 205 acn ath ccn gtn ytn ytn gay ath gcn gar mgn acn ggn aay atg mgn     672
Thr Ile Pro Val Leu Leu Asp Ile Ala Glu Arg Thr Gly Asn Met Arg
    210                 215                 220 gar tty ath aay wsn ccn tty mgn gay ath tay tay mgn ggn car acn     720
Glu Phe Ile Asn Ser Pro Phe Arg Asp Ile Tyr Tyr Arg Gly Gln Thr
225                 230                 235                 240 wsn ytn cay ath gcn ath gar mgn mgn tgy aar cay tay gtn gar ytn     768
Ser Leu His Ile Ala Ile Glu Arg Arg Cys Lys His Tyr Val Glu Leu
                245                 250                 255 ytn gtn gcn car ggn gcn gay gtn cay gcn car gcn mgn ggn mgn tty     816
Leu Val Ala Gln Gly Ala Asp Val His Ala Gln Ala Arg Gly Arg Phe
            260                 265                 270 tty car ccn aar gay gar ggn ggn tay tty tay tty ggn gar ytn ccn     864
Phe Gln Pro Lys Asp Glu Gly Gly Tyr Phe Tyr Phe Gly Glu Leu Pro
        275                 280                 285 ytn wsn ytn gcn gcn tgy acn aay car ccn cay ath gtn aay tay ytn     912
Leu Ser Leu Ala Ala Cys Thr Asn Gln Pro His Ile Val Asn Tyr Leu
    290                 295                 300 acn gar aay ccn cay aar aar gcn gay atg mgn mgn car gay wsn mgn     960
Thr Glu Asn Pro His Lys Lys Ala Asp Met Arg Arg Gln Asp Ser Arg
305                 310                 315                 320
```

-continued

```
ggn aay acn gtn ytn cay gcn ytn gtn gcn ath gcn gay aay acn mgn    1008
Gly Asn Thr Val Leu His Ala Leu Val Ala Ile Ala Asp Asn Thr Arg
            325                 330                 335 gar aay acn aar tty gtn acn aar atg tay gay ytn ytn ytn aar        1056
Glu Asn Thr Lys Phe Val Thr Lys Met Tyr Asp Leu Leu Leu Lys
        340                 345                 350 tgy wsn mgn ytn tty ytn gay wsn aay ytn gar acn gtn ytn aay aay    1104
Cys Ser Arg Leu Phe Leu Asp Ser Asn Leu Glu Thr Val Leu Asn Asn
            355                 360                 365 gay ggn ytn wsn ccn ytn atg atg gcn gcn aar acn ggn aar ath ggn    1152
Asp Gly Leu Ser Pro Leu Met Met Ala Ala Lys Thr Gly Lys Ile Gly
            370                 375                 380 gtn tty car cay ath ath mgn mgn gar gtn acn gay gar acn mgn        1200
Val Phe Gln His Ile Ile Arg Arg Glu Val Thr Asp Glu Thr Arg
385                 390                 395                 400 cay ytn wsn mgn aar tty aar gay tgg gcn tay ggn ccn gtn tay wsn    1248
His Leu Ser Arg Lys Phe Lys Asp Trp Ala Tyr Gly Pro Val Tyr Ser
                    405                 410                 415 wsn ytn tay gay ytn wsn wsn ytn gay acn tgy ggn gar gtn wsn        1296
Ser Leu Tyr Asp Leu Ser Ser Leu Asp Thr Cys Gly Glu Glu Val Ser
            420                 425                 430 gtn ytn gar ath ytn gtn tay aay wsn aar ath gar aay mgn cay gar    1344
Val Leu Glu Ile Leu Val Tyr Asn Ser Lys Ile Glu Asn Arg His Glu
            435                 440                 445 atg ytn gcn gtn gar ccn ath aay gar ytn ytn mgn gay aar tgg mgn    1392
Met Leu Ala Val Glu Pro Ile Asn Glu Leu Leu Arg Asp Lys Trp Arg
450                 455                 460 aar tty ggn gcn gtn wsn tty tay ath aay gtn gtn wsn tay ytn tgy    1440
Lys Phe Gly Ala Val Ser Phe Tyr Ile Asn Val Val Ser Tyr Leu Cys
465                 470                 475                 480 gcn atg gtn ath tty acn ytn acn gcn tay tay car ccn ytn gar ggn    1488
Ala Met Val Ile Phe Thr Leu Thr Ala Tyr Tyr Gln Pro Leu Glu Gly
                485                 490                 495 acn ccn ccn tay ccn tay mgn acn acn gtn gay tay ytn mgn ytn gcn    1536
Thr Pro Pro Tyr Pro Tyr Arg Thr Thr Val Asp Tyr Leu Arg Leu Ala
            500                 505                 510 ggn gar gtn ath acn ytn tty acn ggn gtn ytn tty tty tty acn wsn    1584
Gly Glu Val Ile Thr Leu Phe Thr Gly Val Leu Phe Phe Phe Thr Ser
            515                 520                 525 ath aar gay ytn tty acn aar aar tgy ccn ggn gtn aay wsn ytn tty    1632
Ile Lys Asp Leu Phe Thr Lys Lys Cys Pro Gly Val Asn Ser Leu Phe
530                 535                 540 gtn gay ggn wsn tty car ytn ytn tay tty ath tay wsn gtn ytn gtn    1680
Val Asp Gly Ser Phe Gln Leu Leu Tyr Phe Ile Tyr Ser Val Leu Val
545                 550                 555                 560 gtn gtn wsn gcn gcn ytn tay ytn gcn ggn ath gar gcn tay ytn gcn    1728
Val Val Ser Ala Ala Leu Tyr Leu Ala Gly Ile Glu Ala Tyr Leu Ala
                565                 570                 575 gtn atg gtn tty gcn ytn gtn ytn ggn tgg atg aay gcn ytn tay tty    1776
Val Met Val Phe Ala Leu Val Leu Gly Trp Met Asn Ala Leu Tyr Phe
            580                 585                 590 acn mgn ggn ytn aar ytn acn ggn acn tay wsn ath atg ath car aar    1824
Thr Arg Gly Leu Lys Leu Thr Gly Thr Tyr Ser Ile Met Ile Gln Lys
            595                 600                 605 ath ytn tty aar gay ytn tty mgn tty ytn ytn tay ytn ytn tty        1872
Ile Leu Phe Lys Asp Leu Phe Arg Phe Leu Leu Tyr Leu Leu Phe
        610                 615                 620 atg ath ggn tay gcn wsn gcn ytn gtn acn ytn ytn aay ccn tgy acn    1920
Met Ile Gly Tyr Ala Ser Ala Leu Val Thr Leu Leu Asn Pro Cys Thr
```

-continued

```
625                 630                 635                 640 aay atg aar gtn tgy gay gar gay car wsn aay tgy acn gtn ccn acn      1968
Asn Met Lys Val Cys Asp Glu Asp Gln Ser Asn Cys Thr Val Pro Thr
                645                 650                 655 tay ccn gcn tgy mgn gay wsn gar acn tty wsn gcn tty ytn ytn gay      2016
Tyr Pro Ala Cys Arg Asp Ser Glu Thr Phe Ser Ala Phe Leu Leu Asp
            660                 665                 670 ytn tty aar ytn acn ath ggn atg ggn gay ytn gar atg ytn wsn wsn      2064
Leu Phe Lys Leu Thr Ile Gly Met Gly Asp Leu Glu Met Leu Ser Ser
        675                 680                 685 gcn aar tay ccn gtn gtn tty ath ytn ytn ytn gtn acn tay ath ath      2112
Ala Lys Tyr Pro Val Val Phe Ile Leu Leu Leu Val Thr Tyr Ile Ile
    690                 695                 700 ytn acn tty gtn ytn ytn ytn aay atg ytn ath gcn ytn atg ggn gar      2160
Leu Thr Phe Val Leu Leu Leu Asn Met Leu Ile Ala Leu Met Gly Glu
705                 710                 715                 720 acn gtn ggn car gtn wsn aar gar wsn aar cay ath tgg aar ytn car      2208
Thr Val Gly Gln Val Ser Lys Glu Ser Lys His Ile Trp Lys Leu Gln
                725                 730                 735 tgg gcn acn acn ath ytn gay ath gar mgn wsn tty ccn gtn tty ytn      2256
Trp Ala Thr Thr Ile Leu Asp Ile Glu Arg Ser Phe Pro Val Phe Leu
            740                 745                 750 mgn aar gcn tty mgn wsn ggn gar atg gtn acn gtn ggn aar wsn wsn      2304
Arg Lys Ala Phe Arg Ser Gly Glu Met Val Thr Val Gly Lys Ser Ser
        755                 760                 765 gay ggn acn ccn gay mgn mgn tgg tgy tty mgn gtn gay gar gtn aay      2352
Asp Gly Thr Pro Asp Arg Arg Trp Cys Phe Arg Val Asp Glu Val Asn
    770                 775                 780 tgg wsn cay tgg aay car aay ytn ggn ath ath aay gar gay ccn ggn      2400
Trp Ser His Trp Asn Gln Asn Leu Gly Ile Ile Asn Glu Asp Pro Gly
785                 790                 795                 800 aar wsn gar ath tay car tay tay ggn tty wsn cay acn gtn ggn mgn      2448
Lys Ser Glu Ile Tyr Gln Tyr Tyr Gly Phe Ser His Thr Val Gly Arg
                805                 810                 815 ytn mgn mgn gay mgn tgg wsn wsn gtn gtn ccn mgn gtn gtn gar ytn      2496
Leu Arg Arg Asp Arg Trp Ser Ser Val Val Pro Arg Val Val Glu Leu
            820                 825                 830 aay aar aay wsn wsn gcn gay gar gtn gtn gtn ccn ytn gay aay ytn      2544
Asn Lys Asn Ser Ser Ala Asp Glu Val Val Val Pro Leu Asp Asn Leu
        835                 840                 845 ggn aay ccn aay tgy gay ggn cay car car ggn tay gcn ccn aar tgg      2592
Gly Asn Pro Asn Cys Asp Gly His Gln Gln Gly Tyr Ala Pro Lys Trp
    850                 855                 860 mgn acn gay gay gcn ccn ytn                                          2613
Arg Thr Asp Asp Ala Pro Leu
865                 870
```

```
<210> SEQ ID NO 16
<211> LENGTH: 2616
<212> TYPE: DNA
<213> ORGANISM: Homo sapiens
<220> FEATURE:
<221> NAME/KEY: CDS
<222> LOCATION: (1)...(2616)

<400> SEQUENCE: 16 atg gcg gat tcc agc gaa ggc ccc cgc gcg ggg ccc ggg gag gtg gct        48
Met Ala Asp Ser Ser Glu Gly Pro Arg Ala Gly Pro Gly Glu Val Ala
 1               5                  10                  15 gag ctc ccc ggg gat gag agt ggc acc cca ggt ggg gag gct ttt cct        96
Glu Leu Pro Gly Asp Glu Ser Gly Thr Pro Gly Gly Glu Ala Phe Pro
```

-continued

|  | 20 | 25 | 30 |  |
|---|---|---|---|---|
| ctc tcc tcc ctg gcc aat ctg ttt gag ggg gag gat ggc tcc ctt tcg<br>Leu Ser Ser Leu Ala Asn Leu Phe Glu Gly Glu Asp Gly Ser Leu Ser<br>35 40 45 | | | | 144 |
| ccc tca ccg gct gat gcc agt cgc cct gct ggc cca ggc gat ggg cga<br>Pro Ser Pro Ala Asp Ala Ser Arg Pro Ala Gly Pro Gly Asp Gly Arg<br>50 55 60 | | | | 192 |
| cca aat ctg cgc atg aag ttc cag ggc gcc ttc cgc aag ggg gtg ccc<br>Pro Asn Leu Arg Met Lys Phe Gln Gly Ala Phe Arg Lys Gly Val Pro<br>65 70 75 80 | | | | 240 |
| aac ccc atc gat ctg ctg gag tcc acc cta tat gag tcc tcg gtg gtg<br>Asn Pro Ile Asp Leu Leu Glu Ser Thr Leu Tyr Glu Ser Ser Val Val<br>85 90 95 | | | | 288 |
| cct ggg ccc aag aaa gca ccc atg gac tca ctg ttt gac tac ggc acc<br>Pro Gly Pro Lys Lys Ala Pro Met Asp Ser Leu Phe Asp Tyr Gly Thr<br>100 105 110 | | | | 336 |
| tat cgt cac cac tcc agt gac aac aag agg tgg agg aag aag atc ata<br>Tyr Arg His His Ser Ser Asp Asn Lys Arg Trp Arg Lys Lys Ile Ile<br>115 120 125 | | | | 384 |
| gag aag cag ccg cag agc ccc aaa gcc cct gcc cct cag ccg ccc ccc<br>Glu Lys Gln Pro Gln Ser Pro Lys Ala Pro Ala Pro Gln Pro Pro Pro<br>130 135 140 | | | | 432 |
| atc ctc aaa gtc ttc aac cgg cct atc ctc ttt gac atc gtg tcc cgg<br>Ile Leu Lys Val Phe Asn Arg Pro Ile Leu Phe Asp Ile Val Ser Arg<br>145 150 155 160 | | | | 480 |
| ggc tcc act gct gac ctg gac ggg ctc ctc cca ttc ttg ctg acc cac<br>Gly Ser Thr Ala Asp Leu Asp Gly Leu Leu Pro Phe Leu Leu Thr His<br>165 170 175 | | | | 528 |
| aag aaa cgc cta act gat gag gag ttt cga gag cca tct acg ggg aag<br>Lys Lys Arg Leu Thr Asp Glu Glu Phe Arg Glu Pro Ser Thr Gly Lys<br>180 185 190 | | | | 576 |
| acc tgc ctg ccc aag gcc ttg ctg aac ctg agc aat ggc cgc aac gac<br>Thr Cys Leu Pro Lys Ala Leu Leu Asn Leu Ser Asn Gly Arg Asn Asp<br>195 200 205 | | | | 624 |
| acc atc cct gtg ctg ctg gac atc gcg gag cgc acc ggc aac atg cgg<br>Thr Ile Pro Val Leu Leu Asp Ile Ala Glu Arg Thr Gly Asn Met Arg<br>210 215 220 | | | | 672 |
| gag ttc att aac tcg ccc ttc cgt gac atc tac tat cga ggt cag aca<br>Glu Phe Ile Asn Ser Pro Phe Arg Asp Ile Tyr Tyr Arg Gly Gln Thr<br>225 230 235 240 | | | | 720 |
| gcc ctg cac atc gcc att gag cgt cgc tgc aaa cac tac gtg gaa ctt<br>Ala Leu His Ile Ala Ile Glu Arg Arg Cys Lys His Tyr Val Glu Leu<br>245 250 255 | | | | 768 |
| ctc gtg gcc cag gga gct gat gtc cac gcc cag gcc cgt ggg cgc ttc<br>Leu Val Ala Gln Gly Ala Asp Val His Ala Gln Ala Arg Gly Arg Phe<br>260 265 270 | | | | 816 |
| ttc cag ccc aag gat gag ggg ggc tac ttc tac ttt ggg gag ctg ccc<br>Phe Gln Pro Lys Asp Glu Gly Gly Tyr Phe Tyr Phe Gly Glu Leu Pro<br>275 280 285 | | | | 864 |
| ctg tcg ctg gct gcc tgc acc aac cag ccc cac att gtc aac tac ctg<br>Leu Ser Leu Ala Ala Cys Thr Asn Gln Pro His Ile Val Asn Tyr Leu<br>290 295 300 | | | | 912 |
| acg gag aac ccc cac aag aag gcg gac atg cgg cgc cag gac tcg cga<br>Thr Glu Asn Pro His Lys Lys Ala Asp Met Arg Arg Gln Asp Ser Arg<br>305 310 315 320 | | | | 960 |
| ggc aac aca gtg ctg cat gcg ctg gtg gcc att gct gac aac acc cgt<br>Gly Asn Thr Val Leu His Ala Leu Val Ala Ile Ala Asp Asn Thr Arg<br>325 330 335 | | | | 1008 |
| gag aac acc aag ttt gtt acc aag atg tac gac ctg ctg ctg ctc aag | | | | 1056 |

```
                Glu Asn Thr Lys Phe Val Thr Lys Met Tyr Asp Leu Leu Leu Lys
                    340                 345                 350 tgt gcc cgc ctc ttc ccc gac agc aac ctg gag gcc gtg ctc aac aac                 1104
Cys Ala Arg Leu Phe Pro Asp Ser Asn Leu Glu Ala Val Leu Asn Asn
            355                 360                 365 gac ggc ctc tcg ccc ctc atg atg gct gcc aag acg ggc aag att ggg                 1152
Asp Gly Leu Ser Pro Leu Met Met Ala Ala Lys Thr Gly Lys Ile Gly
    370                 375                 380 atc ttt cag cac atc atc cgg cgg gag gtg acg gat gag gac aca cgg                 1200
Ile Phe Gln His Ile Ile Arg Arg Glu Val Thr Asp Glu Asp Thr Arg
385                 390                 395                 400 cac ctg tcc cgc aag ttc aag gac tgg gcc tat ggg cca gtg tat tcc                 1248
His Leu Ser Arg Lys Phe Lys Asp Trp Ala Tyr Gly Pro Val Tyr Ser
                405                 410                 415 tcg ctt tat gac ctc tcc tcc ctg gac acg tgt ggg gaa gag gcc tcc                 1296
Ser Leu Tyr Asp Leu Ser Ser Leu Asp Thr Cys Gly Glu Glu Ala Ser
            420                 425                 430 gtg ctg gag atc ctg gtg tac aac agc aag att gag aac cgc cac gag                 1344
Val Leu Glu Ile Leu Val Tyr Asn Ser Lys Ile Glu Asn Arg His Glu
    435                 440                 445 atg ctg gct gtg gag ccc atc aat gaa ctg ctg cgg gac aag tgg cgc                 1392
Met Leu Ala Val Glu Pro Ile Asn Glu Leu Leu Arg Asp Lys Trp Arg
450                 455                 460 aag ttc ggg gcc gtc tcc ttc tac atc aac gtg gtc tcc tac ctg tgt                 1440
Lys Phe Gly Ala Val Ser Phe Tyr Ile Asn Val Val Ser Tyr Leu Cys
465                 470                 475                 480 gcc atg gtc atc ttc act ctc acc gcc tac tac cag ccg ctg gag ggc                 1488
Ala Met Val Ile Phe Thr Leu Thr Ala Tyr Tyr Gln Pro Leu Glu Gly
                485                 490                 495 aca ccg ccg tac cct tac cgc acc acg gtg gac tac ctg cgg ctg gct                 1536
Thr Pro Pro Tyr Pro Tyr Arg Thr Thr Val Asp Tyr Leu Arg Leu Ala
            500                 505                 510 ggc gag gtc att acg ctc ttc act ggg gtc ctg ttc ttc ttc acc aac                 1584
Gly Glu Val Ile Thr Leu Phe Thr Gly Val Leu Phe Phe Phe Thr Asn
    515                 520                 525 atc aaa gac ttg ttc atg aag aaa tgc cct gga gtg aat tct ctc ttc                 1632
Ile Lys Asp Leu Phe Met Lys Lys Cys Pro Gly Val Asn Ser Leu Phe
530                 535                 540 att gat ggc tcc ttc cag ctg ctc tac ttc atc tac tct gtc ctg gtg                 1680
Ile Asp Gly Ser Phe Gln Leu Leu Tyr Phe Ile Tyr Ser Val Leu Val
545                 550                 555                 560 atc gtc tca gca gcc ctc tac ctg gca ggg atc gag gcc tac ctg gcc                 1728
Ile Val Ser Ala Ala Leu Tyr Leu Ala Gly Ile Glu Ala Tyr Leu Ala
                565                 570                 575 gtg atg gtc ttt gcc ctg gtc ctg ggc tgg atg aat gcc ctt tac ttc                 1776
Val Met Val Phe Ala Leu Val Leu Gly Trp Met Asn Ala Leu Tyr Phe
            580                 585                 590 acc cgt ggg ctg aag ctg acg ggg acc tat agc atc atg atc cag aag                 1824
Thr Arg Gly Leu Lys Leu Thr Gly Thr Tyr Ser Ile Met Ile Gln Lys
    595                 600                 605 att ctc ttc aag gac ctt ttc cga ttc ctg ctc gtc tac ttg ctc ttc                 1872
Ile Leu Phe Lys Asp Leu Phe Arg Phe Leu Leu Val Tyr Leu Leu Phe
610                 615                 620 atg atc ggc tac gct tca gcc ctg gtc tcc ctc ctg aac ccg tgt gcc                 1920
Met Ile Gly Tyr Ala Ser Ala Leu Val Ser Leu Leu Asn Pro Cys Ala
625                 630                 635                 640 aac atg aag gtg tgc aat gag gac cag acc aac tgc aca gtg ccc act                 1968
Asn Met Lys Val Cys Asn Glu Asp Gln Thr Asn Cys Thr Val Pro Thr
                645                 650                 655
```

-continued

```
tac ccc tcg tgc cgt gac agc gag acc ttc agc acc ttc ctc ctg gac    2016
Tyr Pro Ser Cys Arg Asp Ser Glu Thr Phe Ser Thr Phe Leu Leu Asp
        660                 665                 670 ctg ttt aag ctg acc atc ggc atg ggc gac ctg gag atg ctg agc agc    2064
Leu Phe Lys Leu Thr Ile Gly Met Gly Asp Leu Glu Met Leu Ser Ser
675                 680                 685 acc aag tac ccc gtg gtc ttc atc atc ctg ctg gtg acc tac atc atc    2112
Thr Lys Tyr Pro Val Val Phe Ile Ile Leu Leu Val Thr Tyr Ile Ile
        690                 695                 700 ctc acc ttt gtg ctg ctc ctc aac atg ctc att gcc ctc atg ggc gag    2160
Leu Thr Phe Val Leu Leu Leu Asn Met Leu Ile Ala Leu Met Gly Glu
705                 710                 715                 720 aca gtg ggc cag gtc tcc aag gag agc aag cac atc tgg aag ctg cag    2208
Thr Val Gly Gln Val Ser Lys Glu Ser Lys His Ile Trp Lys Leu Gln
                725                 730                 735 tgg gcc acc acc atc ctg gac att gag cgc tcc ttc ccc gta ttc ctg    2256
Trp Ala Thr Thr Ile Leu Asp Ile Glu Arg Ser Phe Pro Val Phe Leu
            740                 745                 750 agg aag gcc ttc cgc tct ggg gag atg gtc acc gtg ggc aag agc tcg    2304
Arg Lys Ala Phe Arg Ser Gly Glu Met Val Thr Val Gly Lys Ser Ser
        755                 760                 765 gac ggc act cct gac cgc agg tgg tgc ttc agg gtg gat gag gtg aac    2352
Asp Gly Thr Pro Asp Arg Arg Trp Cys Phe Arg Val Asp Glu Val Asn
770                 775                 780 tgg tct cac tgg aac cag aac ttg ggc atc atc aac gag gac ccg ggc    2400
Trp Ser His Trp Asn Gln Asn Leu Gly Ile Ile Asn Glu Asp Pro Gly
785                 790                 795                 800 aag aat gag acc tac cag tat tat ggc ttc tcg cat acc gtg ggc cgc    2448
Lys Asn Glu Thr Tyr Gln Tyr Tyr Gly Phe Ser His Thr Val Gly Arg
                805                 810                 815 ctc cgc agg gat cgc tgg tcc tcg gtg gta ccc cgc gtg gtg gaa ctg    2496
Leu Arg Arg Asp Arg Trp Ser Ser Val Val Pro Arg Val Val Glu Leu
            820                 825                 830 aac aag aac tcg aac ccg gac gag gtg gtg gtg cct ctg gac agc atg    2544
Asn Lys Asn Ser Asn Pro Asp Glu Val Val Val Pro Leu Asp Ser Met
        835                 840                 845 ggg aac ccc cgc tgc gat ggc cac cag cag ggt tac ccc cgc aag tgg    2592
Gly Asn Pro Arg Cys Asp Gly His Gln Gln Gly Tyr Pro Arg Lys Trp
850                 855                 860 agg act gag gac gcc ccg ctc tag                                    2616
Arg Thr Glu Asp Ala Pro Leu *
865                 870
```

<210> SEQ ID NO 17
<211> LENGTH: 871
<212> TYPE: PRT
<213> ORGANISM: Homo sapiens

<400> SEQUENCE: 17

```
Met Ala Asp Ser Ser Glu Gly Pro Arg Ala Gly Pro Gly Glu Val Ala
 1               5                  10                  15

Glu Leu Pro Gly Asp Glu Ser Gly Thr Pro Gly Gly Glu Ala Phe Pro
            20                  25                  30

Leu Ser Ser Leu Ala Asn Leu Phe Glu Gly Glu Asp Gly Ser Leu Ser
        35                  40                  45

Pro Ser Pro Ala Asp Ala Ser Arg Pro Ala Gly Pro Gly Asp Gly Arg
    50                  55                  60

Pro Asn Leu Arg Met Lys Phe Gln Gly Ala Phe Arg Lys Gly Val Pro
65                  70                  75                  80
```

```
Asn Pro Ile Asp Leu Leu Glu Ser Thr Leu Tyr Glu Ser Ser Val Val
                85                  90                  95

Pro Gly Pro Lys Lys Ala Pro Met Asp Ser Leu Phe Asp Tyr Gly Thr
            100                 105                 110

Tyr Arg His His Ser Ser Asp Asn Lys Arg Trp Arg Lys Lys Ile Ile
        115                 120                 125

Glu Lys Gln Pro Gln Ser Pro Lys Ala Pro Ala Pro Gln Pro Pro Pro
130                 135                 140

Ile Leu Lys Val Phe Asn Arg Pro Ile Leu Phe Asp Ile Val Ser Arg
145                 150                 155                 160

Gly Ser Thr Ala Asp Leu Asp Gly Leu Leu Pro Phe Leu Leu Thr His
                165                 170                 175

Lys Lys Arg Leu Thr Asp Glu Glu Phe Arg Glu Pro Ser Thr Gly Lys
            180                 185                 190

Thr Cys Leu Pro Lys Ala Leu Leu Asn Leu Ser Asn Gly Arg Asn Asp
        195                 200                 205

Thr Ile Pro Val Leu Leu Asp Ile Ala Glu Arg Thr Gly Asn Met Arg
210                 215                 220

Glu Phe Ile Asn Ser Pro Phe Arg Asp Ile Tyr Tyr Arg Gly Gln Thr
225                 230                 235                 240

Ala Leu His Ile Ala Ile Glu Arg Arg Cys Lys His Tyr Val Glu Leu
                245                 250                 255

Leu Val Ala Gln Gly Ala Asp Val His Ala Gln Ala Arg Gly Arg Phe
            260                 265                 270

Phe Gln Pro Lys Asp Glu Gly Gly Tyr Phe Tyr Phe Gly Glu Leu Pro
        275                 280                 285

Leu Ser Leu Ala Ala Cys Thr Asn Gln Pro His Ile Val Asn Tyr Leu
290                 295                 300

Thr Glu Asn Pro His Lys Lys Ala Asp Met Arg Arg Gln Asp Ser Arg
305                 310                 315                 320

Gly Asn Thr Val Leu His Ala Leu Val Ala Ile Ala Asp Asn Thr Arg
                325                 330                 335

Glu Asn Thr Lys Phe Val Thr Lys Met Tyr Asp Leu Leu Leu Leu Lys
            340                 345                 350

Cys Ala Arg Leu Phe Pro Asp Ser Asn Leu Glu Ala Val Leu Asn Asn
        355                 360                 365

Asp Gly Leu Ser Pro Leu Met Met Ala Ala Lys Thr Gly Lys Ile Gly
370                 375                 380

Ile Phe Gln His Ile Ile Arg Arg Glu Val Thr Asp Glu Asp Thr Arg
385                 390                 395                 400

His Leu Ser Arg Lys Phe Lys Asp Trp Ala Tyr Gly Pro Val Tyr Ser
                405                 410                 415

Ser Leu Tyr Asp Leu Ser Ser Leu Asp Thr Cys Gly Glu Glu Ala Ser
            420                 425                 430

Val Leu Glu Ile Leu Val Tyr Asn Ser Lys Ile Glu Asn Arg His Glu
        435                 440                 445

Met Leu Ala Val Glu Pro Ile Asn Glu Leu Leu Arg Asp Lys Trp Arg
450                 455                 460

Lys Phe Gly Ala Val Ser Phe Tyr Ile Asn Val Val Ser Tyr Leu Cys
465                 470                 475                 480

Ala Met Val Ile Phe Thr Leu Thr Ala Tyr Tyr Gln Pro Leu Glu Gly
                485                 490                 495

Thr Pro Pro Tyr Pro Tyr Arg Thr Thr Val Asp Tyr Leu Arg Leu Ala
```

```
                    500                 505                 510
Gly Glu Val Ile Thr Leu Phe Thr Gly Val Leu Phe Phe Thr Asn
            515                 520                 525
Ile Lys Asp Leu Phe Met Lys Lys Cys Pro Gly Val Asn Ser Leu Phe
            530                 535                 540
Ile Asp Gly Ser Phe Gln Leu Leu Tyr Phe Ile Tyr Ser Val Leu Val
545                 550                 555                 560
Ile Val Ser Ala Ala Leu Tyr Leu Ala Gly Ile Glu Ala Tyr Leu Ala
                565                 570                 575
Val Met Val Phe Ala Leu Val Leu Gly Trp Met Asn Ala Leu Tyr Phe
            580                 585                 590
Thr Arg Gly Leu Lys Leu Thr Gly Thr Tyr Ser Ile Met Ile Gln Lys
            595                 600                 605
Ile Leu Phe Lys Asp Leu Phe Arg Phe Leu Leu Val Tyr Leu Leu Phe
            610                 615                 620
Met Ile Gly Tyr Ala Ser Ala Leu Val Ser Leu Leu Asn Pro Cys Ala
625                 630                 635                 640
Asn Met Lys Val Cys Asn Glu Asp Gln Thr Asn Cys Thr Val Pro Thr
                645                 650                 655
Tyr Pro Ser Cys Arg Asp Ser Glu Thr Phe Ser Thr Phe Leu Leu Asp
                660                 665                 670
Leu Phe Lys Leu Thr Ile Gly Met Gly Asp Leu Glu Met Leu Ser Ser
            675                 680                 685
Thr Lys Tyr Pro Val Val Phe Ile Ile Leu Leu Val Thr Tyr Ile Ile
            690                 695                 700
Leu Thr Phe Val Leu Leu Leu Asn Met Leu Ile Ala Leu Met Gly Glu
705                 710                 715                 720
Thr Val Gly Gln Val Ser Lys Glu Ser Lys His Ile Trp Lys Leu Gln
                725                 730                 735
Trp Ala Thr Thr Ile Leu Asp Ile Glu Arg Ser Phe Pro Val Phe Leu
                740                 745                 750
Arg Lys Ala Phe Arg Ser Gly Glu Met Val Thr Val Gly Lys Ser Ser
            755                 760                 765
Asp Gly Thr Pro Asp Arg Arg Trp Cys Phe Arg Val Asp Glu Val Asn
            770                 775                 780
Trp Ser His Trp Asn Gln Asn Leu Gly Ile Ile Asn Glu Asp Pro Gly
785                 790                 795                 800
Lys Asn Glu Thr Tyr Gln Tyr Tyr Gly Phe Ser His Thr Val Gly Arg
                805                 810                 815
Leu Arg Arg Asp Arg Trp Ser Ser Val Val Pro Arg Val Val Glu Leu
                820                 825                 830
Asn Lys Asn Ser Asn Pro Asp Glu Val Val Val Pro Leu Asp Ser Met
            835                 840                 845
Gly Asn Pro Arg Cys Asp Gly His Gln Gln Gly Tyr Pro Arg Lys Trp
            850                 855                 860
Arg Thr Glu Asp Ala Pro Leu
865                 870

<210> SEQ ID NO 18
<211> LENGTH: 2613
<212> TYPE: DNA
<213> ORGANISM: Artificial Sequence
<220> FEATURE:
<221> NAME/KEY: CDS
<222> LOCATION: (1)...(2613)
```

<223> OTHER INFORMATION: Generic sequence that encompasses all
        nucleotide sequences that encode human TRPV4 having amino acid
        sequence as shown in SEQ ID NO:17
<220> FEATURE:
<221> NAME/KEY: misc_feature
<222> LOCATION: 12,15,69,102,105,138,144,150,165,264,279,282,318,351,
        354,402,477,486,567,609,687,870,957,1080,1116,1209,1248,1251,1266,
        1269,1296,1323,1410,1431,1626,1644,1671,1689,1809,1890,1902,1977,
        1989,2001,2061,2064,2178,2187,2241,2274,2301,2304,2358,2433,2469,
        22508,2541
<223> OTHER INFORMATION: n = A,T,C or G if after TC;
        n = T or C if after AG
<220> FEATURE:
<221> NAME/KEY: misc_feature
<222> LOCATION: 27,168,192,204,228,342,366,372,453,480,537,558,618,657,
        672,696,711,744,747,807,813,945,948,960,1008,1065,1173,1176,1200,
        1212,1338,1380,1392,1509,1530,1782,1848,1983,2238,2259,2271,2322,
        2337,2448,2454,2457,2463,2484,2556,2586,2595
<223> OTHER INFORMATION: n = A,T,C or G if after CG;
        n = A or G if after AG
<220> FEATURE:
<221> NAME/KEY: misc_feature
<222> LOCATION: all "n" not specified above
<223> OTHER INFORMATION: n = A,T,C or G

<400> SEQUENCE: 18

```
atg gcn gay wsn wsn gar ggn ccn mgn gcn ggn ccn ggn gar gtn gcn      48
Met Ala Asp Ser Ser Glu Gly Pro Arg Ala Gly Pro Gly Glu Val Ala
 1               5                  10                  15 gar ytn ccn ggn gay gar wsn ggn acn ccn ggn ggn gar gcn tty ccn      96
Glu Leu Pro Gly Asp Glu Ser Gly Thr Pro Gly Gly Glu Ala Phe Pro
             20                  25                  30 ytn wsn wsn ytn gcn aay ytn tty gar ggn gar gay ggn wsn ytn wsn     144
Leu Ser Ser Leu Ala Asn Leu Phe Glu Gly Glu Asp Gly Ser Leu Ser
         35                  40                  45 ccn wsn ccn gcn gay gcn wsn mgn ccn gcn ggn ccn ggn gay ggn mgn     192
Pro Ser Pro Ala Asp Ala Ser Arg Pro Ala Gly Pro Gly Asp Gly Arg
     50                  55                  60 ccn aay ytn mgn atg aar tty car ggn gcn tty mgn aar ggn gtn ccn     240
Pro Asn Leu Arg Met Lys Phe Gln Gly Ala Phe Arg Lys Gly Val Pro
 65                  70                  75                  80 aay ccn ath gay ytn ytn gar wsn acn ytn tay gar wsn wsn gtn gtn     288
Asn Pro Ile Asp Leu Leu Glu Ser Thr Leu Tyr Glu Ser Ser Val Val
                 85                  90                  95 ccn ggn ccn aar aar gcn ccn atg gay wsn ytn tty gay tay ggn acn     336
Pro Gly Pro Lys Lys Ala Pro Met Asp Ser Leu Phe Asp Tyr Gly Thr
            100                 105                 110 tay mgn cay cay wsn wsn gay aay aar mgn tgg mgn aar aar ath ath     384
Tyr Arg His His Ser Ser Asp Asn Lys Arg Trp Arg Lys Lys Ile Ile
        115                 120                 125 gar aar car ccn car wsn ccn aar gcn ccn gcn ccn car ccn ccn ccn     432
Glu Lys Gln Pro Gln Ser Pro Lys Ala Pro Ala Pro Gln Pro Pro Pro
    130                 135                 140 ath ytn aar gtn tty aay mgn ccn ath ytn tty gay ath gtn wsn mgn     480
Ile Leu Lys Val Phe Asn Arg Pro Ile Leu Phe Asp Ile Val Ser Arg
145                 150                 155                 160 ggn wsn acn gcn gay ytn gay ggn ytn ytn ccn tty ytn ytn acn cay     528
Gly Ser Thr Ala Asp Leu Asp Gly Leu Leu Pro Phe Leu Leu Thr His
                165                 170                 175 aar aar mgn ytn acn gay gar gar tty mgn gar ccn wsn acn ggn aar     576
Lys Lys Arg Leu Thr Asp Glu Glu Phe Arg Glu Pro Ser Thr Gly Lys
            180                 185                 190 acn tgy ytn ccn aar gcn ytn ytn aay ytn wsn aay ggn mgn aay gay     624
Thr Cys Leu Pro Lys Ala Leu Leu Asn Leu Ser Asn Gly Arg Asn Asp
        195                 200                 205
```

```
acn ath ccn gtn ytn gay ath gcn gar mgn ac

| | | | | | | | | | | | | | | | |
|---|---|---|---|---|---|---|---|---|---|---|---|---|---|---|---|
| ath | aar | gay | ytn | tty | atg | aar | aar | tgy | ccn | ggn | gtn | aay | wsn | ytn | tty |
| Ile | Lys | Asp | Leu | Phe | Met | Lys | Lys | Cys | Pro | Gly | Val | Asn | Ser | Leu | Phe |
| | | | | 530 | | | | 535 | | | | 540 | | | |

1632

| | | | | | | | | | | | | | | | |
|---|---|---|---|---|---|---|---|---|---|---|---|---|---|---|---|
| ath | gay | ggn | wsn | tty | car | ytn | ytn | tay | tty | ath | tay | wsn | gtn | ytn | gtn |
| Ile | Asp | Gly | Ser | Phe | Gln | Leu | Leu | Tyr | Phe | Ile | Tyr | Ser | Val | Leu | Val |
| 545 | | | | | 550 | | | | 555 | | | | | 560 | |

1680

| | | | | | | | | | | | | | | | |
|---|---|---|---|---|---|---|---|---|---|---|---|---|---|---|---|
| ath | gtn | wsn | gcn | gcn | ytn | tay | ytn | gcn | ggn | ath | gar | gcn | tay | ytn | gcn |
| Ile | Val | Ser | Ala | Ala | Leu | Tyr | Leu | Ala | Gly | Ile | Glu | Ala | Tyr | Leu | Ala |
| | | | | 565 | | | | | 570 | | | | | 575 | |

1728

| | | | | | | | | | | | | | | | |
|---|---|---|---|---|---|---|---|---|---|---|---|---|---|---|---|
| gtn | atg | gtn | tty | gcn | ytn | gtn | ytn | ggn | tgg | atg | aay | gcn | ytn | tay | tty |
| Val | Met | Val | Phe | Ala | Leu | Val | Leu | Gly | Trp | Met | Asn | Ala | Leu | Tyr | Phe |
| | | | 580 | | | | | 585 | | | | | 590 | | |

1776

| | | | | | | | | | | | | | | | |
|---|---|---|---|---|---|---|---|---|---|---|---|---|---|---|---|
| acn | mgn | ggn | ytn | aar | ytn | acn | ggn | acn | tay | wsn | ath | atg | ath | car | aar |
| Thr | Arg | Gly | Leu | Lys | Leu | Thr | Gly | Thr | Tyr | Ser | Ile | Met | Ile | Gln | Lys |
| | | | 595 | | | | 600 | | | | | 605 | | | |

1824

| | | | | | | | | | | | | | | | |
|---|---|---|---|---|---|---|---|---|---|---|---|---|---|---|---|
| ath | ytn | tty | aar | gay | ytn | tty | mgn | tty | ytn | ytn | gtn | tay | ytn | ytn | tty |
| Ile | Leu | Phe | Lys | Asp | Leu | Phe | Arg | Phe | Leu | Leu | Val | Tyr | Leu | Leu | Phe |
| 610 | | | | | 615 | | | | | 620 | | | | | |

1872

| | | | | | | | | | | | | | | | |
|---|---|---|---|---|---|---|---|---|---|---|---|---|---|---|---|
| atg | ath | ggn | tay | gcn | wsn | gcn | ytn | gtn | wsn | ytn | ytn | aay | ccn | tgy | gcn |
| Met | Ile | Gly | Tyr | Ala | Ser | Ala | Leu | Val | Ser | Leu | Leu | Asn | Pro | Cys | Ala |
| 625 | | | | | 630 | | | | | 635 | | | | | 640 |

1920

| | | | | | | | | | | | | | | | |
|---|---|---|---|---|---|---|---|---|---|---|---|---|---|---|---|
| aay | atg | aar | gtn | tgy | aay | gar | gay | car | acn | aay | tgy | acn | gtn | ccn | acn |
| Asn | Met | Lys | Val | Cys | Asn | Glu | Asp | Gln | Thr | Asn | Cys | Thr | Val | Pro | Thr |
| | | | | 645 | | | | | 650 | | | | | 655 | |

1968

| | | | | | | | | | | | | | | | |
|---|---|---|---|---|---|---|---|---|---|---|---|---|---|---|---|
| tay | ccn | wsn | tgy | mgn | gay | wsn | gar | acn | tty | wsn | acn | tty | ytn | ytn | gay |
| Tyr | Pro | Ser | Cys | Arg | Asp | Ser | Glu | Thr | Phe | Ser | Thr | Phe | Leu | Leu | Asp |
| | | | 660 | | | | | 665 | | | | | 670 | | |

2016

| | | | | | | | | | | | | | | | |
|---|---|---|---|---|---|---|---|---|---|---|---|---|---|---|---|
| ytn | tty | aar | ytn | acn | ath | ggn | atg | ggn | gay | ytn | gar | atg | ytn | wsn | wsn |
| Leu | Phe | Lys | Leu | Thr | Ile | Gly | Met | Gly | Asp | Leu | Glu | Met | Leu | Ser | Ser |
| | | 675 | | | | | 680 | | | | | 685 | | | |

2064

| | | | | | | | | | | | | | | | |
|---|---|---|---|---|---|---|---|---|---|---|---|---|---|---|---|
| acn | aar | tay | ccn | gtn | gtn | tty | ath | ath | ytn | ytn | gtn | acn | tay | ath | ath |
| Thr | Lys | Tyr | Pro | Val | Val | Phe | Ile | Ile | Leu | Leu | Val | Thr | Tyr | Ile | Ile |
| 690 | | | | | 695 | | | | | 700 | | | | | |

2112

| | | | | | | | | | | | | | | | |
|---|---|---|---|---|---|---|---|---|---|---|---|---|---|---|---|
| ytn | acn | tty | gtn | ytn | ytn | ytn | aay | atg | ytn | ath | gcn | ytn | atg | ggn | gar |
| Leu | Thr | Phe | Val | Leu | Leu | Leu | Asn | Met | Leu | Ile | Ala | Leu | Met | Gly | Glu |
| 705 | | | | | 710 | | | | | 715 | | | | | 720 |

2160

| | | | | | | | | | | | | | | | |
|---|---|---|---|---|---|---|---|---|---|---|---|---|---|---|---|
| acn | gtn | ggn | car | gtn | wsn | aar | gar | wsn | aar | cay | ath | tgg | aar | ytn | car |
| Thr | Val | Gly | Gln | Val | Ser | Lys | Glu | Ser | Lys | His | Ile | Trp | Lys | Leu | Gln |
| | | | | 725 | | | | | 730 | | | | | 735 | |

2208

| | | | | | | | | | | | | | | | |
|---|---|---|---|---|---|---|---|---|---|---|---|---|---|---|---|
| tgg | gcn | acn | acn | ath | ytn | gay | ath | gar | mgn | wsn | tty | ccn | gtn | tty | ytn |
| Trp | Ala | Thr | Thr | Ile | Leu | Asp | Ile | Glu | Arg | Ser | Phe | Pro | Val | Phe | Leu |
| | | | 740 | | | | | 745 | | | | | 750 | | |

2256

| | | | | | | | | | | | | | | | |
|---|---|---|---|---|---|---|---|---|---|---|---|---|---|---|---|
| mgn | aar | gcn | tty | mgn | wsn | ggn | gar | atg | gtn | acn | gtn | ggn | aar | wsn | wsn |
| Arg | Lys | Ala | Phe | Arg | Ser | Gly | Glu | Met | Val | Thr | Val | Gly | Lys | Ser | Ser |
| | | 755 | | | | | 760 | | | | | 765 | | | |

2304

| | | | | | | | | | | | | | | | |
|---|---|---|---|---|---|---|---|---|---|---|---|---|---|---|---|
| gay | ggn | acn | ccn | gay | mgn | mgn | tgg | tgy | tty | mgn | gtn | gay | gar | gtn | aay |
| Asp | Gly | Thr | Pro | Asp | Arg | Arg | Trp | Cys | Phe | Arg | Val | Asp | Glu | Val | Asn |
| | | 770 | | | | | 775 | | | | | 780 | | | |

2352

| | | | | | | | | | | | | | | | |
|---|---|---|---|---|---|---|---|---|---|---|---|---|---|---|---|
| tgg | wsn | cay | tgg | aay | car | aay | ytn | ggn | ath | ath | aay | gar | gay | ccn | ggn |
| Trp | Ser | His | Trp | Asn | Gln | Asn | Leu | Gly | Ile | Ile | Asn | Glu | Asp | Pro | Gly |
| 785 | | | | | 790 | | | | | 795 | | | | | 800 |

2400

| | | | | | | | | | | | | | | | |
|---|---|---|---|---|---|---|---|---|---|---|---|---|---|---|---|
| aar | aay | gar | acn | tay | car | tay | tay | ggn | tty | wsn | cay | acn | gtn | ggn | mgn |
| Lys | Asn | Glu | Thr | Tyr | Gln | Tyr | Tyr | Gly | Phe | Ser | His | Thr | Val | Gly | Arg |
| | | | | 805 | | | | | 810 | | | | | 815 | |

2448

| | | | | | | | | | | | | | | | |
|---|---|---|---|---|---|---|---|---|---|---|---|---|---|---|---|
| ytn | mgn | mgn | gay | mgn | tgg | wsn | wsn | gtn | gtn | ccn | mgn | gtn | gtn | gar | ytn |
| Leu | Arg | Arg | Asp | Arg | Trp | Ser | Ser | Val | Val | Pro | Arg | Val | Val | Glu | Leu |
| | | | 820 | | | | | 825 | | | | | 830 | | |

2496

| | | | | | | | | | | | | | | | |
|---|---|---|---|---|---|---|---|---|---|---|---|---|---|---|---|
| aay | aar | aay | wsn | aay | ccn | gay | gar | gtn | gtn | gtn | ccn | ytn | gay | wsn | atg |
| Asn | Lys | Asn | Ser | Asn | Pro | Asp | Glu | Val | Val | Val | Pro | Leu | Asp | Ser | Met |

2544

-continued

```
                   835                 840                 845
ggn aay ccn mgn tgy gay ggn cay car car ggn tay ccn mgn aar tgg      2592
Gly Asn Pro Arg Cys Asp Gly His Gln Gln Gly Tyr Pro Arg Lys Trp
    850                 855                 860 mgn acn gar gay gcn ccn ytn                                          2613
Arg Thr Glu Asp Ala Pro Leu
865                 870

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide probe that hybridizes to mouse
      TRPV3-encoding nucleic acid

<400> SEQUENCE: 19
tgacatgatc ctgctgagga gtg                                              23

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 20
acgaggcagg cgaggtattc tt                                               22

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 21
cagcgtatgc agaggctcca gggtcag                                          27

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 22
ttgaagtcct cagccaccgt cacca                                            25

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
caccagcgcg tgcaggatgt                                                  20

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide primer
```

```
<400> SEQUENCE: 24
tcgttctcct cagcgaaggc aagcaga                                27

<210> SEQ ID NO 25
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 25
ccttctatct ccaggaagaa gtgtgc                                 26

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 26
gtcaccagcg cgtgcaggat gttgt                                  25

<210> SEQ ID NO 27
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 27
aggcccatac gcccagtccg tgaac                                  25

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 28
catgcccata gactggaagc c                                      21

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 29
gatggcgatg ttcagcgctg tctgc                                  25

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 30
gctgccaaga tgggcaaggc tgaga                                  25

<210> SEQ ID NO 31
<211> LENGTH: 24
```

```
<212> TYPE: DNA
<213> ORGANISM: Artificial Sequence
<220> FEATURE:
<223> OTHER INFORMATION: Oligonucleotide primer

<400> SEQUENCE: 31
cctgggctgg gcgaacatgc tcta                                    24

<210> SEQ ID NO 32
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 32
gcgccagatg cgttcacttt ctttgga                                 27

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 33
tgacatgatc ctgctgagga gtg                                     23

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 34
acgaggcagg cgaggtattc tt                                      22

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 35
tccaagctgt gcttgtgata                                         20

<210> SEQ ID NO 36
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 36
cttgagcatg tagtttcaca caaa                                    24

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 37
```
gtgttttcca ttccgtccac                                              20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 38
cgacgtttct gggaattcat                                              20

<210> SEQ ID NO 39
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 39
cttgagcatg tagtttcaca caaa                                         24

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 40
tcctcctcct caacatgctc                                              20

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 41
tggaaatcaa aacagtattt caatg                                        25

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 42
ctcttcaagc tcaccatagg c                                            21

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 43
cgacgtttct gggaattcat                                              20

<210> SEQ ID NO 44
<211> LENGTH: 20
<212> TYPE: DNA
<213> ORGANISM: Artificial Sequence

```
<220> FEATURE:
<223> OTHER INFORMATION: Oligonucleotide primer

<400> SEQUENCE: 44
gtgttttcca ttccgtccac                                               20

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 45
ccctctgtta ccgcagacac                                               20

<210> SEQ ID NO 46
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 46
actccagcct gggtgaca                                                 18

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 47
atggtctcca gctcccagtt                                               20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 48
aggaggacga aggtgaggat                                               20

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 49
agcctcaggt ctgaagtgga                                               20

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 50
gccagatgcg ttcactttct                                               20
```

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 51
ggcaaatttc ttccatttcg                                              20

<210> SEQ ID NO 52
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 52
agatgcgttc gctctcctt                                               19

<210> SEQ ID NO 53
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 53
tgcacacttc ttcctggaga t                                            21

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 54
ttcctcatgc acaagctgac                                              20

<210> SEQ ID NO 55
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 55
tcttcctgga gatagaaggg att                                          23

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 56
cgatgatttc cagcacagag                                              20

<210> SEQ ID NO 57
<211> LENGTH: 23
<212> TYPE: DNA
<213> ORGANISM: Artificial Sequence
<220> FEATURE:
<223> OTHER INFORMATION: Oligonucleotide primer

```
<400> SEQUENCE: 57
ctcaccaatg tagacacaac gac                                              23

<210> SEQ ID NO 58
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 58
taccagcatg aaggcttcta ttt                                              23

<210> SEQ ID NO 59
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 59
ataagcactg ctgtgatgtc tcc                                              23

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 60
gtcagcttgt gcatgaggaa                                                  20

<210> SEQ ID NO 61
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 61
tgacagagac cccatccaat cccaaca                                          27

<210> SEQ ID NO 62
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 62
ctcttgtgat atggctttct gg                                               22

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 63
gagaaggagt gggtgagctg                                                  20

<210> SEQ ID NO 64
```

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 64
ccttctccca gagtccacag                                                   20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 65
agcaggcagg aaaatgagag                                                   20

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 66
ccaaagatgg tccagaaagc                                                   20

<210> SEQ ID NO 67
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 67
ctcttgtgat atggctttct gg                                                22

<210> SEQ ID NO 68
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 68
aactgtgatg acatggactc tcccccag                                          28

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 69
aactgtgatg acatggactc                                                   20

<210> SEQ ID NO 70
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 70
```
caggatgatg tgacagagac cccatc      26

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 71
atgatcctgc tgaggagtgg      20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 72
aggatgacac aggcccatac      20

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 73
atcctcacct tcgtcctcct      20

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 74
cattccgtcc acttcacctc      20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 75
tggttttgct gttgttcctg      20

<210> SEQ ID NO 76
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 76
catgtaaatc aacgcagaag tca      23

<210> SEQ ID NO 77
<211> LENGTH: 20
<212> TYPE: PRT

```
<213> ORGANISM: Mus musculus

<400> SEQUENCE: 77

Cys Asp Asp Met Asp Ser Pro Gln Ser Pro Gln Asp Asp Val Thr Glu
 1               5                  10                  15

Thr Pro Ser Asn
            20

<210> SEQ ID NO 78
<211> LENGTH: 14
<212> TYPE: PRT
<213> ORGANISM: Mus musculus

<400> SEQUENCE: 78

Lys Ile Gln Asp Ser Ser Arg Ser Asn Ser Lys Thr Thr Leu
 1               5                  10

<210> SEQ ID NO 79
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 79
ctcatgcaca agctgacagc ct                                          22

<210> SEQ ID NO 80
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 80
aggcctcttc cgtgtactca gcgttg                                      26

<210> SEQ ID NO 81
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 81
atctggcacc acaccttcta caa                                         23

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 82
gccagccagg tccagacgca                                             20

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 83
```
ctcatgcaca agctgacagc ct                                           22

<210> SEQ ID NO 84
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 84
aggcctcttc cgtgtactca gcgttg                                       26

<210> SEQ ID NO 85
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 85
ccctgggctg ggcgaacatg ctcta                                        25

<210> SEQ ID NO 86
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 86
cttggcagcc atcatgagag gcgaa                                        25

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 87
gcagtggtaa caacgcagag                                              20

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 88
aggtcagatc tgtggcaggt                                              20

<210> SEQ ID NO 89
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 89
cgtgaggtga cagatgagga                                              20

<210> SEQ ID NO 90
<211> LENGTH: 20
<212> TYPE: DNA
<213> ORGANISM: Artificial Sequence

```
<220> FEATURE:
<223> OTHER INFORMATION: Oligonucleotide primer

<400> SEQUENCE: 90
ccagtatggc agatcctggt                                              20

<210> SEQ ID NO 91
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 91
atggcagatc ctggtgatg                                               19

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 92
cccaggcact actgaggact                                              20

<210> SEQ ID NO 93
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 93
agggctacgc tcccaagt                                                18

<210> SEQ ID NO 94
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 94
gtgctggctt aggtgactcc                                              20

<210> SEQ ID NO 95
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 95
tgaggatgac ataggtgatg ag                                           22

<210> SEQ ID NO 96
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 96
ccaaggacaa aaaggactgc                                              20
```

```
<210> SEQ ID NO 97
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 97
caagtttgtc cgcctctttc                                              20

<210> SEQ ID NO 98
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 98
aactgtctgg agctggcagt                                              20

<210> SEQ ID NO 99
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 99
caagtttgtc cgcctctttc                                              20

<210> SEQ ID NO 100
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 100
actgccagct ccagacagtt                                              20

<210> SEQ ID NO 101
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 101
ccttcgatgt gctggctctg ggcataa                                      27

<210> SEQ ID NO 102
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 102
ccttgccttt cttccccaga gtctcaa                                      27

<210> SEQ ID NO 103
<211> LENGTH: 25
<212> TYPE: DNA
<213> ORGANISM: Artificial Sequence
<220> FEATURE:
<223> OTHER INFORMATION: Oligonucleotide primer
```

<400> SEQUENCE: 103
gcaaagtttt tggctccacc cgtca 25

<210> SEQ ID NO 104
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 104
gccagtgctg ggtcagcagt tcgta 25

<210> SEQ ID NO 105
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 105
ttcaggaggt catgttcacg gctctca 27

<210> SEQ ID NO 106
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 106
gtaccggaac ctgcagatcg ccaaga 26

<210> SEQ ID NO 107
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 107
gcaagatccc ttgtgtggtg gtgga 25

<210> SEQ ID NO 108
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 108
cagcctggtg gaggtggagg atgtt 25

<210> SEQ ID NO 109
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 109
cggaacctgc agatcgccaa gaact 25

<210> SEQ ID NO 110

```
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 110
gcgtggccag acagggatc ctaag                                              25

<210> SEQ ID NO 111
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 111
ccacacagca aagaggaaca                                                   20

<210> SEQ ID NO 112
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 112
ggagccgcag aaatggtact                                                   20

<210> SEQ ID NO 113
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 113
tctcattggc ctcatttctg                                                   20

<210> SEQ ID NO 114
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 114
atatgagacc cgagcagtgg                                                   20
```

TRANSIENT RECEPTOR POTENTIAL CHANNEL TRPV3 AND ITS USE

CROSS-REFERENCE TO RELATED APPLICATIONS

This patent application is a continuation of U.S. patent application Ser. No. 10/171,319 filed on Jun. 13, 2002 issued as U.S. Pat. No. 7,115,414. U.S. patent application Ser. No. 10/171,319 in turn claims the benefit of priority to U.S. Provisional Application No. 60/297,835 filed on Jun. 13, 2001, U.S. Provisional Application No. 60/351,238, filed on Jan. 22, 2002, U.S. Provisional Application No. 60/352,914, filed on Jan. 29, 2002, U.S. Provisional Application No. 60/357,161, filed on Feb. 12, 2002, U.S. Provisional Application No. 60/381,086, filed on May 15, 2002, and U.S. Provisional Application No. 60/381,739, filed on May 16, 2002. These previously filed patent applications are incorporated herein by reference in their entirety and for all purposes.

COPYRIGHT NOTIFICATION

Pursuant to 37 C.F.R. 1.71(e), a portion of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention pertains to novel vanilloid receptor (VR) related nucleic acids and polypeptides. In particular, the invention relates to proteins that are homologous to known VRs, nucleic acids encoding such proteins, identification of trkA$^+$ pain-specific genes, and the use of these genes and polypeptides in methods of diagnosing pain, methods of identifying compounds useful in treating pain and methods of treating pain.

2. Background

Pain has been defined as the sensory experience perceived by nerve tissue distinct from sensations of touch, pressure, heat and cold. Individuals suffering from pain typically describe it by such terms as bright, dull, aching, pricking, cutting, burning, etc. This range of sensations, as well as the variation in perception of pain by different individuals, makes a precise definition of pain difficult. Pain as suffering, however, is generally considered to include both the original sensation and the reaction to that sensation. Where pain results from the stimulation of nociceptive receptors and transmitted over intact neural pathways, this is termed nociceptive pain. Alternatively, pain may be caused by damage to neural structures, often manifesting itself as neural supersensitivity, and is referred to as neuropathic pain.

Neuropathic pain is a particular type of pain that has a complex and variable etiology. It is generally a chronic condition attributable to complete or partial transection of a nerve or trauma to a nerve plexus or soft tissue. This condition is characterized by hyperesthesia (enhanced sensitivity to a natural stimulus), hyperalgesia (abnormal sensitivity to pain), allodynia (widespread tenderness, characterized by hypersensitivity to tactile stimuli) and/or spontaneous burning pain. In humans, neuropathic pain tends to be chronic and debilitating, and occurs during conditions such as trigeminal neuralgia, diabetic neuropathy, post-herpetic neuralgia, late-stage cancer, amputation or physical nerve damage.

Most drugs including conventional opioids and antidepressants are not practical against chronic pain such as neuropathic pain, either because they are not effective or have serious side effects. For these reasons, alternate therapies for the management of chronic or neuropathic pain are widely sought.

Stimuli such as heat, cold, stretch, and pressure are detected by specialized sensory neurons within the Dorsal Root Ganglia (DRG). These neurons fire action potentials in response to these mechanical and thermal stimuli, although the molecular mechanism for such detection is not known. Recently, two channels, vanilloid receptor 1 (VR1) and vanilloid receptor-like protein 1 (VRL1), have been isolated from DRG that respond to different thresholds of high heat, and hence act as pain receptors. These channels belong to a family of TRP channels that in *C. elegans* and *D. melanogaster* are involved in mechano- and osmoregulation.

The VR1 is a calcium channel with six transmembrane domains and a putative pore domain. The channel can be activated by many distinct reagents, including heat, low pH (high proton concentration is present during injury and inflammation), and capsaicin (the active ingredient in hot chili peppers). The knockout of VR1 in mice has demonstrated that this channel plays a role in pain propagation; however, since the phenotype is rather subtle, it also implies that VR1 is not the sole receptor for high heat and pain. To date, one other homologue of VR1 is known in mammals—the VRL1. VRL1 is structurally very similar to VR1, but is expressed on DRG neurons that are not involved in pain reception (in contrast to VR1).

The somatic sensory neurons detect external stimuli such as heat, cold and noxious stimuli through the activation of thermal and mechanical receptors/channels. The VR family represents the first example of molecules expressed within the DRG that have such activation capabilities. Since these molecules are relatively specific to sensory neurons (for example, VR1 knockout mice do not have phenotypes outside of pain perception), they represent highly promising targets for developing drugs against pain or other thermal noxious stimuli. VR1 knockout mice have demonstrated that other molecules have to be involved in pain perception. However, despite the large amount of interest generated in the scientific community concerning this class of receptors, so far, no other receptors of this class have been identified.

In view of the role of the VR members in pain perception, the identification of new members of VR would allow the development of therapeutic candidates specifically designed to block these new TRP channels, which would enable the treatment of various disorders associated with chronic pain. In addition, the identification of new VR members would permit the screening of various drugs to identify those compounds suitable for further, in-depth studies of therapeutic applications.

SUMMARY OF THE INVENTION

The present invention relates to members of the VR family, in particular TRPV3 (previously known as VRLS, VRLX, VR4 and TRPV7), TRPV4 (previously known as VRL3 and OTRPC4) and TRPM8 (previously known as TRPX) nucleic acids and polypeptides, recombinant materials and methods for their production. In another aspect, the present invention relates to the identification of trkA$^+$ pain-specific genes expressed in the DRG. In yet another aspect, the present invention relates to methods for using the TRPV3, TRPV4, TRPM8 and trkA+ pain-specific nucleic acids and polypeptides, including methods for treating pain, inflammation, skin disorders and cancer, methods of diagnosing pain, inflammation, skin disorders and cancer, methods of identifying agents useful in the treatment of pain, inflammation, skin disorders and cancer and in methods of monitoring the efficacy of a treatment for pain, inflammation, skin disorders and cancer.

TRPV3

The invention provides isolated and/or purified TRPV3 nucleic acid molecules, such as: a) a polynucleotide that encodes a mouse TRPV3 protein comprising amino acid residues 1-791 of SEQ ID NO: 2; b) a polynucleotide that encodes a mouse TRPV3 protein comprising amino acid residues 2-791 of SEQ ID NO: 2; c) a polynucleotide that encodes a functional domain of a mouse TRPV3 protein; d) a polynucleotide that encodes a human TRPV3 protein comprising amino acid residues 1-791 of SEQ ID NO 5; e) a polynucleotide that encodes a human TRPV3 protein comprising amino acid residues 2-791 of SEQ ID NO 5; f) a polynucleotide that encodes a functional domain of a human TRPV3 protein; and g) a polynucleotide that is complementary to a polynucleotide of a) through f). In some embodiments, the nucleic acid molecule is a) or b) and comprises a first polynucleotide that is 80% or more identical to a second polynucleotide having a nucleotide sequence as set forth in SEQ ID NO: 3 (mouse TRPV3), or is d) or e) and comprises a first polynucleotide 80% or more identical to a second polynucleotide having a nucleotide sequence as set forth in SEQ ID NO: 6 (human TRPV3). The nucleic acids can be 90% or more, or 95% or more, identical to a second polynucleotide having a nucleotide sequence as set forth in SEQ ID NO: 3 or SEQ ID NO: 6, or can be identical to the respective polynucleotide. Examples of TRPV3 nucleic acids of the invention include polynucleotides that are 80% or more, 90% or more, or 95% or more, identical to a second polynucleotide having a nucleotide sequence as set forth in nucleotides 65-2440 of SEQ ID NO: 1 (mouse TRPV3) or nucleotides 57-2432 of SEQ ID NO: 4 (human TRPV3).

The invention also provides isolated TRPV3 nucleic acid molecules that encode polypeptides that include one or more functional domains of a mammalian (e.g., human or mouse) TRPV3 polypeptide. The polypeptides encoded by these nucleic acid molecules can include, for example, one or more functional domains such as ankyrin domains, transmembrane regions, pore loop regions, and coiled-coil domains. As an example, the polypeptides can include a pore loop region flanked by two transmembrane regions, and/or four ankyrin domains.

Also provided by the invention are isolated and/or purified TRPV3 polypeptides. Such polypeptides include, for example, a) a mouse TRPV3 protein comprising amino acid residues 1-791 of SEQ ID NO: 2; b) a mouse TRPV3 protein comprising amino acid residues 2-791 of SEQ ID NO: 2; c) one or more functional domains of a mouse TRPV3 protein; d) a human TRPV3 protein comprising amino acid residues 1-791 of SEQ ID NO 5; e) a human TRPV3 protein comprising amino acid residues 2-791 of SEQ ID NO 5; and f) one or more functional domains of a human TRPV3 protein. For example, the TRPV3 polypeptides can include one or more functional domains selected from the group consisting of an ankyrin domain, a transmembrane region, a pore loop region, and a coiled-coil domain. In some embodiments, the polypeptides include a pore loop region flanked by two transmembrane regions, and/or four ankyrin domains.

Methods for identifying an agent that modulates TRPV3-mediated cation passage through a membrane are also provided by the invention. These methods involve: a) providing a membrane that comprises a TRPV3 polypeptide; b) contacting the membrane with a candidate agent; and c) determining whether passage of one or more cations through the membrane is increased in the presence of the candidate agent compared to passage in the absence of the candidate agent. In some embodiments, the membrane is a cell membrane and cation passage through the membrane is detected by measuring cation influx or efflux across the membrane into or out of the cell. The assay is conducted at a temperature of at least 33° C., in some embodiments. Also provided are methods in which a candidate agent that reduces cation passage is further tested for ability to treat pain by administering the candidate agent to a test animal and determining whether the candidate agent decreases the test animal's response to a pain stimulus. A pain stimulus can include, for example exposure to a temperature above 33° C.

The invention also provides methods for reducing pain associated with TRPV3 activity. These methods involve administering to a subject suffering from pain an analgesically effective amount of a compound that reduces TRPV3-mediated cation passage through a membrane or reduces signal transduction from a TRPV3 polypeptide to a DRG neuron. The pain can be with, for example, one or more of heat exposure, inflammation, and tissue damage. Suitable compounds can include, for example, an antibody that specifically binds to a TRPV3 polypeptide; an antisense polynucleotide, ribozyme, or an interfering RNA that reduces expression of a TRPV3 polypeptide; and/or a chemical compound that reduces cation passage through a membrane that comprises a TRPV3 polypeptide.

Methods for determining whether pain in a subject is mediated by TRPV3 are also provided by the invention. These methods can involve: obtaining a sample from a region of the subject at which the pain is felt; and testing the sample to determine whether a TRPV3 polypeptide or TRPV3 polynucleotide is present and/or active in the sample. In some embodiments, the presence of a TRPV3 polypeptide in the sample is detected by determining whether cation passage across membranes of cells in the sample is mediated by a TRPV3 polypeptide. For example, TRPV3 involvement in mediating cation passage across membranes of the cells can be determined by detecting an increase in cation passage across membranes of the cells when assayed above 33° C. compared to cation passage when assayed below 33° C. To distinguish between TRPV3 involvement in mediating cation passage and involvement by other ion channels (e.g., TRPV1 or TRPV2), the assay can be conducted at a temperature above the activation threshold of TRPV3 but below the activation threshold of the other receptor (e.g., below about 43° C. or below about 52° C., respectively, for TRPV1 and TRPV2). As an alternative to assaying for TRPV3-mediated ion channel activity, one can detect the presence of a TRPV3 polypeptide in the sample by contacting the sample with a reagent that specifically binds to a TRPV3 polypeptide, or detect the presence of a TRPV3 polynucleotide in the sample by contacting nucleic acids from the sample with a test polynucleotide that can hybridize to a TRPV3 polynucleotide.

TRPV4

The invention also provides isolated TRPV4 nucleic acid molecules. These include, for example, a) a polynucleotide that encodes a mouse TRPV4 protein comprising amino acid residues 1-871 of SEQ ID NO: 14; b) a polynucleotide that encodes a mouse TRPV4 protein comprising amino acid residues 2-871 of SEQ ID NO: 14; c) a polynucleotide that encodes a polypeptide that comprises one or more functional domains of a mouse TRPV4 protein; d) a polynucleotide that encodes a human TRPV4 protein comprising amino acid residues 1-871 of SEQ ID NO 17; e) a polynucleotide that encodes a human TRPV4 protein comprising amino acid residues 2-871 of SEQ ID NO 17; f) a polynucleotide that encodes a polypeptide that comprises one or more functional domains of a human TRPV4 protein; and g) a polynucleotide that is complementary to a polynucleotide of a) through f). In some embodiments, the nucleic acid molecule is a) or b) and comprises a first polynucleotide that is 80% or more identical to a second polynucleotide having a nucleotide sequence as set forth in SEQ ID NO: 15 (mouse TRPV4), or is d) or e) and comprises a first polynucleotide 80% or more identical to a second polynucleotide having a nucleotide sequence as set forth in SEQ ID NO: 18 (human TRPV4). The nucleic acids can be 90% or more, or 95% or more, identical to a second polynucleotide having a nucleotide sequence as set forth in SEQ ID NO: 15 or SEQ ID NO: 18, or can be identical to the respective polynucleotide. Examples of TRPV4 nucleic acids of the invention include polynucleotides that are 80% or more, 90% or more, or 95% or more, identical to a second polynucleotide having a nucleotide sequence as set forth in nucleotides 156-2771 of SEQ ID NO: 13 (mouse TRPV4) or to a nucleotide sequence as set forth in SEQ ID NO: 16 (human TRPV4).

The invention also provides isolated TRPV4 nucleic acid molecules that encode polypeptides that include one or more functional domains of a mammalian (e.g., human or mouse) TRPV4 polypeptide. The polypeptides encoded by these nucleic acid molecules can include, for example, one or more functional domains such as ankyrin domains, transmembrane regions, pore loop regions, and coiled-coil domains. As an example, the polypeptides can include a pore loop region flanked by two transmembrane regions, and/or three ankyrin domains.

Also provided by the invention are isolated and/or purified TRPV4 polypeptides. Such polypeptides include, for example, a) a mouse TRPV4 protein comprising amino acid residues 1-871 of SEQ ID NO: 14; b) a mouse TRPV4 protein comprising amino acid residues 2-871 of SEQ ID NO: 14; c) one or more functional domains of a mouse TRPV4 protein; d) a human TRPV4 protein comprising amino acid residues 1-871 of SEQ ID NO 17; e) a human TRPV4 protein comprising amino acid residues 2-871 of SEQ ID NO 17; and f) one or more functional domains of a human TRPV4 protein. For example, the TRPV4 polypeptides can include one or more functional domains selected from the group consisting of an ankyrin domain, a transmembrane region, a pore loop region, and a coiled-coil domain. In some embodiments, the polypeptides include a pore loop region flanked by two transmembrane regions, and/or three ankyrin domains.

Methods for identifying an agent that modulates TRPV4-mediated cation passage through a membrane are also provided by the invention. These methods involve: a) providing a membrane that comprises a TRPV4 polypeptide; b) contacting the membrane with a candidate agent; and c) determining whether passage of one or more cations through the membrane is increased in the presence of the candidate agent compared to passage in the absence of the candidate agent. Cation influx and/or efflux can be measured as described above for TRPV3. In some embodiments, candidate agents that reduce cation passage are further tested for ability to treat pain by administering the candidate agent to a test animal and determining whether the candidate agent decreases the test animal's response to a pain stimulus.

Methods for reducing pain associated with TRPV4 activity are provided by the invention. These methods involve administering to a subject suffering from pain an analgesically effective amount of a compound that reduces TRPV4-mediated cation passage through a membrane or reduces signal transduction from a TRPV4 polypeptide to a DRG neuron. The compounds are suitable for treating, for example, neuropathic pain, and can include: a) an antibody that specifically binds to a TRPV4 polypeptide; b) an antisense polynucleotide, ribozyme, or an interfering RNA that reduces expression of a TRPV4 polypeptide; and c) a chemical compound that reduces cation passage through a membrane that comprises a TRPV4 polypeptide.

The invention also provides methods for determining whether pain in a subject is mediated by TRPV4. These methods involve obtaining a sample from a region of the subject at which the pain is felt, and testing the sample to determine whether a TRPV4 polypeptide or TRPV4 polynucleotide is present and/or active in the sample. The presence and/or activity of the TRPV4 polypeptide can be detected, for example, by determining whether cation passage across membranes of cells in the sample is mediated by a TRPV4 polypeptide, or by contacting the sample with a reagent that specifically binds to a TRPV4 polypeptide. One can detect the presence of a TRPV4 polynucleotide by, for example, contacting nucleic acids from the sample with a test polynucleotide that can hybridize to a TRPV4 polynucleotide.

TRPM8

Isolated and/or purified TRPM8 nucleic acid molecules are also provided by the invention. These TRPM8 nucleic acid molecules include, for example, a) a polynucleotide that encodes a mouse TRPM8 protein comprising amino acid residues 1-1104 of SEQ ID NO: 8; b) a polynucleotide that encodes a mouse TRPM8 protein comprising amino acid residues 2-1104 of SEQ ID NO: 8; c) a polynucleotide that encodes a polypeptide that comprises one or more functional domains of a mouse TRPM8 protein; d) a polynucleotide that encodes a human TRPM8 protein comprising amino acid residues 1-1268 of SEQ ID NO 11; e) a polynucleotide that encodes a human TRPM8 protein comprising amino acid residues 2-1268 of SEQ ID NO 11; f) a polynucleotide that encodes a polypeptide that comprises one or more functional domains of a human TRPM8 protein; and g) a polynucleotide that is complementary to a polynucleotide of a) through f). In some embodiments, the nucleic acid molecule is a) or b) and comprises a first polynucleotide that is 80% or more identical to a second polynucleotide having a nucleotide sequence as set forth in SEQ ID NO: 9 (mouse TRPM8), or is d) or e) and comprises a first polynucleotide 80% or more identical to a second polynucleotide having a nucleotide sequence as set forth in SEQ ID NO: 12 (human TRPM8). The nucleic acids can be 90% or more, or 95% or more, identical to a second polynucleotide having a nucleotide sequence as set forth in SEQ ID NO: 9 or SEQ ID NO: 12, or can be identical to the respective polynucleotide. Examples of TRPM8 nucleic acids of the invention include polynucleotides that are 80% or more, 90% or more, or 95% or more, identical to a second polynucleotide having a nucleotide sequence as set forth in nucleotides 448-3762 of SEQ ID NO: 7 (mouse TRPM8) or nucleotides 61-4821 of SEQ ID NO: 10 (human TRPM8).

The invention also provides isolated TRPM8 nucleic acid molecules that encode polypeptides that include one or more functional domains of a mammalian (e.g., human or mouse) TRPM8 polypeptide. The polypeptides encoded by these nucleic acid molecules can include, for example, one or more functional domains such as transmembrane regions, pore loop regions, and coiled-coil domains. As an example, the polypeptides can include a pore loop region flanked by two transmembrane regions.

The invention also provides isolated and/or purified TRPM8 polypeptides. The TRPM8 polypeptides include, for example, a) a mouse TRPM8 protein comprising amino acid residues 1-1104 of SEQ ID NO: 8; b) a mouse TRPM8 protein comprising amino acid residues 2-1104 of SEQ ID NO: 8; c) one or more functional domains of a mouse TRPM8 protein; d) a human TRPM8 protein comprising amino acid residues 1-1268 of SEQ ID NO 11; e) a human TRPM8 protein comprising amino acid residues 2-1268 of SEQ ID NO 11; and f) one or more functional domains of a human TRPM8 protein. For example, the TRPM8 polypeptides can include one or more functional domains selected from the group consisting of a transmembrane region, a pore loop region, and a coiled-coil domain. In some embodiments, the TRPM8 polypeptides of the invention include a pore loop region flanked by two transmembrane regions.

Methods for identifying an agent that modulates TRPM8-mediated cation passage through a membrane are also provided by the invention. These methods involve: a) providing a membrane that comprises a TRPM8 polypeptide; b) contacting the membrane with a candidate agent; and c) determining whether passage of one or more cations through the membrane is increased in the presence of the candidate agent compared to passage in the absence of the candidate agent. In some embodiments, the membrane is a cell membrane and cation passage through the membrane is detected by measuring cation influx or efflux across the membrane into or out of the cell. To identify antagonists that reduce TRPM8-mediated cation passage, the assay typically is conducted under conditions in which TRPM8 allows cation passage in the absence of the antagonist; e.g., at a temperature of about 20° C. or less, or in the presence of menthol. Also provided are methods in which a candidate agent that reduces cation passage is further tested for ability to treat pain by administering the candidate agent to a test animal and determining whether the candidate agent decreases the test animal's response to a pain stimulus. A pain stimulus can include, for example exposure to a temperature below 20° C.

In other embodiments, the invention provides methods for identifying an agent that stimulates TRPM8-mediated cation passage through a membrane. These screens for identifying TRPM8 agonists generally are conducted under conditions in which the TRPM8 polypeptides do not mediate cation passage. Such conditions include, for example, temperatures above about 20° C. Agonists of TRPM8-mediated cation passage are useful as flavor enhancers, fragrances, and the like.

The invention also provides methods of reducing pain associated with TRPM8 activity. These methods involve administering to a subject suffering from pain an analgesically effective amount of a compound that reduces TRPM8-mediated cation passage through a membrane or reduces signal transduction from a TRPM8 polypeptide to a DRG neuron. These methods are useful for treating pain that results from, for example, cold exposure, inflammation, tissue damage, and the like. The compounds can be, for example, a) an antibody that specifically binds to a TRPM8 polypeptide; b) an antisense polynucleotide, ribozyme, or an interfering RNA that reduces expression of a TRPM8 polypeptide; or c) a chemical compound that reduces cation passage through a membrane that comprises a TRPM8 polypeptide.

Methods for determining whether pain in a subject is mediated by TRPM8 are also provided by the invention. These methods involve obtaining a sample from a region of the subject at which the pain is felt; and testing the sample to determine whether a TRPM8 polypeptide or TRPM8 polynucleotide is present and/or active in the sample. In some embodiments, the presence of a TRPM8 polypeptide in the sample is detected by determining whether cation passage across membranes of cells in the sample is mediated by a TRPM8 polypeptide. TRPM8 involvement in mediating cation passage across membranes of the cells can be determined, for example, by detecting an increase or decrease in cation passage across membranes of the cells when assayed below 20° C. and/or in the presence of menthol, compared to cation passage when assayed above 20° C. and/or in the absence of menthol. Alternatively, or additionally, the presence of a TRPM8 polypeptide in the sample is detected by contacting the sample with a reagent that specifically binds to a TRPM8 polypeptide. The presence of a TRPM8 polynucleotide in the sample can be detected by, for example, contacting nucleic acids from the sample with a test polynucleotide that can hybridize to a TRPM8 polynucleotide.

The invention also provides methods for identifying an agent useful in the modulation of a mammalian sensory response. These methods involve: a) contacting a candidate agent with a test system that comprises a receptor polypeptide selected from the group consisting of TRPM8, TRPV3 and TRPV4; and b) detecting a change in activity of the receptor polypeptide in the presence of the candidate agent as compared to the activity of the receptor polypeptide in the absence of the agent, thereby identifying an agent that modulates receptor activity.

Also provided by the invention are methods for monitoring the efficacy of a treatment of a subject suffering from pain. These methods involve: a) obtaining, at two or more time points in the course of treatment for pain, a sample from a region of the subject at which the pain is felt; and b) testing the samples to determine whether a reduction is observed in amount or activity of one or more members selected from the group consisting of: a TRPV3 polypeptide, a TRPV3 mRNA, a TRPV4 polypeptide, a TRPV4 mRNA, a TRPM8 polypeptide, and a TRPM8 mRNA. In some embodiments, one of the time points is prior to or simultaneously with administration of the treatment, and the other time point is after treatment has begun.

The invention provides assays capable of detecting the expression of one or more of TRPV3, TRPV4 or TRPM8 in human tissue. The assays are selected from the group consisting of: a) an assay comprising contacting a human tissue sample with monoclonal antibodies binding to TRPV3, TRPV4 or TRPM8 and determining whether the monoclonal antibodies bind to polypeptides in the sample; and b) an assay comprising contacting a human tissue sample with an oligonucleotide that is capable of hybridizing to a nucleic acid that encodes TRPV3, TRPV4 or TRPM8.

Methods of treating pain provided by the invention include methods in which a patient suffering from pain mediated by one or more polypeptides selected from the group consisting of TRPV3, TRPV4 and TRPM8 is identified by measuring expression of the polypeptide in tissue from such patient, and administering to such patient an analgesically effective amount of an agent which inhibits the polypeptide.

The invention also provides methods for identifying an agent useful in the treatment of pain. These methods involve: a) administering a candidate agent to a mammal suffering from pain; b) in a sample obtained from the mammal, detecting an activity or amount of one or more members selected from the group consisting of: a TRPV3 polypeptide, a TRPV3 mRNA, a TRPV4 polypeptide, a TRPV4 mRNA, a TRPM8 polypeptide, and a TRPM8 mRNA; and c) comparing the amount or activity of the member in the presence of the candidate agent with the amount or activity of the member in a sample obtained from the mammal in the absence of the candidate agent, wherein a decrease in amount or activity of the member in the sample in the presence of the candidate agent relative to the amount or activity in the absence of the candidate agent is indicative of an agent useful in the treatment of pain.

Also provided are methods for identifying an agent that binds to and/or modulates the activity of an mRNA or polypeptide encoded by a TRPV3, TRPV4, or TRPM8 nucleic acid. These methods involve: a) contacting an isolated cell which expresses a heterologous TRPV3, TRPV4, or TRPM8 nucleic acid encoding a polypeptide with the agent; and b) determining binding and/or modulation of the activity of the mRNA or polypeptide by the agent, to identify agents which bind with and/or modulate the activity of the polypeptide.

BRIEF DESCRIPTION OF THE DRAWINGS

FIG. 1A: mRNA levels of TRPV3 are increased in a rat model of chronic neuropathic pain. The human cDNA sequence of TRPV3 is used to search the Celera mouse genomic DNA database and two primers are derived from regions that are identical from human and mouse sequences. The primers are used to amplify the rat TRPV3 from total RNA samples from the Chung model (L4 and L5 DRG) and sham-operated animals in a standard reverse-transcriptase polymerase chain reaction (RT-PCR) protocol. The top panel shows the gel image from one RT-PCR experiment and the bottom shows the average fold of regulation of TRPV3 in L4 and L5 DRG neurons from Chung model from three independent experiments. FIG. 1B: TRPV4 is up-regulated in a rat model of chronic neuropathic pain. For analysis TRPV4 expression in the Chung model (28- and 50-day), first-strand cDNA equivalent to 30 ng of total RNA is used per reaction and amplified between 32/35 cycles for higher expressing genes and 35/38 cycles for lower-expressing genes. Due to the constraints on the amount of total RNA available, half the volume of the PCR reaction is removed at the lower cycle and the remaining reaction is continued for a further 3 cycles. All the samples are resolved on 4-20% TBE gels and densitometry carried out on the clearest, non-saturated bands.

FIG. 2A: Rooted tree showing protein sequence relationship of different members of the TRPV ion channel family. FIG. 2B: Relative position of TRPV1 (VR1) and TRPV3 coding sequences on mouse (11B4) and human (17p13) chromosomes. FIG. 2C: Comparison of mouse TRPV3 protein sequence to other TRPVs (excluding C-terminal half containing transmembrane domains). Identical sequences are highlighted in dark gray; conserved residues, in light gray. Predicted coiled-coil and ankyrin domains are marked and coffespond to regions for TRPV3 only. The protein alignment is generated using Megalign and Boxshade at http://biowb.sdsc.edu/CGI/BW.cgi. The coiled -coil domains are predicted using the program Coils http://searchlauncher-.bcm.tmc.edu/seq-search/struc-predict.html). The ankyrin domains are predicted using the PFAM protein search http://pfam.wustl.edu/hmmsearch.shtml). FIG. 2D: A schematic of TRPV3 and predicted membrane topology. FIG. 2E: Kyte Doolittle hydrophobicity plot of TRPV3 sequences showing the 6 transmembrane domains (1-6) and the pore domain (P).

FIG. 2F: Coiled-coil domain prediction of TRPV3 sequence by Coils shows two 14-mer peaks at the N -terminal, prior to ankyrin sequences.

FIG. 3A: Inward current to temperature ramp, $V_h=-60$ mV, in calcium free external solutions. FIG. 3B: Heat evoked currents of the same cell in $Ca^{2+}$-free and subsequently in $Ca^{2+}$ containing solutions showing increased inward current in $Ca^{2+}$ conditions. FIG. 3C: Semilogarithmic plot of current against temperature with double exponential fitted line for the same trace as FIG. 3A. Note the discontinuity at ~32° C. (arrow). FIG. 3D: Current-voltage relationship in calcium containing external solution showing the pronounced outward rectification of TRPV3 at 48° C. but not at room temperature. Note the small outward currents at room temperature.

FIG. 4A: Repeated heat steps from 25-45° C. evoke increased inward current responses. FIG. 4B: The outward rectification becomes more pronounced with repeated voltage ramps in 48° C. external solution. Both experiments are conducted in the presence of 2 mM $CaCl_2$ in the external solution. FIG. 4C: Control protocol for antagonist experiments. Note that the responses continue to sensitize with repeated heat steps in the absence of putative antagonists. FIG. 4D: 1 µM ruthenium red attenuates the sensitization and inhibits the heat response.

FIGS. 6A-6D show results of an analysis of the nucleotide and amino acid sequences of TRPM8. FIG. 6A: Comparison of mouse TRPM8 protein sequence to some of its closest relatives, TRPM1 (human Melastatin, GI 6006023), TRPM2 (human, GI 4507688) and TRPM7 (mouse Chak, GI 14211382). The alignment is generated using Megalign and Boxshade. Identical or conserved residues are shown in white letters on a black background. FIG. 6B: Phylogenetic tree showing protein sequence relationship of different members of the TRP ion channel super-family. TRPs are subdivided into three main subfamilies: TRPMs, TRPVs and TRPCs. The TRPMs do not contain any Ankyrin domains in their N-terminal domains. The transmembrane domains have the highest homology among different classes of TRP channels. FIG. 6C: Kyte Doolittle hydrophobicity plot of TRPM8 sequences showing the eight hydrophobic peaks demarking the potential transmembrane regions of the protein that spans from 695-1024 amino acids. Figure 6D: Coiled-coil domain prediction of TRPM8 sequence by the program coils shows multiple 14-mer peaks at the N- and C-terminus of the transmembrane spanning domains http://searchlauncher.bcm.tmc.edu/seq-search/struc-predict.html).

FIG. 7A: mTRPM8 CHO cells show a rapid increase in $[Ca^{2+}]_i$ when the temperature reaches ~15° C. Non-transfected CHO cells do not show a response to cold. Removal of external $Ca^{2+}$ completely abolishes the response to cooling. FIG. 7B: The estimated average threshold temperature at which $[Ca^{2+}]_i$ begins to increase is approximately 23° C. for mTRPM8. TRPM8-expressing CHO cells are cooled from 33-23° C., upon which an increase in $Ca^{2+}$ is observed. Continuous cooling of the cells to 20° C. shows a marked $Ca^{2+}$ increase followed by a rapid return to near-basal levels upon warming to 33° C. FIG. 7C: TRPM8 responses, evoked by repeated applications of a 23° C. temperature stimulus show little desensitization in calcium-containing standard bath solution. FIG. 7D: TRPM8 responds to menthol at 25° C. Intensity of the TRPM8 response is dependent on menthol concentrations. A 10-fold increase in menthol concentration results in a larger influx of $Ca^{2+}$. This response is suppressed in the absence of extracellular $Ca^{2+}$. Non-transfected CHO cells exhibit no increase in $[Ca^{2+}]_i$ upon application of menthol. FIG. 7E: At 33° C., 10 µM menthol does not elicit an influx of $Ca^{2+}$. When the temperature of the bath solution is lowered to 30° C., a marked increase in intracellular $Ca^{2+}$ is observed. Additionally, repeated applications of menthol do not appear to desensitize TRPM8-expressing cells. These experiments suggest that menthol simulates the effect of cooling in TRPM8-expressing cells. This identification of a cold-sensing TRP channel involved in thermoreception reveals an expanded role for this family in somatic sensory detection.

FIG. 8A: TRPM8-transfected CHO cells show a rapid increase in $[Ca^{2+}]_i$ when the temperature is lowered from 25° C. to 15° C. The stimulus period is indicated below the traces. Non-transfected CHO cells do not show a response to cold. Removal of external $Ca^{2+}$ completely suppresses the response to cooling. Experiments are performed in triplicate. The average response (±SEM) of 20-30 cells from a representative experiment is presented. FIG. 8B: Increase in $[Ca^{2+}]_i$ due to decrease in temperature from 35° C. to 13° C. in TRPM8+ cells. The panel shows mean±SEM for 34 individual cells. Note the increase starts to occur between 22° C. and 25° C.

FIG. 9A: Outward currents evoked at +60 mV by reducing the temperature from 35° C. to 10° C. In this cell the current activates at 19.3° C. as indicated in the right hand panel. FIG. 9B: Current-voltage relationship for currents activated at 20.5° C. and 33.5° C. Increasing the temperature reduces the amplitude of outward currents.

FIG. 10A: Inward currents evoked by 1 mM menthol ($V_h=-60$ mV) are inactivated by increasing the temperature from 25° C. to 45° C. FIG. 10B: Current-voltage relationship for response to 1 mM menthol. Currents show pronounced outward-rectification in the presence of menthol not seen in the absence of this agonist.

FIG. 11A: Single examples, from two different cells, of current evoked by applying 0.1, 0.5, 1 and 10 mM menthol at 22° C. and 35° C. FIG. 11B: Comparison of response (mean±SEM, n=5 for all points) of current evoked by menthol either at 22° C. or 35° C.

DESCRIPTION OF THE SEQUENCE LISTING

Figure 1:
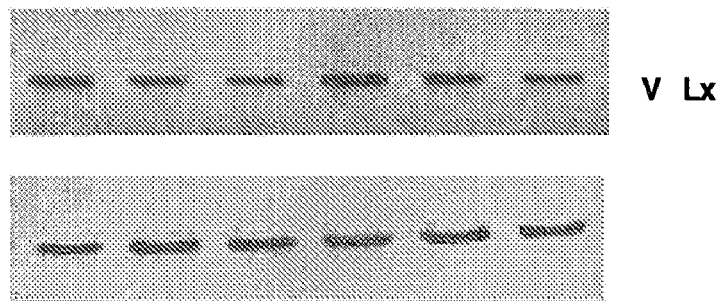
FIGS. 1A and 1B show differential expression of TRPV3 and TRPV4 genes in the Chung model.
Figure 1:
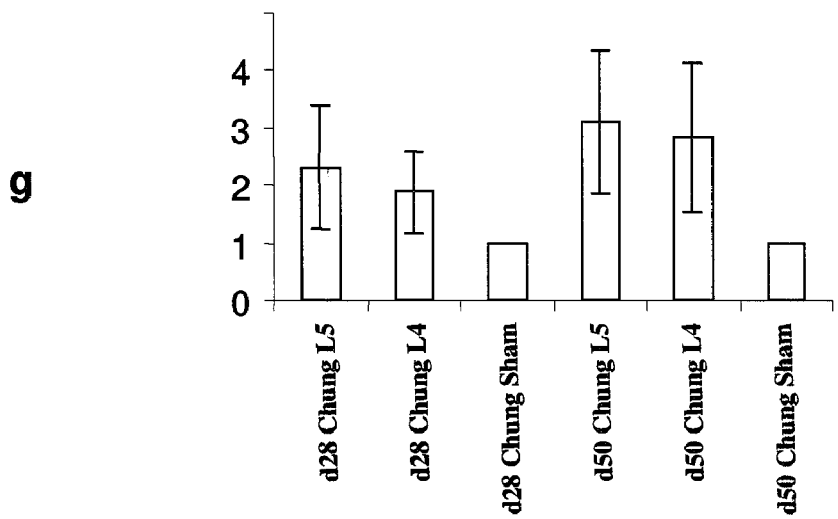
Figure 1:
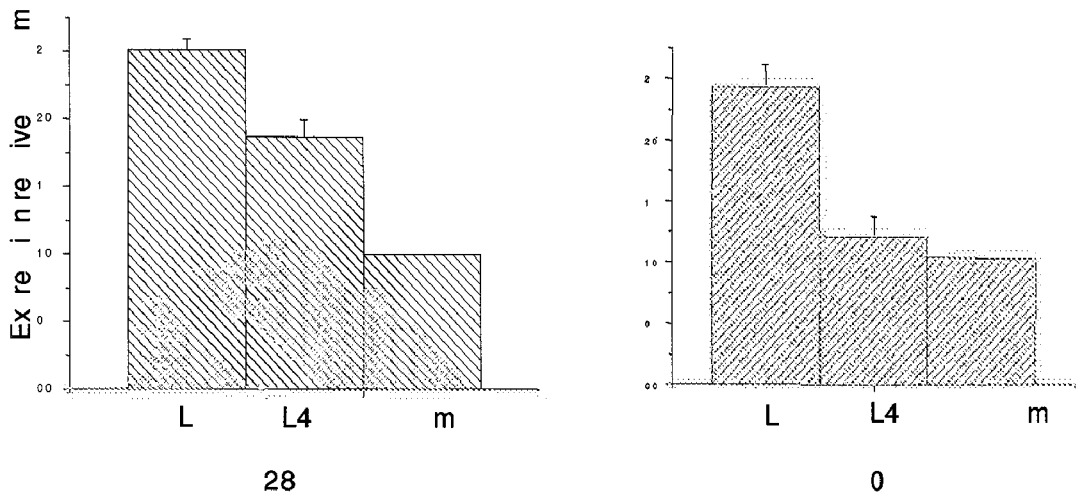

SEQ ID NO: 1 provides a nucleotide sequence that encodes a mouse TRPV3 polypeptide, and upstream and downstream regions. The open-reading frame extends from nucleotides 65-2440.

SEQ ID NO: 2 provides an amino acid sequence of a mouse TRPV3 polypeptide.

SEQ ID NO: 3 provides nucleotide sequences for all polynucleotides that code for the mouse TRPV3 amino acid sequence presented in SEQ ID NO: 2.

SEQ ID NO: 4 provides a nucleotide sequence that encodes a human TRPV3 polypeptide, and an upstream non-coding region. The open-reading frame extends from nucleotides 57-2432.

SEQ ID NO: 5 provides an amino acid sequence of a human TRPV3 polypeptide.

SEQ ID NO: 6 provides nucleotide sequences for all polynucleotides that code for the human TRPV3 amino acid sequence presented in SEQ ID NO: 5.

SEQ ID NO: 7 provides a nucleotide sequence that encodes a mouse TRPM8 polypeptide, and upstream and downstream non-coding regions. The coding region extends from nucleotides 448-3762.

SEQ ID NO: 8 provides an amino acid sequence of a mouse TRPM8 polypeptide.

SEQ ID NO: 9 provides nucleotide sequences for all polynucleotides that code for the mouse TRPM8 amino acid sequence presented in SEQ ID NO: 8.

SEQ ID NO: 10 provides a nucleotide sequence that encodes a human TRPM8 polypeptide, and upstream and downstream non-coding regions. The coding region extends from nucleotides 61-4821.

SEQ ID NO: 11 provides an amino acid sequence of a human TRPM8 polypeptide.

SEQ ID NO: 12 provides nucleotide sequences for all polynucleotides that code for the human TRPM8 amino acid sequence presented in SEQ ID NO: 11.

SEQ ID NO: 13 provides a nucleotide sequence that encodes a mouse TRPV4 polypeptide, and upstream and downstream regions. The open-reading frame extends from nucleotides 156-2771.

SEQ ID NO: 14 provides an amino acid sequence of a mouse TRPV4 polypeptide.

SEQ ID NO: 15 provides nucleotide sequences for all polynucleotides that code for the mouse TRPV4 amino acid sequence presented in SEQ ID NO: 14.

SEQ ID NO: 16 provides a nucleotide sequence that encodes a human TRPV4 polypeptide.

SEQ ID NO: 17 provides an amino acid sequence of a human TRPV4 polypeptide.

SEQ ID NO: 18 provides nucleotide sequences for all polynucleotides that code for the human TRPV4 amino acid sequence presented in SEQ ID NO: 17.

DETAILED DESCRIPTION

Definitions

A "host cell," as used herein, refers to a prokaryotic or eukaryotic cell that contains heterologous DNA that has been introduced into the cell by any means, e.g., electroporation, calcium phosphate precipitation, microinjection, transformation, viral infection and the like.

"Heterologous" as used herein means "of different natural origin" or represent a non-natural state. For example, if a host cell is transformed with a DNA or gene derived from another organism, particularly from another species, that gene is heterologous with respect to that host cell and also with respect to descendants of the host cell which carry that gene. Similarly, heterologous refers to a nucleotide sequence derived from and inserted into the same natural, original cell type, but which is present in a non-natural state, e.g., a different copy number, or under the control of different regulatory elements.

A "vector" molecule is a nucleic acid molecule into which heterologous nucleic acid may be inserted which can then be introduced into an appropriate host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes".

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well-known, published procedures. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The terms "nucleic acid", "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally-occurring nucleotides. Although polynucleotide sequences presented herein recite "T" (for thymidine), which is found only in DNA, the sequences also encompass the corresponding RNA molecules in which each "T" in the DNA sequence is replaced by "U" for uridine.

The term "isolated" refers to material that is substantially or essentially free from components which normally accompany the material as found in its native state. Thus, the polypeptides and nucleic acids of the invention do not include materials normally associated with their in situ environment. An isolated nucleic acid, for example, is not associated with all or part of the chromosomal DNA that would otherwise flank the nucleic acid. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well-known in the art, such as polyacrylamide gel electrophoresis of a protein sample, followed by visualization upon staining. For certain purposes high resolution will be needed and HPLC or a similar means for purification utilized.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical", in the context of two nucleic acids or polypeptides, refers to two or more sequences or subsequences that have at least 70%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J. Mol. Biol.*, 48:443 (1970), by the search for similarity method of Pearson & Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al., *J Mol. Biol.*, 215:403-410 (1990) and Altschuel et al., *Nucleic Acids Res.*, 25:3389-3402 (1977), respectively. Software for performing BLAST analyses is publicly available through the National Center for Biotechnology Information http://www.ncbi.nlm.nih.gov/). This algorithm involves first identifying high-scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters wordlength (W), T and X determine the sensitivity and speed of the alignment. The BLASTN program (for nucleotide sequences) uses as defaults a W of 11, an expectation (E) of 10, M=5, N=−4, and a comparison of both strands. For amino acid sequences, the BLASTP program uses as defaults a W of 3, an E of 10 and the BLOSUM62 scoring matrix (see Henikoff & Henikoff, *Proc. Natl. Acad. Sci. USA*, 89:10915 (1989)). Percent identities, where specified herein, are typically calculated using the Blast 2.0 implementation using the default parameters.

In addition to calculating percent sequence identity, the BLAST algorithm also performs a statistical analysis of the similarity between two sequences (see, e.g., Karlin & Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two polynucleotides are substantially identical is that the polynucleotides hybridize to each other under specified hybridization conditions. Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC or deionized water. In general, hybridization incubation times are from 5 minutes to 24 hours, with 1, 2 or more washing steps, and wash incubation times are about 1, 2 or 15 minutes. SSC is 0.15 M NaCl and 15 mM citrate buffer. It is understood that equivalents of SSC using other buffer systems can be employed.

A further indication that two nucleic acid sequences or polypeptides are substantially identical is that the polypeptide encoded by the first nucleic acid is immunologically cross-reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations". Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art (see, e.g., Creighton, Proteins, W.H. Freeman and Company (1984)). Individual substitutions, deletions or additions which alter, add or delete a single amino acid or a small percentage of amino acids in an encoded sequence are also "conservatively modified variations".

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells can contain genes that are not found within the native (non-recombinant) form of the cell or can express native genes that are otherwise abnormally expressed, under expressed or not expressed at all. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation and related techniques.

The term "modulate" refers to a change in the activity and/or amount of TRPV3, TRPV4 or TRPM8 proteins. For example, modulation may cause an increase or a decrease in protein activity, binding characteristics, or any other biological, functional or immunological properties of such proteins. The term "modulation" also refers to a change in the increase or decrease in the level of expression of mRNA or protein encoded by the TRPV3, TRPV4, and TRPM8 genes.

The term "operably-linked", as used herein, refer to functionally-related nucleic acid sequences. A promoter is operably associated or operably-linked with a coding sequence if the promoter controls the translation of the encoded polypeptide. While operably-linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "agonist", as used herein, refers to a molecule which, when bound to the TRPV3, TRPV4 and TRPM8 proteins, increases or prolongs the duration of the effect of the biological or immunological activity of such proteins. Agonists may include proteins, nucleic acids, carbohydrates or any other molecules which bind to and modulate the effect of these proteins.

The term "antagonist", as used herein, refers to a molecule which, when bound to TRPV3, TRPV4 and TRPM8 proteins, decreases the amount or the duration of the effect of the biological or immunological activity of these proteins. Antagonists may include proteins, nucleic acids, carbohydrates, antibodies or any other molecules which decrease the effect of these proteins. The term "antagonist" can also refer to a molecule which decreases the level of expression of mRNA and/or translation of protein encoded by TRPV3, TRPV4, and TRPM8 genes. Examples of such antagonists include antisense polynucleotides, ribozymes and double-stranded RNAs.

In practicing the present invention, many conventional techniques in molecular biology, microbiology and recombinant DNA are used. These techniques are well-known and are explained in, e.g., *Current Protocols in Molecular Biology*, Vols. I, II and III, F. M. Ausubel, ed. (1997); Sambrook et al.,

*Molecular Cloning: A Laboratory Manual*, 3rd Edition, Cold Spring Harbor Laboratory Press, Cold Spring Harbor, N.Y. (2001); *DNA Cloning: A Practical Approach*, Vols. I and II, D. N. Glover, ed. (1985); *Oligonucleotide Synthesis*, M. L. Gait, ed. (1984); *Nucleic Acid Hybridization*, Hames and Higgins (1985); *Transcription and Translation*, Hames and Higgins, eds. (1984); *Animal Cell Culture*, R. I. Freshney, ed. (1986); *Immobilized Cells and Enzymes*, IRL Press (1986); Perbal, *A Practical Guide to Molecular Cloning; the series, Methods in Enzymology*, Academic Press, Inc. (1984); *Gene Transfer Vectors for Mammalian Cells*, J. H. Miller and M. P. Calos, eds., Cold Spring Harbor Laboratory Press, Cold Spring Harbor, N.Y. (1987); and *Methods in Enzymology*, Vols. 154 and 155, Wu and Grossman, and Wu, eds., respectively.

DESCRIPTION OF THE PREFERRED EMBODIMENTS

The present invention relates to novel nucleic acids known as TRPV3 (previously known as VRLX, VRL-S, VR4 and TRPV7), TRPV4 (previously known as VRL3 and OTRPC4), and TRPM8 (previously known as TRPX) that are homologous to the VR1, polypeptides encoded by these nucleic acids, recombinant materials and methods for their production. The specific names given to the three genes follow the nomenclature suggested in Montell et al., *Molecular Cell*, 9:229-231 (2002). The genes have been found to be expressed either in keratinocytes or the DRG, and both TRPV3 and TRPM8 proteins function in temperature sensation. In addition, expression of the TRPV3 and TRPV4 genes is up-regulated in a rat injury model (see Examples 4 and 6). The present invention also relates to the identification of trkA+ pain-specific genes that are expressed in the DRG. Since the aforementioned genes are expressed in keratinocytes and the DRG, function in temperature sensation, and are up-regulated in response to injury, these genes and their related polypeptides can serve as specific therapeutic targets for the design of drugs to treat chronic and nociceptive pain, inflammation and skin disorders. Accordingly, the invention also relates to methods for identifying agents useful in treating pain, inflammation and skin disorders, methods for treating pain, inflammation and skin disorders and methods of monitoring the efficacy of a treatment, utilizing these genes and polypeptides. These genes and related polypeptides can also be utilized in diagnostic methods for the detection of pain, inflammation and skin disorders.

TRPV3, TRPV4 and TRPM8 belong to the VR family. A Hidden Markov Model (HMM) of the VR1 and VRL1 proteins from different mammalian species including human and an HMM model against Transmembrane 6 (TM6) domain of all known TRP/VRs has been constructed. The six-frame translation of the Human Celera database has been searched against the VR model. Multiple new putative exons with high homology (70% identical and 82% similar in conserved regions among the different VR/TRPs) to Transmembrane 4 (TM4) and TM6 domains to the known TRPs have been identified. These exons map to bacterial artificial chromosomes containing specific human sequences from the High Throughput Genome Sequence (HTGS) database. All the newly-identified exons belong to three new genes of the VR family. Subsequently, RT-PCR has confirmed that these genes are expressed in the DRG or keratinocytes. The structural homology to known TRP channels, the genes' expression in DRG or keratinocytes, their function as temperature-sensitive channels, and the up-regulation of TRPV3 and TRPV4 gene expression observed in a rat injury model in the DRG, indicate that the new genes act as important sensory receptors.

TRPV3: An Ion Channel Responsive to Warm and Hot Temperatures

TRPV3 is the first molecule described to be activated at warm and hot temperatures, and to be expressed in skin cells (see Examples 2 and 3). TRPV3 signaling mediates a cell-autonomous response in keratinocytes upon exposure to heat. The heat-induced TRPV3 signal is transferred to nearby free nerve endings, thereby contributing to conscious sensations of warm and hot. This is supported by indirect evidence that skin cells can act as thermal receptors. For instance, while dissociated DRG neurons can be directly activated by heat and cold, warm receptors have only been demonstrated in experiments where skin-nerve connectivity is intact (see Hensel et al., *Pfugers Arch.*, 329:1-8 (1971), Hensel et al., *J. Physio.*, 204:99-112 (1969)). TRPV3 has an activation threshold around 33-35° C. The presence of such a warm receptor in skin (with a resting temperature of 34° C.) and not DRG neurons (with a resting temperature of 37° C. at the cell body) prevents a warm-channel like TRPV3 from being constitutively active at core 37° C. temperatures. The residual heat sensitivity in TRPV1 knockout mice also involves skin cells: while dissociated DRG neurons from TRPV1-null animals do not respond to moderate noxious stimulus at all, skin-nerve preparations from such animals do respond (see Caterina et al., *Science*, 288:306-13 (2000); Davis et al., *Nature*, 405:183-187 (2000); Roza et al., Paper presented at the 31st Annual meeting for the Society of Neuroscience, San Diego, Calif. (2001)). Collectively these data indicate that a warm/heat receptor is present in the skin, in addition to the heat receptors in DRGs. While synapses have not been found between keratinocytes and sensory termini; ultrastructural studies have shown that keratinocytes contact, and often surround, DRG nerve fibers through membrane-membrane apposition (see Hilliges et al., *J. Invest. Dermatol.*, 104:134-137 (1995) and Cauna., *J. Anat.*, 115:277-288 (1973)). Therefore, heat-activated TRPV3 signal from keratinocytes can be transduced to DRG neurons through direct chemical signaling. One potential signaling mechanism can involve ATP. P2X3, an ATP-gated channel, is present in sensory endings, and analysis of P2X3 knockout mice show a strong deficit in coding of warm temperatures (see Souslova et al., *Nature*, 407:1015-1017 (2000); Cockayne et al., *Nature*, 407:1011-1015 (2000)). Furthermore, release of ATP from damaged keratinocytes has been shown to cause action potentials in nociceptors via the P2X receptors (see Cook et al., *Pain*, 95:41-47 (2002)). Since TRPV3 is activated at innocuous warm and noxious hot temperatures and is expressed in skin, this gene can serve as a therapeutic target for the design of drugs useful in treating pain, inflammation and skin disorders, e.g., those associated with sunburn and other sensitized states.

In one aspect, the invention provides isolated nucleic acids encoding a mammalian TRPV3 protein. These include an isolated and/or recombinant nucleic acid molecule that encodes a mouse TRPV3 protein having an amino acid sequence as shown in SEQ ID NO: 2. For example, the TRPV3-encoding nucleic acids of the invention include those that have a nucleotide sequence as set forth in SEQ ID NO: 1, from nucleotides 65-2440. The nucleic acids of the invention can include not only the coding region, but also the non-coding regions that are upstream and downstream of the coding region and also are provided in SEQ ID NO: 1. The invention also provides an isolated mouse TRPV3 polypeptide having an amino acid sequence as shown in SEQ ID NO:

2. Also provided are numerous other nucleic acids that encode this mouse TRPV3 polypeptide; the nucleotide sequences of these nucleic acids are shown in SEQ ID NO: 3.

Human TRPV3 polypeptides and polynucleotides are also provided by the invention. For example, the invention provides an isolated and/or recombinant human TRPV3-encoding polynucleotide encoding a human TRPV3 polypeptide having an amino acid sequence as set forth in SEQ ID NO: 5. These nucleic acid molecules include those that have a nucleotide sequence as set forth in nucleotides 57-2432 of SEQ ID NO: 4. Upstream and downstream non-coding regions are also provided in SEQ ID NO: 4. Also provided by the invention are isolated human TRPV3 polypeptides having an amino acid sequence as set forth in SEQ ID NO: 5. The invention also provides numerous other nucleic acids that encode this human TRPV3 polypeptide; the nucleotide sequences of these nucleic acids are shown in SEQ ID NO: 6.

TRPV4: An Ion Channel that is Activated by Pain

TRPV4 is a TRP channel protein that is expressed in adult mouse kidney, newborn dorsal root ganglion and adult trigeminal tissue (see Example 5). TRPV4 is a nonselective cation channel that is activated by decreases in, and is inhibited by increases in, extracellular osmolarity indicating that this channel functions as an osmosensor channel (see, e.g., Strotmann et al., *Nat. Cell Biol.*, 2:695-702 (2000)). In addition, expression of the TRPV4 gene is up-regulated in a rat injury model (see Example 6). Accordingly, the TRPV4 gene can serve as a therapeutic target for the design of drugs to treat pain, kidney disorders and migraine.

The invention provides isolated nucleic acids that encode a mammalian TRPV4 protein. These include the isolated and/or recombinant nucleic acid molecule that encodes mouse TRPV4 protein having an amino acid sequence as set forth in SEQ ID NO: 14. Included among these nucleic acid molecules are those that have a nucleotide sequence as set forth in nucleotides 156-2771 of SEQ ID NO: 13. Upstream and downstream non-coding sequences are also provided. Also provided by the invention are isolated mouse TRPV4 polypeptides having an amino acid sequence as set forth in SEQ ID NO: 14. Numerous other nucleic acids that encode this mouse TRPV4 polypeptide are also provided by the invention. The nucleotide sequences of such nucleic acids are shown in SEQ ID NO: 15.

The mammalian TRPV4-encoding nucleic acids also include the isolated and/or recombinant nucleic acid molecules that encode human TRPV4 protein that has an amino acid sequence as set forth in SEQ ID NO: 17. Such nucleic acid molecules include those having a nucleotide sequence as set forth in SEQ ID NO: 16. Also provided are isolated human TRPV4 polypeptides having an amino acid sequence as set forth in SEQ ID NO: 17. The invention also provides numerous other nucleic acids that encode this human TRPV4 polypeptide; the nucleotide sequences of these nucleic acids are shown in SEQ ID NO: 18.

TRPM8: An Ion Channel Responsive to Cold Temperatures and to Menthol

TRPM8 is activated by cold stimuli and a cooling agent (menthol) and is expressed in a select group of DRG neurons that share characteristics of thermoreceptive neurons (see Examples 8 and 9).

Cells over-expressing TRPM8 show increased intracellular calcium levels when subjected to cold temperatures ranging from 23° C. to 10° C. (the lower limit of our temperature-controlled perfusion system). The calcium influx and electrophysiological studies described below demonstrate that TRMP8 is a non-selective, plasma membrane cation channel activated by cold temperatures. The ionic permeability of TRPM8 is similar to that of other TRP channels, which are permeable to both monovalent and divalent cations, although calcium permeability estimates ($P_{Ca}/P_{Na}$) vary from 0.3 to 14 (see, e.g., Harteneck et al., *Trends Neurosci.*, 23:159-166 (2000)). Menthol is a cooling compound that likely acts on endogenous cold-sensitive channel(s) (see Schafer et al., *J. Gen. Physiol.*, 88:757-776 (1986)). That TRPM8-expressing cells are activated and modulated by menthol reinforces the idea that TRPM8 indeed functions as a cold-sensitive channel in vivo. The finding that the sensitivity to menthol is dependent on temperature is consistent with the behavior of a subset of isolated DRG neurons that show a raised 'cold' threshold in the presence of menthol (see Reid and Flonta, *Nature*, 413: 480 (2001)). With respect to the mechanism of TRPM8 activation, TRPM8 could be directly gated by cold stimulus through a conformational change, or cold temperatures could act through a second messenger system that in turn activates TRPM8. The rapid activation by menthol suggests a direct gating mechanism, at least for this mode of activation.

The expression pattern observed for TRPM8 is consistent with a role in cold thermoception. First, TRPM8 mRNA is highly-specific to DRG neurons. Within the DRG, TRPM8 is expressed in the small-diameter non-myelinated neurons, which correspond to the c-fiber thermoreceptor and nociceptors (see Scott, *Sensory Neurons: Diversity, Development and Plasticity*, Oxford University Press, NY (1992)). The lack of TRPM8 expression in trkA knockout mice, whose DRGs lack all thermoreceptor and nociceptive neurons, corroborates this finding. Furthermore, the lack of co-expression with VR1, CGRP or IB4 in the adult suggests that TRPM8 is expressed in a unique population of DRG neurons distinct from well-characterized heat nociceptors. Both soma size of neurons that express VRL1 (medium-large neurons) and their co-expression with NF200 (80% co-expression (see Caterina et al., *Nature*, 398:436-441(1999)) strongly argues that cells expressing TRPM8 and VRL1 are also distinct. Therefore, by using various markers it is shown below that TRPM8 is expressed in a sub-class of nociceptors/thermoreceptors that is distinct from noxious heat sensing neurons, and this correlates well with physiological studies of cold-sensitive DRG neurons (see Hensel, *Thermoreception and Temperature Regulation*, Academic Press, London (1981)). A human gene with a high degree of similarity to mouse TRPM8 but no known function was recently shown to be expressed in prostate tissue (see Tsavaler et al., *Cancer Res.*, 61:3760-3769 (2001)).

As the first molecule to respond to cold temperatures and menthol, TRPM8 offers interesting insight into the fundamental biology of cold perception. Modulation of TRPM8 activity is also relevant for therapeutic applications: cold treatment is often used as a method of pain relief, and in some instances, hypersensitivity to cold can lead to cold allodynia in patients suffering from neuropathic pain. Modulation of TRPM8 activity is also relevant for treating acute pain, e.g., toothache and other trigeminal focused pain; and for treating cancer, particularly prostate cancer and other prostate disorders.

The invention provides isolated nucleic acids encoding a TRPM8 mammalian protein. These include the isolated and/or recombinant nucleic acid molecules that encode mouse TRPM8 protein that have an amino acid sequence as set forth in SEQ ID NO: 8. For example, the invention provides recombinant and/or isolated nucleic acid molecules that have a nucleotide sequence as set forth in nucleotides 448-3762 of SEQ ID NO: 7. Upstream and downstream non-coding regions are also provided. The invention also provides isolated mouse TRPM8 polypeptides that include an amino acid sequence as set forth in SEQ ID NO: 8. Also provided are numerous other nucleic acids that encode this mouse TRPM8 polypeptide. Nucleotide sequences of these nucleic acids are provided in SEQ ID NO: 9.

The nucleic acids encoding a mammalian TRPM8 protein also include isolated and/or recombinant nucleic acid molecules that encode a human TRPM8 protein comprising an amino acid sequence as set forth in SEQ ID NO: 11. For example, the invention provides an isolated and/or recombinant nucleic acid molecule that includes a nucleotide sequence as set forth from nucleotides 61-4821 of SEQ ID NO: 10. Upstream and downstream non-coding regions are also provided by the invention. The invention also provides isolated human TRPM8 polypeptides having an amino acid sequence as set forth in SEQ ID NO: 11. The TRPM8 protein is responsive to cold and menthol.

Nucleic Acid Molecules

Nucleic acid molecules of the present invention also include isolated nucleic acid molecules that have at least 80% sequence identity, preferably at least 90% identity, preferably at least 95% identity, more preferably at least 98% identity, and most preferably at least 99% identity to a nucleic acid encoding a polypeptide comprising the amino acid sequence of SEQ ID NO: 2, SEQ ID NO: 5, SEQ ID NO: 8, SEQ ID NO: 11, SEQ ID NO: 14 or SEQ ID NO: 17, respectively, over the entire coding region or over a subsequence thereof. Such nucleic acid molecules include a nucleic acid having a nucleotide sequence as set forth in SEQ ID NO: 1, SEQ ID NO: 3, SEQ ID NO: 4, SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 16 or SEQ ID NO: 18, as set forth above.

Nucleic acids of the present invention include isolated nucleic acid molecules encoding polypeptide variants which comprise the amino acid sequences of SEQ ID NO: 2, SEQ ID NO: 5, SEQ ID NO: 8, SEQ ID NO: 11, SEQ ID NO: 14 or SEQ ID NO: 17, respectively. Nucleic acids that are amplified using a primer pair disclosed herein are also encompassed by the present invention.

Further nucleic acids of the present invention also include fragments of the aforementioned nucleic acid molecules. These oligonucleotide probes are preferably of sufficient length to specifically hybridize only to complementary transcripts of the above identified gene(s) of interest under the desired hybridization conditions (e.g., stringent conditions). As used herein, the term "oligonucleotide" refers to a single-stranded nucleic acid. Generally the oligonucleotides probes will be at least 16-20 nucleotides in length, although in some cases longer probes of at least 20-25 nucleotides will be desirable.

The oligonucleotide probes can be labeled with one or more labeling moieties to permit detection of the hybridized probe/target polynucleotide complexes. Labeling moieties can include compositions that can be detected by spectroscopic, biochemical, photochemical, bioelectronic, immunochemical, electrical optical or chemical means. Examples of labeling moieties include, but are not limited to, radioisotopes, e.g., $^{32}P$, $^{33}P$, $^{35}S$, chemiluminescent compounds, labeled binding proteins, heavy metal atoms, spectroscopic markers, such as fluorescent markers and dyes, linked enzymes, mass spectrometry tags and magnetic labels.

Oligonucleotide probe arrays for expression monitoring can be prepared and used according to techniques which are well known to those skilled in the art as described, e.g., in Lockhart et al., *Nature Biotech.*, 14:1675-1680 (1996); McGall et al., *Proc. Natl. Acad. Sci. USA*, 93:13555-13460 (1996); and U.S. Pat. No. 6,040,138.

The invention also provides isolated nucleic acid molecules that are complementary to all the above described isolated nucleic acid molecules.

An isolated nucleic acid encoding one of the above polypeptides including homologs from species other than mouse or human, may be obtained by a method which comprises the steps of screening an appropriate library under stringent conditions with a labeled probe having the sequence of SEQ ID NO: 1, SEQ ID NO: 3, SEQ ID NO: 4, SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 16 or SEQ ID NO: 18, or a fragment thereof; and isolating full-length cDNA and genomic clones containing the nucleotide sequences. Such hybridization techniques are well-known to a skilled artisan.

Nucleic acid molecules of the present invention may be obtained, using standard cloning and screening techniques, from a cDNA library derived from mRNA in cells of the DRG using the expressed sequence tag (EST) analysis (see Adams et al., *Science*, 252:1651-1656 (1991); Adams et al., *Nature*, 355:632-634 (1992); Adams et al., *Nature*, 377;Suppl. 3:174 (1995)). Polynucleotides of the invention can also be obtained from natural sources such as genomic DNA libraries or can be synthesized using well-known and commercially available techniques.

It is also appreciated by one skilled in the art, that an isolated cDNA sequence can be incomplete, in that the region coding for the polypeptide is short at the 5' end of the DNA. This can occur due to the failure of the reverse transcriptase to complete a DNA copy of the mRNA transcript during the synthesis of the first strand of cDNA. Methods for obtaining full-length cDNAs, or to extend short cDNAs, are well-known in the art, e.g., those based on the method of RACE as described in Frohman et al., *Proc. Natl. Acad. Sci. USA*, 85:8998-9002 (1988). The RACE technique has been modified as exemplified by Marathon™ technology (Clontech Laboratories, Inc.), wherein cDNAs have been prepared from mRNA extracted from a selected tissues and an adaptor sequence is ligated to each end. Subsequently, nucleic acid amplification (PCR) is carried out to amplify the missing 5-end of the cDNA using a combination of gene specific and adaptor specific oligonucleotide primers. The PCR reaction is repeated using primers known as nested primers that are designed to anneal with the amplified product, which is generally an adaptor specific primer that anneals further 3' in the adaptor sequence and a gene specific primer that anneals further 5' in the known gene sequence. The reaction products are then analyzed by DNA sequencing and a full-length cDNA is prepared either by directly joining the product to the existing cDNA to provide a complete sequence, or by carrying out a separate full-length PCR using the new sequence information for the design of the 5' primer.

When nucleic acid molecules of the present invention are utilized for the recombinant production of polypeptides of the present invention, the polynucleotide can include the coding sequence for the mature polypeptide, by itself; or the coding sequence for the mature polypeptide in reading frame with other coding sequences, such as those encoding a leader or secretory sequence, a pre-, pro- or prepro-protein sequence, or other fusion peptide portions. For example, a marker sequence which facilitates purification of the fused polypeptide can be encoded, e.g., a hexa-histidine peptide, as provided in the pQE vector (Qiagen, Inc.) and described in Gentz et al., *Proc. Natl. Acad. Sci. USA*, 86:821-824 (1989), or is an HA tag. The nucleic acid molecule can also contain non-coding 5' and 3' sequences, such as transcribed, non-translated sequences, splicing and polyadenylation signals, ribosome binding sites and sequences that stabilize mRNA.

Polypeptides and Antibodies

In another aspect, the present invention relates to mammalian TRPV3, TRPV4 and TRPM8 polypeptides. These include the mouse TRPV3 polypeptide comprising an amino acid sequence as set forth in SEQ ID NO: 2, the human TRPV3 polypeptide comprising an amino acid sequence as set forth in SEQ ID: 5, the mouse TRPV4 polypeptide comprising an amino acid sequence as set forth in SEQ ID NO: 14, the human TRPV4 polypeptide comprising an amino acid sequence as set forth in SEQ ID NO: 17, the mouse TRPM8 polypeptide comprising an amino acid sequence as set forth in SEQ ID NO: 8, and the human TRPM8 polypeptide having an amino acid sequence as set forth in SEQ ID NO: 11.

Further polypeptides of the present invention include isolated polypeptides, i.e., variants, in which the amino acid sequence has at least 90% identity, preferably at least 95% identity, more preferably at least 98% identity and most preferably at least 99% identity, to the amino acid sequences as set forth in SEQ ID NO: 2, SEQ ID NO: 5, SEQ ID NO: 8, SEQ ID NO: 11, SEQ ID NO: 14 or SEQ ID NO: 17 over the entire length of these sequences, or a subsequence thereof. Such sequences include the sequences of SEQ ID NO: 2, SEQ ID NO: 5, SEQ ID NO: 8, SEQ ID NO: 11, SEQ ID NO: 14 and SEQ ID NO: 17.

The polypeptides of the present invention also include fragments of the aforementioned sequences. For example, the polypeptides of the invention can include amino acids that comprise one or more functional domains of a TRPV3, TRPV4, or TRPM8 polypeptide of the invention. Examples of such domains are described below; other functional domains can be determined using methods known to those of skill in the art.

The aforementioned TRPV3, TRPV4 and TRPM8 polypeptides can be obtained by a variety of means. Smaller peptides (generally less than 50 amino acids long) may be conveniently synthesized by standard chemical techniques. These polypeptides may also be purified from biological sources by methods well known in the art (see *Protein Purification, Principles and Practice*, 2$^{nd}$ Edition, Scopes, Springer Verlag, NY (1987)). They may also be produced in their naturally occurring, truncated or fusion protein forms by recombinant DNA technology using techniques well-known in the art. These methods include, for example, in vitro recombinant DNA techniques, synthetic techniques and in vivo genetic recombination (see, e.g., the techniques described in Sambrook et al., *Molecular Cloning, A Laboratory Manual*, 3$^{rd}$ Edition, Cold Spring Harbor Press, NY (2001); and Ausubel et al., eds., *Short Protocols in Molecular Biology*, 4$^{th}$ Edition, John Wiley & Sons, Inc., NY (1999)). Alternatively, RNA encoding the proteins may be chemically synthesized (see, e.g., the techniques described in *Oligonucleotide Synthesis*, Gait, Ed., IRL Press, Oxford (1984)). Obtaining large quantities of these polypeptides is preferably by recombinant techniques as further described herein.

Accordingly, another aspect of the present invention relates to a method for producing a TRPV3, TRPV4 or TRPM8 polypeptide. These methods generally involve:

a) obtaining a DNA sequence encoding the TRPV3, TRPV4 or TRPM8 polypeptide as defined above; and b) inserting the DNA into a host cell and expressing the TRPV3, TRPV4 or TRPM8 polypeptide. In some embodiments, the methods further include:

c) isolating the TRPV3, TRPV4 or TRPM8 polypeptide.

The nucleic acid molecules described herein can be expressed in a suitable host cell to produce active TRPV3, TRPV4 or TRPM8 protein. Expression occurs by placing a nucleotide sequence encoding these proteins into an appropriate expression vector and introducing the expression vector into a suitable host cell, growing the transformed host cell, inducing the expression of one of these proteins, and purifying the recombinant proteins from the host cell to obtain purified, and preferably active, TRPV3, TRPV4 or TRPM8 protein. Appropriate expression vectors are known in the art. For example, pET-14b, pcDNA1Amp and pVL1392 are available from Novagen and Invitrogen and are suitable vectors for expression in *E. Coli*, COS cells and baculovirus infected insect cells, respectively. These vectors are illustrative of those that are known in the art. Suitable host cells can be any cell capable of growth in a suitable media and allowing purification of the expressed TRPV3, TRPV4 or TRPM8 protein. Examples of suitable host cells include bacterial cells, such as *E. Coli*, Streptococci, Staphylococci, *Streptomyces* and *Bacillus subtilis* cells; fungal cells, such as yeast cells, e.g., *Pichia* and *Aspergillus* cells; insect cells, such as *Drosophila* S2 and *Spodoptera* Sf9 cells; mammalian cells, such as CHO, COS, HeLa; and plant cells.

Growth of the transformed host cells can occur under conditions that are known in the art. The conditions will generally depend upon the host cell and the type of vector used. Suitable induction conditions may be used such as temperature and chemicals and will depend on the type of promoter utilized.

Purification of the TRPV3, TRPV4 or TRPM8 protein can be accomplished using known techniques without performing undue experimentation. Generally, the transformed cells expressing one of these proteins are broken, crude purification occurs to remove debris and some contaminating proteins, followed by chromatography to further purify the protein to the desired level of purity. Cells can be broken by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well-known techniques for refolding proteins may be used to obtain the active conformation of the protein when the protein is denatured during intracellular synthesis, isolation or purification.

In another aspect, the present invention relates to antibodies that recognize epitopes within the amino acid sequence of SEQ ID NO: 2, SEQ ID NO: 5, SEQ ID NO: 8, SEQ ID NO: 11, SEQ ID NO: 14 or SEQ ID NO: 17. As used herein, the term "antibody" includes, but is not limited to, polyclonal antibodies, monoclonal antibodies, humanized or chimeric antibodies and biologically-functional antibody fragments which are those fragments sufficient for binding of the antibody fragment to the protein. Antibodies specific for proteins encoded by the aforementioned sequences have utilities in several types of applications. These may include, e.g., the production of diagnostic kits for use in detecting and diagnosing pain, particularly in differentiating among different types of pain. Another use would be to link such antibodies to therapeutic agents, such as chemotherapeutic agents, followed by administration to subjects suffering from pain. These and other uses are described in more detail below.

For the production of antibodies to a protein encoded by one of the disclosed genes, various host animals may be immunized by injection with the polypeptide, or a portion thereof. Such host animals may include but are not limited to rabbits, mice and rats, to name but a few. Various adjuvants may be used to increase the immunological response, depending on the host species, including but not limited to Freund's (complete and incomplete), mineral gels such as aluminum hydroxide, surface active substances, such as lysolecithin, pluronic polyols, polyanions, peptides, oil emulsions, keyhole limpet hemocyanin, dinitrophenol, and potentially useful human adjuvants, such as BCG (Bacille Calmette-Guerin) and *Corynebacterium parvum.*

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to the hybridoma technique of Kohler and Milstein, *Nature,* 256:495-497 (1975); and U.S. Pat. No. 4,376,110, the human B-cell hybridoma technique (see Kosbor et al., *Immunology Today,* 4:72 (1983); Cole et al., *Proc. Natl. Acad. Sci. USA,* 80:2026-2030 (1983), and the EBV-hybridoma technique (see Cole et al., *Monoclonal Antibodies and Cancer Therapy*, Alan R. Liss, Inc., pp. 77-96 (1985)). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (see Morrison et al., *Proc. Natl. Acad. Sci. USA,* 81:6851-6855 (1984); Neuberger et al., *Nature,* 312:604-608 (1984); Takeda et al., *Nature,* 314:452-454 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived from a murine mAb and a human immunoglobulin constant region.

Alternatively, techniques described for the production of single chain antibodies (see U.S. Pat. No. 4,946,778; Bird, *Science,* 242:423-426 (1988); Huston et al., *Proc. Natl. Acad. Sci. USA,* 85:5879-5883 (1988); and Ward et al., *Nature,* 334:544-546 (1989)) can be adapted to produce differentially expressed gene single-chain antibodies. Single-chain antibodies are formed by linking the heavy and light chain fragments of the Fv region via an amino acid bridge, resulting in a single-chain polypeptide.

Most preferably, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (see Huse et al., *Science,* 246:1275-1281 (1989)) to allow rapid and easy identification of monoclonal Fab fragments with the desired specificity.

Assays for Expression of TRPV3, TRPV4 and TRPM8

In another aspect, diagnostic assays are provided which are capable of detecting the expression of one or more of TRPV3, TRPV4 or TRPM8 in human tissue. Such assays are particularly useful in identifying subjects suffering from pain and differentiating among different types of pain. As stated above, expression of the TRPV3 and TRPV4 genes are up-regulated in a rat injury model. Accordingly, up-regulation of the TRPV3 and TRPV4 genes in a sample obtained from a subject suffering from pain compared with a normal value of expression of these genes, e.g., a sample obtained from a subject not suffering from pain, or a pre-established control for which expression of the gene was determined at an earlier time, is indicative of a subject suffering from pain. Expression of one or more of these genes can be detected by measuring either protein encoded by the gene or mRNA corresponding to the gene in a tissue sample, particularly from a human tissue sample obtained from a site of pain.

Expression of the TRPV3, TRPV4 and TRPM8 proteins can be detected by a probe which is detectably-labeled, or which can be subsequently-labeled. Generally, the probe is an antibody which recognizes the expressed protein as described above, especially a monoclonal antibody. Accordingly, in one embodiment, an assay capable of detecting the expression of one or more of TRPV3, TRPV4 or TRPM8 genes comprises contacting a human tissue sample with antibodies preferably monoclonal antibodies, that bind to TRPV3, TRPV4 or TRPM8 polypeptides and determining whether the monoclonal antibodies bind to the polypeptides in the sample.

Immunoassay methods which utilize the antibodies include, but are not limited to, dot blotting, western blotting, competitive and non-competitive protein binding assays, enzyme-linked immunosorbant assays (ELISA), immunohistochemistry, fluorescence-activated cell sorting (FACS) and others commonly used and widely-described in scientific and patent literature, and many employed commercially.

Particularly preferred, for ease of detection, is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule, followed by incubation for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well-known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the protein expressed by the gene of interest, e.g., TRPV3 or a fragment thereof.

The most commonly used reporter molecules in this type of assay are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of TRPV3, TRPV4 or TRPM8 protein which is present in the tissue sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well-established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

The level of expression of mRNA corresponding to the TRPV3, TRPV4 and TRPM8 genes can be detected utilizing methods well-known to those skilled in the art, e.g., northern blotting, RT-PCR, real time quantitative PCR, high density arrays and other hybridization methods. Accordingly, in another embodiment, an assay capable of detecting the expression of one or more of TRPV3, TRPV4 or TRPM8 genes in a sample of tissue, preferably human tissue, is provided which comprises contacting a human tissue sample with an oligonucleotide, i.e., a primer, that is capable of hybridizing to a nucleic acid, particularly a mRNA, that encodes TRPV3, TRPV4 or TRPM8. The oligonucleotide primer is generally from 10-20 nucleotides in length, but longer sequences can also be employed.

RNA can be isolated from the tissue sample by methods well-known to those skilled in the art as described, e.g., in Ausubel et al., *Current Protocols in Molecular Biology*, John Wiley and Sons, Inc., 1:4.1.1-4.2.9 and 4.5.1-4.5.3 (1996).

One preferred method for detecting the level of mRNA transcribed from the TRPV3, TRPV3, and TRPM8 genes is RT-PCR. In this method, an mRNA species is first transcribed to complementary DNA (cDNA) with use of the enzyme reverse transcriptase. Methods of reverse transcribing RNA into cDNA are well-known and described in Sambrook et al., supra. The cDNA is then amplified as in a standard PCR reaction (referred to as PCR) which is described in detail in U.S. Pat. Nos. 4,683,195; 4,683,202; and 4,800,159.

Briefly, in PCR, two primer sequences are prepared which are complementary to regions on opposite complementary strands of the target nucleic acid sequence. An excess of deoxynucleoside triphosphates are added to a reaction mixture along with a DNA polymerase, e.g., Taq polymerase. The primers will bind to the target nucleic acid and the polymerase will cause the primers to be extended along the target nucleic acid sequence by adding on nucleotides. By raising and lowering the temperature of the reaction mixture, the extended primers will dissociate from the target nucleic acid to form reaction products, excess primers will bind to the target nucleic acid and to the reaction products and the process is repeated.

Another preferred method for detecting the level of mRNA transcripts obtained from more than one of the disclosed genes involves hybridization of labeled mRNA to an ordered array of oligonucleotides. Such a method allows the level of transcription of a plurality of these genes to be determined simultaneously to generate gene expression profiles or patterns. In particularly useful embodiments, a gene expression profile derived from a tissue sample obtained from a subject suffering from pain can be compared with a gene expression profile derived from a sample obtained from a normal subject, i.e., a subject not suffering from pain, to determine whether one or more of the TRPV3, TRPV4 and TRPM8 genes are over-expressed in the sample obtained from the subject suffering from pain relative to the genes in the sample obtained from the normal subject, and thereby determine which gene is responsible for the pain. Ligase chain reaction is another assay that is suitable for detecting the presence of a TRPV3, TRPV4, or TRPM8 polynucleotide.

The oligonucleotides utilized in this hybridization method typically are bound to a solid support. Examples of solid supports include, but are not limited to, membranes, filters, slides, paper, nylon, wafers, fibers, magnetic or nonmagnetic beads, gels, tubing, polymers, polyvinyl chloride dishes, etc. Any solid surface to which the oligonucleotides can be bound, either directly or indirectly, either covalently or non-covalently, can be used. A particularly preferred solid substrate is a high density array or DNA chip. These high density arrays contain a particular oligonucleotide probe in a pre-selected location on the array. Each pre-selected location can contain more than one molecule of the particular probe. Because the oligonucleotides are at specified locations on the substrate, the hybridization patterns and intensities (which together result in a unique expression profile or pattern) can be interpreted in terms of expression levels of particular genes.

The oligonucleotide probes are preferably of sufficient length to specifically hybridize only to complementary transcripts of the above identified gene(s) of interest. As used herein, the term "oligonucleotide" refers to a single-stranded nucleic acid. Generally the oligonucleotides probes will be at least 16-20 nucleotides in length, although in some cases longer probes of at least 20-25 nucleotides will be desirable.

The oligonucleotide probes can be labeled with one or more labeling moieties to permit detection of the hybridized probe/target polynucleotide complexes. Labeling moieties can include compositions that can be detected by spectroscopic, biochemical, photochemical, bioelectronic, immunochemical, electrical optical or chemical means. Examples of labeling moieties include, but are not limited to, radioisotopes, e.g., $^{32}P$, $^{33}P$, $^{35}S$, chemiluminescent compounds, labeled binding proteins, heavy metal atoms, spectroscopic markers, such as fluorescent markers and dyes, linked enzymes, mass spectrometry tags and magnetic labels.

Oligonucleotide probe arrays for expression monitoring can be prepared and used according to techniques which are well-known to those skilled in the art as described, e.g., in Lockhart et al., supra); McGall et al., supra; and U.S. Pat. No. 6,040,138.

In another aspect, kits are provided for detecting the level of expression of one or more of the TRPV3, TRPV4 and TRPM8 genes in a sample of tissue, e.g., a sample of tissue from a site of pain. For example, the kit can comprise a labeled compound or agent capable of detecting a protein encoded by, or mRNA corresponding to, at least one of the genes TRPV3, TRPV4 and TRPM8; or fragment of the protein, means for determining the amount of protein encoded by or mRNA corresponding to the gene or fragment of the protein; and means for comparing the amount of protein encoded by or mRNA corresponding to the gene or fragment of the protein, obtained from the subject sample with a standard level of expression of the gene, e.g., from a sample obtained from a subject not suffering pain. With respect to detection of TRPV3, TRPV4 and TRPM8 proteins, the agent can be an antibody specific for these proteins. With respect to detection of mRNA, the agent can be pre-selected primer pairs that selectively hybridize to mRNA corresponding to SEQ ID NO: 1, SEQ ID NO: 3, SEQ ID NO: 4, SEQ ID NO: 6, SEQ ID NO: 7, SEQ ID NO: 9, SEQ ID NO: 10, SEQ ID NO: 12, SEQ ID NO: 13, SEQ ID NO: 15, SEQ ID NO: 16 and SEQ ID NO: 18. The compound or agent can be packaged in a suitable container. The kit can further comprise instructions for using the kit to detect protein encoded by or mRNA corresponding to the gene.

In another aspect, the present invention is based on the identification of novel genes that are specific for trkA$^+$ pain-specific DRG neurons. DRG neurons can be classified into several distinct subpopulations with different functional, biochemical and morphological characteristics. The only known early markers differentially expressed by the DRG subtypes are the trk family of neurotrophin receptors. Gene-targeted deletion of the mouse neurotrophins and trks (receptor tyrosine kinases) have demonstrated that neurotrophin signaling is required for the survival of the different subpopulations of DRG neurons that trks specifically mark. For example, trkA knockout mice lack the nociceptive and thermoceptive neurons that sense pain and temperature.

Identification of Agonists and Antagonists

In another aspect, the present invention relates to the use of the TRPV3, TRPV4 and TRPM8 genes in methods for identifying agents useful in treating pain, or modulating responses to heat and cold, as flavor enhancers (e.g., menthol mimetics that one can identify using TRPM8 in a screening assay) and as cosmetic additives that provide a cool or warm sensation to the skin (e.g., menthol mimetics, capsaicin mimetics or other compounds identified using TRPM8 or TRPV3 in screening assays). These methods comprise assaying for the ability of various agents to bind and/or modulate the activity of the proteins encoded by these genes, and/or decrease or increase the level of expression of mRNA corresponding to or protein encoded by these genes. The candidate agent may function as an antagonist or agonist. Examples of various candidate agents include, but are not limited to, natural or synthetic molecules such as antibodies, proteins or fragments thereof, antisense nucleotides, double-stranded RNA, ribozymes, organic or inorganic compounds, etc. Methods for identifying such candidate agents can be carried out in cell-based systems and in animal models.

For example, proteins encoding these genes expressed in a recombinant host cell such as CHO or COS may be used to identify candidate agents that bind to and/or modulate the activity of the protein, or that increase or decrease the level of expression of mRNA corresponding to or encoded by these genes. In this regard, the specificity of the binding of a candidate agent showing affinity for the protein can be shown by measuring the affinity of the agents for cells expressing the receptor or membranes from these cells. This can be achieved by measuring the specific binding of labeled, e.g., radioactive agent to the cell, cell membranes or isolated protein, or by measuring the ability of the candidate agent to displace the specific binding of standard labeled ligand.

Cells expressing proteins encoded by these genes can also be utilized to identify agents that modulate the protein's activity. For example, one method for identifying compounds useful for treating pain, or for use as a flavor or fragrance, comprises, providing a cell that expresses one of these proteins, e.g., TRPV3, TRPV4 or TRPM8, combining a candidate agent with the cell and measuring the effect of the candidate agent on the protein's activity. The cell can be a mammalian cell, a yeast cell, bacterial cell, insect cell or any other cell expressing the TRPV3 protein. The candidate compound is evaluated for its ability to elicit an appropriate response, e.g., the stimulation of cellular depolarization or increase in intracellular calcium ion levels due to calcium ion influx.

The level of intracellular calcium can be assessed using a calcium ion-sensitive fluorescent indicator such as a calcium ion-sensitive fluorescent dye, including, but not limited to, quin-2 (see, e.g., Tsien et al., *J. Cell Biol.*, 94:325 (1982)), fura-2 (see, e.g., Grynkiewicz et al., *J. Biol. Chem.*, 260:3440 (1985)), fluo-3 (see, e.g., Kao et al., *J. Biol. Chem.*, 264:8179 (1989)) and rhod-2 (see, e.g., Tsien et al., *J. Biol. Chem., Abstract* 89a (1987)).

Membrane depolarization of recombinant cells expressing the above proteins can be monitored using a fluorescent dye that is sensitive to changes in membrane potential, including, but not limited to, carbocyanaines such as 3,3'-dipentyloxacarbocyanine iodide (DiOC$_5$) and 3,3'-dipropylthiadicarbocyanine iodide (DiSC$_3$), oxonols, such as bis-(1,3-dibutyl-barbituric acid) pentamethine oxonol (DiBAC$_4$ (Biotrend Chemikalien GmbH, Cologne, Germany)) or bis-(1,3-dibutylbarbituric acid) pentamethine oxonol, etc. Cellular fluorescence can be monitored using a fluorometer.

The assays to identify antagonists of ion channel activity are preferably performed under conditions in which the particular ion channel is active. Conversely, when seeking to identify an agonist, one would preferably perform the screening under conditions in which the ion channel is not active in the absence of the agonist. For example, TRPV3 is activated (i.e., mediates ion passage through a membrane) at temperatures of about 33° C. and above. Accordingly, it is preferred to screen for antagonists of TRPV3 at a temperature of above about 33° C. (e.g., 35°, 40°, 45°, or above), and to screen for agonists of TRPV3 at a temperature below 33° C. (e.g., 30°, 25°, 20° C., or below). In some assays, it is desirable to discriminate between TRPV3-mediated ion transport and ion transport mediated by a different TRP ion channel. For example, to discriminate between TRPV3-mediated cation transport and cation transport mediated by, for example, TRPV1 or TRPV2, the assay can be conducted at a temperature above the activation threshold of TRPV3 but below the activation threshold of the other receptor (e.g., below about 43° C. or below about 52° C., respectively, for TRPV1 and TRPV2). Thus, an assay temperature of between about 35° C. and about 40° C. would result in active TRPV3, but inactive TRPV1 and TRPV2.

Similarly, assays to identify antagonists of TRPM8 cation channel activity are preferably conducted under conditions in which the TRPM8 conducts cations in the absence of an antagonist. For example, since the threshold activation temperature of TRPM8 is approximately 15° C., one could screen for antagonists at a temperature below 15° C. (e.g., 10°, 5°, 0° C., and the like). TRPM8 also is activated by menthol, so instead of or in addition to regulating activity by temperature, one could conduct the assay for antagonists in the presence of menthol. To identify an agonist of TRPM8, it is preferred to conduct the assay under conditions in which TRPM8 does not exhibit significant ion channel activity, such as a temperature above 15° C. (e.g., 20° C., 25° C., 30° C., etc.). To distinguish between TRPM8-mediated cation channel activity and that of other TRP ion channels, the assay for agonists can be conducted at a temperature below 33° C. (the activation temperature of TRPV3). For example, a temperature between 20° C. and 30° C. would result in TRPM8 being inactive in the absence of an agonist, and TRPV3, TRPV1 and TRPV2 also being inactive.

The TRPV3, TRPV4, and TRPM8 cation channels function to transport not only divalent cations (e.g., $Ca^{2++}$), but also monovalent cations (e.g., $Na^+$, $K^+$).

The assay can be carried out manually or using an automated system. For high throughput screening assays to identify ligands of such proteins, an automated system is preferred. For example, one type of automated system provides a 96-well, 384-well, or 1536-well, culture plate wherein a recombinant cell comprising a nucleotide sequence encoding such a protein is cultured to express the protein. The plate is loaded into a fluorescence imaging plate reader (e.g., "FLIPR®" commercially available from Molecular Devices Corp., Sunnyvale, Calif.) which measure the kinetics of intracellular calcium influx in each of the wells. The FLIPR® can quantitatively transfer fluids into and from each well of the plate and thus can be utilized to add the calcium-ion sensitive fluorescent indicator dye, a candidate agent, etc. Membrane potential dyes suitable for high throughput assays include the FLIPR® Membrane Potential Assay Kit as sold by Molecular Devices Corp.

Once a candidate compound is identified as an agonist, such agonists can be added to cells expressing such proteins followed by the addition of various candidate agents to determine which agents function as antagonists.

The nucleic acids and polypeptides of the present invention can also be utilized to identify candidate agents that modulate, i.e., increase or decrease the level of expression of mRNA and proteins in cells expressing these proteins. For example, expression of the TRPV4 gene is shown to be up-regulated in a rat injury model (see Example 3). The level of expression of mRNA and protein can be detected utilizing methods well-known to those skilled in the art as described above.

After initial screening assays have identified agents that inhibit the protein's activity or level of expression of mRNA or protein, these agents can then be assayed in conventional live animal models of pain to assess the ability of the agent to ameliorate the pathological effects produced in these models and/or inhibit expression levels of mRNA or protein. For example, in the case of the TRPV4 gene which is shown to be up-regulated in a rat injury model, one method for identifying an agent useful in the treatment of pain comprises:

a) administering a candidate agent, e.g., an antisense nucleotide derived from the sequence of the TRPV4 gene, to a subject such as a rat model of pain; and b) determining reversal of established pain in the animal.

Various animal models utilized in neuropathic pain are well-known in the art, e.g., the partial sciatic ligation model, i.e., the Seltzer model, the chronic constriction injury model, i.e., the CCI model and the spinal nerve ligation model, i.e., the Chung model.

For example, in the partial sciatic ligation (see, the Seltzer model as described in Seltzer et al., *Pain,* 43:205-218 (1990)), rats are anesthetized and a small incision made mid-way up one thigh (usually the left) to expose the sciatic nerve. The nerve is carefully cleared of surrounding connective tissues at a site near the trochanter just distal to the point at which the posterior biceps semitendinosus nerve branches off the common sciatic nerve. A 7-0 silk suture is inserted into the nerve with a ⅜ curved, reversed-cutting mini-needle, and tightly ligated so that the dorsal ⅓ to ½ of the nerve thickness is held within the ligature. The muscle and skin are closed with sutures and clips and the wound dusted with antibiotic powder. In sham animals the sciatic nerve is exposed but not ligated and the wound closed as before.

In the chronic constriction model (the CCI model as described in Bennett et al., *Pain,* 33:87-107 (1988)) rats are anesthetized and a small incision is made midway up one thigh to expose the sciatic nerve. The nerve is freed of surrounding connective tissue and four ligatures of chromic gut are tied loosely around the nerve with approximately 1 mM between each, so that the ligatures just barely construct the surface of the nerve. The wound is closed with sutures and clips. In sham animals the sciatic nerve is exposed but not ligated and the wound is closed.

In the spinal nerve ligation (see, the Chung model as described in Kim et al., *Pain,* 50:355-363 (1992)) rats are anesthetized and placed into a prone position and an incision made to the left of the spine at the L4-S2 level. A deep dissection through the paraspinal muscles and separation of the muscles from the spinal processes at the L4-S2 level will reveal part of the sciatic nerve as it branches to form the L4, L5 and L6 spinal nerves. The L6 transverse process is carefully removed with a small rongeur enabling visualization of these spinal nerves. The L5 spinal nerve is isolated and tightly ligated with 7-0 silk suture. The wound is closed with a single muscle suture (6-0 silk) and one or two skin closure clips and dusted with antibiotic powder. In sham animals the L5 nerve is exposed as before but not ligated and the wound closed as before.

Male Wistar rats (120-140 g) are used for each of the three models. Mechanical hyperalgesia is then assessed in rat by measuring paw withdrawal thresholds of both hindpaws to an increasing pressure stimulus using an Analgesymeter (Ugo-Basile, Milan). Thermal hyperalgesia is assessed by measuring withdrawal latencies to a noxious thermal stimuls applied to the underside of each hindpaw. With all models, mechanical hyperalgesia and allodynia and thermal hyperalgesis develop within 1-3 days following surgery and persist for at least 50 days. Reversal of mechanical hyperalgesia and allodynia and thermal hyperalgesia is assessed following administration of the agent, e.g., the antisense nucleotide specific for the TRPV4 gene.

Another example of a method for identifying agents useful in treating pain comprises:

a) administering a candidate agent to a subject such as a rat model of pain;

b) detecting a level of expression of a protein encoded by or mRNA corresponding to one of genes described herein, e.g., TRPV4, in a sample obtained from the subject; and c) comparing the level of expression of the protein or mRNA in the sample in the presence of the agent with a level of expression of the protein or mRNA obtained from the sample of the subject in the absence of the agent, wherein a decreased level of expression of the protein or mRNA in the sample in the presence of the agent relative to the level of expression of the protein or mRNA in the absence of the agent is indicative that the agent is useful in the treatment of pain.

The present invention also provides a method for identifying an agent useful in the modulation of a mammalian sensory response. The method comprises a) contacting a candidate agent with a test system that comprises a receptor polypeptide selected from the group consisting of TRPM8, TRPV3, and TRPV4; and b) detecting a change in activity of the receptor polypeptide in the presence of the candidate agent as compared to the activity of the receptor polypeptide in the absence of the agent, thereby identifying an agent that modulates receptor activity.

In particularly useful embodiments of this method, the sensory response is response to cold and the polypeptide is a TRPM8 polypeptide preferably having an amino acid sequence selected from the group consisting of SEQ ID NO: 8 and SEQ ID NO: 11. The method can further include the step of administering the agent that modulates receptor activity to a test subject, and thereafter detecting a change in the sensory response in the test subject.

The test system that is contacted with a candidate agent can comprise, e.g., a membrane that comprises the receptor polypeptide or a cell that expresses a heterologous polynucleotide that encodes the receptor polypeptide. In a useful embodiment, the heterologous polynucleotide comprises a nucleotide sequence as set forth in nucleotides 448-3762 of SEQ ID NO: 7 or as set forth in nucleotides 61-4821 of SEQ ID NO: 10, and the receptor polypeptide is a TRPM8 polypeptide. The cell can be substantially isolated wherein the step of contacting of the cell with the candidate agent is performed in vitro or the cell can be present in an organism wherein the step of contacting is performed in vivo.

In particularly useful embodiments, the receptor activity comprises increased or decreased $Ca^{2+}$ passage through the membrane comprising the receptor polypeptide, wherein the membrane can be, e.g., a substantially purified cell membrane or a membrane comprising a liposome.

Pharmaceutical Compositions and Methods

The present invention also provides for therapeutic methods of treating a subject suffering from pain utilizing the aforementioned genes, i.e., TRPV3, TRPV4, and TRPM8. Examples of suitable therapeutic agents include, but are not limited to, antisense nucleotides, ribozymes, double-stranded RNAs, antagonists and agonists, as described in detail below.

As used herein, the term "antisense" refers to nucleotide sequences that are complementary to a portion of an RNA expression product of at least one of the disclosed genes. "Complementary" nucleotide sequences refer to nucleotide sequences that are capable of base-pairing according to the standard Watson-Crick complementary rules. That is, purines will base pair with pyrimidine to form combinations of guanine:cytosine and adenine:thymine in the case of DNA, or adenine:uracil in the case of RNA. Other less common bases, e.g., inosine, 5-methylcytosine, 6-methyladenine, hypoxanthine and others may be included in the hybridizing sequences and will not interfere with pairing.

When introduced into a host cell, antisense nucleotide sequences specifically hybridize with the cellular mRNA and/or genomic DNA corresponding to the gene(s) so as to inhibit expression of the encoded protein, e.g., by inhibiting transcription and/or translation within the cell.

The isolated nucleic acid molecule comprising the antisense nucleotide sequence can be delivered, e.g., as an expression vector, which when transcribed in the cell, produces RNA which is complementary to at least a unique portion of the encoded mRNA of the gene(s). Alternatively, the isolated nucleic acid molecule comprising the antisense nucleotide sequence is an oligonucleotide probe which is prepared ex vivo and, which when introduced into the cell results in inhibiting expression of the encoded protein by hybridizing with the mRNA and/or genomic sequences of the gene(s).

Preferably, the oligonucleotide contains artificial internucleotide linkages which render the antisense molecule resistant to exonucleases and endonucleases, and thus are stable in the cell. Examples of modified nucleic acid molecules for use as antisense nucleotide sequences are phosphoramidate, phosporothioate and methylphosphonate analogs of DNA as described, e.g., in U.S. Pat. Nos. 5,176,996; 5,264, 564; and 5,256,775. General approaches to preparing oligomers useful in antisense therapy are described, e.g., in Van der Krol., *BioTechniques*, 6:958-976 (1988); and Stein et al., *Cancer Res.*, 48:2659-2668 (1988).

Typical antisense approaches, involve the preparation of oligonucleotides, either DNA or RNA, that are complementary to the encoded mRNA of the gene. The antisense oligonucleotides will hybridize to the encoded mRNA of the gene and prevent translation. The capacity of the antisense nucleotide sequence to hybridize with the desired gene will depend on the degree of complementarity and the length of the antisense nucleotide sequence. Typically, as the length of the hybridizing nucleic acid increases, the more base mismatches with an RNA it may contain and still form a stable duplex or triplex. One skilled in the art can determine a tolerable degree of mismatch by use of conventional procedures to determine the melting point of the hybridized complexes.

Antisense oligonucleotides are preferably designed to be complementary to the 5' end of the mRNA, e.g., the 5' untranslated sequence up to and including the regions complementary to the mRNA initiation site, i.e., AUG. However, oligonucleotide sequences that are complementary to the 3' untranslated sequence of mRNA have also been shown to be effective at inhibiting translation of mRNAs as described e.g., in Wagner, *Nature*, 372:333 (1994). While antisense oligonucleotides can be designed to be complementary to the mRNA coding regions, such oligonucleotides are less efficient inhibitors of translation.

Regardless of the mRNA region to which they hybridize, antisense oligonucleotides are generally from about 15 to about 25 nucleotides in length.

The antisense nucleotide can also comprise at least one modified base moiety, e.g., 3-methylcytosine, 5-methylcytosine, 7-methylguanine, 5-fluorouracil, 5-bromouracil and may also comprise at least one modified sugar moiety, e.g., arabinose, hexose, 2-fluorarabinose and xylulose.

In another embodiment, the antisense nucleotide sequence is an alpha-anomeric nucleotide sequence. An alpha-anomeric nucleotide sequence forms specific double stranded hybrids with complementary RNA, in which, contrary to the usual beta-units, the strands run parallel to each other as described e.g., in Gautier et al., *Nucl. Acids. Res.*, 15:6625-6641 (1987).

Antisense nucleotides can be delivered to cells which express the described genes in vivo by various techniques, e.g., injection directly into the target tissue site, entrapping the antisense nucleotide in a liposome, by administering modified antisense nucleotides which are targeted to the target cells by linking the antisense nucleotides to peptides or antibodies that specifically bind receptors or antigens expressed on the cell surface.

However, with the above-mentioned delivery methods, it may be difficult to attain intracellular concentrations sufficient to inhibit translation of endogenous mRNA. Accordingly, in a preferred embodiment, the nucleic acid comprising an antisense nucleotide sequence is placed under the transcriptional control of a promoter, i.e., a DNA sequence which is required to initiate transcription of the specific genes, to form an expression construct. The use of such a construct to transfect cells results in the transcription of sufficient amounts of single-stranded RNAs to hybridize with the endogenous mRNAs of the described genes, thereby inhibiting translation of the encoded mRNA of the gene. For example, a vector can be introduced in vivo such that it is taken up by a cell and directs the transcription of the antisense nucleotide sequence. Such vectors can be constructed by standard recombinant technology methods. Typical expression vectors include bacterial plasmids or phage, such as those of the pUC or Bluescript™ plasmid series, or viral vectors such as adenovirus, adeno-associated virus, herpes virus, vaccinia virus and retrovirus, adapted for use in eukaryotic cells. Expression of the antisense nucleotide sequence can be achieved by any promoter known in the art to act in mammalian cells. Examples of such promoters include, but are not limited to, the promoter contained in the 3' long terminal repeat of Rous sarcoma virus as described, e.g., in Yamamoto et al., *Cell*, 22:787-797 (1980); the herpes thymidine kinase promoter as described, e.g., in Wagner et al., *Proc. Natl. Acad. Sci. USA*, 78:1441-1445 (1981); the SV40 early promoter region as described e.g., in Bemoist and Chambon, *Nature*, 290:304-310 (1981); and the regulatory sequences of the metallothionein gene as described, e.g., in Brinster et al., *Nature*, 296:39-42 (1982).

Ribozymes are RNA molecules that specifically cleave other single-stranded RNA in a manner similar to DNA restriction endonucleases. By modifying the nucleotide sequences encoding the RNAs, ribozymes can be synthesized to recognize specific nucleotide sequences in a molecule and cleave it as described, e.g., in Cech, *J. Amer. Med. Assn.*, 260:3030 (1988). Accordingly, only mRNAs with specific sequences are cleaved and inactivated.

Two basic types of ribozymes include the "hammerhead" type as described, e.g., in Rossie et al., *Pharmac. Ther.*, 50:245-254 (1991); and the hairpin ribozyme as described, e.g., in Hampel et al., *Nucl. Acids Res.*, 18:299-304 (1999) and U.S. Pat. No. 5,254,678. Intracellular expression of hammerhead and hairpin ribozymes targeted to mRNA corresponding to at least one of the disclosed genes can be utilized to inhibit protein encoded by the gene.

Ribozymes can either be delivered directly to cells, in the form of RNA oligonucleotides incorporating ribozyme sequences, or introduced into the cell as an expression vector encoding the desired ribozymal RNA. Ribozyme sequences can be modified in essentially the same manner as described for antisense nucleotides, e.g., the ribozyme sequence can comprise a modified base moiety.

Double-stranded RNA, i.e., sense-antisense RNA, corresponding to at least one of the disclosed genes can also be utilized to interfere with expression of at least one of the disclosed genes. Interference with the function and expression of endogenous genes by double-stranded RNA has been shown in various organisms such as *C. elegans* as described e.g., in Fire et al., *Nature*, 391:806-811 (1998); *Drosophila* as described, e.g., in Kennerdell et al., *Cell*, 23;95(7):1017-1026 (1998); and mouse embryos as described, e.g., in Wianni et al., *Nat. Cell Biol.*, 2(2):70-75 (2000). Such double-stranded RNA can be synthesized by in vitro transcription of single-stranded RNA read from both directions of a template and in vitro annealing of sense and antisense RNA strands. Double-stranded RNA can also be synthesized from a cDNA vector construct in which the gene of interest is cloned in opposing orientations separated by an inverted repeat. Following cell transfection, the RNA is transcribed and the complementary strands reanneal. Double-stranded RNA corresponding to at least one of the disclosed genes could be introduced into a cell by cell transfection of a construct such as that described above.

The term "antagonist" with respect to methods of treatment refers to a molecule which, when bound to the protein encoded by the gene, inhibits its activity. Antagonists can include, but are not limited to, peptides, proteins, carbohydrates and small molecules (generally, a molecule having a molecular weight of about 1000 daltons or less).

The term "agonist" with respect to methods of treatment refers to a molecule which, when bound to the protein encoded by the gene, activates its activity. Agonists can include, but are not limited to, peptides, proteins, carbohydrates and small molecules.

In a particularly useful embodiment, the antagonist is an antibody-specific for the cell-surface protein expressed by one of the genes, e.g., TRPV3. Antibodies useful as therapeutics encompass the antibodies as described above, and are preferably monoclonal antibodies. The antibody alone may act as an effector of therapy or it may recruit other cells to actually effect cell killing. The antibody may also be conjugated to a reagent such as a chemotherapeutic, radionuclide, ricin A chain, cholera toxin, pertussis toxin, etc. and serve as a target agent. Alternatively, the effector may be a lymphocyte carrying a surface molecule that interacts, either directly or indirectly, with a tumor target. Various effector cells include, cytotoxic T cells and NK cells.

Examples of the antibody-therapeutic agent conjugates which can be used in therapy include, but are not limited to: 1) antibodies coupled to radionuclides, such as $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re, and as described, e.g., in Goldenberg et al., *Cancer Res.*, 41:4354-4360 (1981); Carrasquillo et al., *Cancer Treat. Rep.*, 68:317-328 (1984); Zalcberg et al., *J. Natl. Cancer Inst.*, 72:697-704 (1984); Jones et al., *Int. J. Cancer*, 35:715-720 (1985); Lange et al., *Surgery*, 98:143-150 (1985); Kaltovich et al., *J. Nucl. Med.*, 27:897 (1986); Order et al., *Int. J. Radiother. Oncol. Biol. Phys.*, 8:259-261 (1982); Courtenay-Luck et al., *Lancet*, 1: 1441-1443 (1984) and Ettinger et al., *Cancer Treat. Rep.*, 66:289-297 (1982); 2) antibodies coupled to drugs or biological response modifiers, such as methotrexate, adriamycin and lymphokines, such as interferon as described, e.g., in Chabner et al., *Cancer, Principles and Practice of Oncology*, J.B. Lippincott Co., Philadelphia, Pa., 1:290-328 (1985); Oldham et al., *Cancer, Principles and Practice of Oncology*, J.B. Lippincott Co., Philadelphia, Pa., 2:2223-2245 (1985); Deguchi et al., *Cancer Res.*, 46:3751-3755 (1986); Deguchi et al., *Fed. Proc.*, 44:1684 (1985); Embleton et al., *Br. J. Cancer*, 49:559-565 (1984); and Pimm et al., *Cancer Immunol. Immunother.*, 12:125-134 (1982); 3) antibodies coupled to toxins, as described, e.g., in Uhr et al., *Monoclonal Antibodies and Cancer*, Academic Press, Inc., pp. 85-98 (1983); Vitetta et al., *Biotechnology and Bio. Frontiers*, P. H. Abelson, Ed., pp. 73-85 (1984) and Vitetta et al., *Science*, 219:644-650 (1983); 4) heterofunctional antibodies, for example, antibodies coupled or combined with another antibody so that the complex binds both to the carcinoma and effector cells, e.g., killer cells, such as T cells, as described, e.g., in Perez et al., *J. Exper. Med.*, 163:166-178 (1986); and Lau et al., *Proc. Natl. Acad. Sci. USA*, 82:8648-8652 (1985); and 5) native, i.e., non-conjugated or non-complexed, antibodies, as described in, e.g., in Herlyn et al., *Proc. Natl. Acad. Sci. USA*, 79:4761-4765 (1982); Schulz et al., *Proc. Natl.*

*Acad. Sci. USA,* 80:5407-5411 (1983); Capone et al., *Proc. Natl. Acad. Sci. USA,* 80:7328-7332 (1983); Sears et al., *Cancer Res.,* 45:5910-5913 (1985); Nepom et al., *Proc. Natl. Acad. Sci. USA,* 81:2864-2867 (1984); Koprowski et al., *Proc. Natl. Acad. Sci. USA,* 81:216-219 (1984); and Houghton et al., *Proc. Natl. Acad. Sci. USA,* 82:1242-1246 (1985).

Methods for coupling an antibody or fragment thereof to a therapeutic agent as described above are well-known in the art and are described, e.g., in the methods provided in the references above. In yet another embodiment, the antagonist useful as a therapeutic for treating disorders can be an inhibitor of a protein encoded by one of the disclosed genes.

In the case of treatment with an antisense nucleotide, the method comprises administering a therapeutically effective amount of an isolated nucleic acid molecule comprising an antisense nucleotide sequence derived from at least one of the disclosed genes, wherein the antisense nucleotide has the ability to decrease the transcription/translation of one of the genes. The term "isolated" nucleic acid molecule means that the nucleic acid molecule is removed from its original environment (e.g., the natural environment if it is naturally occurring). For example, a naturally-occurring nucleic acid molecule is not isolated, but the same nucleic acid molecule, separated from some or all of the coexisting materials in the natural system, is isolated, even if subsequently reintroduced into the natural system. Such nucleic acid molecules could be part of a vector or part of a composition, and still be isolated in that such vector or composition is not part of its natural environment.

With respect to treatment with a ribozyme or double-stranded RNA molecule, the method comprises administering a therapeutically effective amount of a nucleotide sequence encoding a ribozyme, or a double-stranded RNA molecule, wherein the nucleotide sequence encoding the ribozyme/double-stranded RNA molecule has the ability to decrease the transcription/translation of one of the genes.

In the case of treatment with an antagonist, the method comprises administering to a subject a therapeutically effective amount of an antagonist that inhibits a protein encoded by one of these genes.

In the case of treatment with an agonist, the method comprises administering to a subject a therapeutically effective amount of an agonist that inhibits a protein encoded by one of these genes. In particularly useful embodiments, the gene is TRPV8 and the agonist can include compounds that are derivatives of menthol and other compounds known to be cool-feeling agents including, but not limited to, camphor, thymol, peppermint oil, thymol and the like. Such compounds can be particular useful in alleviating pain associated with skin inflammation by providing a cool sensation to the skin.

A "therapeutically effective amount" of an isolated nucleic acid molecule comprising an antisense nucleotide, nucleotide sequence encoding a ribozyme, double-stranded RNA, agonist or antagonist, refers to a sufficient amount of one of these therapeutic agents to treat a subject suffering from pain. The determination of a therapeutically effective amount is well within the capability of those skilled in the art. For any therapeutic, the therapeutically effective dose can be estimated initially either in cell culture assays, or in animal models, usually mice, rats, rabbits, dogs or pigs. The animal model may also be used to determine the appropriate concentration range and route of administration. Such information can then be used to determine useful doses and routes for administration in humans.

The present invention also provides for methods of treating pain, wherein the method comprises identifying a patient suffering from a TRPV3-, TRPV4- or TRPM8-mediated pain by measuring expression of protein encoded by or mRNA corresponding to the TRPV3, TRPV4 or TRPM8 gene, and then administering to such a patient an analgesically effective amount of an agent which decreases or increases the activity or expression of one of these genes. The agent can be a therapeutic agent as described above.

An "analgesically effective amount" can be a therapeutically effective amount as described above.

Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Antisense nucleotides, ribozymes, double-stranded RNAs, agonists, antagonists and other agents which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight and gender of the subject, diet, time and frequency of administration, drug combination(s), reaction sensitivities and tolerance/response to therapy.

Normal dosage amounts may vary from 0.1-100,000 mg, up to a total dose of about 1 g, depending upon the route of administration. Guidance as to particular dosages and methods of delivery is provided in the literature and generally available to practitioners in the art. Those skilled in the art will employ different formulations for nucleotides than for antagonists.

For therapeutic applications, the antisense nucleotides, nucleotide sequences encoding ribozymes, double-stranded RNAs (whether entrapped in a liposome or contained in a viral vector), antibodies or other agents are preferably administered as pharmaceutical compositions containing the therapeutic agent in combination with one or more pharmaceutically acceptable carriers. The compositions may be administered alone or in combination with at least one other agent, such as stabilizing compound, which may be administered in any sterile, biocompatible pharmaceutical carrier, including, but not limited to, saline, buffered saline, dextrose and water. The compositions may be administered to a patient alone, or in combination with other agents, drugs or hormones.

The pharmaceutical compositions may be administered by any number of routes including, but not limited to, oral, intravenous, intramuscular, intraarticular, intraarterial, intramedullary, intrathecal, intraventricular, transdermal, subcutaneous, intraperitoneal, intranasal, enteral, topical, sublingual or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences, Maack Publishing Co., Easton, Pa.

Pharmaceutical compositions for oral administration can be formulated using pharmaceutically acceptable carriers well-known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins, such as gelatin and collagen. If desired, disintegrating or solubilizing agents may be added, such as the cross-linked polyvinyl pyrrolidone, agar, alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid or liquid polyethylene glycol with or without stabilizers.

Pharmaceutical formulations suitable for parenteral administration may be formulated in aqueous solutions, preferably in physiologically compatible buffers, such as Hank's solution, Ringer's solution or physiologically buffered saline. Aqueous injection suspensions may contain substances which increase the viscosity of the suspension, such as sodium carboxymethyl cellulose, sorbitol or dextran. Additionally, suspensions of the active compounds may be prepared as appropriate oily injection suspensions. Suitable lipophilic solvents or vehicles include fatty oils, such as sesame oil or synthetic fatty acid esters, such as ethyl oleate or triglycerides or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1-2% sucrose, and 2-7% mannitol, at a pH range of 4.5-5.5, that is combined with buffer prior to use.

After pharmaceutical compositions have been prepared, they can be placed in an appropriate container and labeled for treatment of an indicated condition. For administration of the antisense nucleotide or antagonist, such labeling would include amount, frequency and method of administration. Those skilled in the art will employ different formulations for antisense nucleotides than for antagonists, e.g., antibodies or inhibitors. Pharmaceutical formulations suitable for oral administration of proteins are described, e.g., in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561.

In another aspect, the treatment of a subject, e.g., a rat injury model, with a therapeutic agent such as those described above, can be monitored by detecting the level of expression of mRNA or protein encoded by at least one of the disclosed genes, or the activity of the protein encoded by the gene. These measurements will indicate whether the treatment is effective or whether it should be adjusted or optimized. Accordingly, one or more of the genes described herein can be used as a marker for the efficacy of a drug during clinical trials.

In a particularly useful embodiment, a method for monitoring the efficacy of a treatment of a subject suffering from pain with an agent (e.g., an antagonist, protein, nucleic acid, small molecule or other therapeutic agent or candidate agent identified by the screening assays described herein) is provided comprising:

a) obtaining a pre-administration sample from a subject prior to administration of the agent;

b) detecting the level of expression of mRNA or protein encoded by the gene, or activity of the protein encoded by the gene in the pre-administration sample;

c) obtaining one or more post-administration samples from the subject;

d) detecting the level of expression of mRNA or protein encoded by the gene, or activity of the protein encoded by the gene in the post-administration sample or samples;

e) comparing the level of expression of expression of mRNA or protein encoded by the gene, or activity of the protein encoded by the gene in the pre-administration sample with the level of expression of mRNA or protein encoded by the gene, or activity of the protein encoded by the gene in the post-administration sample or samples; and f) adjusting the administration of the agent accordingly.

For example, increased administration of the agent may be desirable to decrease the level of expression or activity of the gene to lower levels than detected, i.e., to increase the effectiveness of the agent. Alternatively, decreased administration of the agent may be desirable to increase expression or activity of the gene to higher levels than detected, i.e., to decrease the effectiveness of the agent.

EXAMPLES

The following examples are offered to illustrate, but not to limit the present invention.

Example 1

Identification of New VRs

A. VR Searching

Strategy: Known VR sequences are downloaded (GI Nos. 6782444, 5305598, 7106445, 4589143, 6635238, 2570933, 5263196 and 4589141) from NCBI and assembled using Clustal (Megalign—DNAstar, Madison, Wis.) with the following parameters: Gap Penalty 10, GapLength Penalty 10, Ktuple 1, Window 5 and Diagonals Saved 5. This alignment is saved as a *.MSF file.

This *.MSF file is converted to a hidden Markov model using HMMBUILD 2.0 (Sean Eddy, Washington University, St. Louis) then calibrated using HMMCALIBRATE 2.0 (Sean Eddy), and used to search 6 frame translations (February 20 release) of the Celera human genome data using the default parameters. The protein sequences of these files are retrieved and used as subjects in a BLASTP search of NR. This file is manually inspected identifying three novel candidates for VRs.

B. Identification of VR TRPV3

Mechanical and thermal stimuli activate specialized sensory neurons that terminate in the skin at receptor structures like hair follicles or as free nerve endings. Pain and temperature sensitive neurons belong to the latter category and are thus thought to directly sense stimuli. A TRP channel that is expressed in pain neurons, VR1 is partially responsible for the detection of noxious heat. This Example describes the cloning of TRPV3, a close relative of VR1 that is also activated by noxious heat. Surprisingly, TRPV3 is most highly-expressed in skin cells. Keratinocytes that express TRPV3 show a calcium influx in response to noxious heat. Therefore, skin cells possess molecular tools similar to those of sensory neurons to "sense" heat.

VR1 (TRPV1), the best-characterized receptor in the somatic sensory system, is directly gated by noxious heat. VR1 is expressed in small-diameter, nociceptive DRG neurons that terminate in the skin as free nerve endings to detect noxious heat. Analysis of VR1 knockout mice has demonstrated that this channel is partially responsible for heat sensitivity. VR1 belongs to the family of six transmembrane-containing TRP non-selective cation-channels that function in mechanosensation, osmoregulation and replenishment of intracellular calcium stores. This TRPV family includes at least five members, three of which are expressed in DRG neurons. One of these, VRL1 (TRPV2), is also gated by heat, but has a higher threshold than VR1 (52° C. instead of 43° C.) and is not co-expressed with VR1. Recent experiments have implied that VRL1 expression does not correlate with the heat-sensitive neurons in VR1 knockout mice, suggesting the existence of yet another heat-sensing channel.

Public and Celera databases for VR1-related TRP channels are searched by constructing a Hidden Markov Model (HMM) of the VR1 and VRL1 protein sequences from different mammalian species. With this model, the 6-frame translation of human sequence is queried and has identified multiple new putative exons with a great degree of sequence similarity to the ankyrin and transmembrane domains of VR1. These exons map to two genes, one of which is TRPV4, as described, e.g., in Liedtke et al., *Cell,* 103:525-35 (2000); and Strotmann et al., supra). The other novel gene is known as TRPV3.

The full-length sequence of mouse TRPV3 is derived from a combination of exon-prediction software, PCR and RACE amplification from newborn mouse DRG and skin cDNA. For PCR cloning, primers (5'-TGACATGATCCTGCTGAG-GAGTG-3' (SEQ ID NO: 19) and 5'-ACGAGGCAGGC-GAGGTATTCTT-3' (SEQ ID NO: 20)) are designed from the HMM sequences for TRPV3 as a result of blast hits to the ankyrin and transmembrane domains and used to amplify a 699-nucleotide fragment of TRPV3 from newborn DRG cDNA. From this initial fragment, Rapid Amplification of cDNA Ends (RACE) PCR (Clontech) is used to obtain the 5' and 3' ends of TRPV3 from mouse newborn skin and DRG cDNA. In order to characterize the genomic locus of VR1 and TRPV3, primers are designed from predicted HMM TRPV3 exon sequences and used to screen a genomic BAC Mouse (RPCI22) library (Roswell Park Cancer Institute). Primers utilized are shown in Table 1. Additionally, mouse VR1 BACs are identified by hybridizing a 320 bp probe spanning the mouse VR1 ankyrin region to the same BAC library. Positive BAC clones are further characterized by restriction digest mapping, pulse field gel electrophoresis, and Southern blotting as previously described using probes specific to the 5' and 3' ends of the VR1 and TRPV3 genes. BAC clones positive for TRPV3 included 5J3. BAC clones that were positive for both VR1 and TRPV3 included 9e22, 27I14, 82c1 and 112g17. BACs positive for VR1 included 137N13, 137O13, 234J23, 246D9 and 285G11.

TABLE 1

TRPV3 Primers

|  |  | SEQ ID NO: |
|---|---|---|
| 5' RACE |  |  |
| AP40 | CAGCGTATGCAGAGGCTCCAGGGTCAG | 21 |
| AP4 | TTGAAGTCCTCAGCCACCGTCACCA | 22 |
| Mvr4ANK | CACCAGCGCGTGCAGGATGT | 23 |
| AP105 RACE-rev | tcgttctcctcagcgaaggcaagcaga | 24 |
| AP110R (nested) | CCTTCTATCTCCAGGAAGAAGTGTGC | 25 |
| ap113r (race) | GTCACCAGCGCGTGCAGGATGTTGT | 26 |
| ap36 | AGGCCCATACGCCCAGTCCGTGAAC | 27 |
| ap33R | CATGCCCATAGACTGGAAGCC | 28 |
| ap71 | GATGGCGATGTTCAGCGCTGTCTGC | 29 |
| 3' RACE |  |  |
| AP37 | GCTGCCAAGATGGGCAAGGCTGAGA | 30 |
| Ap31 | CCTGGGCTGGGCGAACATGCTCTA | 31 |
| TM6VR4RACE | GCGCCAGATGCGTTCACTTTCTTTGGA | 32 |
| Primers to amplify partial and/or full-length TRPV transcript | | |
| mVR4-F | TGACATGATCCTGCTGAGGAGTG | 33 |
| mVR4-R | ACGAGGCAGGCGAGGTATTCTT | 34 |
| AP72F | TCCAAGCTGTGCTTGTGATA | 35 |
| AP73R | CTTGAGCATGTAGTTTCACACAAA | 36 |
| AP74R | GTGTTTTCCATTCCGTCCAC | 37 |
| AP75R | CGACGTTTCTGGGAATTCAT | 38 |
| AP76R | CTTGAGCATGTAGTTTCACACAAA | 39 |
| AP77F | TCCTCCTCCTCAACATGCTC | 40 |
| AP78R | TGGAAATCAAAACAGTATTTCAATG | 41 |
| AP79F | CTCTTCAAGCTCACCATAGGC | 42 |

TABLE 1-continued

TRPV3 Primers

| | | SEQ ID NO: |
|---|---|---|
| AP80R | CGACGTTTCTGGGAATTCAT | 43 |
| AP81R | GTGTTTTCCATTCCGTCCAC | 44 |
| AP82R | CCCTCTGTTACCGCAGACAC | 45 |
| AP83F | ACTCCAGCCTGGGTGACA | 46 |
| AP84R | ATGGTCTCCAGCTCCCAGTT | 47 |
| AP85R | AGGAGGACGAAGGTGAGGAT | 48 |
| AP86F | AGCCTCAGGTCTGAAGTGGA | 49 |
| AP87R | GCCAGATGCGTTCACTTTCT | 50 |
| AP88R | GGCAAATTTCTTCCATTTCG | 51 |
| AP89R | AGATGCGTTCGCTCTCCTT | 52 |
| AP102F | TGCACACTTCTTCCTGGAGAT | 53 |
| AP103F | TTCCTCATGCACAAGCTGAC | 54 |
| AP104F | TCTTCCTGGAGATAGAAGGGATT | 55 |
| AP106R | CGATGATTTCCAGCACAGAG | 56 |
| AP107F | CTCACCAATGTAGACACAACGAC | 57 |
| AP108F | TACCAGCATGAAGGCTTCTATTT | 58 |
| AP109R | ATAAGCACTGCTGTGATGTCTCC | 59 |
| AP111R | GTCAGCTTGTGCATGAGGAA | 60 |
| AP112F | TGACAGAGACCCCATCCAATCCCAACA | 61 |
| AP114F | CTCTTGTGATATGGCTTTCTGG | 62 |
| AP115F | GAGAAGGAGTGGGTGAGCTG | 63 |
| AP116R | CCTTCTCCCAGAGTCCACAG | 64 |
| AP117F | AGCAGGCAGGAAAATGAGAG | 65 |
| AP118R | CCAAAGATGGTCCAGAAAGC | 66 |
| AP115F | CTCTTGTGATATGGCTTTCTGG | 67 |
| AP116F | AACTGTGATGACATGGACTCTCCCCAG | 68 |
| AP118F | AACTGTGATGACATGGACTC | 69 |
| AP119F | CAGGATGATGTGACAGAGACCCCATC | 70 |
| AP128F | ATGATCCTGCTGAGGAGTGG | 71 |
| AP129R | AGGATGACACAGGCCCATAC | 72 |
| AP130F | ATCCTCACCTTCGTCCTCCT | 73 |
| AP131R | CATTCCGTCCACTTCACCTC | 74 |
| AP204R (3'UTR) | TGGTTTTGCTGTTGTTCCTG | 75 |
| AP205R (POLYA) | CATGTAAATCAACGCAGAAGTCA | 76 |

Several murine ESTs from skin tissues contain 3' UTR TRPV3 sequence (BB148735, BB148088, BB151430 and AI644701), and recently the human TRPV3 sequence has been annotated (see GI: 185877, 18587705 and Peng et al., *Genomics*, 76:99-109 (2001)).

Figure 2:
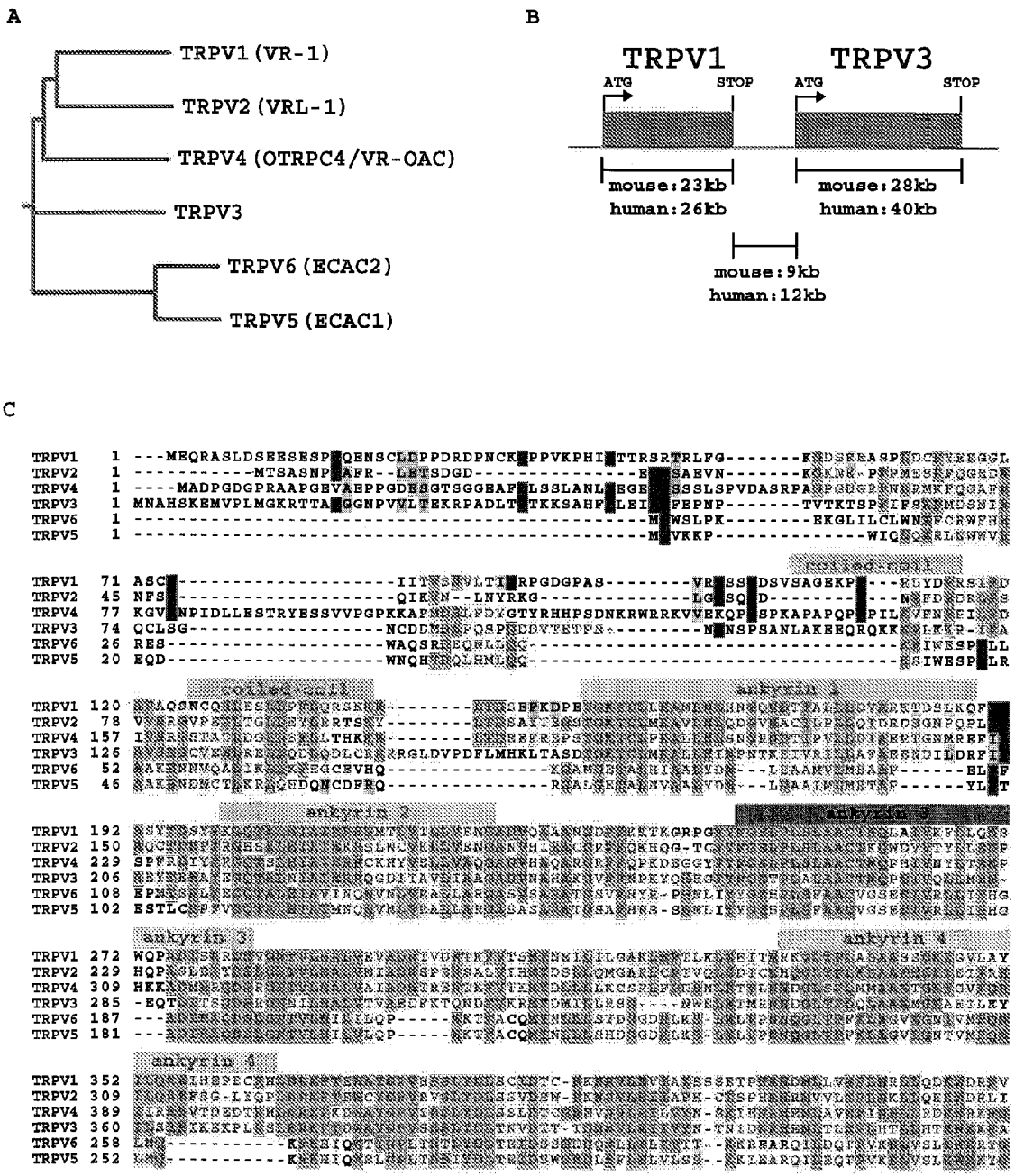
FIGS. 2A-2F show the TRPV3 sequence and genomic localization.
Figure 2D:
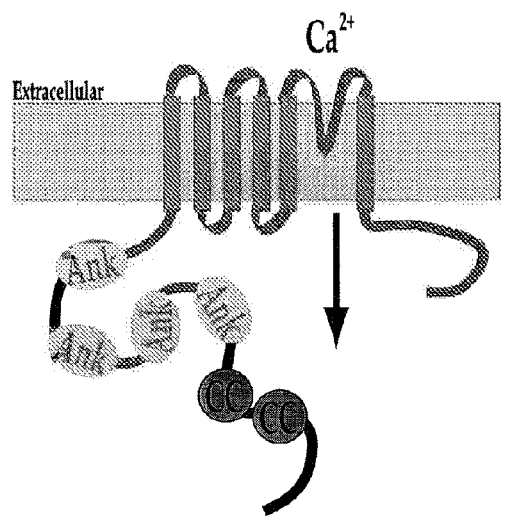
Figure 2E:
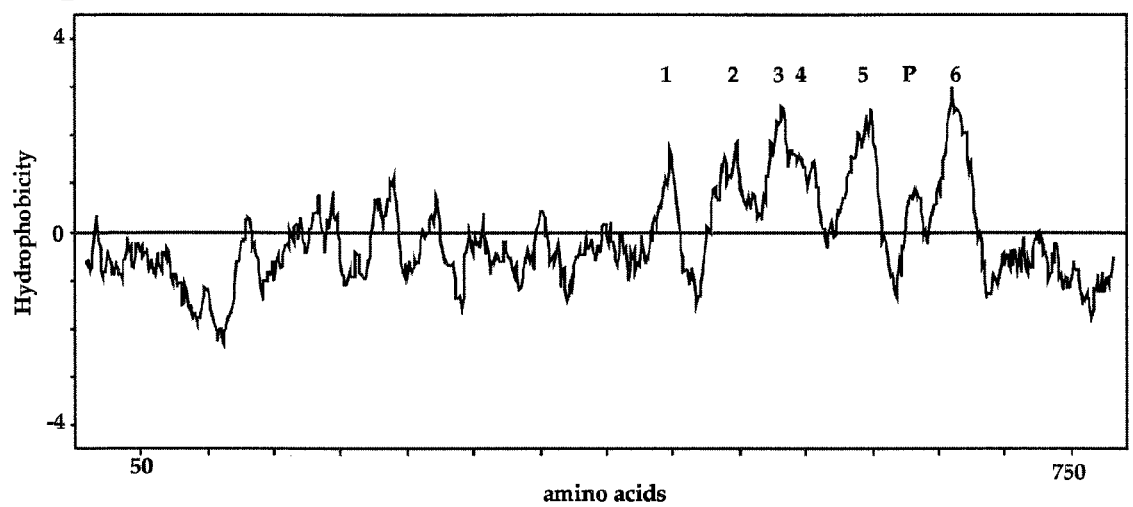
Figure 2F:
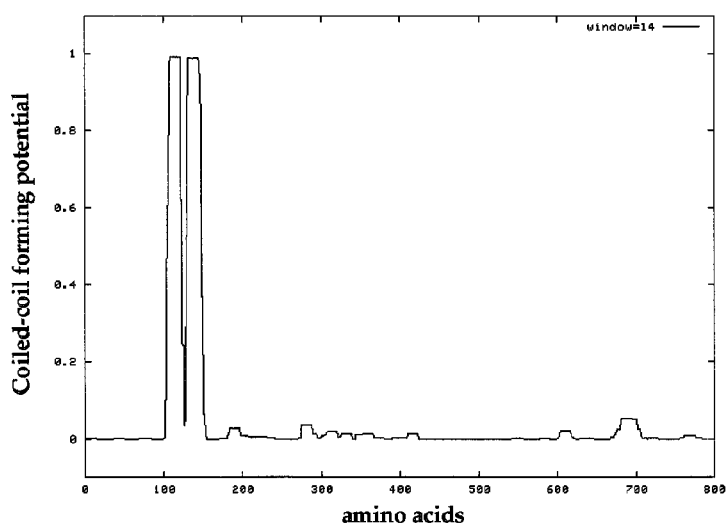

As predicted from the nucleotide sequence, TRPV3 is composed of 791 amino acid residues. The overall sequence of mouse TRPV3 has 43% identity to TRPV1 (VR1) and TRPV4; 41% to TRPV2 (VRL1); and 20% to TRPV5 (ECAC) and TRPV6 (see FIG. 2C). TRPV3 has four, instead of the usual three, predicted N-terminal ankyrin domains that are thought to be involved in protein-protein interactions, TM6 domains and a pore loop region between the last two membrane spanning regions. Two coiled-coil domains N-terminus to the ankyrin domains in TRPV3 are also identified (see FIG. 2F). Coiled-coil domains are implicated in oligomerization of GABA-B channels, and have been previously reported to be present in some TRP channels, but not for TRPVs. Further examination shows that VR1, but not the other members of the TRPV family, also has putative coiled-coil domains in the same N-terminal location. Phylogenetic analysis illustrates that TRPV3 is indeed a member of the OTRP/TRPV sub-family, which is part of the larger TRP ion channel family (see FIG. 2A). The same BAC genomic clone in the public database contains the sequence of TRPV3 and VR1. Both genes map to human chromosome 17p13 and mouse chromosome 11B4. Mapping analysis of these BAC clones, and later the assembled human and mouse genome sequences reveals the distance between the two genes to be about 10 kb (see FIG. 2B). This suggests that TRPV3 and VR1 are derived from a single duplication event.

Example 2

Localization of TRPV3 Expression

A. Northern Blot Analysis

For Northern blot analyses approximately 3 µg of polyA+ RNA extracted from adult mouse and newborn tissue are electrophoresed on 1% glyoxal gels, transferred and hybridized at high-stringency with a $^{32}$P labeled probe representing the entire full-length TRPV3 sequence. Commercial Northern blots (Clontech) are hybridized with the same TRPV3 full-length probe. For human skin specific expression, Northern blots are prepared from 20 µg of total RNA from primary keratinocytes and cell lines CRL-2309 and CRL-2404 (ATCC) or from 2 µg of polyA+ adult and fetal skin RNA (Stratagene). Blots are hybridized with a probe corresponding to the ankryin 1-TM2 region of the TRPV3 human sequence. For VR1 hybridizations, a probe corresponding to nucleotides 60-605, encoding the amino terminus of rat VR1 are used on mouse blots. The entire coding sequence of human VR1 are used as a probe on human Northern blots.

As stated above, to determine the overall tissue distribution of TRPV3, the full-length mouse TRPV3 sequence is used as a probe for Northern blot analysis. No TRPV3 expression is detected using commercial Northern blots. Blots from adult rat are then used that include tissues relevant to somatic sensation, including DRG, spinal cord and different sources of skin. A mRNA of approximately 6.5 kb is present in tissues derived from skin but not in DRGs. Probing the same adult blot with a TRPV1-specific probe confirms its strong expression in DRG while demonstrating a lack of expression in skin tissues. Northern blot analysis of human adult and fetal skin also shows expression of TRPV3. Cultured primary mouse keratinocytes as well as several epidermal cell lines do not show any TRPV3 expression by Northern blots. These finding suggest that TRPV3 expression may get down regulated after tissue dissociation and long-term culture. Northern blots from newborn and adult mice that include tissues relevant for somatic sensation, including DRG, spinal cord and different sources in skin also show TRPV3 expression in skin tissues with weak expression in the DRG.

B. In Situ Hybridization

For in situ hybridizations, newborn and adult tissues are dissected, fixed in 4% paraformaldehyde in PBS, cryoprotected and frozen in liquid nitrogen in OCT mounting medium. Cryostat sections (10 µm) are processed and probed with either a digoxygenin cRNA probe or a $^{35}$S-labeled probe generated by in vitro transcription as described in Wilkinson, in *Essential Developmental Biology, A Practical Approach*, C. Stem, P. Holland, eds., Oxford Univ. Press, NY, pp. 258-263 (1993). Two mouse TRPV3-specific antisense riboprobes are used, one corresponding to nucleotides 235-1020 encoding the amino terminus and the other spanning nucleotides 980-1675 corresponding to the region between the third ankyrin and TM4 domains.

Digoxygenin-labeled probes show specific expression in specialized skin tissues, such as hair follicles in both newborn and adult mice. Expression in epidermis is difficult to assess, because of high background observed in this tissue with the sense probe. To circumvent this problem, and to gain more sensitivity, $^{35}$S-radioactive in situ hybridizations are carried out on cross-sections of newborn mice. Clear expression is detected in the epidermis and hair follicles. No significant expression is detected in DRGs.

C. Immunohistochemical Staining Assays

For immunohistochemistry, rabbits are immunized (AnimalPharm Services, Healdsburg, Calif.) with KLH conjugated peptide corresponding to either the N-terminus of mouse TRPV3 (CDDMDSPQSPQDDVTETPSN (SEQ ID NO: 77)) or a C-terminus peptide (KIQDSSRSNSKTTL (SEQ ID NO: 78)). Affinity purified antiserum recognizes a band of relative molecular mass ~85 kDa in whole-cell extracts prepared from CHO cells stably transfected with mouse TRPV3 (not shown). For peptide competition, diluted antibody solutions (1:5000) of TRPV3 are pre-incubated (room temperature, 2 hours) with TRPV3 antigenic peptide (9 µgmL$^{-1}$) prior to incubation with tissue sections. Immunofluorescence are performed on fixed frozen and paraffin sections using rabbit anti-TRPV3 (1:5000), pan cytokeratin (Abcam) cytokeratin (1:300, Abcam), cytokeratin 10 (K8.60, Sigma), pan-basal Cytokeratin (Abcam), PGP9.5 (Abcam) followed by FITC-labeled goat anti-rabbit (10 µg/mL$^{-1}$) and Cy-3-labeled donkey anti-mouse (Jackson Immunoresearch) antibodies.

Using polyclonal antibodies produced against TRPV3 peptides from either the N-terminus or the C-terminus, intense TRPV3 immunoreactivity is observed in most keratinocytes at the epidermal layer and in hair follicles from newborn and adult rodent tissues. In the epidermis, staining is absent in the outermost layers (stratum corneum and lucidum) as well as the basement membrane. In hair follicles, expression is localized to the outer root sheath and absent from the matrix cells, inner root sheath and sebaceous glands. Developmentally, expression in hair follicles increases from newborn to adult stages. High magnification of these images indicates staining in the cytoplasm and at high levels in the plasma membrane.

Coexpression with various keratinocyte-specific markers shows that TRPV3 is expressed in the basal keratinocytes, which in vitro require low calcium concentrations to maintain their undifferentiated state, as well as in some of the more differentiated suprabasal layers of the epidermis. Temperature-sensing neurons are thought to terminate as free nerve endings mainly at the level of dermis, but some processes do extend into the epidermis (see Hilliges et al., supra; and Cauna, supra. Cutaneous termini can be labeled with the immunohistochemical marker protein gene product 9.5 (PGP 9.5), and it is observed that these epidermal endings indeed co-localize with TRPV3.

D. GFP-fusion Constructs

The full-length mouse TRPV3 is amplified and subcloned into pcDNA3.1/CT-GFP-TOPO (Invitrogen). In vitro transcription/translation (TnT System, Promega) confirms the integrity of the constructs. Cells are viewed live or fixed in 4% paraformaldehyde 48-72 hours after transfection, counter-stained with propidium iodide and mounted in Slowfade (Molecular probes).

Confocal fluorescence microscopy on cells transiently transfected with a C-terminally GFP-tagged TRPV3 protein construct also finds the protein mainly localized at the plasma membrane. This pattern of expression at the cell membrane is consistent with TRPV3 having a role as an ion channel. In sum, the expression analysis suggests that TRPV3 is most prominently expressed in plasma membrane of keratinocytes in both rodents and humans.

Example 3

Activation of TRPV3 Protein by Heat

A. Effect of Heat, Capsazepine and Ruthenium Red Upon Conductance

Given the high degree of homology of TRPV3 to TRPV family members, TRPV3 is tested to determine whether it responds to stimuli known to activate other closely-related family members. Accordingly, the effects of heat upon TRPV3 activity in mediating conductance are examined using whole-cell patch-clamp analysis of transfected CHO cell lines expressing TRPV3.

Mouse TRPV3 and rat TRPV1 cDNA are subcloned into pcDNA5 (Invitrogen) and transfected into CHO-K1/FRT cells using Fugene 6 (Roche). The transfected cells are selected by growth in MEM medium containing 200 µg/mL hygromycin (Gibco BRL). Populations are frozen at early passages and these stocks are used for further studies. Stable clones that express the mRNAs are identified by Northern blot analysis as well as Southern blotting to confirm integration site. Long-term cultures are subsequently maintained at 33° C.

TRPV3 expressing CHO cells are assayed electrophysiologically using whole cell voltage clamped techniques. Currents are recorded via pCLAMP8 suite of software via an Axopatch 200A and filtered at 5 kHz. Series-resistance compensation for all experiments is 80% using 2-5 MΩ resistance, fire-polished pipettes. Unless stated, the holding potential for most experiments is −60 mV, apart from the current-voltage relationship studies (2 second ramp from −100 to +80 mV). Cells are normally bathed in a medium containing (mM): NaCl, 140; KCl, 5; Glucose; 10, HEPES, 10; CaCl$_2$, 2; MgCl$_2$ 1; titrated to pH 7.4 with NaOH, apart from the monovalent permeability studies, when NaCl is replaced by equimolar KCl or CsCl with the omission of KCl, 5 mM. For the divalent permeability studies, the solutions either contain 1 mM Ca$^{2+}$ or Mg$^{2+}$ and (mM) NaCl, 100; Glucose, 10; Hepes, 10; sucrose, 80 or 30 mM test ion, in the above solution minus sucrose. The experiments in calcium free media have no added CaCl$_2$ with the addition of 100 µM EGTA. Pipette solution is always (mM) CsCl, 140; CaCl$_2$, 1; EGTA, 10; HEPES, 10; MgATP, 2; titrated to pH7.4 with CsOH. For the permeability, ratios for the monovalent cations relative to Na ($P_X/P_{Na}$) are calculated as follows:

$$P_X/P_{Na} = E_{shift} = \{RT/F\}\log(P_X/P_{Na}[X]_O/[Na]_O)$$

where F is Faraday's constant, R is the universal gas constant, and T is absolute temperature. For the divalent ions, $P_{Ca}$ or $P_{Mg}/P_{Na}$ is calculated as follows:

$$E_{shift} = \{RT/F\}\log\{[Na]_O + 4B'[X]_{O(2)}\}/\{[Na]_O 4B'[X]_{O(1)}\}$$

where $B' = P'_X/P_{Na}$ and $P'_X = P_X/(1+e^{EF/RT})$ and $[X]_{O(1)}$ and $[X]_{O(2)}$ refer to the two different concentrations of the divalent ion tested.

Figure 3:
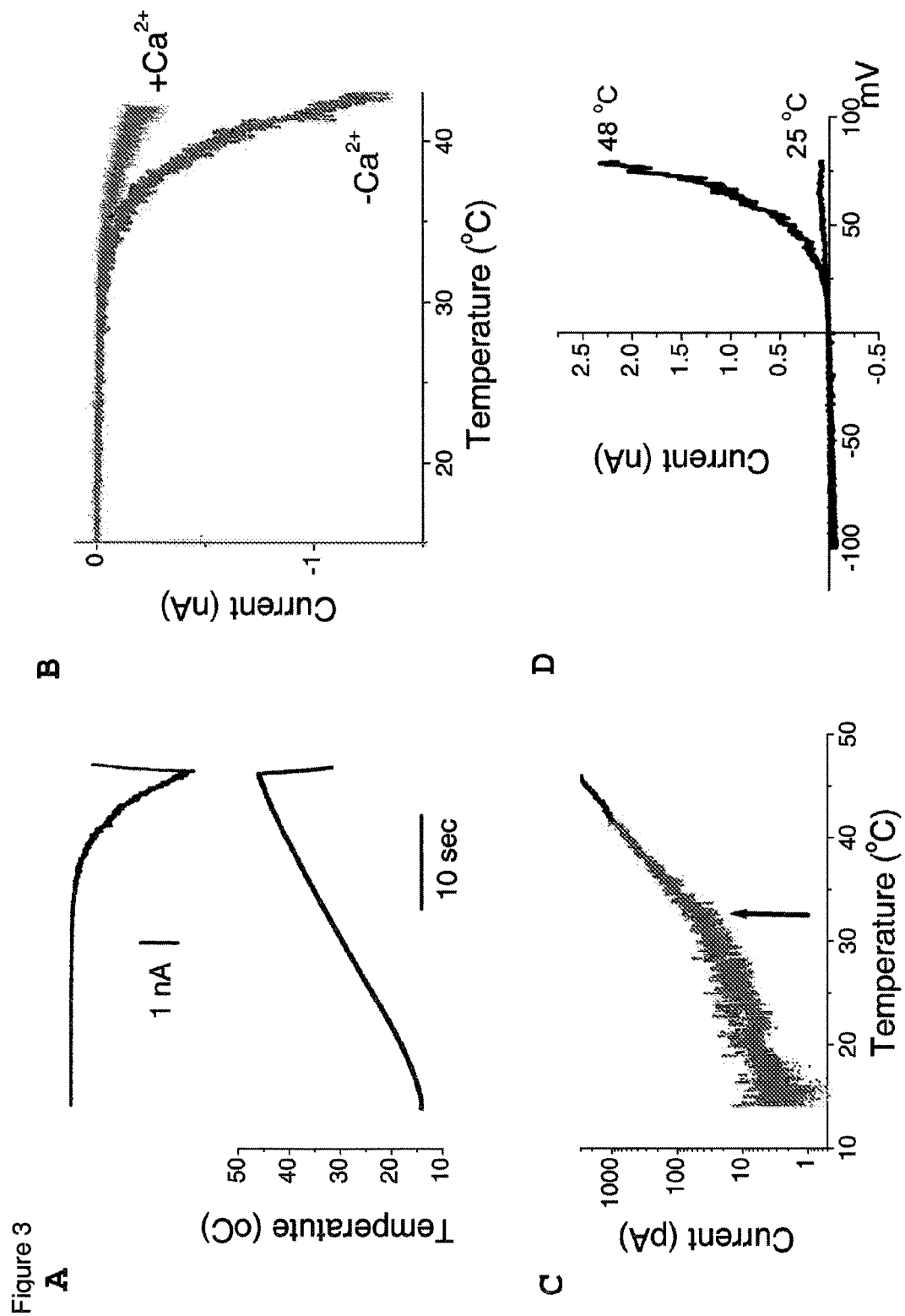
FIGS. 3A-3D demonstrate that TRPV3 is activated by heat. Currents evoked by heat in TRPV3 expressing Chinese Hamster Ovary (CHO) cells.

The results from transfected cells assayed electrophysiologically via whole cell voltage clamped techniques are described below. Capsaicin (1 µM), an activator of TRPV1, does not evoke a response in TRPV3-expressing cells. Similarly no current responses are seen when TRPV3-expressing cells are challenged with a hypo-osmotic solution containing 70 mM NaCl or with low pH (5.4). However, raising the temperature of superperfused external solution from room temperature to 45° C. evokes currents in TRPV3 expressing cells. Analysis of currents evoked by temperature ramps from ~15' C. to ~48° C. (see FIG. 3A) shows that little current is elicited until temperatures rise above ~33° C. and that the current continues to increase in the noxious temperature range (>42° C.). With these findings, TRPV3-expressing cells are subsequently maintained at 33° C. to avoid constitutive activation. The current amplitude is influenced by the presence or absence of $Ca^{2+}$ in the external medium, with reduced current amplitudes in the presence of 2 mM $Ca^{2+}$ after a prior challenge in $Ca^{2+}$-free solution (see FIG. 3B). This finding is reminiscent of the channel properties of TRPV5 and TRPV6 (see Nilius et al., *J. Physiol.*, 527:239-248 (2000)). As shown in FIG. 3C, the heat evoked current in TRPV3-expressing CHO cells increases exponentially at temperatures above 35° C. with an e-fold increase per 5.29±0.35° C. (n=12), corresponding to a mean $Q_{10}$ of 6.62. This temperature dependence is considerably greater than that seen for most ion channel currents, which typically have $Q_{10}$ values in the range 1.5-2.0, but is less than the values noted for TRPV1 (VR1, Q10=17.8) (see Vyklicky et al., *J. Physiol.*, 517:181-192 (1999)). In some cells it is difficult to see a sharp threshold temperature. However, measurable temperature dependent currents below 30° C. show an e-fold increase for a 22.72±3.31° C. (n=12) increase in temperature ($Q_{10}$=1.69).

The elevated temperature evoked currents, in TRPV3-expressing cells, shows a pronounced outward rectification (see FIG. 3D) with a reversal potential in the standard recording solution of −1.22±1 mV. Reducing the NaCl in the external solution to 70 mM (from 140 mM) shifts the reversal potential by −19 mV as expected for a cation selective conductance (shift =−17.5 mV). Differences in reversal potentials are also used to determine the ionic selectivity of TRPV3 channels. In simplified external solutions, the reversal potentials of the heat activated currents are very similar when NaCl ($E_{rev}$=−1.22±1.08 mV, n=5) is replaced with either KCl ($E_{rev}$=−0.40±0.77 mV, n=6) or CsCl ($E_{rev}$=−1.14±0.53 mV, n=6), which yields relative permeability ratios $P_K/P_{Na}$ and $P_{Cs}/P_{Na}$ close to 1 (see Funayama et al., *Brain Res. Mol. Brain Res.*, 43:259-266 (1996)). The relative permeability of $Ca^{2+}$ and $Mg^{2+}$ are estimated from the shift in reversal potentials when their concentrations are raised from 1 mM to 30 mM in a 100 mM NaCl solution containing the divalent cation under investigation. The reversal potential shifts (from −9.1+1.40 mV to +11.29+0.38 mV for $Ca^{2+}$ and from −8.41±0.50 mV to +10.34±2.38 mV for $Mg^{2+}$) correspond to $P_{Ca}/P_{Na}$=2.57 and $P_{Mg}/P_{Na}$=2.18. These data show that TRPV3 is a non-selective cation channel that discriminates poorly between the tested monovalent cations and has significant divalent cation permeability.

Figure 4:
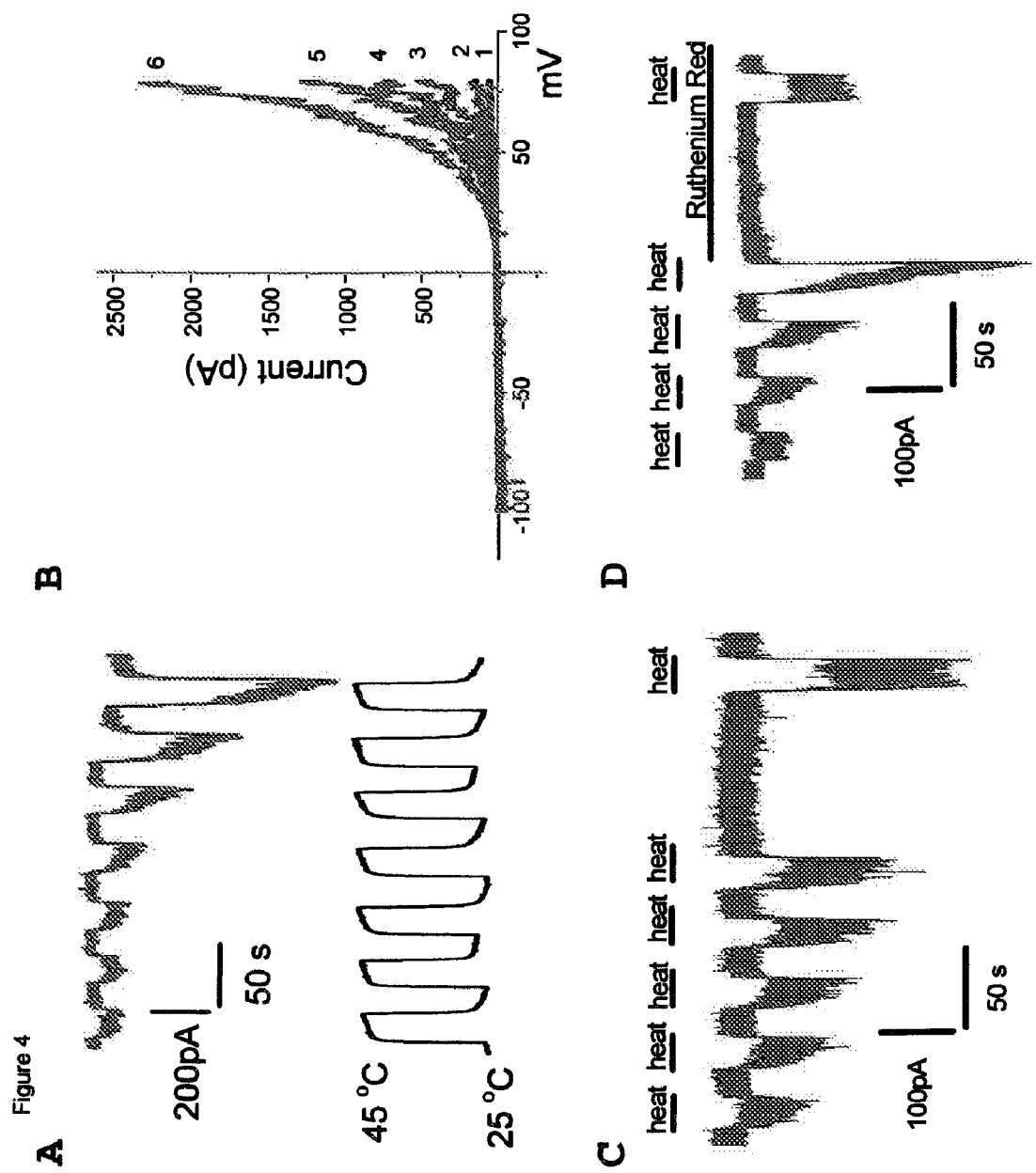
FIGS. 4A-4D. TRPV3 becomes sensitized to repeated applications of the heat stimulus.
Figure 5:
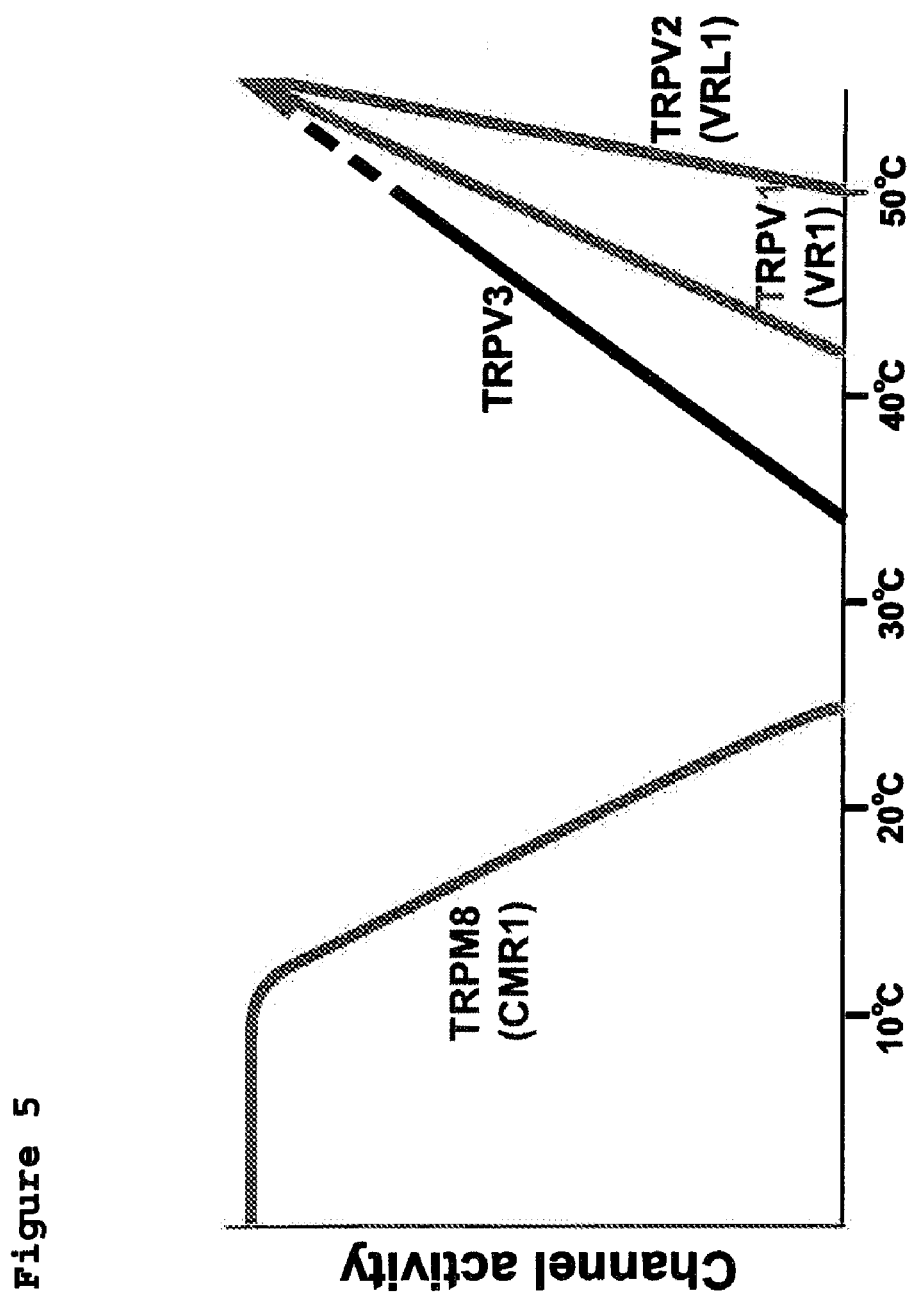
FIG. 5. TRP Channels in thermosensation. Four TRP channels implicated in thermosensation cover most but not all physiologically relevant temperatures.

Heat activation of TRPV3 shows a marked sensitization with repeated heat stimulation. This is studied at a steady membrane potential of −60 mV and with voltage ramps. The first response to a step increase from room temperature to ~48° C. is often very small, but the current response grew with repeated heat steps (see FIG. 4A). Sensitization to heat has also been observed for TRPV1 and TRPVL (see Caterina et al., supra and Jordt et al., *Cell*, 108:421-430 (2002)). Application of voltage ramps shows that sensitization is associated with an increase in outward rectification (see FIG. 4B). A protocol of repeated temperature challenges is used to investigate if antagonists of TRPV1 (VR1) are inhibitors of TRPV3. Under normal conditions, a heat challenge delivered 2 minutes after 4-5 sensitizing heat steps evokes a current that is 1.57±0.25 (n=4) times the amplitude of the preceding response (see FIG. 4C). Application of 10 µM capsazepine, a competitive capsaicin antagonist at TRPV1, for 2 minutes prior to the test heat challenge does not reduce the current amplitude (2.31±0.36 times the amplitude of the preceding response, n=4). In contrast, a similar exposure to 1 µM ruthenium red, a non-competitive inhibitor of other TRPV channels, reduces the relative amplitude of the heat response to 0.34±0.03, n=5 (see FIG. 4D). Taken together, these results indicate that TRPV3 is a cation permeable channel activated by warm and hot temperatures and has channel properties reminiscent of other TRPV channels.

Example 4

Gene Expression Analysis of TRPV3 in the Rat Chung Model

These studies discussed below measure relative levels of RNA expression for TRPV3 in the Chung neuropathic pain model using RT-PCR.

A. Spinal Nerve Ligation (Chung) Model

This model is established according to the methods described by Kim and Chung, supra, 1992. Rats are anesthetized and placed into a prone position and an incision made to the left of the spine at the L4-S2 level. A deep dissection through the paraspinal muscles and separation of the muscles from the spinal processes at the L4-S2 level will reveal part of the sciatic nerve as it branches to form the L4, L5 and L6 spinal nerves. The L6 transverse process is carefully removed with a small rongeur enabling visualization of these spinal nerves. The L5 spinal nerve is isolated and tightly ligated with 7-0 silk suture. The wound is closed with a single muscle suture (6-0 silk) and one or two skin closure clips and dusted with antibiotic powder. In sham animals the L5 nerve is exposed as before but not ligated and the wound closed as before.

Male Wistar rats (120-140 g) are used for each procedure. Mechanical hyperalgesia is assessed by measuring paw withdrawal thresholds of both hindpaws to an increasing pressure stimulus using an Analgesymeter (Ugo-Basile, Milan). Mechanical allodynia is assessed by measuring withdrawal thresholds to non-noxious mechanical stimuli applied with von Frey hairs to the plantar surface of both hindpaws. Thermal hyperalgesia is assessed by measuring withdrawal latencies to a noxious thermal stimulus applied to the underside of each hindpaw. With all models, mechanical hyperalgesia and allodynia and thermal hyperalgesia develop within 1-3 days following surgery and persist for at least 50 days. Drugs may be applied before and after surgery to assess their effect on the development of hyperalgesia, or approximately 14 days following surgery to determine their ability to reverse established hyperalgesia.

B. RT-PCR mRNA Analysis

One microgram of total RNA samples from the Chung model (L4 and L5 DRG) and sham-operated animals are used for first-strand cDNA synthesis using 50 pmol of oligo (dt) 24 primer in a 20 μL total reaction with 200 units Superscript II (LTI). The cDNA is then diluted to 100 μL with Tris-EDTA buffer (10 mM Tris Cl, pH 8.0 and 1 mM EDTA). Three μL of the diluted cDNA is used to amplify the message for TRPV3 with gene-specific primers (sequences in 5' to 3' orientation: TRPV3 forward primer, CTCATGCACAAGCTGACAGCCT (SEQ ID NO: 79); TRPV3 reverse primer, AGGCCTCTTCCGTGTACTCAGCGTTG (SEQ ID NO: 80)) in a 15 μL PCR reaction using NotStart Taq DNA polymerase (Qiagen) for 25-38 cycles. Neuropeptide Y (NPY) is used as positive control.

For normalization 1 μL of the diluted cDNA is used to amplify actin using the following primers:

```
5'actin primer:
ATC TGG CAC CAC ACC TTC TAC AA    (SEQ ID NO: 81)

3'actin primer:
GCC AGC CAG GTC CAG ACG CA        (SEQ ID NO: 82)
```

A portion of the samples are then analyzed on a 4-20 TBE Criterion polyacrylamide gel (BioRad), stained with SYBR GREEN I (Molecular Probes) and visualized on a Phosphorimager.

FIG. 1A shows the average fold regulation of TRPV3 (VRLX) in L4 and L5 DRG neurons from the Chung model from three independent experiments. As shown in FIG. 1A the positive control, NPY and TRPV3 message are elevated in the injured DRG relative to sham and non-ligated DRGs.

Example 5

Identification of TRPV4

Primers are designed to amplify distinct regions of the candidate genes that had been identified through the computer model. Based on the human sequence obtained, PCR primers are designed to also amplify the mouse homologue of TRPV4 (mTRPV4) (TRPV4 forward: CTCATGCACAAGCTGACAGCCT (SEQ ID NO: 83); TRP4 reverse: AGGCCTCTTCCGTGTACTCAGCGTTG (SEQ ID NO: 84)). These PCR products are subsequently sequenced and the mouse EST database is searched using these sequences. One EST clone (ID No. AI510567) is identified and obtained from the IMAGE consortium. The EST is further characterized and found to contain a ~2.4 kb insert which is sequenced. Primers are designed from this sequence and used to obtain the full length cDNA using the RACE protocol (Clontech). Both 5' and 3' RACE products are obtained and sequenced. This approach results in the amplification of the full length cDNA of mTRPV4 from mouse kidney and DRG cDNA using primers designed from the very 5' and 3' end of the RACE products. All primers utilized in the characterization of mTRPV4 are shown in Table 2. A novel full length cDNA of 3.2 kb is identified, which includes an open-reading frame of ~2.5 kb, a 5' UTR consisting of ~145 bp and a 3' UTR encompassing ~400-500 nucleotides. The gene encodes a 3.4 kb transcript that contains three ankyrin-repeat regions and TM6 domains. The protein sequence includes ~1000 amino acids and is set forth in SEQ ID NO: 14. Clustal W alignments to the rat VR (GenBank Ascession No. AF029310) reveals 34% identity and 64% similarity to VR1 in the region spanning the Ank2 through the TM4 region.

TABLE 2

TRPV4 Primers

| | | SEQ ID NO: |
|---|---|---|
| Primers used for RACE | | |
| 3' RACE | CCCTGGGCTGGGCGAACATGCTCTA | 85 |
| VR3RACE5' | CTTGGCAGCCATCATGAGAGGCGAA | 86 |
| Primers to amplify partial/full length TRPV4 | | |
| AP19 | GCAGTGGTAACAACGCAGAG | 87 |
| AP20 | AGGTCAGATCTGTGGCAGGT | 88 |
| AP21 | CGTGAGGTGACAGATGAGGA | 89 |
| AP32 | CCAGTATGGCAGATCCTGGT | 90 |
| AP25 | ATGGCAGATCCTGGTGATG | 91 |
| AP26 | CCCAGGCACTACTGAGGACT | 92 |
| AP27 | AGGGCTACGCTCCCAAGT | 93 |
| AP28 | GTGCTGGCTTAGGTGACTCC | 94 |
| AP22 | TGAACTTGCGAGACAGATGC | 95 |

A combination of RT-PCR and Northern blot analyses are utilized to characterize expression of TRPV4. Total RNA is prepared from adult mouse kidney, newborn DRG and adult trigeminal tissue. RT-PCR is carried out using cDNA prepared from these three mouse tissues and primers within the ankyrin and the TM domain of mTRPV4. The expected 403 bp product is observed in all three tissues. This PCR product also serves as a probe on Northern blots (Clontech MTN blots). The expected 3.4 kb transcript is observed in kidney and other tissues.

The genomic structure of hTRPV4 is predicted from the high throughput genomic sequence database (GenBank Accession No. AC007834). HVR3 encompasses ~17 exons. A comparison of the amino acid sequence of the rat VR1 sequence (GenBank Accession No. AF029310) and the mouse VR3 protein reveals 34% identity and 64% similarity in the sequence spanning the ankyrin 2 region and the TM4 domain. The nucleotide and amino acid sequences of hTRPV4 are shown in SEQ ID NO: 16 and SEQ ID NO: 17, respectively.

Example 6

Gene Expression Analysis of TRPV4 in the Rat Chung Model

These studies discussed below measure relative levels of RNA expression for TRPV4 in the Chung neuropathic pain model using RT-PCR.

A. Spinal Nerve Ligation (Chung) Model

This model is established according to the methods described by Kim and Chung, supra, and is described in Example 4.

B. RT-PCR mRNA Analysis

One microgram of total RNA samples from the Chung model (L4 and L5 DRG) and sham-operated animals are used for first-strand cDNA synthesis using 50 pmol of oligo (dt) 24 primer in a 20 μL total reaction with 200 units Superscript II (LTI). The cDNA is then diluted to 100 μL with Tris-EDTA buffer (10 mM Tris Cl, pH 8.0 and 1 mM EDTA). Three μL of the diluted cDNA is used to amplify the message for TRPV4 with gene-specific primers (Sequences in 5' to 3' orientation: TRPV4 forward primer, 99 TGAGGATGACATAGGTGAT- GAG 120 (SEQ ID NO: 96), TRPV4 reverse primer, 255 CCAAGGACAAAAAGGACTGC 236 (SEQ ID NO: 97)) in a 15 μL PCR reaction using NotStart Taq DNA polymerase (Qiagen) for 25-38 cycles. NPY is used as positive control.

For normalization 1 μL of the diluted cDNA is used to amplify actin using the following primers:

```
5'actin primer:
ATC TGG CAC CAC ACC TTC TAC AA    (SEQ ID NO: 81)

3'actin primer:
GCC AGC CAG GTC CAG ACG CA        (SEQ ID NO: 82)
```

A portion of the samples are then analyzed on a 4-20 TBE Criterion polyacrylamide gel (BioRad), stained with SYBR GREEN I (Molecular Probes) and visualized on a Phosphorimager.

First-strand cDNA from the Chung model (50 days post-ligation) is normalized using a house-keeping gene; beta-actin. FIGS. 1A and 1B shows the expression of TRPV4 and NPY in the Chung Model (50- and 28-day post-ligation, respectively). The positive control, NPY and TRPV4 message are elevated in the injured DRG relative to sham and non-ligated DRGs. Accordingly, TRPV4 serves as a target for neuropathic pain.

Example 7

Identification of VR TRPM8

To identify novel TRP channels, genomic DNA databases are searched by constructing a HMM from the known TRP protein sequences of different mammalian species. With this model, the 6-frame translation of all available human sequences is queried and identifies multiple novel putative exons with similarity to the TM4 and TM6 domains of VR1. A fragment of the mouse homologue of one novel TRP channel is amplified by RT-PCR from mouse DRG RNA. Full-length sequence of this gene is derived from a combination of exon-prediction software, PCR and RACE amplification from newborn mouse DRGs.

For PCR cloning, primers 163f (5'-CAAGTTTGTCCGC-CTCTTTC (SEQ ID NO: 98)) and 164r (5'-AACTGTCTG-GAGCTGGCAGT (SEQ ID NO: 99)) are designed from the HMM sequences for TRPM8 as a result of blast hits and used to amplify a 699-nucleotide fragment of TRPM8 from newborn DRG cDNA. From this initial sequence and exon prediction programs, RACE PCR (Clontech) is used to obtain the 5' and 3' ends of TRPM8 from mouse newborn DRG cDNA following the manufacturer's protocol. Primers used in these experiments are shown in Table 3.

TABLE 3

Primers to Amplify Mouse TRPM8 cDNA

| | | SEQ ID NO: |
|---|---|---|
| Putative trp candidate 2KMHMR5R44-MOD CELERA HUMAN CONTIG | | |
| FOR MOUSE: Probes designed for in situ hyb analysis | | |
| AP163F | CAAGTTTGTCCGCCTCTTTC | 100 |
| AP164R | ACTGCCAGCTCCAGACAGTT | 101 |

TABLE 3-continued

Primers to Amplify Mouse TRPM8 cDNA

| | | SEQ ID NO: |
|---|---|---|
| Rapid amplification of cDNA ends (RACE) | | |
| 5' RACE primers 5' RACE (nested) | ccttcgatgtgctggctctgggcataa | 102 |
| 5' RACE | CCTTGCCTTTCTTCCCCAGAGTCTCAA | 103 |
| AP220 5' RACE | GCAAAGTTTTTGGCTCCACCCGTCA | 104 |
| AP221 5' RACE (nested) | GCCAGTGCTGGGTCAGCAGTTCGTA | 105 |
| 3' RACE primers 3' RACE I | TTCAGGAGGTCATGTTCACGGCTCTCA | 106 |
| 3' RACE I (nested) | GTACCGGAACCTGCAGATCGCCAAGA | 107 |
| AP218 3'RACE TRPXII | GCAAGATCCCTTGTGTGGTGGTGGA | 108 |
| AP219 3' (nested) | CAGCCTGGTGGAGGTGGAGGATGTT | 109 |
| 3' RACE #3 | CGGAACCTGCAGATCGCCAAGAACT | 110 |
| 3' RACE primer in TMS region of TRPM8 AP225 | GCGTGGCCAGACAGGGGATCCTAAG | 111 |
| 3' REVERSE primer in TMS region of TRPM8 AP226 | CCACACAGCAAAGAGGAACA | 112 |
| To amplify longer piece of mouse TRPM8 216F | GGAGCCGCAGAAATGGTACT | 113 |
| Primers used for Northern probe Amplifies around 1.2 kB band | | |
| AP258 | TCTCATTGGCCTCATTTCTG | 114 |
| AP247 | ATATGAGACCCGAGCAGTGG | 115 |

The protein TRPM8, has been named following the nomenclature suggested in Clapham et al., Cell, 108:595-598 (2001). Several human ESTs, many of which have been isolated from various cancer tissues, contain fragments of TRPM8 (Genbank GI Nos. 8750489, 9149390, 9335992 and 2223353).

Figure 6B:
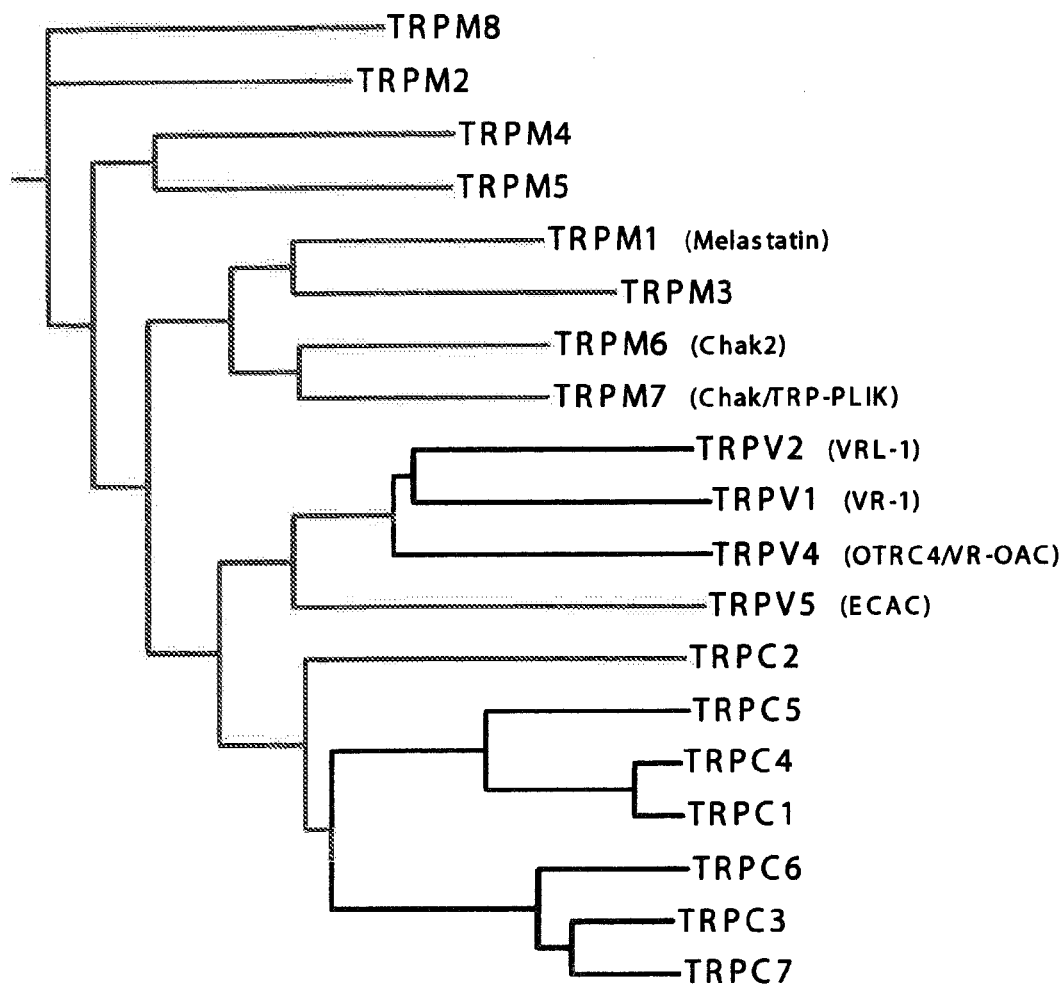
Figure 6C:
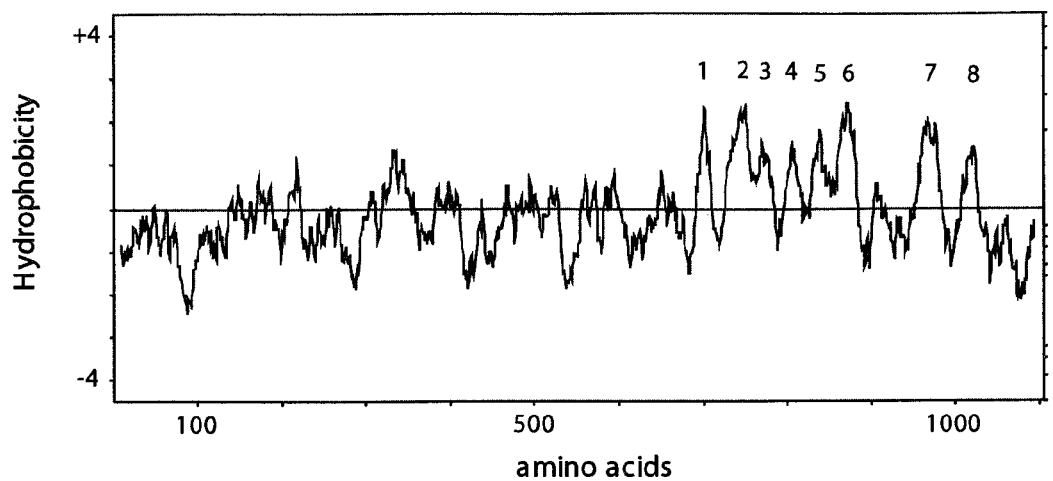
Figure 6D:
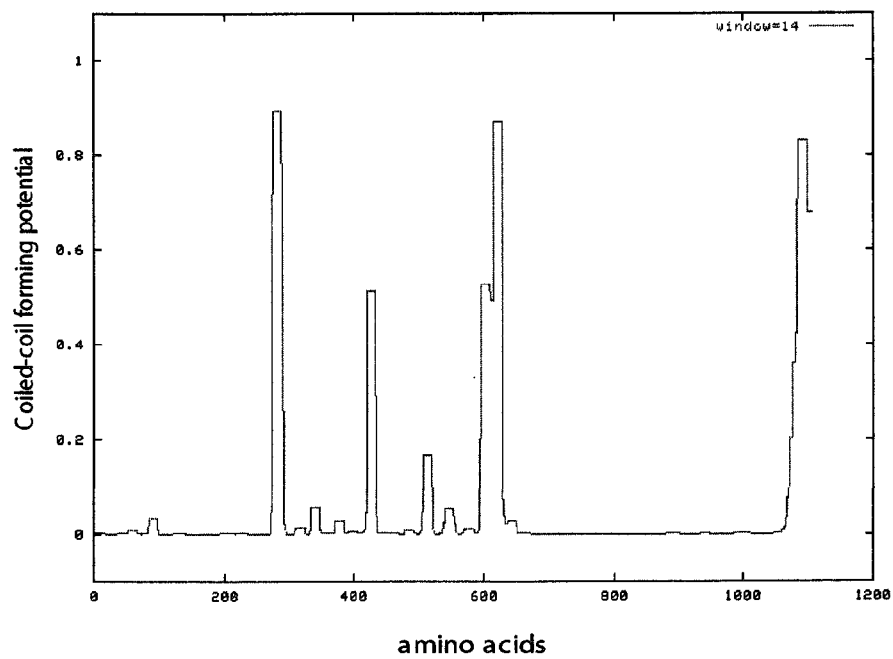

Translation of the nucleotide sequence of TRPM8 predicts a protein composed of 1104 amino acid residues (see SEQ ID NO: 8). The overall sequence of mouse TRPM8 is 93% identical to that of the human gene (see FIG. 6A). Its closest relative is TRPM2 (42% identity) (see FIGS. 6A and 6B). TRPM8 belongs to the "long" or Melastatin subfamily of TRP channels, a group of TRPs characterized by their lack of ankyrin domains in the N-terminus. TRP channels are predicted to contain TM6 domains, although at least one is predicted to have seven membrane-spanning domains (see Nagamine et al., Genomics, 54:124-131 (1998)). A Kyte-Doolittle plot suggests the presence of eight distinct hydrophobic peaks in TRPM8 sequence, which could represent six to eight predicted transmembrane domains. Overall, the predicted transmembrane domains are within amino acids 695-1024 of TRPM8. Outside of this region, the only predicted secondary structures are coiled-coil domains present both in the N- and C-terminal portion of the protein (data not shown) (see Burkhard et al., Trends Cell. Biol., 11:82-88 (2001)). Coiled-coil domains are implicated in oligomerization of GABA-B channels, and have been previously predicted in some TRP channels (see Funayama et al., supra; and Margeta-Mitrovic et al., *Neuron*, 27:97-106 (2000)).

Example 8

Localization of TRPM8 Expression

A. Northern Blot Analysis

Northern blots are made as followed: Total RNA are purified from mouse newborn and adult tissues using TRIzol LS (Invitrogen/Gibco Life technologies), followed by polyA$^+$ purification with Oligotex (Qiagen) according to the manufacturer's protocols. Approximately 3 mg of sample are electrophoresed on 1% glyoxal gels, transferred and hybridized at high-stringency with a $^{32}$P-labeled probe representing nucleotides 1410-1980 of the mouse full-length TRPM8 sequence. Commercial Northern blots (Clontech) are hybridized with the same TRPM8 probe. Blots are hybridized for 3 hours at 68° C. in ExpressHyb hybridization solution (Clontech) and washed according to the manufacturer's high-stringency washing protocol and exposed to a phosphoimager screen for 1-3 days.

The results from this analysis are described below. No TRPM8 expression is detected using commercial Northern blots. Blots from newborn and adult mice are used that include tissues relevant for somatic sensation, including DRG, spinal cord and different sources of skin. One mRNA species of approximately 6.3 kb is present predominantly in DRGs.

B. In Situ Hybridization

For in situ hybridizations, newborn and adult tissues are dissected, fixed in 4% paraformaldehyde in PBS, cryoprotected and frozen in liquid nitrogen in OCT mounting medium. Cryostat sections (10 μm) are processed and hybridized with a digoxygenin cRNA probe generated by in vitro transcription (Roche Biochemicals). The mouse TRPM8 mRNA-specific antisense riboprobe corresponds to nucleotides 1410-1980 of the mTRPM8 sequence. Fluorescence detection and double-labeling experiments are carried out with the tyramide signal amplification kit (TSA; NEN) essentially as previously described (see Dong et al., *Cell*, 106:619-632 (2001)).

Digoxygenin-labeled probes show specific expression in DRG and trigeminal ganglia (cranial sensory neurons innervating the mouth and jaw) in newborn and adult mouse, but not in day 13 embryos. TRPM8 expression is restricted to approximately 5-10% of adult DRG neurons. The average size of the neurons positive for TRPM8 is 18±3.1 μm (mean±standard deviation, n=69), and can be classified as small-diameter c-fiber-containing neurons, which in mouse are defined as smaller than 25 μm. TRPM8 is not expressed in heavily-myelinated neurons marked by Neurofilament (NF) antibodies, which correlates well with TRPM8 expression in small-sized neurons. TRPM8$^+$ neurons thus appear to belong to a subset of nociceptive or thermoceptive neurons that express trkA, an NGF receptor, during development (see Huang and Reichardt, *Ann. Rev. Neurosci.*, 24:677-736 (2001)). In the absence of NGF or trkA, DRG neurons that normally express this receptor die through apoptosis during embryonic development (Huang and Reichardt, supra). To prove that TRPM8 is expressed in trkA-dependent neurons, TRPM8 expression is evaluated in DRGs from newborn trkA-null mice. The expression of TRPM8 is completely abolished in the mutant ganglia. In addition, TRPM8 is not co-expressed with VR1, which marks a class of nociceptors that respond to capsaicin and noxious heat. This observation is confirmed by the lack of TRPM8 co-expression with either CGRP or IB4, two well-characterized antigenic markers found on nociceptive neurons (see Snider and McMahon, *Neuron*, 20:629-632 (1998); Tominaga et al., *Neuron*, 21:531-543 (1998)). This data strongly indicates that TRPM8 is expressed in a subpopulation of thermoceptive/nociceptive neurons distinct from the well-characterized heat and pain sensing neurons marked by VR1, CGRP or IB4.

Following in situ hybridization, immunofluorescence is performed with anti-CGRP (1:100; Biogenesis), IB-4 (10 μg/mL; Sigma), anti-VR1 (1/2000; Abcam), anti-NF150 (1/1000; Chemicon) and detected with FITC or CY3 (10 μg/mL; Jackson Immunoresearch). Although all panels shown in these studies demonstrate lack of co-expression, this is not due to technical issues since additional probes/antibodies are used as controls to ensure our double-labeling protocol with the TRPM8 in situ probe is working.

Example 9

Activation of TRPM8 Protein by Cold and Menthol

A. Effect of Heat, Capsaicin, Cold and Menthol Upon Intracellular Calcium

Given the similarity of TRPM8 protein to TRPV family members and its unique expression pattern, the effects of heat, capsaicin, cold and menthol in mediating calcium influx are examined using transfected CHO-K1/FRT cells expressing TRPM8 protein and a fluorescent calcium imaging method as described in detail below.

To generate mouse TRPM8-expressing CHO cell lines, mouse TRPM8 cDNA are subcloned in pcDNA5 (Invitrogen), transfected into CHO-K1/FRT cells using Fugene 6 (Roche). The transfected cells are selected by growth in MEM medium containing 200 μg/μL$^{-1}$ hygromycin (Gibco BRL). Populations are frozen at early passage numbers and these stocks are used for further studies. Stable clones that express the mRNAs are identified by Northern blot analysis as well as Southern blotting to confirm integration site (not shown). CHO cells do not express an endogenous TRPM8 isoform and therefore serve as a control along with a cell line stably transfected with a VR1-expressing plasmid.

Calcium imaging experiments are performed essentially as previously described (see Savidge et al., *Neuroscience*, 102: 177-184 (2001)). Briefly, cells are plated on glass coverslips and loaded with Fura-2 acetoxymethyl ester (2.5-5 mM) and incubated for 30-60 minutes at room temperature in 1.5 mM of pluronic acid (Molecular Probes, Eugene, Oreg.) in a HEPES-buffered saline (2 mM Ca 2+). Coverslips are placed in a laminar flow perfusion chamber (Warner Instrument Corp.) and constantly perfused with HEPES-buffered saline (2 mM Ca$^{2+}$) via a local perfusion pipette through which buffer and chilled solutions are also applied. Chilled stimulations consist of a linear decrease (~1-1.5° C. sec$^{-1}$) in perfusate temperature from 33° C. to 10° C. Perfusate temperature is controlled by a regulated Peltier device and is monitored in the cell chamber by a miniature thermocouple. Alternatively, cells are plated on 24-well tissue culture plates, loaded with Fura-2 and application of solutions is performed with a 3 cc syringe over a period of 10 seconds. Images of Fura-2 loaded cells with the excitation wavelength alternating between 340 and 380 nM are captured with a cooled CCD camera. Following subtraction of background fluorescence, the ratio of fluorescence intensity at the two wavelengths is calculated. Ratio levels in groups of 20-40 individual cells are analyzed using MetaFluor (Universal Imaging Corporation). All graphs are averaged responses from groups of 20-30 individual cells from representative single experiments. All experiments are repeated on three separate occasions and similar results obtained. Hanks balanced salt solution (HBSS), phosphate buffered saline (PBS) and all cell culture reagents are obtained from Gibco BRL. Ruthenium red, capsaicin and menthol are obtained from Sigma.

Figure 7A:
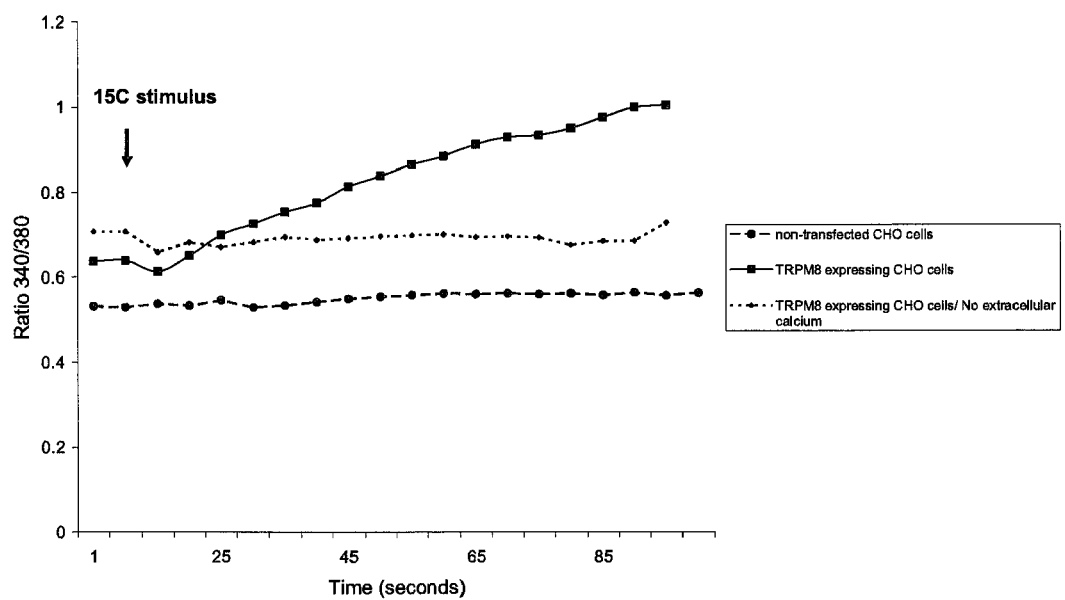
FIGS. 7A-7E: Increase in intracellular calcium concentration ($[Ca^{2+}]_i$) in TRPM8-expressing CHO cells in response to cold and menthol.
Figure 8:
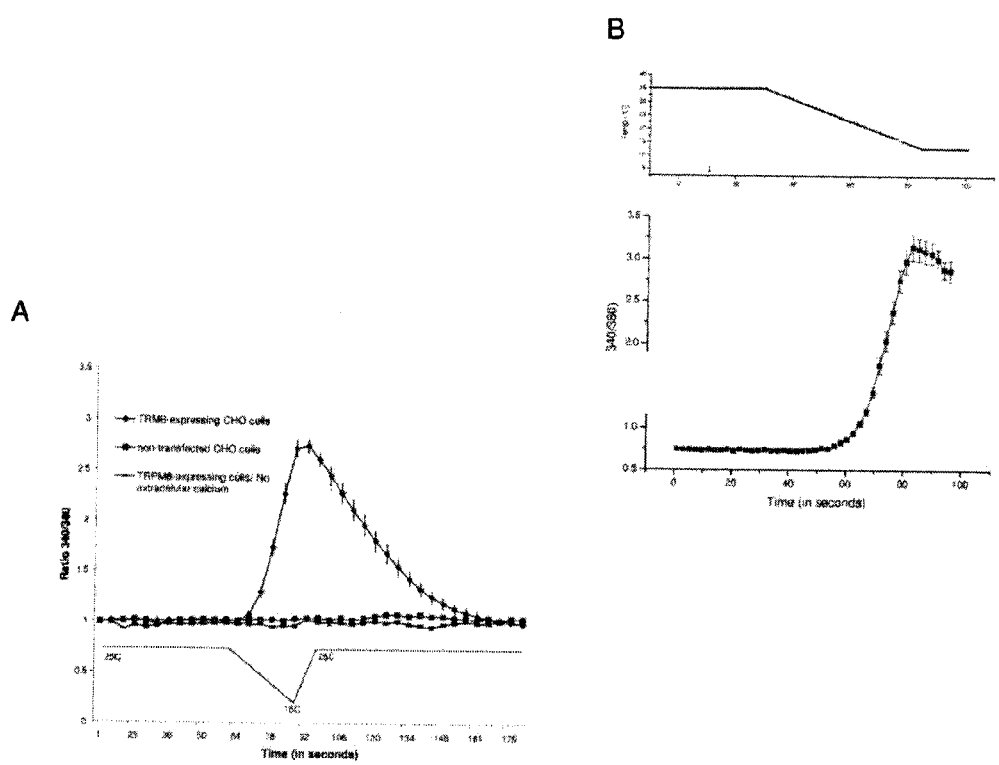
FIGS. 8A-8B show an increase in intracellular calcium concentration $[Ca^{2+}]_i$ in TRPM8-expressing CHO cells in response to cold.

The results of the above calcium imaging experiments are described below. Capsaicin (10 µM), an activator of VR1, does not evoke a response in TRPM8 expressing cells. Neither hypo-osmotic solutions, known to generate $Ca^{2+}$ responses in TRPV3-expressing cells, or hypertonic buffer elicit a response in TRPM8 expressing cell lines (see Liedtke et al., supra; and Strotmann et al., supra)). An increase in temperature (25-50° C.), a potent stimulus for VR1, also does not alter intracellular calcium levels. However, when the temperature is lowered from 25° C. to 15° C., an increase in intracellular calcium is observed in TRPM8 expressing cells (FIGS. 7A and 8A). This response is not observed in non-transfected CHO cells or the VR1-expressing cell line (FIGS. 7A and 8A). Addition of a 10° C. stimulus also evokes an influx of $Ca^{2+}$. This response is dependent on $Ca^{2+}$ in the buffer, because removal of extracellular calcium suppresses the temperature response (FIGS. 7A and 8A). The dependence on outside calcium is indicative of a cation-permeable channel localized at the plasma membrane. A potent blocker of the heat response for VR1, ruthenium red (at 5 µM), does not suppress the temperature response.

Figure 7B:
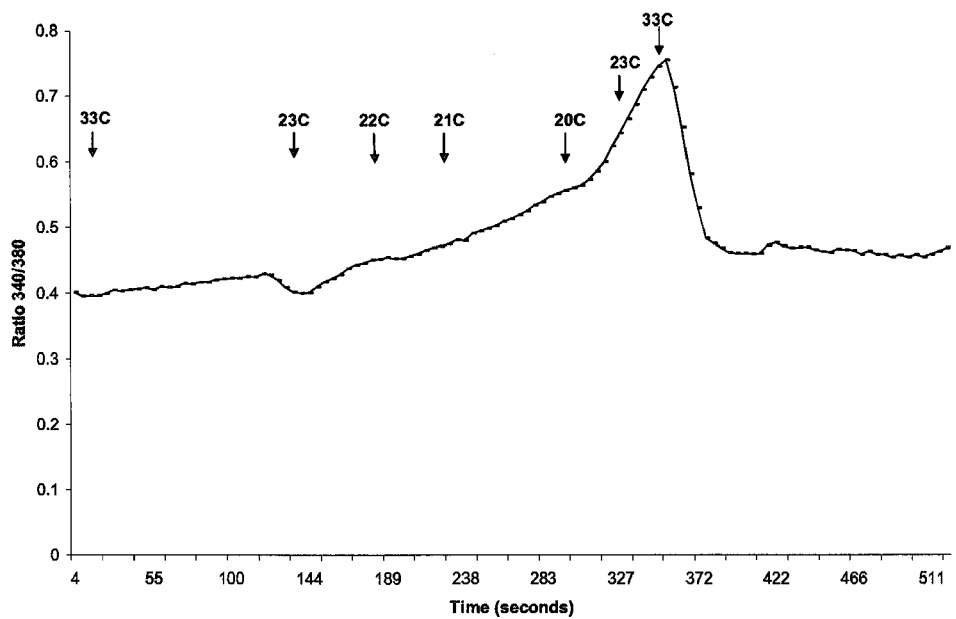
Figure 7C:
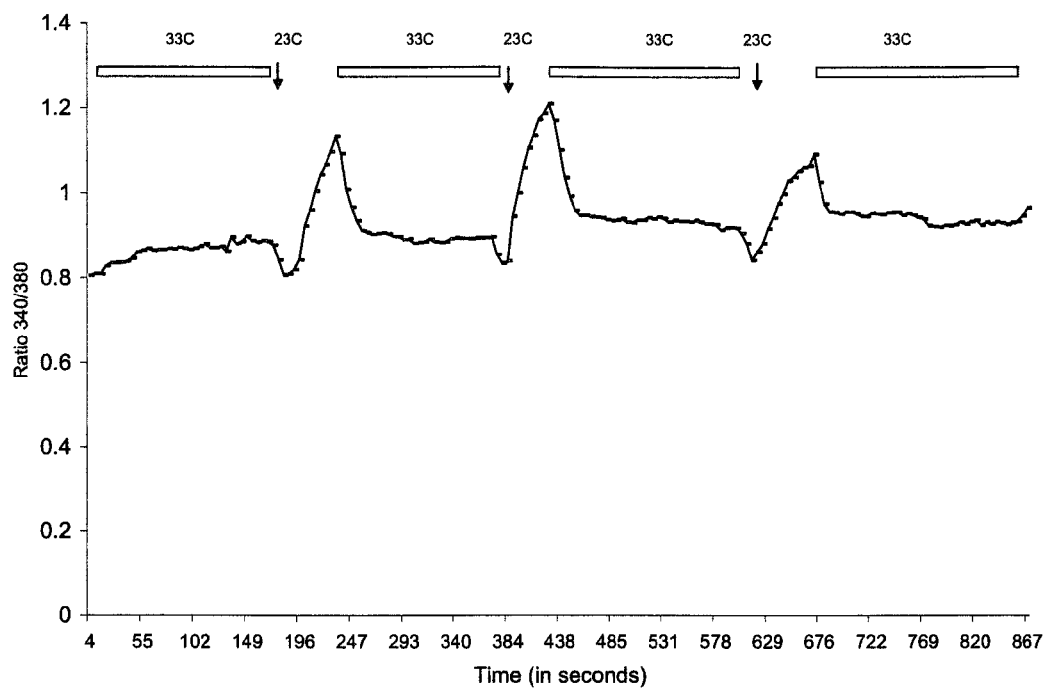

Since TRPM8 responds to a decrease in temperature, additional experiments are carried out to investigate the temperature threshold at which intracellular calcium ($[Ca^{2+}]_i$) begins to rise in TRPM8 expressing cells. Cells are incubated at 35° C. (normal skin temperature) for several minutes followed by a decrease in temperature to 13° C. The temperature response in mouse TRPM8-CHO cells shows a threshold of 22-25° C. at which $[Ca^{2+}]_i$ starts to increase (FIG. 7B), followed by a marked increase when the temperature of the buffer reached ~15° C. These experiments indicate that at physiological relevant temperatures, the upper activation threshold for TRPM8 is ~23° C. (FIG. 7C).

Figure 7D:
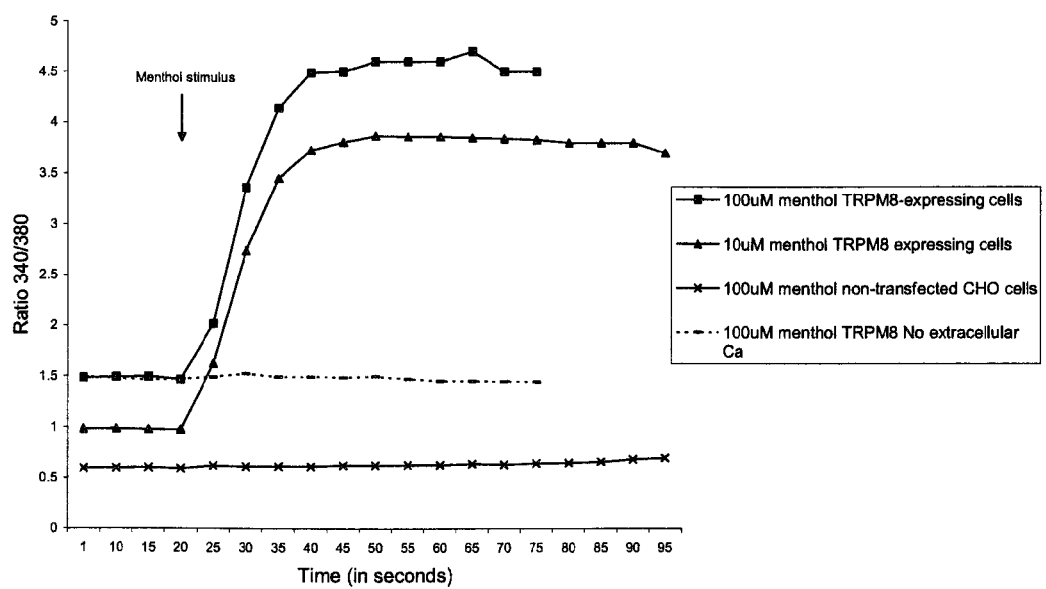
Figure 7E:
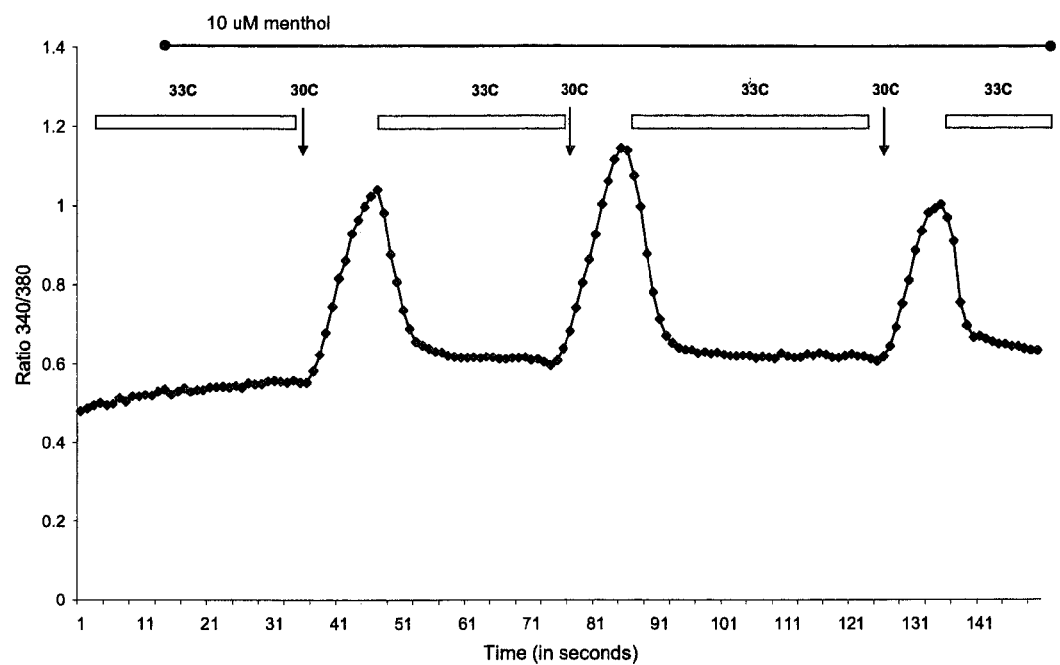

Menthol, a compound commonly used for its cooling properties, is tested as a stimulus on TRPM8 expressing CHO cells. Non-transfected CHO cells are completely insensitive to menthol (tested up to 1 mM) (FIG. 7D). However, upon treatment of TRPM8 cells (incubated at 25° C.), intracellular fluorescence increases significantly within seconds in response to menthol concentrations of 10 and 100 µM (FIG. 7D). Additionally, as with the temperature stimulus, depletion of calcium from the extracellular buffer suppresses the calcium response (FIG. 7D). The effect that menthol has at different temperatures is also examined. Incubation of TRPM8 expressing cells at 33° C., reveals that µM menthol does not induce a calcium response as observed at 25° C., but upon lowering the temperature to 30° C., intracellular calcium levels increases (FIG. 7E). Menthol thus appears to mimic the effect of lowering the temperature on TRPM8 expressing cells.

B. Effect of Cold and Menthol Upon Conductance

To investigate the membrane responses to cold and menthol, voltage clamp experiments are carried out on TRPM8 expressing cells which are prepared as described above.

Cells are plated onto poly-D-lysine coated cover-slips for recording purposes and recordings undertaken 18-24 hours later. Experiments are carried out at room temperature using whole-cell voltage clamp technique, with an Axopatch 2B amplifier, filtered at 5 kHz and pClamp suite of software (Axon Instruments). Series resistant compensation is 80% for all experiments, using 2-5 MΩ fire-polished pipettes. Recording solutions are as follows; pipette solution for all experiments is (mM) CsCl, 140; $CaCl_2$, 1; EGTA, 10; HEPES, 10; MgATP, 2; titrated to pH 7.4 with CsOH. For menthol and cold activated currents the bath solution is (mM): NaCl, 140; KCl, 5; Glucose; 10, HEPES, 10; $CaCl_2$, 2; $MgCl_2$, 1; titrated to pH 7.4 with NaOH. Current-voltage relationships are used to evaluate reversal potentials with voltage ramps from –100 to +60 mV (2 second duration). For the permeability studies for the monovalent ions the NaCl in a simplified bath solution (mM): NaCl, 140; Glucose; 10, HEPES, 10; $CaCl_2$, 2; $MgCl_2$, 1, is substituted by either equimolar CsCl or KCl (titrated with CsOH or KOH). For calcium permeability estimates, the bath solutions contains (mM) NaCl, 100; Glucose, 10 mM; Hepes, 10 mM (titrated with NaOH) plus 1 or 30 mM $CaCl_2$. Osmolarity of solutions are adjusted by addition of sucrose. Permeability ratios for the monovalent cations to Na ($P_X/P_{Na}$) are calculated as follows:

$$P_X/P_{Na}=E_{shift}=\{RT/F\}\log(P_X/P_{Na}[X]_O/[Na]_O)$$

where F is Faraday's constant, R is the universal gas constant and T is absolute temperature. For measurements of calcium permeability $P_{Ca}/P_{Na}$ is calculated as follows:

$$E_{shift}=\{RT/F\}\log\{[Na]_O+4B[Ca]_{P(2)}\}/\{[Na]_O AB [Ca]_{O(1)}\}$$

where $B'=P'_{Ca}/P_{Na}$ and $P'Ca=P_{Ca}/(1+e^{EF/RT})$ and $[Ca]_{O(1)}$ and $[Ca]_{O(2)}$ refer to the two different calcium concentrations. Local perfusion of menthol is via a $TC^2$bip temperature controller. A Marlow temperature controller is used for the cooling ramps.

Figure 9:
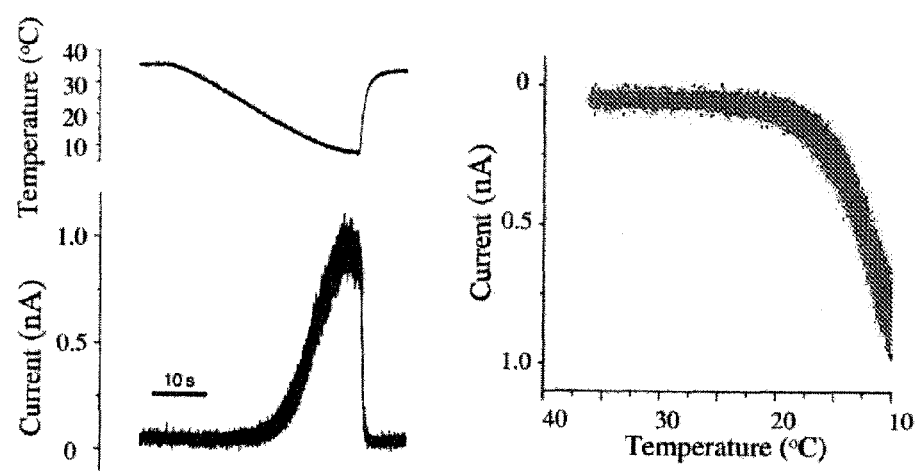
FIGS. 9A-9B show that current is evoked by reduction in temperature in TRPM8-expressing CHO cells.
Figure 9:
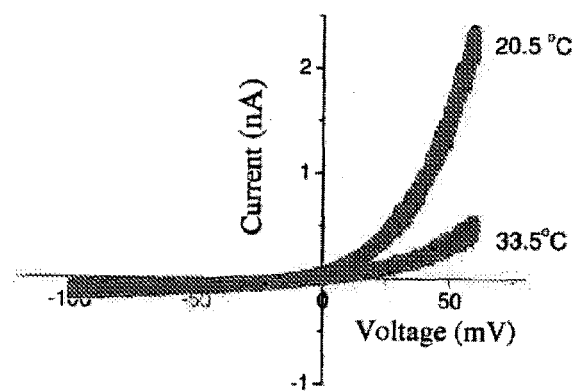

The results of the voltage clamp studies carried out on TRPM8 expressing cells are described below. Temperature ramps from 35° C. to 7-13° C. evoke inward currents at a holding potential of –60 mV and outward currents at +40 or +60 mV. Currents increase in amplitude as the temperature is lowered and usually show some degree of desensitization at the coldest temperatures tested <10° C. (FIG. 9A). The temperature threshold for current activation shows no dependence on membrane potential and individual cells activated at temperatures between 19° C. and 25° C., with a mean threshold of 21.79±0.64° C. (n=5). Analysis of the current-voltage relationships of the response to a cold stimulus with CsCl filled recording pipettes and a typical NaCl-based external solution reveals an outwardly rectifying current with a reversal potential ($E_{rev}$) close to 0 mV which is typical of a non-selective cation channel (FIG. 9B).

Figure 10:
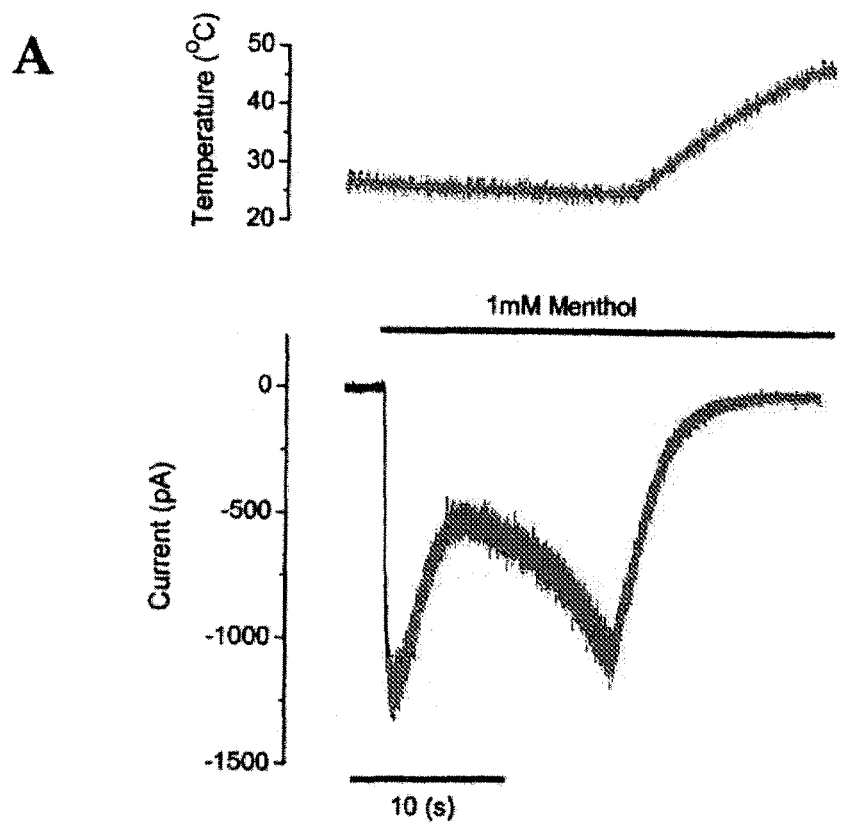
FIGS. 10A-10B show that current is evoked by menthol in TRPM8-expressing CHO cells.
Figure 10:
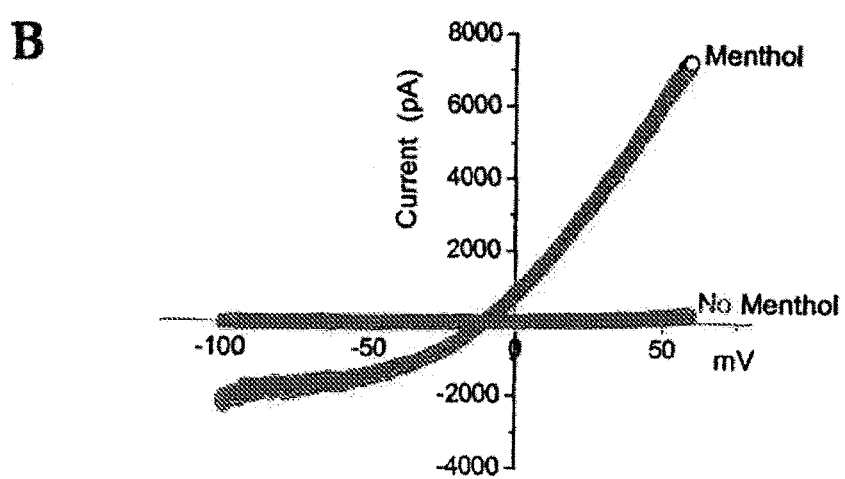
Figure 11:
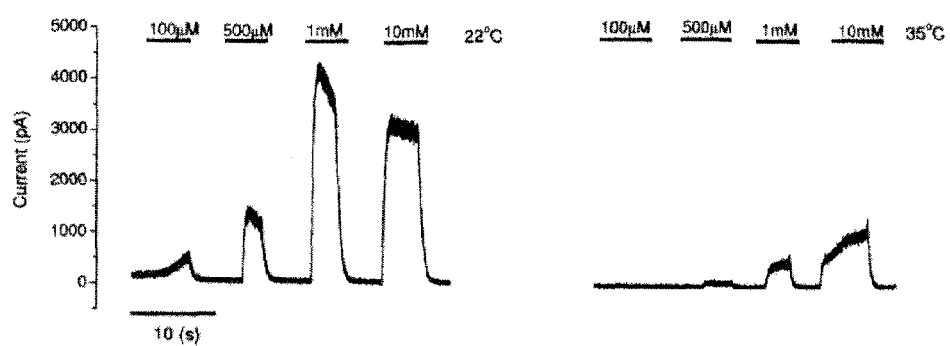
FIGS. 11A-11B show a dose-response curve for menthol-stimulated current in TRPM8-expressing CHO cells. The voltage employed was +60 mV.
Figure 11:
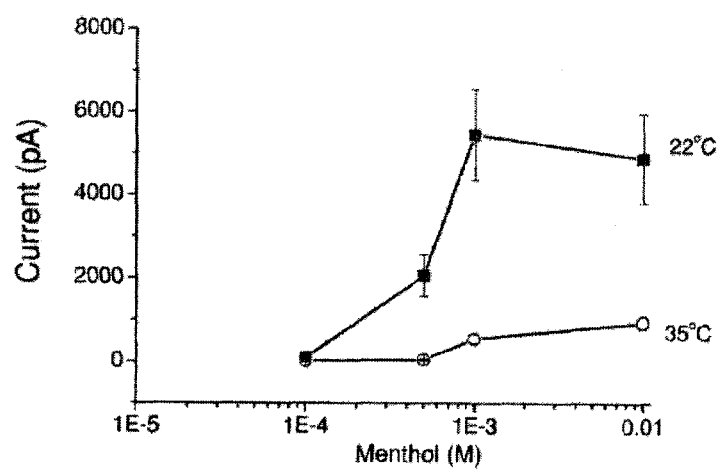

Application of menthol evokes rapidly activating currents in TRPM8 expressing, but not in non-transfected CHO cells at temperatures above the threshold for cold activation (>23° C., FIG. 10A). The menthol activated current shows pronounced outward rectification (FIG. 10B) with an $E_{rev}$ of –9.28±0.75 mV (n=12) that is similar to the $E_{rev}$ for the cold-activated current under the same ionic conditions. These currents could be inactivated by raising the temperature (see FIG. 10A) suggesting that menthol shifts the threshold for activation to higher temperatures, which agrees with the calcium imaging experiments. To test this idea further, concentration-response curves for menthol-evoked currents at two temperatures (22° C. and 35° C.) are obtained using positive membrane potentials to increase the size of the currents (FIGS. 11A and 11B). The concentration-response relationship is shifted to the left at the lower temperature with a marked increase in the maximum amplitudes (FIGS. 11A and 11B). Changes in $E_{rev}$ are used to determine the ion selectivity of the menthol activated current. Isotonic replacement of the NaCl in the solution with KCl or CsCl, causes small positive shifts in $E_{rev}$ indicating that the TRPM8 channel discriminates poorly between these cations (data not shown). From the changes in $E_{rev}$ measured on individual cells (external NaCl to KCl gives a shift of +7.38±1.43 mV, n=7; NaCl to CsCl gives a shift of +9.09±0.36 mV, n=5) a permeability sequence of Cs>K>Na is calculated with $P_{Cs}/P_{Na}$=1.43 and $P_K/P_{Na}$=1.34. Relative calcium permeability is calculated from the $E_{rev}$ values measured with different external calcium concentrations. Increasing the external calcium from 1-30 mM, in the absence of external $Mg^{2+}$ ions, shifts $E_{rev}$ by +11.67±1.20 mV, which corresponds to $P_{Ca}/P_{Na}$=0.97. Thus TRPM8 is permeable to the monovalent cations, Na, K and Cs as well as the divalent cation calcium.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

---

We claim:

1. An isolated TRPV3 polypeptide comprising amino acid residues 1-791 of SEQ ID NO: 5 or amino acid residues 2-791 of SEQ ID NO: 5.

2. The TRPV3 polypeptide of claim 1, wherein the TRPV3 polypeptide comprises amino acid residues 1-791 of SEQ ID NO: 5.

3. The TRPV3 polypeptide of claim 1, wherein the TRPV3 polypeptide comprises amino acids 2-791 of SEQ ID NO: 5.

* * * * *